(12) United States Patent
Duvick et al.

(10) Patent No.: US 6,737,562 B1
(45) Date of Patent: May 18, 2004

(54) AMINO POLYOL AMINE OXIDASE POLYNUCLEOTIDES AND RELATED POLYPEPTIDES AND METHODS OF USE

(75) Inventors: Jonathan P. Duvick, Des Moines, IA (US); Jacob T. Gilliam, Norwalk, IA (US); Joyce R. Maddox, Des Moines, IA (US)

(73) Assignee: Pioneer Hi-Bred International, Inc., Johnston, IA (US)

(*) Notice: Subject to any disclaimer, the term of this patent is extended or adjusted under 35 U.S.C. 154(b) by 0 days.

(21) Appl. No.: 09/771,045

(22) Filed: Jan. 26, 2001

Related U.S. Application Data

(63) Continuation of application No. 09/352,159, filed on Jul. 12, 1999, now Pat. No. 6,211,434, and a continuation of application No. 09/352,168, filed on Jul. 12, 1999, now Pat. No. 6,211,435.
(60) Provisional application No. 60/135,391, filed on May 21, 1999, and provisional application No. 60/092,936, filed on Jul. 15, 1998.

(51) Int. Cl.[7] .................. C12N 15/09; C12N 15/31; C12N 15/82; A01H 5/00; A01H 5/10
(52) U.S. Cl. .................. 800/279; 800/278; 800/298; 800/295; 800/320; 800/320.1; 800/320.2; 800/320.3; 800/312; 800/314; 800/322; 800/306
(58) Field of Search .................. 800/279, 278, 800/298, 295, 320, 320.1, 312, 314, 322, 306, 288, 317.4, 320.2; 435/320.1, 419, 468, 183, 195, 196; 536/23.2, 23.7, 24.1

(56) References Cited

U.S. PATENT DOCUMENTS

| | | | |
|---|---|---|---|
| 4,988,586 A | 1/1991 | Toyoda et al. | 424/93.2 |
| 5,178,863 A | 1/1993 | Toyoda et al. | 424/93.48 |
| 5,262,306 A | 11/1993 | Robeson et al. | 435/29 |
| 5,716,820 A | 2/1998 | Duvick et al. | 435/196 |
| 5,792,931 A * | 8/1998 | Duvick et al. | 800/205 |

OTHER PUBLICATIONS

Lazar et al. Molecular and Cellular Biology, vol. 8(3), pp. 1247–1252, 1988.*
Broun et al. Science, vol. 282, pp. 131–133, 1998.*
Adams et al. Accession No. AQ280543, pp. 1 and 2, deposited 1998.*
Abbas, et al., 1992, *Weed Technology*, 6: 548–552, "Phytotoxicity of Fumonisin $B_1$ on Weed and Crop Species[1]".
Blackwell, et al., 1994, *J. of AOAC International*, 77(2): 506–511, "Production of Carbon 14–Labeled Fumonisin in Liquid Culture".
Gelderblom, et al., 1993, *Food Chem. Toxic.*, 31(6): 407–414, "Structure–Activity Relationships of Fumonisins in Short–Term Carcinogenesis and Cytotoxicity Assays".
Duvick, et al., 1998, *Mol. Genetics of Host–Specific Toxins in Plant Disease*, 369–381, "Detoxification of Mycotoxins In Planta as a Strategy for Improving Grain Quality and Disease Resistance: Identification of Fumonisin–Degrading Microbes from Maize".
Blackwell, B.A., et al., 1999, *Natural Toxins*, 7(1):31–38, "Oxidative Deamination of Hydrolyzed Fumonisin $B_1$ ($AP_1$) by Cultures of Exophiala spinifera".
Schilling, B., et al., 1995, *Mol. Gen. Genet.*, 247:430–438, "Cloning, sequencing and heterologous expression of the monoamine oxidase gene from *Aspergillus niger*".
Anzai, et al., 1989, *Mol. Gen. Genet.*, 219: 492–494, "Transgenic tobacco resistant to a bacterial disease by the detoxification of a pathogenic toxin".
Kunst, F., et al., 1997, *XP 002121402, EMBL Accession No. Z99107*, "Bacillus subtilis complete genome".
Papoff, et al., 1996, *J. of Immunology*, 156(12): 4622–4630, "An N–Terminal Domain Shared by Fas/Apo–1 (CD 95) Soluble Variants Prevents Cell Death in Vitro[1,2]".
Alvarez, et al., 1997, *Oxidative Stress and the Molecular Biology of Antioxidant Defenses*, "Oxidative Burst–mediated Defense Responses in Plant Disease Resistance".
Lamb, et al., 1997, *Annu. Rev. Plant Physiol. Plant Mol. Biol.*, 48: 251–275, "The Oxidative Burst in Plant Disease Resistance".
Schrader, et al., 1996, *App. Microbiol Biotechnol*, 45: 458–464, "Studies on the inactivation of the flavoprotein $_D$–amino acid oxidase from *Trigonopsis variabilis*".
Lamprecht, et al., 1994, *Phytopathology*, 84: 383–391, "Phytotoxicity of Fumonisins and TA–Toxin to Corn and Tomato".
Itagaki, et al., 1996, *J. of Biol. Chem.*, 33: 20102–20107, "Expression and Characterization of a Modified Flavin–containing Monooxygenase 4 from Humans*".
Toyoda, et al., 1988, *Phytopathology*, 78(10):1307–1311, "Detoxification of Fusaric Acid by a Fusaric Acid–Resistant Mutant of Pseudomonas solanacearum and its Application to Biological Control of Fusarium Wilt of Tomato".
Bunz, et al., 1993, *Biodegradation*, 4: 171–178, "Purification of two isofunctional hydrolases (EC 3.7.1.8) in the degradative pathway for dibenzofuran in Sphingomonas sp. Strain RW1".
Duvick, et al., 1992, *J. of Biol. Chem.*, 267(26): 18814–18820, "Purification and Characterization of a Novel Antimicrobial Peptide from Maize (*Zea mays* L.) Kernels*".
Kraus, et al., 1992, *J. of Agri and Food Chem.*, 40(12):2331–2332, "Synthesis of Analogs of Fumonisin B1".

(List continued on next page.)

*Primary Examiner*—Amy J. Nelson
*Assistant Examiner*—Medina A. Ibrahim
(74) *Attorney, Agent, or Firm*—McKee, Voorhees & Sease, P.L.C.

(57) ABSTRACT

The present invention provides polynucleotides and related polypeptides of the enzyme APAO isolated from *Exophiala spinfera* and *Rhinocladiella atrovirens*. Additionally, the polynucleotides encoding for the APAO enzyme can be used to transform plant cells normally susceptible to Fusarium. Plants can be regenerated from the transformed plant cells.

8 Claims, No Drawings

OTHER PUBLICATIONS

Lotti, et al., 1993, *Gene,* 124:45–55, "Cloning and analysis of Canidida cylindracea lipase sequences".

Cygler, et al., 1993, *Protein Science,* 2: 366–382, "Relationship between sequence conservation and three–dimensional structure in a large family of esterases, lipases, and related proteins".

Arpagaus, et al., 1991, *J. of Biol. Chem.,* 266(11): 6966–6974, "Use of the Polymerase Chain Reaction for Homology Probing of Butyrylcholinesterase from Several Vertebrates".

Van Asch, et al., 1992, *Phytopathology,* 82: 1330–1332, "Phytotoxicity of Fumonisin B1, Moniliformin, and T–2 Toxin to Corn Callus Cultures".

Lagu, et al., 1992, *$204^{th}$ American Chemical Society National Meeting, Washington, D.C., USA,* "Synthesis Fumonisin Analogs, Abstracts of Papers (Part 2)".

Zeiss, Hans–Joachim, 1991, *J. Org. Chem.,* 56(5) 1783–1788, "Enantioselective Synthesis of Both Enantiomers of Phosphinothricin via Asymmetric Hydrogenation of α–Acylamido Acrylates".

Ishizuka, H., et al, 1995, *XP002121274 Swissprot Accession No. 40974,* "Putriscine oxidase".

Horinouchi, S., et al., 1993, *XP002121474 EMBL Accession No. D12511,* "M. Rubens gene for putrescine oxidase, complete cds".

Van Asch, et al., 1992, *Phytopathology,* 82(11): 1330–1332, "Phytotoxicity of Fumonisin $B_1$, Moniliformin, and T–2 Toxin to Corn Callus Cultures".

Vesonder, et al., 1993, *Arch. Environ. Contam. Toxicol.,* 24: 473–477, "Comparison of the Cytotoxicities of Fusarium Metabolites and Alternaria Metabolite AAL–Toxin to Cultured Mammalian Cell Lines".

Tanaka, et al., 1993, *Phytochemistry,* 33(4): 779–785, "Structure–Dependent Phytotoxicity of Fumonisins and Related Compounds in a Duckweek Bioassay".

He P., et al., 1992, *Applied and Environmental Microbiology,* 58(12): 3857–3863, "Microbial Transformation of Deoxynivalenol (Vomitoxin)".

Kneusel, et al., 1994, *The J. of Biological Chemistry,* 269(5): 3449–3456, "Molecular Characterization and Cloning of an Esterase Which Inactivates the Macrolide Toxin Brefeldin A*".

Miller, J.D., et al., 1986, *Canadian J. of Plant Pathology,*8: 147–150, "Degradation of deoxynivalenol by suspension cultures of the fusarium head blight resistant wheat cultivar Frontant".

Ueno, et al., 1983, *Applied and Environmental Microbiology,* 46: 120–127, "Metabolism of T–2 Toxin in Curtobacterium sp. Strain 114–2".

Utsumi, et al., 1991, *Agric. Biol. Chem.,* 55: 1913–1918, "Molecular Cloning and Characterization of the Fusaric Acid–resistance Gene from *Pseudomonas cepacia*".

Vesonder, et al., 1992, *Arch. Environ. Contam. Toxicol.,* 23: 464–467, Comparative Phytotoxicity of the Fumonisins, AAL–Toxin and Yeast Sphingolipids in *Lemna minor* L. (Duckweed).

Marth, et al., 1978, *J. Food Technol.,* 33: 81–87, "Update on molds: degradation of aflatoxin".

Kneusel, et al., 1990, *FEBS Letters,* 275(1–2): 107–110, "Detoxification of the macrolide toxin brefeldin A by *Bacillus subtilis*".

Quinet, et al., 1993, *J. of Biol. Chem.,* 23: 16891–16894, "Inhibition of the Cellular Secretion of Cholesteryl Ester Transfer Protein by a Variant Protein Formed by Alternative Splicing of mRNA*".

Bhat, et al., 1996, *Protein Engineering,* 9(8): 713–718, "Expression of recombinant α–$A^{ins}$–crystallin and not αA–crystallin inhibits bacterial growth".

Przemylaw, 1997, *Biochem J.,* 322: 681–692, "Oxidative burst: an early plant response to pathogen infection".

Aguirre, et al., 1989, *J. Bacteriol,* 171: 6243–6250, "Oxidation of *Neurospora crassa* NADP–Specific Glutamate dehydrogenase by Activated Oxygen Species".

Gould, et al., 1989, *J. Cell Biol.,* 108: 1657–1664, "A Conserved Tripeptide Sorts Proteins to Peroxisomes".

Gilchrist, et al., 1992, *Mycopathologia,* 117: 57–64, "Genetic and physiological response to fumonisin and AAL–toxin by intact tissue of a higher plant".

Schmiedeknecht, et al., 1996, *Eur. J. Biochem.,* 242(2) 339–351, "Isolation and characterization of a 14.5–kDa trichloroacetic–acid–soluble translational inhibitor protein from human monocytes that is upregulated upon cellular differentiation".

Samuel, et al., 1997, *Hepatology,* 25(5) 1213–1222, "Hrp12, a Novel Heat–Responsive, Tissue–Specific Phosphorylated Protein Isolated From Mouse Liver".

* cited by examiner

SEQUENCE LISTING

```
<160> NUMBER OF SEQ ID NOS: 54

<210> SEQ ID NO 1
<211> LENGTH: 372
<212> TYPE: DNA
<213> ORGANISM: Exophiala spinifera
<220> FEATURE:
<221> NAME/KEY: misc_feature
<222> LOCATION: (346)..(346)
<223> OTHER INFORMATION: n = A, T, C, or G

<400> SEQUENCE: 1
gggccccggc gttctcgtag gctgcgcgga gttggtccca gacagacttt tgtcgtacct      60
gcttggactg ttgggaccac ttccgtcccg ggtctccgac catgaaacag gtaatggacc     120
attgtcgatc gacgtcgatg ctggtatctc tggcaaatga gatggggtca cagctcgatt     180
ggaggacgcc cgagaagcct tgttcgcgcc accacggctt gtcccatacg aagactatct     240
```

```
tgctatagta gcccaggata gaattttccg ccaatgcttg cttctcggcg ggaagaggtg    300
gtgaaaatgt caaggtggga tacaaggttg tcggtaacga aaccancacc tttttgcttc    360
ggaacacggc gc                                                        372
```

<210> SEQ ID NO 2
<211> LENGTH: 182
<212> TYPE: DNA
<213> ORGANISM: Exophiala spinifera

<400> SEQUENCE: 2

```
gaattttccg ccaatgcttg cttctcggcg ggaagaggtg gtgaaaatgt caaggtggga     60
tacaaggttg tcggtaacga aaccaccacc tttttgcttc ggaacacggc gcccgaggcc    120
gatcgtactg tacagccgga tgccgactgc tcaatttcag cgacggcggt gttgaggtgc    180
ac                                                                   182
```

<210> SEQ ID NO 3
<211> LENGTH: 29
<212> TYPE: DNA
<213> ORGANISM: Artificial Sequence
<220> FEATURE:
<223> OTHER INFORMATION: Designed oligonucleotide for 3' RACE N21965
      (Exophiala spinifera)

<400> SEQUENCE: 3

```
tggtttcgtt accgacaacc ttgtatccc                                       29
```

<210> SEQ ID NO 4
<211> LENGTH: 28
<212> TYPE: DNA
<213> ORGANISM: Artificial Sequence
<220> FEATURE:
<223> OTHER INFORMATION: Designed oligonucleotide for 5' RACE 21968

<400> SEQUENCE: 4

```
gagttggtcc cagacagact tttgtcgt                                        28
```

<210> SEQ ID NO 5
<211> LENGTH: 1389
<212> TYPE: DNA
<213> ORGANISM: Exophiala spinifera
<220> FEATURE:
<221> NAME/KEY: CDS
<222> LOCATION: (1)..(1386)
<223> OTHER INFORMATION:

<400> SEQUENCE: 5

```
gac aac gtt gcg gac gtg gta gtg gtg ggc gct ggc ttg agc ggt ttg       48
Asp Asn Val Ala Asp Val Val Val Val Gly Ala Gly Leu Ser Gly Leu
1               5                   10                  15 gag acg gca cgc aaa gtc cag gcc gcc ggt ctg tcc tgc ctc gtt ctt       96
Glu Thr Ala Arg Lys Val Gln Ala Ala Gly Leu Ser Cys Leu Val Leu
            20                  25                  30 gag gcg atg gat cgt gta ggg gga aag act ctg agc gta caa tcg ggt      144
Glu Ala Met Asp Arg Val Gly Gly Lys Thr Leu Ser Val Gln Ser Gly
        35                  40                  45 ccc ggc agg acg act atc aac gac ctc ggc gct gcg tgg atc aat gac      192
Pro Gly Arg Thr Thr Ile Asn Asp Leu Gly Ala Ala Trp Ile Asn Asp
    50                  55                  60 agc aac caa agc gaa gta tcc aga ttg ttt gaa aga ttt cat ttg gag      240
Ser Asn Gln Ser Glu Val Ser Arg Leu Phe Glu Arg Phe His Leu Glu
65                  70                  75                  80
```

```
ggc gag ctc cag agg acg act gga aat tca atc cat caa gca caa gac         288
Gly Glu Leu Gln Arg Thr Thr Gly Asn Ser Ile His Gln Ala Gln Asp
            85                  90                  95 ggt aca acc act aca gct cct tat ggt gac tcc ttg ctg agc gag gag         336
Gly Thr Thr Thr Thr Ala Pro Tyr Gly Asp Ser Leu Leu Ser Glu Glu
                100                 105                 110 gtt gca agt gca ctt gcg gaa ctc ctc ccc gta tgg tct cag ctg atc         384
Val Ala Ser Ala Leu Ala Glu Leu Leu Pro Val Trp Ser Gln Leu Ile
        115                 120                 125 gaa gag cat agc ctt caa gac ctc aag gcg agc cct cag gcg aag cgg         432
Glu Glu His Ser Leu Gln Asp Leu Lys Ala Ser Pro Gln Ala Lys Arg
    130                 135                 140 ctc gac agt gtg agc ttc gcg cac tac tgt gag aag gaa cta aac ttg         480
Leu Asp Ser Val Ser Phe Ala His Tyr Cys Glu Lys Glu Leu Asn Leu
145                 150                 155                 160 cct gct gtt ctc ggc gta gca aac cag atc aca cgc gct ctg ctc ggt         528
Pro Ala Val Leu Gly Val Ala Asn Gln Ile Thr Arg Ala Leu Leu Gly
                165                 170                 175 gtg gaa gcc cac gag atc agc atg ctt ttt ctc acc gac tac atc aag         576
Val Glu Ala His Glu Ile Ser Met Leu Phe Leu Thr Asp Tyr Ile Lys
            180                 185                 190 agt gcc acc ggt ctc agt aat att ttc tcg gac aag aaa gac ggc ggg         624
Ser Ala Thr Gly Leu Ser Asn Ile Phe Ser Asp Lys Lys Asp Gly Gly
        195                 200                 205 cag tat atg cga tgc aaa aca ggt atg cag tcg att tgc cat gcc atg         672
Gln Tyr Met Arg Cys Lys Thr Gly Met Gln Ser Ile Cys His Ala Met
    210                 215                 220 tca aag gaa ctt gtt cca ggc tca gtg cac ctc aac acc ccc gtc gct         720
Ser Lys Glu Leu Val Pro Gly Ser Val His Leu Asn Thr Pro Val Ala
225                 230                 235                 240 gaa att gag cag tcg gca tcc ggc tgt aca gta cga tcg gcc tcg ggc         768
Glu Ile Glu Gln Ser Ala Ser Gly Cys Thr Val Arg Ser Ala Ser Gly
                245                 250                 255 gcc gtg ttc cga agc aaa aag gtg gtg gtt tcg tta ccg aca acc ttg         816
Ala Val Phe Arg Ser Lys Lys Val Val Val Ser Leu Pro Thr Thr Leu
            260                 265                 270 tat ccc acc ttg aca ttt tca cca cct ctt ccc gcc gag aag caa gca         864
Tyr Pro Thr Leu Thr Phe Ser Pro Pro Leu Pro Ala Glu Lys Gln Ala
        275                 280                 285 ttg gcg gaa aat tct atc ctg ggc tac tat agc aag ata gtc ttc gta         912
Leu Ala Glu Asn Ser Ile Leu Gly Tyr Tyr Ser Lys Ile Val Phe Val
    290                 295                 300 tgg gac aag ccg tgg tgg cgc gaa caa ggc ttc tcg ggc gtc ctc caa         960
Trp Asp Lys Pro Trp Trp Arg Glu Gln Gly Phe Ser Gly Val Leu Gln
305                 310                 315                 320 tcg agc tgt gac ccc atc tca ttt gcc aga gat acc agc atc gac gtc        1008
Ser Ser Cys Asp Pro Ile Ser Phe Ala Arg Asp Thr Ser Ile Asp Val
                325                 330                 335 gat cga caa tgg tcc att acc tgt ttc atg gtc gga gac ccg gga cgg        1056
Asp Arg Gln Trp Ser Ile Thr Cys Phe Met Val Gly Asp Pro Gly Arg
            340                 345                 350 aag tgg tcc caa cag tcc aag cag gta cga caa aag tct gtc tgg gac        1104
Lys Trp Ser Gln Gln Ser Lys Gln Val Arg Gln Lys Ser Val Trp Asp
        355                 360                 365 caa ctc cgc gca gcc tac gag aac gcc ggg gcc caa gtc cca gag ccg        1152
Gln Leu Arg Ala Ala Tyr Glu Asn Ala Gly Ala Gln Val Pro Glu Pro
    370                 375                 380 gcc aac gtg ctc gaa atc gag tgg tcg aag cag cag tat ttc caa gga        1200
Ala Asn Val Leu Glu Ile Glu Trp Ser Lys Gln Gln Tyr Phe Gln Gly
```

-continued

```
                    385                 390                 395                 400
gct ccg agc gcc gtc tat ggg ctg aac gat ctc atc aca ctg ggt tcg              1248
Ala Pro Ser Ala Val Tyr Gly Leu Asn Asp Leu Ile Thr Leu Gly Ser
                405                 410                 415 gcg ctc aga acg ccg ttc aag agt gtt cat ttc gtt gga acg gag acg              1296
Ala Leu Arg Thr Pro Phe Lys Ser Val His Phe Val Gly Thr Glu Thr
            420                 425                 430 tct tta gtt tgg aaa ggg tat atg gaa ggg gcc ata cga tcg ggt caa              1344
Ser Leu Val Trp Lys Gly Tyr Met Glu Gly Ala Ile Arg Ser Gly Gln
        435                 440                 445 cga ggt gct gca gaa gtt gtg gct agc ctg gtg cca gca gca tag                  1389
Arg Gly Ala Ala Glu Val Val Ala Ser Leu Val Pro Ala Ala
    450                 455                 460

<210> SEQ ID NO 6
<211> LENGTH: 462
<212> TYPE: PRT
<213> ORGANISM: Exophiala spinifera

<400> SEQUENCE: 6

Asp Asn Val Ala Asp Val Val Val Gly Ala Gly Leu Ser Gly Leu
1               5                   10                  15

Glu Thr Ala Arg Lys Val Gln Ala Ala Gly Leu Ser Cys Leu Val Leu
                20                  25                  30

Glu Ala Met Asp Arg Val Gly Gly Lys Thr Leu Ser Val Gln Ser Gly
            35                  40                  45

Pro Gly Arg Thr Thr Ile Asn Asp Leu Gly Ala Ala Trp Ile Asn Asp
        50                  55                  60

Ser Asn Gln Ser Glu Val Ser Arg Leu Phe Glu Arg Phe His Leu Glu
65                  70                  75                  80

Gly Glu Leu Gln Arg Thr Thr Gly Asn Ser Ile His Gln Ala Gln Asp
                85                  90                  95

Gly Thr Thr Thr Thr Ala Pro Tyr Gly Asp Ser Leu Leu Ser Glu Glu
            100                 105                 110

Val Ala Ser Ala Leu Ala Glu Leu Leu Pro Val Trp Ser Gln Leu Ile
        115                 120                 125

Glu Glu His Ser Leu Gln Asp Leu Lys Ala Ser Pro Gln Ala Lys Arg
130                 135                 140

Leu Asp Ser Val Ser Phe Ala His Tyr Cys Glu Lys Glu Leu Asn Leu
145                 150                 155                 160

Pro Ala Val Leu Gly Val Ala Asn Gln Ile Thr Arg Ala Leu Leu Gly
                165                 170                 175

Val Glu Ala His Glu Ile Ser Met Leu Phe Leu Thr Asp Tyr Ile Lys
            180                 185                 190

Ser Ala Thr Gly Leu Ser Asn Ile Phe Ser Asp Lys Lys Asp Gly Gly
        195                 200                 205

Gln Tyr Met Arg Cys Lys Thr Gly Met Gln Ser Ile Cys His Ala Met
    210                 215                 220

Ser Lys Glu Leu Val Pro Gly Ser Val His Leu Asn Thr Pro Val Ala
225                 230                 235                 240

Glu Ile Glu Gln Ser Ala Ser Gly Cys Thr Val Arg Ser Ala Ser Gly
                245                 250                 255

Ala Val Phe Arg Ser Lys Lys Val Val Ser Leu Pro Thr Thr Leu
            260                 265                 270

Tyr Pro Thr Leu Thr Phe Ser Pro Pro Leu Pro Ala Glu Lys Gln Ala
        275                 280                 285
```

-continued

```
Leu Ala Glu Asn Ser Ile Leu Gly Tyr Tyr Ser Lys Ile Val Phe Val
    290                 295                 300

Trp Asp Lys Pro Trp Trp Arg Glu Gln Gly Phe Ser Gly Val Leu Gln
305                 310                 315                 320

Ser Ser Cys Asp Pro Ile Ser Phe Ala Arg Asp Thr Ser Ile Asp Val
                325                 330                 335

Asp Arg Gln Trp Ser Ile Thr Cys Phe Met Val Gly Asp Pro Gly Arg
            340                 345                 350

Lys Trp Ser Gln Gln Ser Lys Gln Val Arg Gln Lys Ser Val Trp Asp
        355                 360                 365

Gln Leu Arg Ala Ala Tyr Glu Asn Ala Gly Ala Gln Val Pro Glu Pro
    370                 375                 380

Ala Asn Val Leu Glu Ile Glu Trp Ser Lys Gln Gln Tyr Phe Gln Gly
385                 390                 395                 400

Ala Pro Ser Ala Val Tyr Gly Leu Asn Asp Leu Ile Thr Leu Gly Ser
                405                 410                 415

Ala Leu Arg Thr Pro Phe Lys Ser Val His Phe Val Gly Thr Glu Thr
            420                 425                 430

Ser Leu Val Trp Lys Gly Tyr Met Glu Gly Ala Ile Arg Ser Gly Gln
        435                 440                 445

Arg Gly Ala Ala Glu Val Val Ala Ser Leu Val Pro Ala Ala
    450                 455                 460
```

<210> SEQ ID NO 7
<211> LENGTH: 1442
<212> TYPE: DNA
<213> ORGANISM: Exophiala spinifera
<220> FEATURE:
<221> NAME/KEY: CDS
<222> LOCATION: (1)..(645)
<223> OTHER INFORMATION:
<220> FEATURE:
<221> NAME/KEY: Intron
<222> LOCATION: (646)..(698)
<223> OTHER INFORMATION:
<220> FEATURE:
<221> NAME/KEY: CDS
<222> LOCATION: (699)..(1439)
<223> OTHER INFORMATION:

<400> SEQUENCE: 7

```
gac aac gtt gcg gac gtg gta gtg gtg ggc gct ggc ttg agc ggt ttg      48
Asp Asn Val Ala Asp Val Val Val Val Gly Ala Gly Leu Ser Gly Leu
1               5                  10                  15 gag acg gca cgc aaa gtc cag gcc gcc ggt ctg tcc tgc ctc gtt ctt      96
Glu Thr Ala Arg Lys Val Gln Ala Ala Gly Leu Ser Cys Leu Val Leu
            20                  25                  30 gag gcg atg gat cgt gta ggg gga aag act ctg agc gta caa tcg ggt     144
Glu Ala Met Asp Arg Val Gly Gly Lys Thr Leu Ser Val Gln Ser Gly
        35                  40                  45 ccc ggc agg acg act atc aac gac ctc ggc gct gcg tgg atc aat gac     192
Pro Gly Arg Thr Thr Ile Asn Asp Leu Gly Ala Ala Trp Ile Asn Asp
    50                  55                  60 agc aac caa agc gaa gta tcc aga ttg ttt gaa aga ttt cat ttg gag     240
Ser Asn Gln Ser Glu Val Ser Arg Leu Phe Glu Arg Phe His Leu Glu
65                  70                  75                  80 ggc gag ctc cag agg acg act gga aat tca atc cat caa gca caa gac     288
Gly Glu Leu Gln Arg Thr Thr Gly Asn Ser Ile His Gln Ala Gln Asp
                85                  90                  95 ggt aca acc act aca gct cct tat ggt gac tcc ttg ctg agc gag gag     336
```

-continued

| | | | | | | | | | | | | |
|---|---|---|---|---|---|---|---|---|---|---|---|---|
| Gly | Thr | Thr | Thr | Thr | Ala | Pro | Tyr | Gly | Asp | Ser | Leu | Leu | Ser | Glu | Glu |
| | | | 100 | | | | | 105 | | | | | 110 | | |

```
gtt gca agt gca ctt gcg gaa ctc ctc ccc gta tgg tct cag ctg atc    384
Val Ala Ser Ala Leu Ala Glu Leu Leu Pro Val Trp Ser Gln Leu Ile
            115                 120                 125 gaa gag cat agc ctt caa gac ctc aag gcg agc cct cag gcg aag cgg    432
Glu Glu His Ser Leu Gln Asp Leu Lys Ala Ser Pro Gln Ala Lys Arg
130                 135                 140 ctc gac agt gtg agc ttc gcg cac tac tgt gag aag gaa cta aac ttg    480
Leu Asp Ser Val Ser Phe Ala His Tyr Cys Glu Lys Glu Leu Asn Leu
145                 150                 155                 160 cct gct gtt ctc ggc gta gca aac cag atc aca cgc gct ctg ctc ggt    528
Pro Ala Val Leu Gly Val Ala Asn Gln Ile Thr Arg Ala Leu Leu Gly
                165                 170                 175 gtg gaa gcc cac gag atc agc atg ctt ttt ctc acc gac tac atc aag    576
Val Glu Ala His Glu Ile Ser Met Leu Phe Leu Thr Asp Tyr Ile Lys
                180                 185                 190 agt gcc acc ggt ctc agt aat att ttc tcg gac aag aaa gac ggc ggg    624
Ser Ala Thr Gly Leu Ser Asn Ile Phe Ser Asp Lys Lys Asp Gly Gly
            195                 200                 205 cag tat gtg cga tgc aaa aca ggtgcgtgtg gtgtcgtctc aggtggggga       675
Gln Tyr Val Arg Cys Lys Thr
        210                 215 ctcgtttctc agtggtcatt cca ggt atg cag tcg att tgc cat gcc atg tca  728
                        Gly Met Gln Ser Ile Cys His Ala Met Ser
                                        220                 225 aag gaa ctt gtt cca ggc tca gtg cac ctc aac acc ccc gtc gct gaa    776
Lys Glu Leu Val Pro Gly Ser Val His Leu Asn Thr Pro Val Ala Glu
                230                 235                 240 att gag cag tcg gca tcc ggc tgt aca gta cga tcg gcc tcg ggc gcc    824
Ile Glu Gln Ser Ala Ser Gly Cys Thr Val Arg Ser Ala Ser Gly Ala
            245                 250                 255 gtg ttc cga agc aaa aag gtg gtg gtt tcg tta ccg aca acc ttg tat    872
Val Phe Arg Ser Lys Lys Val Val Val Ser Leu Pro Thr Thr Leu Tyr
            260                 265                 270 ccc acc ttg aca ttt tca cca cct ctt ccc gcc gag aag caa gca ttg    920
Pro Thr Leu Thr Phe Ser Pro Pro Leu Pro Ala Glu Lys Gln Ala Leu
        275                 280                 285 gcg gaa aat tct atc ctg ggc tac tat agc aag ata gtc ttc gta tgg    968
Ala Glu Asn Ser Ile Leu Gly Tyr Tyr Ser Lys Ile Val Phe Val Trp
290                 295                 300                 305 gac aag ccg tgg tgg cgc gaa caa ggc ttc tcg ggc gtc ctc caa tcg    1016
Asp Lys Pro Trp Trp Arg Glu Gln Gly Phe Ser Gly Val Leu Gln Ser
            310                 315                 320 agc tgt gac ccc atc tca ttt gcc aga gat acc agc atc gac gtc gat    1064
Ser Cys Asp Pro Ile Ser Phe Ala Arg Asp Thr Ser Ile Asp Val Asp
        325                 330                 335 cga caa tgg tcc att acc tgt ttc atg gtc gga gac ccg gga cgg aag    1112
Arg Gln Trp Ser Ile Thr Cys Phe Met Val Gly Asp Pro Gly Arg Lys
        340                 345                 350 tgg tcc caa cag tcc aag cag gta cga caa aag tct gtc tgg gac caa    1160
Trp Ser Gln Gln Ser Lys Gln Val Arg Gln Lys Ser Val Trp Asp Gln
355                 360                 365 ctc cgc gca gcc tac gag aac gcc ggg gcc caa gtc cca gag ccg gcc    1208
Leu Arg Ala Ala Tyr Glu Asn Ala Gly Ala Gln Val Pro Glu Pro Ala
370                 375                 380                 385 aac gtg ctc gaa atc gag tgg tcg aag cag cag tat ttc caa gga gct    1256
Asn Val Leu Glu Ile Glu Trp Ser Lys Gln Gln Tyr Phe Gln Gly Ala
            390                 395                 400
```

```
ccg agc gcc gtc tat ggg ctg aac gat ctc atc aca ctg ggt tcg gcg      1304
Pro Ser Ala Val Tyr Gly Leu Asn Asp Leu Ile Thr Leu Gly Ser Ala
        405                 410                 415 ctc aga acg ccg ttc aag agt gtt cat ttc gtt gga acg gag acg tct      1352
Leu Arg Thr Pro Phe Lys Ser Val His Phe Val Gly Thr Glu Thr Ser
        420                 425                 430 tta gtt tgg aaa ggg tat atg gaa ggg gcc ata cga tcg ggt caa cga      1400
Leu Val Trp Lys Gly Tyr Met Glu Gly Ala Ile Arg Ser Gly Gln Arg
    435                 440                 445 ggt gct gca gaa gtt gtg gct agc ctg gtg cca gca gca tag              1442
Gly Ala Ala Glu Val Val Ala Ser Leu Val Pro Ala Ala
450                 455                 460

<210> SEQ ID NO 8
<211> LENGTH: 462
<212> TYPE: PRT
<213> ORGANISM: Exophiala spinifera

<400> SEQUENCE: 8

Asp Asn Val Ala Asp Val Val Val Gly Ala Gly Leu Ser Gly Leu
1               5                   10                  15

Glu Thr Ala Arg Lys Val Gln Ala Ala Gly Leu Ser Cys Leu Val Leu
                20                  25                  30

Glu Ala Met Asp Arg Val Gly Gly Lys Thr Leu Ser Val Gln Ser Gly
            35                  40                  45

Pro Gly Arg Thr Thr Ile Asn Asp Leu Gly Ala Ala Trp Ile Asn Asp
    50                  55                  60

Ser Asn Gln Ser Glu Val Ser Arg Leu Phe Glu Arg Phe His Leu Glu
65                  70                  75                  80

Gly Glu Leu Gln Arg Thr Thr Gly Asn Ser Ile His Gln Ala Gln Asp
                85                  90                  95

Gly Thr Thr Thr Thr Ala Pro Tyr Gly Asp Ser Leu Leu Ser Glu Glu
            100                 105                 110

Val Ala Ser Ala Leu Ala Glu Leu Leu Pro Val Trp Ser Gln Leu Ile
        115                 120                 125

Glu Glu His Ser Leu Gln Asp Leu Lys Ala Ser Pro Gln Ala Lys Arg
    130                 135                 140

Leu Asp Ser Val Ser Phe Ala His Tyr Cys Glu Lys Glu Leu Asn Leu
145                 150                 155                 160

Pro Ala Val Leu Gly Val Ala Asn Gln Ile Thr Arg Ala Leu Leu Gly
                165                 170                 175

Val Glu Ala His Glu Ile Ser Met Leu Phe Leu Thr Asp Tyr Ile Lys
            180                 185                 190

Ser Ala Thr Gly Leu Ser Asn Ile Phe Ser Asp Lys Lys Asp Gly Gly
        195                 200                 205

Gln Tyr Val Arg Cys Lys Thr Gly Met Gln Ser Ile Cys His Ala Met
    210                 215                 220

Ser Lys Glu Leu Val Pro Gly Ser Val His Leu Asn Thr Pro Val Ala
225                 230                 235                 240

Glu Ile Glu Gln Ser Ala Ser Gly Cys Thr Val Arg Ser Ala Ser Gly
                245                 250                 255

Ala Val Phe Arg Ser Lys Lys Val Val Ser Leu Pro Thr Thr Leu
            260                 265                 270

Tyr Pro Thr Leu Thr Phe Ser Pro Pro Leu Pro Ala Glu Lys Gln Ala
        275                 280                 285

Leu Ala Glu Asn Ser Ile Leu Gly Tyr Tyr Ser Lys Ile Val Phe Val
```

-continued

```
                290                 295                 300
Trp Asp Lys Pro Trp Trp Arg Glu Gln Gly Phe Ser Gly Val Leu Gln
305                 310                 315                 320

Ser Ser Cys Asp Pro Ile Ser Phe Ala Arg Asp Thr Ser Ile Asp Val
                325                 330                 335

Asp Arg Gln Trp Ser Ile Thr Cys Phe Met Val Gly Asp Pro Gly Arg
                340                 345                 350

Lys Trp Ser Gln Gln Ser Lys Gln Val Arg Gln Lys Ser Val Trp Asp
                355                 360                 365

Gln Leu Arg Ala Ala Tyr Glu Asn Ala Gly Ala Gln Val Pro Glu Pro
                370                 375                 380

Ala Asn Val Leu Glu Ile Glu Trp Ser Lys Gln Gln Tyr Phe Gln Gly
385                 390                 395                 400

Ala Pro Ser Ala Val Tyr Gly Leu Asn Asp Leu Ile Thr Leu Gly Ser
                405                 410                 415

Ala Leu Arg Thr Pro Phe Lys Ser Val His Phe Val Gly Thr Glu Thr
                420                 425                 430

Ser Leu Val Trp Lys Gly Tyr Met Glu Gly Ala Ile Arg Ser Gly Gln
                435                 440                 445

Arg Gly Ala Ala Glu Val Val Ala Ser Leu Val Pro Ala Ala
                450                 455                 460
```

<210> SEQ ID NO 9
<211> LENGTH: 458
<212> TYPE: PRT
<213> ORGANISM: Exophiala spinifera

<400> SEQUENCE: 9

```
Asp Asn Val Ala Asp Val Val Val Gly Ala Gly Leu Ser Gly Leu
1               5                   10                  15

Glu Thr Ala Arg Lys Val Gln Ala Ala Gly Leu Ser Cys Leu Val Leu
                20                  25                  30

Glu Ala Met Asp Arg Val Gly Gly Lys Thr Leu Ser Val Gln Ser Gly
                35                  40                  45

Pro Gly Arg Thr Thr Ile Asn Asp Leu Gly Ala Ala Trp Ile Asn Asp
                50                  55                  60

Ser Asn Gln Ser Glu Val Ser Arg Leu Phe Glu Arg Phe His Leu Glu
65              70                  75                  80

Gly Glu Leu Gln Arg Thr Thr Gly Asn Ser Ile His Gln Ala Gln Asp
                85                  90                  95

Gly Thr Thr Thr Thr Ala Pro Tyr Gly Asp Ser Leu Leu Ser Glu Glu
                100                 105                 110

Val Ala Ser Ala Leu Ala Glu Leu Leu Pro Val Trp Ser Gln Leu Ile
                115                 120                 125

Glu Glu His Ser Leu Gln Asp Leu Lys Ala Ser Pro Gln Ala Lys Arg
                130                 135                 140

Leu Asp Ser Val Ser Phe Ala His Tyr Cys Glu Lys Glu Leu Asn Leu
145                 150                 155                 160

Pro Ala Val Leu Gly Val Ala Asn Gln Ile Thr Arg Ala Leu Leu Gly
                165                 170                 175

Val Glu Ala His Glu Ile Ser Met Leu Phe Leu Thr Asp Tyr Ile Lys
                180                 185                 190

Ser Ala Thr Gly Leu Ser Asn Ile Phe Ser Asp Lys Lys Asp Gly Gly
                195                 200                 205
```

```
Gln Tyr Val Arg Cys Lys Thr Gly Ala Cys Gly Val Ser Gly Gly
    210                 215                 220

Gly Leu Val Ser Gln Trp Ser Phe Gln Val Cys Ser Arg Phe Ala Met
225                 230                 235                 240

Pro Cys Gln Arg Asn Leu Phe Gln Ala Gln Cys Thr Ser Thr Pro Pro
                245                 250                 255

Ser Leu Lys Leu Ser Ser Arg His Pro Ala Val Gln Tyr Asp Arg Pro
            260                 265                 270

Arg Ala Pro Cys Ser Glu Ala Lys Arg Trp Trp Phe Arg Tyr Arg Gln
        275                 280                 285

Pro Cys Ile Pro Pro His Phe His Leu Phe Pro Pro Arg Ser Lys
    290                 295                 300

His Trp Arg Lys Ile Leu Ser Trp Ala Thr Ile Ala Arg Ser Ser Tyr
305                 310                 315                 320

Gly Thr Ser Arg Gly Gly Ala Asn Lys Ala Ser Arg Ala Ser Ser Asn
                325                 330                 335

Arg Ala Val Thr Pro Ser His Leu Pro Glu Ile Pro Ala Ser Thr Ser
                340                 345                 350

Ile Asp Asn Gly Pro Leu Pro Val Ser Trp Ser Glu Thr Arg Asp Gly
            355                 360                 365

Ser Gly Pro Asn Ser Pro Ser Arg Tyr Asp Lys Ser Leu Ser Gly Thr
        370                 375                 380

Asn Ser Ala Gln Pro Thr Arg Thr Pro Gly Pro Lys Ser Gln Ser Arg
385                 390                 395                 400

Pro Thr Cys Ser Lys Ser Ser Gly Arg Ser Ser Ile Ser Lys Glu
                405                 410                 415

Leu Arg Ala Pro Ser Met Gly Thr Ile Ser Ser His Trp Val Arg Arg
                420                 425                 430

Ser Glu Arg Arg Ser Arg Val Phe Ile Ser Leu Glu Arg Arg Leu
            435                 440                 445

Phe Gly Lys Gly Ile Trp Lys Gly Pro Tyr
    450                 455

<210> SEQ ID NO 10
<211> LENGTH: 1392
<212> TYPE: DNA
<213> ORGANISM: Exophiala spinifera
<220> FEATURE:
<221> NAME/KEY: CDS
<222> LOCATION: (1)..(1389)
<223> OTHER INFORMATION:
<220> FEATURE:
<221> NAME/KEY: misc_feature
<222> LOCATION: (1)..(3)
<223> OTHER INFORMATION: Extra lysine in K:trAPAO

<400> SEQUENCE: 10 aaa gac aac gtt gcg gac gtg gta gtg gtg ggc gct ggc ttg agc ggt      48
Lys Asp Asn Val Ala Asp Val Val Val Val Gly Ala Gly Leu Ser Gly
1               5                   10                  15 ttg gag acg gca cgc aaa gtc cag gcc gcc ggt ctg tcc tgc ctc gtt     96
Leu Glu Thr Ala Arg Lys Val Gln Ala Ala Gly Leu Ser Cys Leu Val
                20                  25                  30 ctt gag gcg atg gat cgt gta ggg gga aag act ctg agc gta caa tcg    144
Leu Glu Ala Met Asp Arg Val Gly Gly Lys Thr Leu Ser Val Gln Ser
            35                  40                  45 ggt ccc ggc agg acg act atc aac gac ctc ggc gct gcg tgg atc aat    192
Gly Pro Gly Arg Thr Thr Ile Asn Asp Leu Gly Ala Ala Trp Ile Asn
        50                  55                  60
```

-continued

| | |
|---|---|
| gac agc aac caa agc gaa gta tcc aga ttg ttt gaa aga ttt cat ttg<br>Asp Ser Asn Gln Ser Glu Val Ser Arg Leu Phe Glu Arg Phe His Leu<br>65                70                  75                80 | 240 |
| gag ggc gag ctc cag agg acg act gga aat tca atc cat caa gca caa<br>Glu Gly Glu Leu Gln Arg Thr Thr Gly Asn Ser Ile His Gln Ala Gln<br>                85                  90                  95 | 288 |
| gac ggt aca acc act aca gct cct tat ggt gac tcc ttg ctg agc gag<br>Asp Gly Thr Thr Thr Thr Ala Pro Tyr Gly Asp Ser Leu Leu Ser Glu<br>100                   105                  110 | 336 |
| gag gtt gca agt gca ctt gcg gaa ctc ctc ccc gta tgg tct cag ctg<br>Glu Val Ala Ser Ala Leu Ala Glu Leu Leu Pro Val Trp Ser Gln Leu<br>            115                  120                  125 | 384 |
| atc gaa gag cat agc ctt caa gac ctc aag gcg agc cct cag gcg aag<br>Ile Glu Glu His Ser Leu Gln Asp Leu Lys Ala Ser Pro Gln Ala Lys<br>130                   135                  140 | 432 |
| cgg ctc gac agt gtg agc ttc gcg cac tac tgt gag aag gaa cta aac<br>Arg Leu Asp Ser Val Ser Phe Ala His Tyr Cys Glu Lys Glu Leu Asn<br>145                 150                  155                  160 | 480 |
| ttg cct gct gtt ctc ggc gta gca aac cag atc aca cgc gct ctg ctc<br>Leu Pro Ala Val Leu Gly Val Ala Asn Gln Ile Thr Arg Ala Leu Leu<br>                   165                  170                  175 | 528 |
| ggt gtg gaa gcc cac gag atc agc atg ctt ttt ctc acc gac tac atc<br>Gly Val Glu Ala His Glu Ile Ser Met Leu Phe Leu Thr Asp Tyr Ile<br>180                   185                  190 | 576 |
| aag agt gcc acc ggt ctc agt aat att ttc tcg gac aag aaa gac ggc<br>Lys Ser Ala Thr Gly Leu Ser Asn Ile Phe Ser Asp Lys Lys Asp Gly<br>            195                  200                  205 | 624 |
| ggg cag tat atg cga tgc aaa aca ggt atg cag tcg att tgc cat gcc<br>Gly Gln Tyr Met Arg Cys Lys Thr Gly Met Gln Ser Ile Cys His Ala<br>210                   215                  220 | 672 |
| atg tca aag gaa ctt gtt cca ggc tca gtg cac ctc aac acc ccc gtc<br>Met Ser Lys Glu Leu Val Pro Gly Ser Val His Leu Asn Thr Pro Val<br>225                 230                  235                  240 | 720 |
| gct gaa att gag cag tcg gca tcc ggc tgt aca gta cga tcg gcc tcg<br>Ala Glu Ile Glu Gln Ser Ala Ser Gly Cys Thr Val Arg Ser Ala Ser<br>                   245                  250                  255 | 768 |
| ggc gcc gtg ttc cga agc aaa aag gtg gtg gtt tcg tta ccg aca acc<br>Gly Ala Val Phe Arg Ser Lys Lys Val Val Val Ser Leu Pro Thr Thr<br>260                   265                  270 | 816 |
| ttg tat ccc acc ttg aca ttt tca cca cct ctt ccc gcc gag aag caa<br>Leu Tyr Pro Thr Leu Thr Phe Ser Pro Pro Leu Pro Ala Glu Lys Gln<br>            275                  280                  285 | 864 |
| gca ttg gcg gaa aat tct atc ctg ggc tac tat agc aag ata gtc ttc<br>Ala Leu Ala Glu Asn Ser Ile Leu Gly Tyr Tyr Ser Lys Ile Val Phe<br>290                   295                  300 | 912 |
| gta tgg gac aag ccg tgg tgg cgc gaa caa ggc ttc tcg ggc gtc ctc<br>Val Trp Asp Lys Pro Trp Trp Arg Glu Gln Gly Phe Ser Gly Val Leu<br>305                 310                  315                  320 | 960 |
| caa tcg agc tgt gac ccc atc tca ttt gcc aga gat acc agc atc gac<br>Gln Ser Ser Cys Asp Pro Ile Ser Phe Ala Arg Asp Thr Ser Ile Asp<br>                   325                  330                  335 | 1008 |
| gtc gat cga caa tgg tcc att acc tgt ttc atg gtc gga gac ccg gga<br>Val Asp Arg Gln Trp Ser Ile Thr Cys Phe Met Val Gly Asp Pro Gly<br>                340                  345                  350 | 1056 |
| cgg aag tgg tcc caa cag tcc aag cag gta cga caa aag tct gtc tgg<br>Arg Lys Trp Ser Gln Gln Ser Lys Gln Val Arg Gln Lys Ser Val Trp<br>355                   360                  365 | 1104 |
| gac caa ctc cgc gca gcc tac gag aac gcc ggg gcc caa gtc cca gag<br>Asp Gln Leu Arg Ala Ala Tyr Glu Asn Ala Gly Ala Gln Val Pro Glu | 1152 |

```
         370                375                 380
ccg gcc aac gtg ctc gaa atc gag tgg tcg aag cag cag tat ttc caa    1200
Pro Ala Asn Val Leu Glu Ile Glu Trp Ser Lys Gln Gln Tyr Phe Gln
385                 390                 395                 400 gga gct ccg agc gcc gtc tat ggg ctg aac gat ctc atc aca ctg ggt    1248
Gly Ala Pro Ser Ala Val Tyr Gly Leu Asn Asp Leu Ile Thr Leu Gly
                405                 410                 415 tcg gcg ctc aga acg ccg ttc aag agt gtt cat ttc gtt gga acg gag    1296
Ser Ala Leu Arg Thr Pro Phe Lys Ser Val His Phe Val Gly Thr Glu
            420                 425                 430 acg tct tta gtt tgg aaa ggg tat atg gaa ggg gcc ata cga tcg ggt    1344
Thr Ser Leu Val Trp Lys Gly Tyr Met Glu Gly Ala Ile Arg Ser Gly
        435                 440                 445 caa cga ggt gct gca gaa gtt gtg gct agc ctg gtg cca gca gca tag    1392
Gln Arg Gly Ala Ala Glu Val Val Ala Ser Leu Val Pro Ala Ala
    450                 455                 460

<210> SEQ ID NO 11
<211> LENGTH: 463
<212> TYPE: PRT
<213> ORGANISM: Exophiala spinifera
<220> FEATURE:
<221> NAME/KEY: misc_feature
<222> LOCATION: (1)..(3)
<223> OTHER INFORMATION: Extra lysine in K:trAPAO

<400> SEQUENCE: 11

Lys Asp Asn Val Ala Asp Val Val Val Gly Ala Gly Leu Ser Gly
1               5                   10                  15

Leu Glu Thr Ala Arg Lys Val Gln Ala Ala Gly Leu Ser Cys Leu Val
            20                  25                  30

Leu Glu Ala Met Asp Arg Val Gly Gly Lys Thr Leu Ser Val Gln Ser
        35                  40                  45

Gly Pro Gly Arg Thr Thr Ile Asn Asp Leu Gly Ala Ala Trp Ile Asn
    50                  55                  60

Asp Ser Asn Gln Ser Glu Val Ser Arg Leu Phe Glu Arg Phe His Leu
65                  70                  75                  80

Glu Gly Glu Leu Gln Arg Thr Thr Gly Asn Ser Ile His Gln Ala Gln
                85                  90                  95

Asp Gly Thr Thr Thr Ala Pro Tyr Gly Asp Ser Leu Leu Ser Glu
            100                 105                 110

Glu Val Ala Ser Ala Leu Ala Glu Leu Leu Pro Val Trp Ser Gln Leu
        115                 120                 125

Ile Glu Glu His Ser Leu Gln Asp Leu Lys Ala Ser Pro Gln Ala Lys
    130                 135                 140

Arg Leu Asp Ser Val Ser Phe Ala His Tyr Cys Glu Lys Glu Leu Asn
145                 150                 155                 160

Leu Pro Ala Val Leu Gly Val Ala Asn Gln Ile Thr Arg Ala Leu Leu
                165                 170                 175

Gly Val Glu Ala His Glu Ile Ser Met Leu Phe Leu Thr Asp Tyr Ile
            180                 185                 190

Lys Ser Ala Thr Gly Leu Ser Asn Ile Phe Ser Asp Lys Lys Asp Gly
        195                 200                 205

Gly Gln Tyr Met Arg Cys Lys Thr Gly Met Gln Ser Ile Cys His Ala
    210                 215                 220

Met Ser Lys Glu Leu Val Pro Gly Ser Val His Leu Asn Thr Pro Val
225                 230                 235                 240
```

```
Ala Glu Ile Glu Gln Ser Ala Ser Gly Cys Thr Val Arg Ser Ala Ser
                245                 250                 255

Gly Ala Val Phe Arg Ser Lys Lys Val Val Ser Leu Pro Thr Thr
            260                 265                 270

Leu Tyr Pro Thr Leu Thr Phe Ser Pro Pro Leu Pro Ala Glu Lys Gln
            275                 280                 285

Ala Leu Ala Glu Asn Ser Ile Leu Gly Tyr Tyr Ser Lys Ile Val Phe
        290                 295                 300

Val Trp Asp Lys Pro Trp Trp Arg Glu Gln Gly Phe Ser Gly Val Leu
305                 310                 315                 320

Gln Ser Ser Cys Asp Pro Ile Ser Phe Ala Arg Asp Thr Ser Ile Asp
                325                 330                 335

Val Asp Arg Gln Trp Ser Ile Thr Cys Phe Met Val Gly Asp Pro Gly
            340                 345                 350

Arg Lys Trp Ser Gln Gln Ser Lys Gln Val Arg Gln Lys Ser Val Trp
            355                 360                 365

Asp Gln Leu Arg Ala Ala Tyr Glu Asn Ala Gly Ala Gln Val Pro Glu
        370                 375                 380

Pro Ala Asn Val Leu Glu Ile Glu Trp Ser Lys Gln Gln Tyr Phe Gln
385                 390                 395                 400

Gly Ala Pro Ser Ala Val Tyr Gly Leu Asn Asp Leu Ile Thr Leu Gly
                405                 410                 415

Ser Ala Leu Arg Thr Pro Phe Lys Ser Val His Phe Val Gly Thr Glu
            420                 425                 430

Thr Ser Leu Val Trp Lys Gly Tyr Met Glu Gly Ala Ile Arg Ser Gly
            435                 440                 445

Gln Arg Gly Ala Ala Glu Val Val Ala Ser Leu Val Pro Ala Ala
        450                 455                 460

<210> SEQ ID NO 12
<211> LENGTH: 34
<212> TYPE: DNA
<213> ORGANISM: Artificial Sequence
<220> FEATURE:
<223> OTHER INFORMATION: Primer sequence designed for cloning DNA into
      expression vectors, N23256

<400> SEQUENCE: 12
ggggaattca aagacaacgt tgcggacgtg gtag                              34

<210> SEQ ID NO 13
<211> LENGTH: 34
<212> TYPE: DNA
<213> ORGANISM: Artificial Sequence
<220> FEATURE:
<223> OTHER INFORMATION: Primer sequence designed for cloning DNA into
      expression vectors N23256

<400> SEQUENCE: 13
ggggcggccg cctatgctgc tggcaccagg ctag                              34

<210> SEQ ID NO 14
<211> LENGTH: 29
<212> TYPE: DNA
<213> ORGANISM: Artificial Sequence
<220> FEATURE:
<223> OTHER INFORMATION: Designed oligonucleotide for 3' RACE, N21965

<400> SEQUENCE: 14
tggtttcgtt accgacaacc ttgtatccc                                    29
```

<210> SEQ ID NO 15
<211> LENGTH: 28
<212> TYPE: DNA
<213> ORGANISM: Artificial Sequence
<220> FEATURE:
<223> OTHER INFORMATION: Designed oligonucleotide for 5' RACE, N21968

<400> SEQUENCE: 15
gagttggtcc cagacagact tttgtcgt                                         28

<210> SEQ ID NO 16
<211> LENGTH: 1673
<212> TYPE: DNA
<213> ORGANISM: Exophiala spinifera
<220> FEATURE:
<221> NAME/KEY: sig_peptide
<222> LOCATION: (1)..(267)
<223> OTHER INFORMATION: yeast alpha mating factor secretion signal
<220> FEATURE:
<221> NAME/KEY: CDS
<222> LOCATION: (1)..(1662)
<223> OTHER INFORMATION:

<400> SEQUENCE: 16

| | | | | | | | | | | | | | | | |
|---|---|---|---|---|---|---|---|---|---|---|---|---|---|---|---|
| atg | aga | ttt | cct | tca | att | ttt | act | gct | gtt | tta | ttc | gca | gca | tcc tcc | 48 |
| Met | Arg | Phe | Pro | Ser | Ile | Phe | Thr | Ala | Val | Leu | Phe | Ala | Ala | Ser Ser | |
| 1 | | | | 5 | | | | | 10 | | | | | 15 | |

| gca | tta | gct | gct | cca | gtc | aac | act | aca | aca | gaa | gat | gaa | acg | gca caa | 96 |
| Ala | Leu | Ala | Ala | Pro | Val | Asn | Thr | Thr | Thr | Glu | Asp | Glu | Thr | Ala Gln | |
| | | 20 | | | | | 25 | | | | | 30 | | | |

| att | ccg | gct | gaa | gct | gtc | atc | ggt | tac | tca | gat | tta | gaa | ggg | gat ttc | 144 |
| Ile | Pro | Ala | Glu | Ala | Val | Ile | Gly | Tyr | Ser | Asp | Leu | Glu | Gly | Asp Phe | |
| | | | 35 | | | | | 40 | | | | | 45 | | |

| gat | gtt | gct | gtt | ttg | cca | ttt | tcc | aac | agc | aca | aat | aac | ggg | tta ttg | 192 |
| Asp | Val | Ala | Val | Leu | Pro | Phe | Ser | Asn | Ser | Thr | Asn | Asn | Gly | Leu Leu | |
| | 50 | | | | | 55 | | | | | 60 | | | | |

| ttt | ata | aat | act | act | att | gcc | agc | att | gct | gct | aaa | gaa | gaa | ggg gta | 240 |
| Phe | Ile | Asn | Thr | Thr | Ile | Ala | Ser | Ile | Ala | Ala | Lys | Glu | Glu | Gly Val | |
| 65 | | | | | 70 | | | | | 75 | | | | | 80 |

| tct | ctc | gag | aaa | aga | gag | gct | gaa | gct | gaa | ttc | aaa | gac | aac | gtt gcg | 288 |
| Ser | Leu | Glu | Lys | Arg | Glu | Ala | Glu | Ala | Glu | Phe | Lys | Asp | Asn | Val Ala | |
| | | | | 85 | | | | | 90 | | | | | 95 | |

| gac | gtg | gta | gtg | gtg | ggc | gct | ggc | ttg | agc | ggt | ttg | gag | acg | gca cgc | 336 |
| Asp | Val | Val | Val | Val | Gly | Ala | Gly | Leu | Ser | Gly | Leu | Glu | Thr | Ala Arg | |
| | | | 100 | | | | | 105 | | | | | 110 | | |

| aaa | gtc | cag | gcc | gcc | ggt | ctg | tcc | tgc | ctc | gtt | ctt | gag | gcg | atg gat | 384 |
| Lys | Val | Gln | Ala | Ala | Gly | Leu | Ser | Cys | Leu | Val | Leu | Glu | Ala | Met Asp | |
| | 115 | | | | | 120 | | | | | 125 | | | | |

| cgt | gta | ggg | gga | aag | act | ctg | agc | gta | caa | tcg | ggt | ccc | ggc | agg acg | 432 |
| Arg | Val | Gly | Gly | Lys | Thr | Leu | Ser | Val | Gln | Ser | Gly | Pro | Gly | Arg Thr | |
| 130 | | | | | 135 | | | | | 140 | | | | | |

| act | atc | aac | gac | ctc | ggc | gct | gcg | tgg | atc | aat | gac | agc | aac | caa agc | 480 |
| Thr | Ile | Asn | Asp | Leu | Gly | Ala | Ala | Trp | Ile | Asn | Asp | Ser | Asn | Gln Ser | |
| 145 | | | | | 150 | | | | | 155 | | | | | 160 |

| gaa | gta | tcc | aga | ttg | ttt | gaa | aga | ttt | cat | ttg | gag | ggc | gag | ctc cag | 528 |
| Glu | Val | Ser | Arg | Leu | Phe | Glu | Arg | Phe | His | Leu | Glu | Gly | Glu | Leu Gln | |
| | | | | 165 | | | | | 170 | | | | | 175 | |

| agg | acg | act | gga | aat | tca | atc | cat | caa | gca | caa | gac | ggt | aca | acc act | 576 |
| Arg | Thr | Thr | Gly | Asn | Ser | Ile | His | Gln | Ala | Gln | Asp | Gly | Thr | Thr Thr | |
| | | | 180 | | | | | 185 | | | | | 190 | | |

| aca | gct | cct | tat | ggt | gac | tcc | ttg | ctg | agc | gag | gag | gtt | gca | agt gca | 624 |
| Thr | Ala | Pro | Tyr | Gly | Asp | Ser | Leu | Leu | Ser | Glu | Glu | Val | Ala | Ser Ala | |
| | 195 | | | | | 200 | | | | | 205 | | | | |

```
ctt gcg gaa ctc ctc ccc gta tgg tct cag ctg atc gaa gag cat agc      672
Leu Ala Glu Leu Leu Pro Val Trp Ser Gln Leu Ile Glu Glu His Ser
    210                 215                 220 ctt caa gac ctc aag gcg agc cct cag gcg aag cgg ctc gac agt gtg      720
Leu Gln Asp Leu Lys Ala Ser Pro Gln Ala Lys Arg Leu Asp Ser Val
225                 230                 235                 240 agc ttc gcg cac tac tgt gag aag gaa cta aac ttg cct gct gtt ctc      768
Ser Phe Ala His Tyr Cys Glu Lys Glu Leu Asn Leu Pro Ala Val Leu
                245                 250                 255 ggc gta gca aac cag atc aca cgc gct ctg ctc ggt gtg gaa gcc cac      816
Gly Val Ala Asn Gln Ile Thr Arg Ala Leu Leu Gly Val Glu Ala His
            260                 265                 270 gag atc agc atg ctt ttt ctc acc gac tac atc aag agt gcc acc ggt      864
Glu Ile Ser Met Leu Phe Leu Thr Asp Tyr Ile Lys Ser Ala Thr Gly
        275                 280                 285 ctc agt aat att ttc tcg gac aag aaa gac ggc ggg cag tat atg cga      912
Leu Ser Asn Ile Phe Ser Asp Lys Lys Asp Gly Gly Gln Tyr Met Arg
    290                 295                 300 tgc aaa aca ggt atg cag tcg att tgc cat gcc atg tca aag gaa ctt      960
Cys Lys Thr Gly Met Gln Ser Ile Cys His Ala Met Ser Lys Glu Leu
305                 310                 315                 320 gtt cca ggc tca gtg cac ctc aac acc ccc gtc gct gaa att gag cag     1008
Val Pro Gly Ser Val His Leu Asn Thr Pro Val Ala Glu Ile Glu Gln
                325                 330                 335 tcg gca tcc ggc tgt aca gta cga tcg gcc tcg ggc gcc gtg ttc cga     1056
Ser Ala Ser Gly Cys Thr Val Arg Ser Ala Ser Gly Ala Val Phe Arg
            340                 345                 350 agc aaa aag gtg gtg gtt tcg tta ccg aca acc ttg tat ccc acc ttg     1104
Ser Lys Lys Val Val Val Ser Leu Pro Thr Thr Leu Tyr Pro Thr Leu
        355                 360                 365 aca ttt tca cca cct ctt ccc gcc gag aag caa gca ttg gcg gaa aat     1152
Thr Phe Ser Pro Pro Leu Pro Ala Glu Lys Gln Ala Leu Ala Glu Asn
    370                 375                 380 tct atc ctg ggc tac tat agc aag ata gtc ttc gta tgg gac aag ccg     1200
Ser Ile Leu Gly Tyr Tyr Ser Lys Ile Val Phe Val Trp Asp Lys Pro
385                 390                 395                 400 tgg tgg cgc gaa caa ggc ttc tcg ggc gtc ctc caa tcg agc tgt gac     1248
Trp Trp Arg Glu Gln Gly Phe Ser Gly Val Leu Gln Ser Ser Cys Asp
                405                 410                 415 ccc atc tca ttt gcc aga gat acc agc atc gac gtc gat cga caa tgg     1296
Pro Ile Ser Phe Ala Arg Asp Thr Ser Ile Asp Val Asp Arg Gln Trp
            420                 425                 430 tcc att acc tgt ttc atg gtc gga gac ccg gga cgg aag tgg tcc caa     1344
Ser Ile Thr Cys Phe Met Val Gly Asp Pro Gly Arg Lys Trp Ser Gln
        435                 440                 445 cag tcc aag cag gta cga caa aag tct gtc tgg gac caa ctc cgc gca     1392
Gln Ser Lys Gln Val Arg Gln Lys Ser Val Trp Asp Gln Leu Arg Ala
    450                 455                 460 gcc tac gag aac gcc ggg gcc caa gtc cca gag ccg gcc aac gtg ctc     1440
Ala Tyr Glu Asn Ala Gly Ala Gln Val Pro Glu Pro Ala Asn Val Leu
465                 470                 475                 480 gaa atc gag tgg tcg aag cag cag tat ttc caa gga gct ccg agc gcc     1488
Glu Ile Glu Trp Ser Lys Gln Gln Tyr Phe Gln Gly Ala Pro Ser Ala
                485                 490                 495 gtc tat ggg ctg aac gat ctc atc aca ctg ggt tcg gcg ctc aga acg     1536
Val Tyr Gly Leu Asn Asp Leu Ile Thr Leu Gly Ser Ala Leu Arg Thr
            500                 505                 510 ccg ttc aag agt gtt cat ttc gtt gga acg gag acg tct tta gtt tgg     1584
Pro Phe Lys Ser Val His Phe Val Gly Thr Glu Thr Ser Leu Val Trp
```

```
            515                 520                 525
aaa ggg tat atg gaa ggg gcc ata cga tcg ggt caa cga ggt gct gca      1632
Lys Gly Tyr Met Glu Gly Ala Ile Arg Ser Gly Gln Arg Gly Ala Ala
            530                 535                 540 gaa gtt gtg gct agc ctg gtg cca gca gca taggcggccg c                 1673
Glu Val Val Ala Ser Leu Val Pro Ala Ala
545                 550
```

<210> SEQ ID NO 17
<211> LENGTH: 554
<212> TYPE: PRT
<213> ORGANISM: Exophiala spinifera

<400> SEQUENCE: 17

```
Met Arg Phe Pro Ser Ile Phe Thr Ala Val Leu Phe Ala Ala Ser Ser
1               5                   10                  15

Ala Leu Ala Ala Pro Val Asn Thr Thr Thr Glu Asp Glu Thr Ala Gln
            20                  25                  30

Ile Pro Ala Glu Ala Val Ile Gly Tyr Ser Asp Leu Glu Gly Asp Phe
        35                  40                  45

Asp Val Ala Val Leu Pro Phe Ser Asn Ser Thr Asn Asn Gly Leu Leu
    50                  55                  60

Phe Ile Asn Thr Thr Ile Ala Ser Ile Ala Ala Lys Glu Glu Gly Val
65                  70                  75                  80

Ser Leu Glu Lys Arg Glu Ala Glu Ala Glu Phe Lys Asp Asn Val Ala
                85                  90                  95

Asp Val Val Val Gly Ala Gly Leu Ser Gly Leu Glu Thr Ala Arg
            100                 105                 110

Lys Val Gln Ala Ala Gly Leu Ser Cys Leu Val Leu Glu Ala Met Asp
        115                 120                 125

Arg Val Gly Gly Lys Thr Leu Ser Val Gln Ser Gly Pro Gly Arg Thr
    130                 135                 140

Thr Ile Asn Asp Leu Gly Ala Ala Trp Ile Asn Asp Ser Asn Gln Ser
145                 150                 155                 160

Glu Val Ser Arg Leu Phe Glu Arg Phe His Leu Glu Gly Glu Leu Gln
                165                 170                 175

Arg Thr Thr Gly Asn Ser Ile His Gln Ala Gln Asp Gly Thr Thr Thr
            180                 185                 190

Thr Ala Pro Tyr Gly Asp Ser Leu Leu Ser Glu Glu Val Ala Ser Ala
        195                 200                 205

Leu Ala Glu Leu Leu Pro Val Trp Ser Gln Leu Ile Glu Glu His Ser
    210                 215                 220

Leu Gln Asp Leu Lys Ala Ser Pro Gln Ala Lys Arg Leu Asp Ser Val
225                 230                 235                 240

Ser Phe Ala His Tyr Cys Glu Lys Glu Leu Asn Leu Pro Ala Val Leu
                245                 250                 255

Gly Val Ala Asn Gln Ile Thr Arg Ala Leu Leu Gly Val Glu Ala His
            260                 265                 270

Glu Ile Ser Met Leu Phe Leu Thr Asp Tyr Ile Lys Ser Ala Thr Gly
        275                 280                 285

Leu Ser Asn Ile Phe Ser Asp Lys Lys Asp Gly Gly Gln Tyr Met Arg
    290                 295                 300

Cys Lys Thr Gly Met Gln Ser Ile Cys His Ala Met Ser Lys Glu Leu
305                 310                 315                 320

Val Pro Gly Ser Val His Leu Asn Thr Pro Val Ala Glu Ile Glu Gln
```

```
            325                 330                 335
Ser Ala Ser Gly Cys Thr Val Arg Ser Ala Ser Gly Ala Val Phe Arg
            340                 345                 350

Ser Lys Lys Val Val Ser Leu Pro Thr Thr Leu Tyr Pro Thr Leu
            355                 360                 365

Thr Phe Ser Pro Pro Leu Pro Ala Glu Lys Gln Ala Leu Ala Glu Asn
370                 375                 380

Ser Ile Leu Gly Tyr Tyr Ser Lys Ile Val Phe Val Trp Asp Lys Pro
385                 390                 395                 400

Trp Trp Arg Glu Gln Gly Phe Ser Gly Val Leu Gln Ser Ser Cys Asp
            405                 410                 415

Pro Ile Ser Phe Ala Arg Asp Thr Ser Ile Asp Val Asp Arg Gln Trp
            420                 425                 430

Ser Ile Thr Cys Phe Met Val Gly Asp Pro Gly Arg Lys Trp Ser Gln
            435                 440                 445

Gln Ser Lys Gln Val Arg Gln Lys Ser Val Trp Asp Gln Leu Arg Ala
450                 455                 460

Ala Tyr Glu Asn Ala Gly Ala Gln Val Pro Glu Pro Ala Asn Val Leu
465                 470                 475                 480

Glu Ile Glu Trp Ser Lys Gln Gln Tyr Phe Gln Gly Ala Pro Ser Ala
            485                 490                 495

Val Tyr Gly Leu Asn Asp Leu Ile Thr Leu Gly Ser Ala Leu Arg Thr
            500                 505                 510

Pro Phe Lys Ser Val His Phe Val Gly Thr Glu Thr Ser Leu Val Trp
            515                 520                 525

Lys Gly Tyr Met Glu Gly Ala Ile Arg Ser Gly Gln Arg Gly Ala Ala
            530                 535                 540

Glu Val Val Ala Ser Leu Val Pro Ala Ala
545                 550

<210> SEQ ID NO 18
<211> LENGTH: 2079
<212> TYPE: DNA
<213> ORGANISM: Unknown
<220> FEATURE:
<223> OTHER INFORMATION: GST:K:trAPAO 2079  for bacterial expression
<220> FEATURE:
<221> NAME/KEY: CDS
<222> LOCATION: (1)..(2076)
<223> OTHER INFORMATION:
<220> FEATURE:
<221> NAME/KEY: misc_feature
<222> LOCATION: (1)..(687)
<223> OTHER INFORMATION: gst fusion + polylinker
<220> FEATURE:
<221> NAME/KEY: misc_feature
<222> LOCATION: (688)..(2076)
<223> OTHER INFORMATION: K:trAPAO
<220> FEATURE:
<221> NAME/KEY: misc_feature
<222> LOCATION: (688)..(690)
<223> OTHER INFORMATION: Extra lysine

<400> SEQUENCE: 18 atg tcc cct ata cta ggt tat tgg aaa att aag ggc ctt gtg caa ccc      48
Met Ser Pro Ile Leu Gly Tyr Trp Lys Ile Lys Gly Leu Val Gln Pro
1               5                   10                  15 act cga ctt ctt ttg gaa tat ctt gaa gaa aaa tat gaa gag cat ttg      96
Thr Arg Leu Leu Leu Glu Tyr Leu Glu Glu Lys Tyr Glu Glu His Leu
            20                  25                  30 tat gag cgc gat gaa ggt gat aaa tgg cga aac aaa aag ttt gaa ttg     144
```

```
                                                                      -continued Tyr Glu Arg Asp Glu Gly Asp Lys Trp Arg Asn Lys Lys Phe Glu Leu
        35                  40                  45 ggt ttg gag ttt ccc aat ctt cct tat tat att gat ggt gat gtt aaa        192
Gly Leu Glu Phe Pro Asn Leu Pro Tyr Tyr Ile Asp Gly Asp Val Lys
 50                  55                  60 tta aca cag tct atg gcc atc ata cgt tat ata gct gac aag cac aac        240
Leu Thr Gln Ser Met Ala Ile Ile Arg Tyr Ile Ala Asp Lys His Asn
 65                  70                  75                  80 atg ttg ggt ggt tgt cca aaa gag cgt gca gag att tca atg ctt gaa        288
Met Leu Gly Gly Cys Pro Lys Glu Arg Ala Glu Ile Ser Met Leu Glu
                 85                  90                  95 gga gcg gtt ttg gat att aga tac ggt gtt tcg aga att gca tat agt        336
Gly Ala Val Leu Asp Ile Arg Tyr Gly Val Ser Arg Ile Ala Tyr Ser
            100                 105                 110 aaa gac ttt gaa act ctc aaa gtt gat ttt ctt agc aag cta cct gaa        384
Lys Asp Phe Glu Thr Leu Lys Val Asp Phe Leu Ser Lys Leu Pro Glu
        115                 120                 125 atg ctg aaa atg ttc gaa gat cgt tta tgt cat aaa aca tat tta aat        432
Met Leu Lys Met Phe Glu Asp Arg Leu Cys His Lys Thr Tyr Leu Asn
    130                 135                 140 ggt gat cat gta acc cat cct gac ttc atg ttg tat gac gct ctt gat        480
Gly Asp His Val Thr His Pro Asp Phe Met Leu Tyr Asp Ala Leu Asp
145                 150                 155                 160 gtt gtt tta tac atg gac cca atg tgc ctg gat gcg ttc cca aaa tta        528
Val Val Leu Tyr Met Asp Pro Met Cys Leu Asp Ala Phe Pro Lys Leu
                165                 170                 175 gtt tgt ttt aaa aaa cgt att gaa gct atc cca caa att gat aag tac        576
Val Cys Phe Lys Lys Arg Ile Glu Ala Ile Pro Gln Ile Asp Lys Tyr
            180                 185                 190 ttg aaa tcc agc aag tat ata gca tgg cct ttg cag ggc tgg caa gcc        624
Leu Lys Ser Ser Lys Tyr Ile Ala Trp Pro Leu Gln Gly Trp Gln Ala
        195                 200                 205 acg ttt ggt ggt ggc gac cat cct cca aaa tcg gat ctg gtt ccg cgt        672
Thr Phe Gly Gly Gly Asp His Pro Pro Lys Ser Asp Leu Val Pro Arg
    210                 215                 220 gga tcc ccg gaa ttc aaa gac aac gtt gcg gac gtg gta gtg gtg ggc        720
Gly Ser Pro Glu Phe Lys Asp Asn Val Ala Asp Val Val Val Val Gly
225                 230                 235                 240 gct ggc ttg agc ggt ttg gag acg gca cgc aaa gtc cag gcc gcc ggt        768
Ala Gly Leu Ser Gly Leu Glu Thr Ala Arg Lys Val Gln Ala Ala Gly
                245                 250                 255 ctg tcc tgc ctc gtt ctt gag gcg atg gat cgt gta ggg gga aag act        816
Leu Ser Cys Leu Val Leu Glu Ala Met Asp Arg Val Gly Gly Lys Thr
            260                 265                 270 ctg agc gta caa tcg ggt ccc ggc agg acg act atc aac gac ctc ggc        864
Leu Ser Val Gln Ser Gly Pro Gly Arg Thr Thr Ile Asn Asp Leu Gly
        275                 280                 285 gct gcg tgg atc aat gac agc aac caa agc gaa gta tcc aga ttg ttt        912
Ala Ala Trp Ile Asn Asp Ser Asn Gln Ser Glu Val Ser Arg Leu Phe
    290                 295                 300 gaa aga ttt cat ttg gag ggc gag ctc cag agg acg act gga aat tca        960
Glu Arg Phe His Leu Glu Gly Glu Leu Gln Arg Thr Thr Gly Asn Ser
305                 310                 315                 320 atc cat caa gca caa gac ggt aca acc act aca gct cct tat ggt gac       1008
Ile His Gln Ala Gln Asp Gly Thr Thr Thr Thr Ala Pro Tyr Gly Asp
                325                 330                 335 tcc ttg ctg agc gag gag gtt gca agt gca ctt gcg gaa ctc ctc ccc       1056
Ser Leu Leu Ser Glu Glu Val Ala Ser Ala Leu Ala Glu Leu Leu Pro
            340                 345                 350
```

```
gta tgg tct cag ctg atc gaa gag cat agc ctt caa gac ctc aag gcg      1104
Val Trp Ser Gln Leu Ile Glu Glu His Ser Leu Gln Asp Leu Lys Ala
        355                 360                 365 agc cct cag gcg aag cgg ctc gac agt gtg agc ttc gcg cac tac tgt      1152
Ser Pro Gln Ala Lys Arg Leu Asp Ser Val Ser Phe Ala His Tyr Cys
370                 375                 380 gag aag gaa cta aac ttg cct gct gtt ctc ggc gta gca aac cag atc      1200
Glu Lys Glu Leu Asn Leu Pro Ala Val Leu Gly Val Ala Asn Gln Ile
385                 390                 395                 400 aca cgc gct ctg ctc ggt gtg gaa gcc cac gag atc agc atg ctt ttt      1248
Thr Arg Ala Leu Leu Gly Val Glu Ala His Glu Ile Ser Met Leu Phe
                405                 410                 415 ctc acc gac tac atc aag agt gcc acc ggt ctc agt aat att ttc tcg      1296
Leu Thr Asp Tyr Ile Lys Ser Ala Thr Gly Leu Ser Asn Ile Phe Ser
            420                 425                 430 gac aag aaa gac ggc ggg cag tat atg cga tgc aaa aca ggt atg cag      1344
Asp Lys Lys Asp Gly Gly Gln Tyr Met Arg Cys Lys Thr Gly Met Gln
        435                 440                 445 tcg att tgc cat gcc atg tca aag gaa ctt gtt cca ggc tca gtg cac      1392
Ser Ile Cys His Ala Met Ser Lys Glu Leu Val Pro Gly Ser Val His
450                 455                 460 ctc aac acc ccc gtc gct gaa att gag cag tcg gca tcc ggc tgt aca      1440
Leu Asn Thr Pro Val Ala Glu Ile Glu Gln Ser Ala Ser Gly Cys Thr
465                 470                 475                 480 gta cga tcg gcc tcg ggc gcc gtg ttc cga agc aaa aag gtg gtg gtt      1488
Val Arg Ser Ala Ser Gly Ala Val Phe Arg Ser Lys Lys Val Val Val
                485                 490                 495 tcg tta ccg aca acc ttg tat ccc acc ttg aca ttt tca cca cct ctt      1536
Ser Leu Pro Thr Thr Leu Tyr Pro Thr Leu Thr Phe Ser Pro Pro Leu
            500                 505                 510 ccc gcc gag aag caa gca ttg gcg gaa aat tct atc ctg ggc tac tat      1584
Pro Ala Glu Lys Gln Ala Leu Ala Glu Asn Ser Ile Leu Gly Tyr Tyr
        515                 520                 525 agc aag ata gtc ttc gta tgg gac aag ccg tgg tgg cgc gaa caa ggc      1632
Ser Lys Ile Val Phe Val Trp Asp Lys Pro Trp Trp Arg Glu Gln Gly
530                 535                 540 ttc tcg ggc gtc ctc caa tcg agc tgt gac ccc atc tca ttt gcc aga      1680
Phe Ser Gly Val Leu Gln Ser Ser Cys Asp Pro Ile Ser Phe Ala Arg
545                 550                 555                 560 gat acc agc atc gac gtc gat cga caa tgg tcc att acc tgt ttc atg      1728
Asp Thr Ser Ile Asp Val Asp Arg Gln Trp Ser Ile Thr Cys Phe Met
                565                 570                 575 gtc gga gac ccg gga cgg aag tgg tcc caa cag tcc aag cag gta cga      1776
Val Gly Asp Pro Gly Arg Lys Trp Ser Gln Gln Ser Lys Gln Val Arg
            580                 585                 590 caa aag tct gtc tgg gac caa ctc cgc gca gcc tac gag aac gcc ggg      1824
Gln Lys Ser Val Trp Asp Gln Leu Arg Ala Ala Tyr Glu Asn Ala Gly
        595                 600                 605 gcc caa gtc cca gag ccg gcc aac gtg ctc gaa atc gag tgg tcg aag      1872
Ala Gln Val Pro Glu Pro Ala Asn Val Leu Glu Ile Glu Trp Ser Lys
610                 615                 620 cag cag tat ttc caa gga gct ccg agc gcc gtc tat ggg ctg aac gat      1920
Gln Gln Tyr Phe Gln Gly Ala Pro Ser Ala Val Tyr Gly Leu Asn Asp
625                 630                 635                 640 ctc atc aca ctg ggt tcg gcg ctc aga acg ccg ttc aag agt gtt cat      1968
Leu Ile Thr Leu Gly Ser Ala Leu Arg Thr Pro Phe Lys Ser Val His
                645                 650                 655 ttc gtt gga acg gag acg tct tta gtt tgg aaa ggg tat atg gaa ggg      2016
Phe Val Gly Thr Glu Thr Ser Leu Val Trp Lys Gly Tyr Met Glu Gly
            660                 665                 670
```

```
gcc ata cga tcg ggt caa cga ggt gct gca gaa gtt gtg gct agc ctg    2064
Ala Ile Arg Ser Gly Gln Arg Gly Ala Ala Glu Val Val Ala Ser Leu
        675                 680                 685 gtg cca gca gca tag                                                2079
Val Pro Ala Ala
    690
```

<210> SEQ ID NO 19
<211> LENGTH: 692
<212> TYPE: PRT
<213> ORGANISM: Unknown
<220> FEATURE:
<223> OTHER INFORMATION: GST:K:trAPAO 2079 for bacterial expression
<220> FEATURE:
<221> NAME/KEY: misc_feature
<222> LOCATION: (1)..(687)
<223> OTHER INFORMATION: gst fusion + polylinker
<220> FEATURE:
<221> NAME/KEY: misc_feature
<222> LOCATION: (688)..(2076)
<223> OTHER INFORMATION: K:trAPAO
<220> FEATURE:
<221> NAME/KEY: misc_feature
<222> LOCATION: (688)..(690)
<223> OTHER INFORMATION: Extra lysine

<400> SEQUENCE: 19

```
Met Ser Pro Ile Leu Gly Tyr Trp Lys Ile Lys Gly Leu Val Gln Pro
1               5                   10                  15

Thr Arg Leu Leu Leu Glu Tyr Leu Glu Glu Lys Tyr Glu Glu His Leu
            20                  25                  30

Tyr Glu Arg Asp Glu Gly Asp Lys Trp Arg Asn Lys Lys Phe Glu Leu
        35                  40                  45

Gly Leu Glu Phe Pro Asn Leu Pro Tyr Tyr Ile Asp Gly Asp Val Lys
    50                  55                  60

Leu Thr Gln Ser Met Ala Ile Ile Arg Tyr Ile Ala Asp Lys His Asn
65                  70                  75                  80

Met Leu Gly Gly Cys Pro Lys Glu Arg Ala Glu Ile Ser Met Leu Glu
                85                  90                  95

Gly Ala Val Leu Asp Ile Arg Tyr Gly Val Ser Arg Ile Ala Tyr Ser
            100                 105                 110

Lys Asp Phe Glu Thr Leu Lys Val Asp Phe Leu Ser Lys Leu Pro Glu
        115                 120                 125

Met Leu Lys Met Phe Glu Asp Arg Leu Cys His Lys Thr Tyr Leu Asn
    130                 135                 140

Gly Asp His Val Thr His Pro Asp Phe Met Leu Tyr Asp Ala Leu Asp
145                 150                 155                 160

Val Val Leu Tyr Met Asp Pro Met Cys Leu Asp Ala Phe Pro Lys Leu
                165                 170                 175

Val Cys Phe Lys Lys Arg Ile Glu Ala Ile Pro Gln Ile Asp Lys Tyr
            180                 185                 190

Leu Lys Ser Ser Lys Tyr Ile Ala Trp Pro Leu Gln Gly Trp Gln Ala
        195                 200                 205

Thr Phe Gly Gly Gly Asp His Pro Pro Lys Ser Asp Leu Val Pro Arg
    210                 215                 220

Gly Ser Pro Glu Phe Lys Asp Asn Val Ala Asp Val Val Val Val Gly
225                 230                 235                 240

Ala Gly Leu Ser Gly Leu Glu Thr Ala Arg Lys Val Gln Ala Ala Gly
                245                 250                 255
```

-continued

```
Leu Ser Cys Leu Val Leu Glu Ala Met Asp Arg Val Gly Gly Lys Thr
            260                 265                 270
Leu Ser Val Gln Ser Gly Pro Gly Arg Thr Thr Ile Asn Asp Leu Gly
            275                 280                 285
Ala Ala Trp Ile Asn Asp Ser Asn Gln Ser Glu Val Ser Arg Leu Phe
290                 295                 300
Glu Arg Phe His Leu Glu Gly Glu Leu Gln Arg Thr Thr Gly Asn Ser
305                 310                 315                 320
Ile His Gln Ala Gln Asp Gly Thr Thr Thr Ala Pro Tyr Gly Asp
                325                 330                 335
Ser Leu Leu Ser Glu Glu Val Ala Ser Ala Leu Ala Glu Leu Leu Pro
            340                 345                 350
Val Trp Ser Gln Leu Ile Glu His Ser Leu Gln Asp Leu Lys Ala
            355                 360                 365
Ser Pro Gln Ala Lys Arg Leu Asp Ser Val Ser Phe Ala His Tyr Cys
            370                 375                 380
Glu Lys Glu Leu Asn Leu Pro Ala Val Leu Gly Val Ala Asn Gln Ile
385                 390                 395                 400
Thr Arg Ala Leu Leu Gly Val Glu Ala His Glu Ile Ser Met Leu Phe
                405                 410                 415
Leu Thr Asp Tyr Ile Lys Ser Ala Thr Gly Leu Ser Asn Ile Phe Ser
            420                 425                 430
Asp Lys Lys Asp Gly Gly Gln Tyr Met Arg Cys Lys Thr Gly Met Gln
            435                 440                 445
Ser Ile Cys His Ala Met Ser Lys Glu Leu Val Pro Gly Ser Val His
            450                 455                 460
Leu Asn Thr Pro Val Ala Glu Ile Glu Gln Ser Ala Ser Gly Cys Thr
465                 470                 475                 480
Val Arg Ser Ala Ser Gly Ala Val Phe Arg Ser Lys Val Val Val
            485                 490                 495
Ser Leu Pro Thr Thr Leu Tyr Pro Thr Leu Thr Phe Ser Pro Pro Leu
            500                 505                 510
Pro Ala Glu Lys Gln Ala Leu Ala Glu Asn Ser Ile Leu Gly Tyr Tyr
            515                 520                 525
Ser Lys Ile Val Phe Val Trp Asp Lys Pro Trp Trp Arg Glu Gln Gly
            530                 535                 540
Phe Ser Gly Val Leu Gln Ser Ser Cys Asp Pro Ile Ser Phe Ala Arg
545                 550                 555                 560
Asp Thr Ser Ile Asp Val Asp Arg Gln Trp Ser Ile Thr Cys Phe Met
                565                 570                 575
Val Gly Asp Pro Gly Arg Lys Trp Ser Gln Ser Lys Gln Val Arg
            580                 585                 590
Gln Lys Ser Val Trp Asp Gln Leu Arg Ala Ala Tyr Glu Asn Ala Gly
            595                 600                 605
Ala Gln Val Pro Glu Pro Ala Asn Val Leu Glu Ile Glu Trp Ser Lys
610                 615                 620
Gln Gln Tyr Phe Gln Gly Ala Pro Ser Ala Val Tyr Gly Leu Asn Asp
625                 630                 635                 640
Leu Ile Thr Leu Gly Ser Ala Leu Arg Thr Pro Phe Lys Ser Val His
                645                 650                 655
Phe Val Gly Thr Glu Thr Ser Leu Val Trp Lys Gly Tyr Met Glu Gly
            660                 665                 670
Ala Ile Arg Ser Gly Gln Arg Gly Ala Ala Glu Val Val Ala Ser Leu
```

675                 680                 685
Val Pro Ala Ala
    690

<210> SEQ ID NO 20
<211> LENGTH: 1464
<212> TYPE: DNA
<213> ORGANISM: Unknown
<220> FEATURE:
<223> OTHER INFORMATION: K:trAPAO translational fusion with barley
      alpha amylase
<220> FEATURE:
<221> NAME/KEY: sig_peptide
<222> LOCATION: (1)..(72)
<223> OTHER INFORMATION: Barley alpha amylase signal sequence
<220> FEATURE:
<221> NAME/KEY: misc_feature
<222> LOCATION: (73)..(1464)
<223> OTHER INFORMATION: K:trAPAO cDNA
<220> FEATURE:
<221> NAME/KEY: CDS
<222> LOCATION: (1)..(1461)
<223> OTHER INFORMATION:
<220> FEATURE:
<221> NAME/KEY: misc_feature
<222> LOCATION: (73)..(75)
<223> OTHER INFORMATION: Added lysine residue

<400> SEQUENCE: 20 atg gcc aac aag cac ctg agc ctc tcc ctc ttc ctc gtg ctc ctc ggc      48
Met Ala Asn Lys His Leu Ser Leu Ser Leu Phe Leu Val Leu Leu Gly
1               5                   10                  15 ctc tcc gcc tcc ctc gcc agc ggc aaa gac aac gtt gcg gac gtg gta      96
Leu Ser Ala Ser Leu Ala Ser Gly Lys Asp Asn Val Ala Asp Val Val
                20                  25                  30 gtg gtg ggc gct ggc ttg agc ggt ttg gag acg gca cgc aaa gtc cag     144
Val Val Gly Ala Gly Leu Ser Gly Leu Glu Thr Ala Arg Lys Val Gln
            35                  40                  45 gcc gcc ggt ctg tcc tgc ctc gtt ctt gag gcg atg gat cgt gta ggg     192
Ala Ala Gly Leu Ser Cys Leu Val Leu Glu Ala Met Asp Arg Val Gly
        50                  55                  60 gga aag act ctg agc gta caa tcg ggt ccc ggc agg acg act atc aac     240
Gly Lys Thr Leu Ser Val Gln Ser Gly Pro Gly Arg Thr Thr Ile Asn
65                  70                  75                  80 gac ctc ggc gct gcg tgg atc aat gac agc aac caa agc gaa gta tcc     288
Asp Leu Gly Ala Ala Trp Ile Asn Asp Ser Asn Gln Ser Glu Val Ser
                85                  90                  95 aga ttg ttt gaa aga ttt cat ttg gag ggc gag ctc cag agg acg act     336
Arg Leu Phe Glu Arg Phe His Leu Glu Gly Glu Leu Gln Arg Thr Thr
            100                 105                 110 gga aat tca atc cat caa gca caa gac ggt aca acc act aca gct cct     384
Gly Asn Ser Ile His Gln Ala Gln Asp Gly Thr Thr Thr Thr Ala Pro
        115                 120                 125 tat ggt gac tcc ttg ctg agc gag gag gtt gca agt gca ctt gcg gaa     432
Tyr Gly Asp Ser Leu Leu Ser Glu Glu Val Ala Ser Ala Leu Ala Glu
    130                 135                 140 ctc ctc ccc gta tgg tct cag ctg atc gaa gag cat agc ctt caa gac     480
Leu Leu Pro Val Trp Ser Gln Leu Ile Glu Glu His Ser Leu Gln Asp
145                 150                 155                 160 ctc aag gcg agc cct cag gcg aag cgg ctc gac agt gtg agc ttc gcg     528
Leu Lys Ala Ser Pro Gln Ala Lys Arg Leu Asp Ser Val Ser Phe Ala
                165                 170                 175 cac tac tgt gag aag gaa cta aac ttg cct gct gtt ctc ggc gta gca     576
His Tyr Cys Glu Lys Glu Leu Asn Leu Pro Ala Val Leu Gly Val Ala
            180                 185                 190

```
aac cag atc aca cgc gct ctg ctc ggt gtg gaa gcc cac gag atc agc      624
Asn Gln Ile Thr Arg Ala Leu Leu Gly Val Glu Ala His Glu Ile Ser
        195                 200                 205 atg ctt ttt ctc acc gac tac atc aag agt gcc acc ggt ctc agt aat      672
Met Leu Phe Leu Thr Asp Tyr Ile Lys Ser Ala Thr Gly Leu Ser Asn
        210                 215                 220 att ttc tcg gac aag aaa gac ggc ggg cag tat atg cga tgc aaa aca      720
Ile Phe Ser Asp Lys Lys Asp Gly Gly Gln Tyr Met Arg Cys Lys Thr
225                 230                 235                 240 ggt atg cag tcg att tgc cat gcc atg tca aag gaa ctt gtt cca ggc      768
Gly Met Gln Ser Ile Cys His Ala Met Ser Lys Glu Leu Val Pro Gly
                245                 250                 255 tca gtg cac ctc aac acc ccc gtc gct gaa att gag cag tcg gca tcc      816
Ser Val His Leu Asn Thr Pro Val Ala Glu Ile Glu Gln Ser Ala Ser
                260                 265                 270 ggc tgt aca gta cga tcg gcc tcg ggc gcc gtg ttc cga agc aaa aag      864
Gly Cys Thr Val Arg Ser Ala Ser Gly Ala Val Phe Arg Ser Lys Lys
                275                 280                 285 gtg gtg gtt tcg tta ccg aca acc ttg tat ccc acc ttg aca ttt tca      912
Val Val Val Ser Leu Pro Thr Thr Leu Tyr Pro Thr Leu Thr Phe Ser
290                 295                 300 cca cct ctt ccc gcc gag aag caa gca ttg gcg gaa aat tct atc ctg      960
Pro Pro Leu Pro Ala Glu Lys Gln Ala Leu Ala Glu Asn Ser Ile Leu
305                 310                 315                 320 ggc tac tat agc aag ata gtc ttc gta tgg gac aag ccg tgg tgg cgc     1008
Gly Tyr Tyr Ser Lys Ile Val Phe Val Trp Asp Lys Pro Trp Trp Arg
                325                 330                 335 gaa caa ggc ttc tcg ggc gtc ctc caa tcg agc tgt gac ccc atc tca     1056
Glu Gln Gly Phe Ser Gly Val Leu Gln Ser Ser Cys Asp Pro Ile Ser
                340                 345                 350 ttt gcc aga gat acc agc atc gac gtc gat cga caa tgg tcc att acc     1104
Phe Ala Arg Asp Thr Ser Ile Asp Val Asp Arg Gln Trp Ser Ile Thr
                355                 360                 365 tgt ttc atg gtc gga gac ccg gga cgg aag tgg tcc caa cag tcc aag     1152
Cys Phe Met Val Gly Asp Pro Gly Arg Lys Trp Ser Gln Gln Ser Lys
370                 375                 380 cag gta cga caa aag tct gtc tgg gac caa ctc cgc gca gcc tac gag     1200
Gln Val Arg Gln Lys Ser Val Trp Asp Gln Leu Arg Ala Ala Tyr Glu
385                 390                 395                 400 aac gcc ggg gcc caa gtc cca gag ccg gcc aac gtg ctc gaa atc gag     1248
Asn Ala Gly Ala Gln Val Pro Glu Pro Ala Asn Val Leu Glu Ile Glu
                405                 410                 415 tgg tcg aag cag cag tat ttc caa gga gct ccg agc gcc gtc tat ggg     1296
Trp Ser Lys Gln Gln Tyr Phe Gln Gly Ala Pro Ser Ala Val Tyr Gly
                420                 425                 430 ctg aac gat ctc atc aca ctg ggt tcg gcg ctc aga acg ccg ttc aag     1344
Leu Asn Asp Leu Ile Thr Leu Gly Ser Ala Leu Arg Thr Pro Phe Lys
                435                 440                 445 agt gtt cat ttc gtt gga acg gag acg tct tta gtt tgg aaa ggg tat     1392
Ser Val His Phe Val Gly Thr Glu Thr Ser Leu Val Trp Lys Gly Tyr
        450                 455                 460 atg gaa ggg gcc ata cga tcg ggt caa cga ggt gct gca gaa gtt gtg     1440
Met Glu Gly Ala Ile Arg Ser Gly Gln Arg Gly Ala Ala Glu Val Val
465                 470                 475                 480 gct agc ctg gtg cca gca gca tag                                     1464
Ala Ser Leu Val Pro Ala Ala
                485
```

<210> SEQ ID NO 21

```
<211> LENGTH: 487
<212> TYPE: PRT
<213> ORGANISM: Unknown
<220> FEATURE:
<223> OTHER INFORMATION: K:trAPAO translational fusion with barley alpha
      amylase
<220> FEATURE:
<221> NAME/KEY: misc_feature
<222> LOCATION: (73)..(1464)
<223> OTHER INFORMATION: K:trAPAO cDNA
<220> FEATURE:
<221> NAME/KEY: misc_feature
<222> LOCATION: (73)..(75)
<223> OTHER INFORMATION: Added lysine residue

<400> SEQUENCE: 21

Met Ala Asn Lys His Leu Ser Leu Ser Leu Phe Leu Val Leu Leu Gly
1               5                   10                  15

Leu Ser Ala Ser Leu Ala Ser Gly Lys Asp Asn Val Ala Asp Val Val
            20                  25                  30

Val Val Gly Ala Gly Leu Ser Gly Leu Glu Thr Ala Arg Lys Val Gln
        35                  40                  45

Ala Ala Gly Leu Ser Cys Leu Val Leu Glu Ala Met Asp Arg Val Gly
    50                  55                  60

Gly Lys Thr Leu Ser Val Gln Ser Gly Pro Gly Arg Thr Thr Ile Asn
65                  70                  75                  80

Asp Leu Gly Ala Ala Trp Ile Asn Asp Ser Asn Gln Ser Glu Val Ser
                85                  90                  95

Arg Leu Phe Glu Arg Phe His Leu Glu Gly Glu Leu Gln Arg Thr Thr
            100                 105                 110

Gly Asn Ser Ile His Gln Ala Gln Asp Gly Thr Thr Thr Thr Ala Pro
        115                 120                 125

Tyr Gly Asp Ser Leu Leu Ser Glu Glu Val Ala Ser Ala Leu Ala Glu
130                 135                 140

Leu Leu Pro Val Trp Ser Gln Leu Ile Glu Glu His Ser Leu Gln Asp
145                 150                 155                 160

Leu Lys Ala Ser Pro Gln Ala Lys Arg Leu Asp Ser Val Ser Phe Ala
                165                 170                 175

His Tyr Cys Glu Lys Glu Leu Asn Leu Pro Ala Val Leu Gly Val Ala
            180                 185                 190

Asn Gln Ile Thr Arg Ala Leu Leu Gly Val Glu Ala His Glu Ile Ser
        195                 200                 205

Met Leu Phe Leu Thr Asp Tyr Ile Lys Ser Ala Thr Gly Leu Ser Asn
210                 215                 220

Ile Phe Ser Asp Lys Lys Asp Gly Gly Gln Tyr Met Arg Cys Lys Thr
225                 230                 235                 240

Gly Met Gln Ser Ile Cys His Ala Met Ser Lys Glu Leu Val Pro Gly
                245                 250                 255

Ser Val His Leu Asn Thr Pro Val Ala Glu Ile Glu Gln Ser Ala Ser
            260                 265                 270

Gly Cys Thr Val Arg Ser Ala Ser Gly Ala Val Phe Arg Ser Lys Lys
        275                 280                 285

Val Val Val Ser Leu Pro Thr Thr Leu Tyr Pro Thr Leu Thr Phe Ser
    290                 295                 300

Pro Pro Leu Pro Ala Glu Lys Gln Ala Leu Ala Glu Asn Ser Ile Leu
305                 310                 315                 320

Gly Tyr Tyr Ser Lys Ile Val Phe Val Trp Asp Lys Pro Trp Trp Arg
                325                 330                 335
```

```
Glu Gln Gly Phe Ser Gly Val Leu Gln Ser Ser Cys Asp Pro Ile Ser
            340                 345                 350

Phe Ala Arg Asp Thr Ser Ile Asp Val Asp Arg Gln Trp Ser Ile Thr
            355                 360                 365

Cys Phe Met Val Gly Asp Pro Gly Arg Lys Trp Ser Gln Gln Ser Lys
370                 375                 380

Gln Val Arg Gln Lys Ser Val Trp Asp Gln Leu Arg Ala Ala Tyr Glu
385                 390                 395                 400

Asn Ala Gly Ala Gln Val Pro Glu Pro Ala Asn Val Leu Glu Ile Glu
                405                 410                 415

Trp Ser Lys Gln Gln Tyr Phe Gln Gly Ala Pro Ser Ala Val Tyr Gly
            420                 425                 430

Leu Asn Asp Leu Ile Thr Leu Gly Ser Ala Leu Arg Thr Pro Phe Lys
            435                 440                 445

Ser Val His Phe Val Gly Thr Glu Thr Ser Leu Val Trp Lys Gly Tyr
            450                 455                 460

Met Glu Gly Ala Ile Arg Ser Gly Gln Arg Gly Ala Ala Glu Val Val
465                 470                 475                 480

Ala Ser Leu Val Pro Ala Ala
                485

<210> SEQ ID NO 22
<211> LENGTH: 1803
<212> TYPE: DNA
<213> ORGANISM: Exophiala spinifera
<220> FEATURE:
<221> NAME/KEY: CDS
<222> LOCATION: (1)..(1800)
<223> OTHER INFORMATION:

<400> SEQUENCE: 22 atg gca ctt gca ccg agc tac atc aat ccc cca aac gtc gcc tcc cca      48
Met Ala Leu Ala Pro Ser Tyr Ile Asn Pro Pro Asn Val Ala Ser Pro
1               5                   10                  15 gca ggg tat tct cac gtc ggc gta ggc cca gac gga ggg agg tat gtg      96
Ala Gly Tyr Ser His Val Gly Val Gly Pro Asp Gly Gly Arg Tyr Val
                20                  25                  30 aca ata gct gga cag att gga caa gac gct tcg ggc gtg aca gac cct     144
Thr Ile Ala Gly Gln Ile Gly Gln Asp Ala Ser Gly Val Thr Asp Pro
            35                  40                  45 gcc tac gag aaa cag gtt gcc caa gca ttc gcc aat ctg cga gct tgc     192
Ala Tyr Glu Lys Gln Val Ala Gln Ala Phe Ala Asn Leu Arg Ala Cys
    50                  55                  60 ctt gct gca gtt gga gcc act tca aac gac gtc acc aag ctc aat tac     240
Leu Ala Ala Val Gly Ala Thr Ser Asn Asp Val Thr Lys Leu Asn Tyr
65                  70                  75                  80 tac atc gtc gac tac gcc ccg agc aaa ctc acc gca att gga gat ggg     288
Tyr Ile Val Asp Tyr Ala Pro Ser Lys Leu Thr Ala Ile Gly Asp Gly
                85                  90                  95 ctg aag gct acc ttt gcc ctt gac agg ctc cct cct tgc acg ctg gtg     336
Leu Lys Ala Thr Phe Ala Leu Asp Arg Leu Pro Pro Cys Thr Leu Val
                100                 105                 110 cca gtg tcg gcc ttg tct tca cct gaa tac ctc ttt gag gtt gat gcc     384
Pro Val Ser Ala Leu Ser Ser Pro Glu Tyr Leu Phe Glu Val Asp Ala
            115                 120                 125 acg gcg ctg gtg ccg gga cac acg acc cca gac aac gtt gcg gac gtg     432
Thr Ala Leu Val Pro Gly His Thr Thr Pro Asp Asn Val Ala Asp Val
130                 135                 140
```

```
                                                        -continued gta gtg gtg ggc gct ggc ttg agc ggt ttg gag acg gca cgc aaa gtc      480
Val Val Val Gly Ala Gly Leu Ser Gly Leu Glu Thr Ala Arg Lys Val
145             150                 155                 160 cag gcc gcc ggt ctg tcc tgc ctc gtt ctt gag gcg atg gat cgt gta      528
Gln Ala Ala Gly Leu Ser Cys Leu Val Leu Glu Ala Met Asp Arg Val
                165                 170                 175 ggg gga aag act ctg agc gta caa tcg ggt ccc ggc agg acg act atc      576
Gly Gly Lys Thr Leu Ser Val Gln Ser Gly Pro Gly Arg Thr Thr Ile
            180                 185                 190 aac gac ctc ggc gct gcg tgg atc aat gac agc aac caa agc gaa gta      624
Asn Asp Leu Gly Ala Ala Trp Ile Asn Asp Ser Asn Gln Ser Glu Val
        195                 200                 205 tcc aga ttg ttt gaa aga ttt cat ttg gag ggc gag ctc cag agg acg      672
Ser Arg Leu Phe Glu Arg Phe His Leu Glu Gly Glu Leu Gln Arg Thr
    210                 215                 220 act gga aat tca atc cat caa gca caa gac ggt aca acc act aca gct      720
Thr Gly Asn Ser Ile His Gln Ala Gln Asp Gly Thr Thr Thr Thr Ala
225                 230                 235                 240 cct tat ggt gac tcc ttg ctg agc gag gag gtt gca agt gca ctt gcg      768
Pro Tyr Gly Asp Ser Leu Leu Ser Glu Glu Val Ala Ser Ala Leu Ala
                245                 250                 255 gaa ctc ctc ccc gta tgg tct cag ctg atc gaa gag cat agc ctt caa      816
Glu Leu Leu Pro Val Trp Ser Gln Leu Ile Glu Glu His Ser Leu Gln
                260                 265                 270 gac ctc aag gcg agc cct cag gcg aag cgg ctc gac agt gtg agc ttc      864
Asp Leu Lys Ala Ser Pro Gln Ala Lys Arg Leu Asp Ser Val Ser Phe
            275                 280                 285 gcg cac tac tgt gag aag gaa cta aac ttg cct gct gtt ctc ggc gta      912
Ala His Tyr Cys Glu Lys Glu Leu Asn Leu Pro Ala Val Leu Gly Val
        290                 295                 300 gca aac cag atc aca cgc gct ctg ctc ggt gtg gaa gcc cac gag atc      960
Ala Asn Gln Ile Thr Arg Ala Leu Leu Gly Val Glu Ala His Glu Ile
305                 310                 315                 320 agc atg ctt ttt ctc acc gac tac atc aag agt gcc acc ggt ctc agt     1008
Ser Met Leu Phe Leu Thr Asp Tyr Ile Lys Ser Ala Thr Gly Leu Ser
                325                 330                 335 aat att ttc tcg gac aag aaa gac ggc ggg cag tat atg cga tgc aaa     1056
Asn Ile Phe Ser Asp Lys Lys Asp Gly Gly Gln Tyr Met Arg Cys Lys
                340                 345                 350 aca ggt atg cag tcg att tgc cat gcc atg tca aag gaa ctt gtt cca     1104
Thr Gly Met Gln Ser Ile Cys His Ala Met Ser Lys Glu Leu Val Pro
            355                 360                 365 ggc tca gtg cac ctc aac acc ccc gtc gct gaa att gag cag tcg gca     1152
Gly Ser Val His Leu Asn Thr Pro Val Ala Glu Ile Glu Gln Ser Ala
        370                 375                 380 tcc ggc tgt aca gta cga tcg gcc tcg ggc gcc gtg ttc cga agc aaa     1200
Ser Gly Cys Thr Val Arg Ser Ala Ser Gly Ala Val Phe Arg Ser Lys
385                 390                 395                 400 aag gtg gtg gtt tcg tta ccg aca acc ttg tat ccc acc ttg aca ttt     1248
Lys Val Val Val Ser Leu Pro Thr Thr Leu Tyr Pro Thr Leu Thr Phe
                405                 410                 415 tca cca cct ctt ccc gcc gag aag caa gca ttg gcg gaa aat tct atc     1296
Ser Pro Pro Leu Pro Ala Glu Lys Gln Ala Leu Ala Glu Asn Ser Ile
                420                 425                 430 ctg ggc tac tat agc aag ata gtc ttc gta tgg gac aag ccg tgg tgg     1344
Leu Gly Tyr Tyr Ser Lys Ile Val Phe Val Trp Asp Lys Pro Trp Trp
            435                 440                 445 cgc gaa caa ggc ttc tcg ggc gtc ctc caa tcg agc tgt gac ccc atc     1392
Arg Glu Gln Gly Phe Ser Gly Val Leu Gln Ser Ser Cys Asp Pro Ile
        450                 455                 460
```

```
tca ttt gcc aga gat acc agc atc gac gtc gat cga caa tgg tcc att    1440
Ser Phe Ala Arg Asp Thr Ser Ile Asp Val Asp Arg Gln Trp Ser Ile
465                 470                 475                 480 acc tgt ttc atg gtc gga gac ccg gga cgg aag tgg tcc caa cag tcc    1488
Thr Cys Phe Met Val Gly Asp Pro Gly Arg Lys Trp Ser Gln Gln Ser
                485                 490                 495 aag cag gta cga caa aag tct gtc tgg gac caa ctc cgc gca gcc tac    1536
Lys Gln Val Arg Gln Lys Ser Val Trp Asp Gln Leu Arg Ala Ala Tyr
            500                 505                 510 gag aac gcc ggg gcc caa gtc cca gag ccg gcc aac gtg ctc gaa atc    1584
Glu Asn Ala Gly Ala Gln Val Pro Glu Pro Ala Asn Val Leu Glu Ile
        515                 520                 525 gag tgg tcg aag cag cag tat ttc caa gga gct ccg agc gcc gtc tat    1632
Glu Trp Ser Lys Gln Gln Tyr Phe Gln Gly Ala Pro Ser Ala Val Tyr
    530                 535                 540 ggg ctg aac gat ctc atc aca ctg ggt tcg gcg ctc aga acg ccg ttc    1680
Gly Leu Asn Asp Leu Ile Thr Leu Gly Ser Ala Leu Arg Thr Pro Phe
545                 550                 555                 560 aag agt gtt cat ttc gtt gga acg gag acg tct tta gtt tgg aaa ggg    1728
Lys Ser Val His Phe Val Gly Thr Glu Thr Ser Leu Val Trp Lys Gly
                565                 570                 575 tat atg gaa ggg gcc ata cga tcg ggt caa cga ggt gct gca gaa gtt    1776
Tyr Met Glu Gly Ala Ile Arg Ser Gly Gln Arg Gly Ala Ala Glu Val
            580                 585                 590 gtg gct agc ctg gtg cca gca gca tag                                1803
Val Ala Ser Leu Val Pro Ala Ala
        595                 600

<210> SEQ ID NO 23
<211> LENGTH: 600
<212> TYPE: PRT
<213> ORGANISM: Exophiala spinifera

<400> SEQUENCE: 23

Met Ala Leu Ala Pro Ser Tyr Ile Asn Pro Asn Val Ala Ser Pro
1               5                   10                  15

Ala Gly Tyr Ser His Val Gly Val Gly Pro Asp Gly Gly Arg Tyr Val
                20                  25                  30

Thr Ile Ala Gly Gln Ile Gly Gln Asp Ala Ser Gly Val Thr Asp Pro
            35                  40                  45

Ala Tyr Glu Lys Gln Val Ala Gln Ala Phe Ala Asn Leu Arg Ala Cys
        50                  55                  60

Leu Ala Ala Val Gly Ala Thr Ser Asn Asp Val Thr Lys Leu Asn Tyr
65                  70                  75                  80

Tyr Ile Val Asp Tyr Ala Pro Ser Lys Leu Thr Ala Ile Gly Asp Gly
                85                  90                  95

Leu Lys Ala Thr Phe Ala Leu Asp Arg Leu Pro Pro Cys Thr Leu Val
                100                 105                 110

Pro Val Ser Ala Leu Ser Ser Pro Glu Tyr Leu Phe Glu Val Asp Ala
            115                 120                 125

Thr Ala Leu Val Pro Gly His Thr Thr Pro Asp Asn Val Ala Asp Val
        130                 135                 140

Val Val Val Gly Ala Gly Leu Ser Gly Leu Glu Thr Ala Arg Lys Val
145                 150                 155                 160

Gln Ala Ala Gly Leu Ser Cys Leu Val Leu Glu Ala Met Asp Arg Val
                165                 170                 175

Gly Gly Lys Thr Leu Ser Val Gln Ser Gly Pro Gly Arg Thr Thr Ile
```

-continued

```
                 180                 185                 190
Asn Asp Leu Gly Ala Ala Trp Ile Asn Asp Ser Asn Gln Ser Glu Val
                195                 200                 205
Ser Arg Leu Phe Glu Arg Phe His Leu Glu Gly Glu Leu Gln Arg Thr
210                 215                 220
Thr Gly Asn Ser Ile His Gln Ala Gln Asp Gly Thr Thr Thr Thr Ala
225                 230                 235                 240
Pro Tyr Gly Asp Ser Leu Leu Ser Glu Val Ala Ser Ala Leu Ala
                245                 250                 255
Glu Leu Leu Pro Val Trp Ser Gln Leu Ile Glu Glu His Ser Leu Gln
                260                 265                 270
Asp Leu Lys Ala Ser Pro Gln Ala Lys Arg Leu Asp Ser Val Ser Phe
                275                 280                 285
Ala His Tyr Cys Glu Lys Glu Leu Asn Leu Pro Ala Val Leu Gly Val
                290                 295                 300
Ala Asn Gln Ile Thr Arg Ala Leu Leu Gly Val Glu Ala His Glu Ile
305                 310                 315                 320
Ser Met Leu Phe Leu Thr Asp Tyr Ile Lys Ser Ala Thr Gly Leu Ser
                325                 330                 335
Asn Ile Phe Ser Asp Lys Lys Asp Gly Gly Gln Tyr Met Arg Cys Lys
                340                 345                 350
Thr Gly Met Gln Ser Ile Cys His Ala Met Ser Lys Glu Leu Val Pro
                355                 360                 365
Gly Ser Val His Leu Asn Thr Pro Val Ala Glu Ile Glu Gln Ser Ala
                370                 375                 380
Ser Gly Cys Thr Val Arg Ser Ala Ser Gly Ala Val Phe Arg Ser Lys
385                 390                 395                 400
Lys Val Val Val Ser Leu Pro Thr Thr Leu Tyr Pro Thr Leu Thr Phe
                405                 410                 415
Ser Pro Pro Leu Pro Ala Glu Lys Gln Ala Leu Ala Glu Asn Ser Ile
                420                 425                 430
Leu Gly Tyr Tyr Ser Lys Ile Val Phe Val Trp Asp Lys Pro Trp Trp
                435                 440                 445
Arg Glu Gln Gly Phe Ser Gly Val Leu Gln Ser Ser Cys Asp Pro Ile
450                 455                 460
Ser Phe Ala Arg Asp Thr Ser Ile Asp Val Asp Arg Gln Trp Ser Ile
465                 470                 475                 480
Thr Cys Phe Met Val Gly Asp Pro Gly Arg Lys Trp Ser Gln Gln Ser
                485                 490                 495
Lys Gln Val Arg Gln Lys Ser Val Trp Asp Gln Leu Arg Ala Ala Tyr
                500                 505                 510
Glu Asn Ala Gly Ala Gln Val Pro Glu Pro Ala Asn Val Leu Glu Ile
                515                 520                 525
Glu Trp Ser Lys Gln Gln Tyr Phe Gln Gly Ala Pro Ser Ala Val Tyr
                530                 535                 540
Gly Leu Asn Asp Leu Ile Thr Leu Gly Ser Ala Leu Arg Thr Pro Phe
545                 550                 555                 560
Lys Ser Val His Phe Val Gly Thr Glu Thr Ser Leu Val Trp Lys Gly
                565                 570                 575
Tyr Met Glu Gly Ala Ile Arg Ser Gly Gln Arg Gly Ala Ala Glu Val
                580                 585                 590
Val Ala Ser Leu Val Pro Ala Ala
                595                 600
```

-continued

```
<210> SEQ ID NO 24
<211> LENGTH: 3003
<212> TYPE: DNA
<213> ORGANISM: unknown
<220> FEATURE:
<223> OTHER INFORMATION: K:trAPAO
<220> FEATURE:
<221> NAME/KEY: misc_feature
<222> LOCATION: (73)..(1575)
<223> OTHER INFORMATION: esp1 mat
<220> FEATURE:
<221> NAME/KEY: misc_feature
<222> LOCATION: (1576)..(1611)
<223> OTHER INFORMATION: spacer sequence
<220> FEATURE:
<221> NAME/KEY: misc_feature
<222> LOCATION: (1612)..(3000)
<223> OTHER INFORMATION: K:trAPAO
<220> FEATURE:
<221> NAME/KEY: CDS
<222> LOCATION: (1)..(3000)
<223> OTHER INFORMATION:
<220> FEATURE:
<221> NAME/KEY: misc_feature
<222> LOCATION: (1612)..(1614)
<223> OTHER INFORMATION: extra lysine

<400> SEQUENCE: 24 atg gcc aac aag cac ctg agc ctc tcc ctc ttc ctc gtg ctc ctc ggc      48
Met Ala Asn Lys His Leu Ser Leu Ser Leu Phe Leu Val Leu Leu Gly
1               5                   10                  15 ctc tcc gcc tcc ctc gcc agc ggc gct cct act gtc aag att gat gct      96
Leu Ser Ala Ser Leu Ala Ser Gly Ala Pro Thr Val Lys Ile Asp Ala
            20                  25                  30 ggg atg gtg gtc ggc acg act act act gtc ccc ggc acc act gcg acc     144
Gly Met Val Val Gly Thr Thr Thr Thr Val Pro Gly Thr Thr Ala Thr
        35                  40                  45 gtc agc gag ttc ttg ggc gtt cct ttt gcc gcc tct ccg aca cga ttt     192
Val Ser Glu Phe Leu Gly Val Pro Phe Ala Ala Ser Pro Thr Arg Phe
    50                  55                  60 gcg cct cct act cgt ccc gtg cct tgg tca acg cct ttg caa gcc act     240
Ala Pro Pro Thr Arg Pro Val Pro Trp Ser Thr Pro Leu Gln Ala Thr
65                  70                  75                  80 gca tat ggt cca gca tgc cct caa caa ttc aat tac ccc gaa gaa ctc     288
Ala Tyr Gly Pro Ala Cys Pro Gln Gln Phe Asn Tyr Pro Glu Glu Leu
                85                  90                  95 cgt gag att acg atg gcc tgg ttc aat aca ccg ccc ccg tca gct ggt     336
Arg Glu Ile Thr Met Ala Trp Phe Asn Thr Pro Pro Pro Ser Ala Gly
            100                 105                 110 gaa agt gag gac tgc ctg aac ctc aac atc tac gtc cca gga act gag     384
Glu Ser Glu Asp Cys Leu Asn Leu Asn Ile Tyr Val Pro Gly Thr Glu
        115                 120                 125 aac aca aac aaa gcc gtc atg gtt tgg ata tac ggt gga gcg ctg gaa     432
Asn Thr Asn Lys Ala Val Met Val Trp Ile Tyr Gly Gly Ala Leu Glu
    130                 135                 140 tat ggt tgg aat tca ttc cac ctt tac gac ggg gct agt ttc gca gcc     480
Tyr Gly Trp Asn Ser Phe His Leu Tyr Asp Gly Ala Ser Phe Ala Ala
145                 150                 155                 160 aat cag gat gtc atc gcc gtg acc atc aac tac aga acg aac att ctg     528
Asn Gln Asp Val Ile Ala Val Thr Ile Asn Tyr Arg Thr Asn Ile Leu
                165                 170                 175 ggg ttc cct gct gcc cct cag ctt cca ata aca cag cga aat ctg ggg     576
Gly Phe Pro Ala Ala Pro Gln Leu Pro Ile Thr Gln Arg Asn Leu Gly
            180                 185                 190
```

```
ttc cta gac caa agg ttt gct ttg gat tgg gta cag cgg aac atc gca        624
Phe Leu Asp Gln Arg Phe Ala Leu Asp Trp Val Gln Arg Asn Ile Ala
        195                 200                 205 gcc ttt ggc ggt gat cct cga aag gtc aca ata ttt ggg cag agt gcg        672
Ala Phe Gly Gly Asp Pro Arg Lys Val Thr Ile Phe Gly Gln Ser Ala
210                 215                 220 ggg ggc aga agt gtc gac gtc ctc ttg acg tct atg cca cac aac cca        720
Gly Gly Arg Ser Val Asp Val Leu Leu Thr Ser Met Pro His Asn Pro
225                 230                 235                 240 ccc ttc cga gca gca atc atg gag tcc ggt gtg gct aac tac aac ttc        768
Pro Phe Arg Ala Ala Ile Met Glu Ser Gly Val Ala Asn Tyr Asn Phe
                245                 250                 255 ccc aag gga gat ttg tcc gaa cct tgg aac acc act gtt caa gct ctc        816
Pro Lys Gly Asp Leu Ser Glu Pro Trp Asn Thr Thr Val Gln Ala Leu
        260                 265                 270 aac tgt acc acc agt atc gac atc ttg agt tgt atg aga aga gtc gat        864
Asn Cys Thr Thr Ser Ile Asp Ile Leu Ser Cys Met Arg Arg Val Asp
            275                 280                 285 ctc gcc act ctg atg aac acg atc gag caa ctc gga ctt ggg ttt gag        912
Leu Ala Thr Leu Met Asn Thr Ile Glu Gln Leu Gly Leu Gly Phe Glu
290                 295                 300 tac acg ttg gac aac gta acg gct gtg tac cgt tct gaa acg gct cgc        960
Tyr Thr Leu Asp Asn Val Thr Ala Val Tyr Arg Ser Glu Thr Ala Arg
305                 310                 315                 320 acg act ggt gac att gct cgt gta cct gtt ctc gtc ggg acg gtg gcc       1008
Thr Thr Gly Asp Ile Ala Arg Val Pro Val Leu Val Gly Thr Val Ala
                325                 330                 335 aac gac gga ctt ctc ttt gtc ctc ggg gag aat gac acc caa gca tat       1056
Asn Asp Gly Leu Leu Phe Val Leu Gly Glu Asn Asp Thr Gln Ala Tyr
        340                 345                 350 ctc gag gag gca atc ccg aat cag ccc gac ctt tac cag act ctc ctt       1104
Leu Glu Glu Ala Ile Pro Asn Gln Pro Asp Leu Tyr Gln Thr Leu Leu
            355                 360                 365 gga gca tat ccc att gga tcc cca ggg atc gga tcg cct caa gat cag       1152
Gly Ala Tyr Pro Ile Gly Ser Pro Gly Ile Gly Ser Pro Gln Asp Gln
370                 375                 380 att gcc gcc att gag acc gag gta aga ttc cag tgt cct tct gcc atc       1200
Ile Ala Ala Ile Glu Thr Glu Val Arg Phe Gln Cys Pro Ser Ala Ile
385                 390                 395                 400 gtg gct cag gac tcc cgg aat cgg ggt atc cct tct tgg cgc tac tac       1248
Val Ala Gln Asp Ser Arg Asn Arg Gly Ile Pro Ser Trp Arg Tyr Tyr
                405                 410                 415 tac aat gcg acc ttt gag aat ctg gag ctt ttc cct ggg tcc gaa gtg       1296
Tyr Asn Ala Thr Phe Glu Asn Leu Glu Leu Phe Pro Gly Ser Glu Val
        420                 425                 430 tac cac agc tct gaa gtc ggg atg gtg ttt ggc acg tat cct gtc gca       1344
Tyr His Ser Ser Glu Val Gly Met Val Phe Gly Thr Tyr Pro Val Ala
            435                 440                 445 agt gcg acc gcc ttg gag gcc cag acg agc aaa tac atg cag ggt gcc       1392
Ser Ala Thr Ala Leu Glu Ala Gln Thr Ser Lys Tyr Met Gln Gly Ala
450                 455                 460 tgg gcg gcc ttt gcc aaa aac ccc atg aat ggg cct ggg tgg aaa caa       1440
Trp Ala Ala Phe Ala Lys Asn Pro Met Asn Gly Pro Gly Trp Lys Gln
465                 470                 475                 480 gtg ccg aat gtc gcg gcg ctt ggc tca cca ggc aaa gcc atc cag gtt       1488
Val Pro Asn Val Ala Ala Leu Gly Ser Pro Gly Lys Ala Ile Gln Val
                485                 490                 495 gac gtc tct cca gcg aca ata gac caa cga tgt gcc ttg tac acg cgt       1536
Asp Val Ser Pro Ala Thr Ile Asp Gln Arg Cys Ala Leu Tyr Thr Arg
        500                 505                 510
```

```
tat tat act gag ttg ggc aca atc gcg ccg agg aca ttt ggc gga ggc      1584
Tyr Tyr Thr Glu Leu Gly Thr Ile Ala Pro Arg Thr Phe Gly Gly Gly
            515                 520                 525 agc ggc gga ggc agc ggc gga ggc agc aaa gac aac gtt gcg gac gtg      1632
Ser Gly Gly Gly Ser Gly Gly Gly Ser Lys Asp Asn Val Ala Asp Val
530                 535                 540 gta gtg gtg ggc gct ggc ttg agc ggt ttg gag acg gca cgc aaa gtc      1680
Val Val Val Gly Ala Gly Leu Ser Gly Leu Glu Thr Ala Arg Lys Val
545                 550                 555                 560 cag gcc gcc ggt ctg tcc tgc ctc gtt ctt gag gcg atg gat cgt gta      1728
Gln Ala Ala Gly Leu Ser Cys Leu Val Leu Glu Ala Met Asp Arg Val
                565                 570                 575 ggg gga aag act ctg agc gta caa tcg ggt ccc ggc agg acg act atc      1776
Gly Gly Lys Thr Leu Ser Val Gln Ser Gly Pro Gly Arg Thr Thr Ile
            580                 585                 590 aac gac ctc ggc gct gcg tgg atc aat gac agc aac caa agc gaa gta      1824
Asn Asp Leu Gly Ala Ala Trp Ile Asn Asp Ser Asn Gln Ser Glu Val
        595                 600                 605 tcc aga ttg ttt gaa aga ttt cat ttg gag ggc gag ctc cag agg acg      1872
Ser Arg Leu Phe Glu Arg Phe His Leu Glu Gly Glu Leu Gln Arg Thr
    610                 615                 620 act gga aat tca atc cat caa gca caa gac ggt aca acc act aca gct      1920
Thr Gly Asn Ser Ile His Gln Ala Gln Asp Gly Thr Thr Thr Thr Ala
625                 630                 635                 640 cct tat ggt gac tcc ttg ctg agc gag gag gtt gca agt gca ctt gcg      1968
Pro Tyr Gly Asp Ser Leu Leu Ser Glu Glu Val Ala Ser Ala Leu Ala
                645                 650                 655 gaa ctc ctc ccc gta tgg tct cag ctg atc gaa gag cat agc ctt caa      2016
Glu Leu Leu Pro Val Trp Ser Gln Leu Ile Glu Glu His Ser Leu Gln
            660                 665                 670 gac ctc aag gcg agc cct cag gcg aag cgg ctc gac agt gtg agc ttc      2064
Asp Leu Lys Ala Ser Pro Gln Ala Lys Arg Leu Asp Ser Val Ser Phe
        675                 680                 685 gcg cac tac tgt gag aag gaa cta aac ttg cct gct gtt ctc ggc gta      2112
Ala His Tyr Cys Glu Lys Glu Leu Asn Leu Pro Ala Val Leu Gly Val
    690                 695                 700 gca aac cag atc aca cgc gct ctg ctc ggt gtg gaa gcc cac gag atc      2160
Ala Asn Gln Ile Thr Arg Ala Leu Leu Gly Val Glu Ala His Glu Ile
705                 710                 715                 720 agc atg ctt ttt ctc acc gac tac atc aag agt gcc acc ggt ctc agt      2208
Ser Met Leu Phe Leu Thr Asp Tyr Ile Lys Ser Ala Thr Gly Leu Ser
                725                 730                 735 aat att ttc tcg gac aag aaa gac ggc ggg cag tat atg cga tgc aaa      2256
Asn Ile Phe Ser Asp Lys Lys Asp Gly Gly Gln Tyr Met Arg Cys Lys
            740                 745                 750 aca ggt atg cag tcg att tgc cat gcc atg tca aag gaa ctt gtt cca      2304
Thr Gly Met Gln Ser Ile Cys His Ala Met Ser Lys Glu Leu Val Pro
        755                 760                 765 ggc tca gtg cac ctc aac acc ccc gtc gct gaa att gag cag tcg gca      2352
Gly Ser Val His Leu Asn Thr Pro Val Ala Glu Ile Glu Gln Ser Ala
    770                 775                 780 tcc ggc tgt aca gta cga tcg gcc tcg ggc gcc gtg ttc cga agc aaa      2400
Ser Gly Cys Thr Val Arg Ser Ala Ser Gly Ala Val Phe Arg Ser Lys
785                 790                 795                 800 aag gtg gtg gtt tcg tta ccg aca acc ttg tat ccc acc ttg aca ttt      2448
Lys Val Val Val Ser Leu Pro Thr Thr Leu Tyr Pro Thr Leu Thr Phe
                805                 810                 815 tca cca cct ctt ccc gcc gag aag caa gca ttg gcg gaa aat tct atc      2496
Ser Pro Pro Leu Pro Ala Glu Lys Gln Ala Leu Ala Glu Asn Ser Ile
```

```
                820                 825                 830
ctg ggc tac tat agc aag ata gtc ttc gta tgg gac aag ccg tgg tgg    2544
Leu Gly Tyr Tyr Ser Lys Ile Val Phe Val Trp Asp Lys Pro Trp Trp
            835                 840                 845 cgc gaa caa ggc ttc tcg ggc gtc ctc caa tcg agc tgt gac ccc atc    2592
Arg Glu Gln Gly Phe Ser Gly Val Leu Gln Ser Ser Cys Asp Pro Ile
850                 855                 860 tca ttt gcc aga gat acc agc atc gac gtc gat cga caa tgg tcc att    2640
Ser Phe Ala Arg Asp Thr Ser Ile Asp Val Asp Arg Gln Trp Ser Ile
865                 870                 875                 880 acc tgt ttc atg gtc gga gac ccg gga cgg aag tgg tcc caa cag tcc    2688
Thr Cys Phe Met Val Gly Asp Pro Gly Arg Lys Trp Ser Gln Gln Ser
                885                 890                 895 aag cag gta cga caa aag tct gtc tgg gac caa ctc cgc gca gcc tac    2736
Lys Gln Val Arg Gln Lys Ser Val Trp Asp Gln Leu Arg Ala Ala Tyr
            900                 905                 910 gag aac gcc ggg gcc caa gtc cca gag ccg gcc aac gtg ctc gaa atc    2784
Glu Asn Ala Gly Ala Gln Val Pro Glu Pro Ala Asn Val Leu Glu Ile
            915                 920                 925 gag tgg tcg aag cag cag tat ttc caa gga gct ccg agc gcc gtc tat    2832
Glu Trp Ser Lys Gln Gln Tyr Phe Gln Gly Ala Pro Ser Ala Val Tyr
        930                 935                 940 ggg ctg aac gat ctc atc aca ctg ggt tcg gcg ctc aga acg ccg ttc    2880
Gly Leu Asn Asp Leu Ile Thr Leu Gly Ser Ala Leu Arg Thr Pro Phe
945                 950                 955                 960 aag agt gtt cat ttc gtt gga acg gag acg tct tta gtt tgg aaa ggg    2928
Lys Ser Val His Phe Val Gly Thr Glu Thr Ser Leu Val Trp Lys Gly
                965                 970                 975 tat atg gaa ggg gcc ata cga tcg ggt caa cga ggt gct gca gaa gtt    2976
Tyr Met Glu Gly Ala Ile Arg Ser Gly Gln Arg Gly Ala Ala Glu Val
            980                 985                 990 gtg gct agc ctg gtg cca gca gca tag                                3003
Val Ala Ser Leu Val Pro Ala Ala
            995                 1000

<210> SEQ ID NO 25
<211> LENGTH: 1000
<212> TYPE: PRT
<213> ORGANISM: unknown
<220> FEATURE:
<223> OTHER INFORMATION: K:trAPAO
<220> FEATURE:
<221> NAME/KEY: misc_feature
<222> LOCATION: (73)..(1575)
<223> OTHER INFORMATION: espl mat
<220> FEATURE:
<221> NAME/KEY: misc_feature
<222> LOCATION: (1576)..(1611)
<223> OTHER INFORMATION: spacer sequence
<220> FEATURE:
<221> NAME/KEY: misc_feature
<222> LOCATION: (1612)..(3000)
<223> OTHER INFORMATION: K:trAPAO
<220> FEATURE:
<221> NAME/KEY: misc_feature
<222> LOCATION: (1612)..(1614)
<223> OTHER INFORMATION: extra lysine

<400> SEQUENCE: 25

Met Ala Asn Lys His Leu Ser Leu Ser Leu Phe Leu Val Leu Leu Gly
1               5                   10                  15

Leu Ser Ala Ser Leu Ala Ser Gly Ala Pro Thr Val Lys Ile Asp Ala
            20                  25                  30

Gly Met Val Val Gly Thr Thr Thr Thr Val Pro Gly Thr Thr Ala Thr
```

-continued

```
            35                  40                  45
Val Ser Glu Phe Leu Gly Val Pro Phe Ala Ser Pro Thr Arg Phe
        50                  55                  60
Ala Pro Pro Thr Arg Pro Val Pro Trp Ser Thr Pro Leu Gln Ala Thr
 65                  70                  75                  80
Ala Tyr Gly Pro Ala Cys Pro Gln Gln Phe Asn Tyr Pro Glu Glu Leu
                 85                  90                  95
Arg Glu Ile Thr Met Ala Trp Phe Asn Thr Pro Pro Ser Ala Gly
                100                 105                 110
Glu Ser Glu Asp Cys Leu Asn Leu Asn Ile Tyr Val Pro Gly Thr Glu
                115                 120                 125
Asn Thr Asn Lys Ala Val Met Val Trp Ile Tyr Gly Gly Ala Leu Glu
130                 135                 140
Tyr Gly Trp Asn Ser Phe His Leu Tyr Asp Gly Ala Ser Phe Ala Ala
145                 150                 155                 160
Asn Gln Asp Val Ile Ala Val Thr Ile Asn Tyr Arg Thr Asn Ile Leu
                165                 170                 175
Gly Phe Pro Ala Ala Pro Gln Leu Pro Ile Thr Gln Arg Asn Leu Gly
                180                 185                 190
Phe Leu Asp Gln Arg Phe Ala Leu Asp Trp Val Gln Arg Asn Ile Ala
                195                 200                 205
Ala Phe Gly Gly Asp Pro Arg Lys Val Thr Ile Phe Gly Gln Ser Ala
210                 215                 220
Gly Gly Arg Ser Val Asp Val Leu Leu Thr Ser Met Pro His Asn Pro
225                 230                 235                 240
Pro Phe Arg Ala Ala Ile Met Glu Ser Gly Val Ala Asn Tyr Asn Phe
                245                 250                 255
Pro Lys Gly Asp Leu Ser Glu Pro Trp Asn Thr Thr Val Gln Ala Leu
                260                 265                 270
Asn Cys Thr Thr Ser Ile Asp Ile Leu Ser Cys Met Arg Arg Val Asp
                275                 280                 285
Leu Ala Thr Leu Met Asn Thr Ile Glu Gln Leu Gly Leu Gly Phe Glu
                290                 295                 300
Tyr Thr Leu Asp Asn Val Thr Ala Val Tyr Arg Ser Glu Thr Ala Arg
305                 310                 315                 320
Thr Thr Gly Asp Ile Ala Arg Val Pro Val Leu Val Gly Thr Val Ala
                325                 330                 335
Asn Asp Gly Leu Leu Phe Val Leu Gly Glu Asn Asp Thr Gln Ala Tyr
                340                 345                 350
Leu Glu Glu Ala Ile Pro Asn Gln Pro Asp Leu Tyr Gln Thr Leu Leu
                355                 360                 365
Gly Ala Tyr Pro Ile Gly Ser Pro Gly Ile Gly Ser Pro Gln Asp Gln
                370                 375                 380
Ile Ala Ala Ile Glu Thr Glu Val Arg Phe Gln Cys Pro Ser Ala Ile
385                 390                 395                 400
Val Ala Gln Asp Ser Arg Asn Arg Gly Ile Pro Ser Trp Arg Tyr Tyr
                405                 410                 415
Tyr Asn Ala Thr Phe Glu Asn Leu Glu Leu Phe Pro Gly Ser Glu Val
                420                 425                 430
Tyr His Ser Ser Glu Val Gly Met Val Phe Gly Thr Tyr Pro Val Ala
                435                 440                 445
Ser Ala Thr Ala Leu Glu Ala Gln Thr Ser Lys Tyr Met Gln Gly Ala
450                 455                 460
```

```
Trp Ala Ala Phe Ala Lys Asn Pro Met Asn Gly Pro Gly Trp Lys Gln
465                 470                 475                 480

Val Pro Asn Val Ala Ala Leu Gly Ser Pro Gly Lys Ala Ile Gln Val
            485                 490                 495

Asp Val Ser Pro Ala Thr Ile Asp Gln Arg Cys Ala Leu Tyr Thr Arg
            500                 505                 510

Tyr Tyr Thr Glu Leu Gly Thr Ile Ala Pro Arg Thr Phe Gly Gly Gly
            515                 520                 525

Ser Gly Gly Gly Ser Gly Gly Gly Ser Lys Asp Asn Val Ala Asp Val
    530                 535                 540

Val Val Val Gly Ala Gly Leu Ser Gly Leu Glu Thr Ala Arg Lys Val
545                 550                 555                 560

Gln Ala Ala Gly Leu Ser Cys Leu Val Leu Glu Ala Met Asp Arg Val
                565                 570                 575

Gly Gly Lys Thr Leu Ser Val Gln Ser Gly Pro Gly Arg Thr Thr Ile
            580                 585                 590

Asn Asp Leu Gly Ala Ala Trp Ile Asn Asp Ser Asn Gln Ser Glu Val
        595                 600                 605

Ser Arg Leu Phe Glu Arg Phe His Leu Glu Gly Glu Leu Gln Arg Thr
    610                 615                 620

Thr Gly Asn Ser Ile His Gln Ala Gln Asp Gly Thr Thr Thr Thr Ala
625                 630                 635                 640

Pro Tyr Gly Asp Ser Leu Leu Ser Glu Glu Val Ala Ser Ala Leu Ala
                645                 650                 655

Glu Leu Leu Pro Val Trp Ser Gln Leu Ile Glu Glu His Ser Leu Gln
                660                 665                 670

Asp Leu Lys Ala Ser Pro Gln Ala Lys Arg Leu Asp Ser Val Ser Phe
            675                 680                 685

Ala His Tyr Cys Glu Lys Glu Leu Asn Leu Pro Ala Val Leu Gly Val
        690                 695                 700

Ala Asn Gln Ile Thr Arg Ala Leu Leu Gly Val Glu Ala His Glu Ile
705                 710                 715                 720

Ser Met Leu Phe Leu Thr Asp Tyr Ile Lys Ser Ala Thr Gly Leu Ser
                725                 730                 735

Asn Ile Phe Ser Asp Lys Lys Asp Gly Gly Gln Tyr Met Arg Cys Lys
                740                 745                 750

Thr Gly Met Gln Ser Ile Cys His Ala Met Ser Lys Glu Leu Val Pro
            755                 760                 765

Gly Ser Val His Leu Asn Thr Pro Val Ala Glu Ile Glu Gln Ser Ala
    770                 775                 780

Ser Gly Cys Thr Val Arg Ser Ala Ser Gly Ala Val Phe Arg Ser Lys
785                 790                 795                 800

Lys Val Val Val Ser Leu Pro Thr Thr Leu Tyr Pro Thr Leu Thr Phe
                805                 810                 815

Ser Pro Pro Leu Pro Ala Glu Lys Gln Ala Leu Ala Glu Asn Ser Ile
            820                 825                 830

Leu Gly Tyr Tyr Ser Lys Ile Val Phe Val Trp Asp Lys Pro Trp Trp
            835                 840                 845

Arg Glu Gln Gly Phe Ser Gly Val Leu Gln Ser Ser Cys Asp Pro Ile
    850                 855                 860

Ser Phe Ala Arg Asp Thr Ser Ile Asp Val Asp Arg Gln Trp Ser Ile
865                 870                 875                 880
```

-continued

```
Thr Cys Phe Met Val Gly Asp Pro Gly Arg Lys Trp Ser Gln Gln Ser
            885                 890                 895

Lys Gln Val Arg Gln Lys Ser Val Trp Asp Gln Leu Arg Ala Ala Tyr
            900                 905                 910

Glu Asn Ala Gly Ala Gln Val Pro Glu Pro Ala Asn Val Leu Glu Ile
            915                 920                 925

Glu Trp Ser Lys Gln Gln Tyr Phe Gln Gly Ala Pro Ser Ala Val Tyr
            930                 935                 940

Gly Leu Asn Asp Leu Ile Thr Leu Gly Ser Ala Leu Arg Thr Pro Phe
945                 950                 955                 960

Lys Ser Val His Phe Val Gly Thr Glu Thr Ser Leu Val Trp Lys Gly
            965                 970                 975

Tyr Met Glu Gly Ala Ile Arg Ser Gly Gln Arg Gly Ala Ala Glu Val
            980                 985                 990

Val Ala Ser Leu Val Pro Ala Ala
            995                 1000
```

<210> SEQ ID NO 26
<211> LENGTH: 2976
<212> TYPE: DNA
<213> ORGANISM: Unknown
<220> FEATURE:
<223> OTHER INFORMATION: Barley alpha amylase signal sequence:BEST1
      mature:artificial spacer:K:trAPAO
<220> FEATURE:
<221> NAME/KEY: sig_peptide
<222> LOCATION: (1)..(72)
<223> OTHER INFORMATION: Barley alpha amylase signal sequence
<220> FEATURE:
<221> NAME/KEY: mat_peptide
<222> LOCATION: (73)..()
<223> OTHER INFORMATION: BEST1 mature
<220> FEATURE:
<221> NAME/KEY: misc_feature
<222> LOCATION: (1546)..(1584)
<223> OTHER INFORMATION: spacer sequence
<220> FEATURE:
<221> NAME/KEY: misc_feature
<222> LOCATION: (1585)..(2973)
<223> OTHER INFORMATION: K:trAPAO
<220> FEATURE:
<221> NAME/KEY: CDS
<222> LOCATION: (1)..(2973)
<223> OTHER INFORMATION:
<220> FEATURE:
<221> NAME/KEY: misc_feature
<222> LOCATION: (1585)..(1587)
<223> OTHER INFORMATION: Extra lysine

<400> SEQUENCE: 26

```
atg gcc aac aag cac ctg agc ctc tcc ctc ttc ctc gtg ctc ctc ggc         48
Met Ala Asn Lys His Leu Ser Leu Ser Leu Phe Leu Val Leu Leu Gly
            -20                 -15                 -10 ctc tcc gcc tcc ctc gcc agc ggc acg gat ttt ccg gtc cgc agg acc         96
Leu Ser Ala Ser Leu Ala Ser Gly Thr Asp Phe Pro Val Arg Arg Thr
        -5                  -1   1                   5 gat ctg ggc cag gtt cag gga ctg gcc ggg gac gtg atg agc ttt cgc        144
Asp Leu Gly Gln Val Gln Gly Leu Ala Gly Asp Val Met Ser Phe Arg
        10                  15                  20 gga ata ccc tat gca gcg ccg ccg gtg ggc ggg ctg cgt tgg aag ccg        192
Gly Ile Pro Tyr Ala Ala Pro Pro Val Gly Gly Leu Arg Trp Lys Pro
25                  30                  35                  40 ccc caa cac gcc cgg ccc tgg gcg ggc gtt cgc ccc gcc acc caa ttt        240
Pro Gln His Ala Arg Pro Trp Ala Gly Val Arg Pro Ala Thr Gln Phe
            45                  50                  55
```

-continued

| | | |
|---|---|---|
| ggc tcc gac tgc ttc ggc gcg gcc tat ctt cgc aaa ggc agc ctc gcc<br>Gly Ser Asp Cys Phe Gly Ala Ala Tyr Leu Arg Lys Gly Ser Leu Ala<br>          60                    65                 70 | 288 | |
| ccc ggc gtg agc gag gac tgt ctt tac ctc aac gta tgg gcg ccg tca<br>Pro Gly Val Ser Glu Asp Cys Leu Tyr Leu Asn Val Trp Ala Pro Ser<br>        75                    80                 85 | 336 | |
| ggc gct aaa ccc ggc cag tac ccc gtc atg gtc tgg gtc tac ggc ggc<br>Gly Ala Lys Pro Gly Gln Tyr Pro Val Met Val Trp Val Tyr Gly Gly<br>      90                    95               100 | 384 | |
| ggc ttc gcc ggc ggc acg gcc gcc atg ccc tac tac gac ggc gag gcg<br>Gly Phe Ala Gly Gly Thr Ala Ala Met Pro Tyr Tyr Asp Gly Glu Ala<br>105              110                  115            120 | 432 | |
| ctt gcc cga cag ggc gtc gtc gtg gtg acg ttt aac tat cgg acg aac<br>Leu Ala Arg Gln Gly Val Val Val Val Thr Phe Asn Tyr Arg Thr Asn<br>              125                  130               135 | 480 | |
| atc ctg ggc ttt ttc gcc cat cct ggt ctc tcg cgc gag agc ccc acc<br>Ile Leu Gly Phe Phe Ala His Pro Gly Leu Ser Arg Glu Ser Pro Thr<br>          140                  145               150 | 528 | |
| gga act tcg ggc aac tac ggc cta ctc gac att ctc gcc gct ctt cgg<br>Gly Thr Ser Gly Asn Tyr Gly Leu Leu Asp Ile Leu Ala Ala Leu Arg<br>              155                  160               165 | 576 | |
| tgg gtg cag agc aac gcc cgc gcc ttc gga ggg gac ccc ggc cga gtg<br>Trp Val Gln Ser Asn Ala Arg Ala Phe Gly Gly Asp Pro Gly Arg Val<br>170              175                  180 | 624 | |
| acg gtc ttt ggt gaa tcg gcc gga gcg agc gcg atc gga ctt ctg ctc<br>Thr Val Phe Gly Glu Ser Ala Gly Ala Ser Ala Ile Gly Leu Leu Leu<br>185              190                  195            200 | 672 | |
| acc tcg ccg ctg agc aag ggt ctc ttc cgt ggc gct atc ctc gaa agt<br>Thr Ser Pro Leu Ser Lys Gly Leu Phe Arg Gly Ala Ile Leu Glu Ser<br>              205                  210               215 | 720 | |
| cca ggg ctg acg cga ccg ctc gcg acg ctc gcc gac agc gcc gcc tcg<br>Pro Gly Leu Thr Arg Pro Leu Ala Thr Leu Ala Asp Ser Ala Ala Ser<br>              220                  225               230 | 768 | |
| ggc gag cgc ctc gac gcc gat ctt tcg cga ctg cgc tcg acc gac cca<br>Gly Glu Arg Leu Asp Ala Asp Leu Ser Arg Leu Arg Ser Thr Asp Pro<br>          235                  240               245 | 816 | |
| gcc acc ctg atg gcg cgc gcc gac gcg gcc cgc ccg gca tcg cgg gac<br>Ala Thr Leu Met Ala Arg Ala Asp Ala Ala Arg Pro Ala Ser Arg Asp<br>250              255                  260 | 864 | |
| ctg cgc agg ccg cgt ccg acc gga ccg atc gtc gat ggc cat gtg ctg<br>Leu Arg Arg Pro Arg Pro Thr Gly Pro Ile Val Asp Gly His Val Leu<br>265              270                  275            280 | 912 | |
| ccg cag acc gac agc gcg gcg atc gcg gcg ggg cag ctg gcg ccg gtt<br>Pro Gln Thr Asp Ser Ala Ala Ile Ala Ala Gly Gln Leu Ala Pro Val<br>              285                  290               295 | 960 | |
| cgg gtc ctg atc gga acc aat gcc gac gaa ggc cgc gcc ttc ctc ggg<br>Arg Val Leu Ile Gly Thr Asn Ala Asp Glu Gly Arg Ala Phe Leu Gly<br>              300                  305               310 | 1008 | |
| cgc gcg ccg atg gag acg cca gcg gac tac caa gcc tat ctg gag gcg<br>Arg Ala Pro Met Glu Thr Pro Ala Asp Tyr Gln Ala Tyr Leu Glu Ala<br>          315                  320               325 | 1056 | |
| cag ttt ggc gac caa gcc gcc gcc gtg gcg gcg tgc tat ccc ctc gac<br>Gln Phe Gly Asp Gln Ala Ala Ala Val Ala Ala Cys Tyr Pro Leu Asp<br>330              335                  340 | 1104 | |
| ggc cgg gcc acg ccc aag gaa atg gtc gcg cgc atc ttc ggc gac aat<br>Gly Arg Ala Thr Pro Lys Glu Met Val Ala Arg Ile Phe Gly Asp Asn<br>345              350                  355            360 | 1152 | |
| cag ttc aat cgg ggg gtc tcg gcc ttc tcg gaa gcg ctt gtg cgc cag<br>Gln Phe Asn Arg Gly Val Ser Ala Phe Ser Glu Ala Leu Val Arg Gln<br>              365                  370               375 | 1200 | |

```
ggc gcg ccc gtg tgg cgt tat cag ttc aac ggt aat acc gag ggt gga    1248
Gly Ala Pro Val Trp Arg Tyr Gln Phe Asn Gly Asn Thr Glu Gly Gly
        380                 385                 390 aga gcg ccg gct acc cac gga gcc gaa att ccc tac gtt ttc ggg gtg    1296
Arg Ala Pro Ala Thr His Gly Ala Glu Ile Pro Tyr Val Phe Gly Val
            395                 400                 405 ttc aag ctc gac gag ttg ggt ctg ttc gat tgg ccg ccc gag ggg ccc    1344
Phe Lys Leu Asp Glu Leu Gly Leu Phe Asp Trp Pro Pro Glu Gly Pro
    410                 415                 420 acg ccc gcc gac cgt gcg ctg ggc caa ctg atg tcc tcc gcc tgg gtc    1392
Thr Pro Ala Asp Arg Ala Leu Gly Gln Leu Met Ser Ser Ala Trp Val
425                 430                 435                 440 cgg ttc gcc aag aat ggc gac ccc gcc ggg gac gcc ctt acc tgg cct    1440
Arg Phe Ala Lys Asn Gly Asp Pro Ala Gly Asp Ala Leu Thr Trp Pro
                445                 450                 455 gcc tat tct acg ggc aag tcg acc atg aca ttc ggt ccc gag ggc cgc    1488
Ala Tyr Ser Thr Gly Lys Ser Thr Met Thr Phe Gly Pro Glu Gly Arg
            460                 465                 470 gcg gcg gtg gtg tcg ccc gga cct tcc atc ccc cct tgc gcg gat ggc    1536
Ala Ala Val Val Ser Pro Gly Pro Ser Ile Pro Pro Cys Ala Asp Gly
        475                 480                 485 gcc aag gcg ggg ggc gga ggc agc ggc gga ggc agc ggc gga ggc agc    1584
Ala Lys Ala Gly Gly Gly Ser Gly Gly Gly Ser Gly Gly Gly Ser
490                 495                 500 aaa gac aac gtt gcg gac gtg gta gtg gtg ggc gct ggc ttg agc ggt    1632
Lys Asp Asn Val Ala Asp Val Val Val Val Gly Ala Gly Leu Ser Gly
505                 510                 515                 520 ttg gag acg gca cgc aaa gtc cag gcc gcc ggt ctg tcc tgc ctc gtt    1680
Leu Glu Thr Ala Arg Lys Val Gln Ala Ala Gly Leu Ser Cys Leu Val
                525                 530                 535 ctt gag gcg atg gat cgt gta ggg gga aag act ctg agc gta caa tcg    1728
Leu Glu Ala Met Asp Arg Val Gly Gly Lys Thr Leu Ser Val Gln Ser
            540                 545                 550 ggt ccc ggc agg acg act atc aac gac ctc ggc gct gcg tgg atc aat    1776
Gly Pro Gly Arg Thr Thr Ile Asn Asp Leu Gly Ala Ala Trp Ile Asn
        555                 560                 565 gac agc aac caa agc gaa gta tcc aga ttg ttt gaa aga ttt cat ttg    1824
Asp Ser Asn Gln Ser Glu Val Ser Arg Leu Phe Glu Arg Phe His Leu
570                 575                 580 gag ggc gag ctc cag agg acg act gga aat tca atc cat caa gca caa    1872
Glu Gly Glu Leu Gln Arg Thr Thr Gly Asn Ser Ile His Gln Ala Gln
585                 590                 595                 600 gac ggt aca acc act aca gct cct tat ggt gac tcc ttg ctg agc gag    1920
Asp Gly Thr Thr Thr Thr Ala Pro Tyr Gly Asp Ser Leu Leu Ser Glu
                605                 610                 615 gag gtt gca agt gca ctt gcg gaa ctc ctc ccc gta tgg tct cag ctg    1968
Glu Val Ala Ser Ala Leu Ala Glu Leu Leu Pro Val Trp Ser Gln Leu
            620                 625                 630 atc gaa gag cat agc ctt caa gac ctc aag gcg agc cct cag gcg aag    2016
Ile Glu Glu His Ser Leu Gln Asp Leu Lys Ala Ser Pro Gln Ala Lys
        635                 640                 645 cgg ctc gac agt gtg agc ttc gcg cac tac tgt gag aag gaa cta aac    2064
Arg Leu Asp Ser Val Ser Phe Ala His Tyr Cys Glu Lys Glu Leu Asn
650                 655                 660 ttg cct gct gtt ctc ggc gta gca aac cag atc aca cgc gct ctg ctc    2112
Leu Pro Ala Val Leu Gly Val Ala Asn Gln Ile Thr Arg Ala Leu Leu
665                 670                 675                 680 ggt gtg gaa gcc cac gag atc agc atg ctt ttt ctc acc gac tac atc    2160
Gly Val Glu Ala His Glu Ile Ser Met Leu Phe Leu Thr Asp Tyr Ile
```

-continued

```
                685                 690                 695
aag agt gcc acc ggt ctc agt aat att ttc tcg gac aag aaa gac ggc      2208
Lys Ser Ala Thr Gly Leu Ser Asn Ile Phe Ser Asp Lys Lys Asp Gly
            700                 705                 710 ggg cag tat atg cga tgc aaa aca ggt atg cag tcg att tgc cat gcc      2256
Gly Gln Tyr Met Arg Cys Lys Thr Gly Met Gln Ser Ile Cys His Ala
        715                 720                 725 atg tca aag gaa ctt gtt cca ggc tca gtg cac ctc aac acc ccc gtc      2304
Met Ser Lys Glu Leu Val Pro Gly Ser Val His Leu Asn Thr Pro Val
    730                 735                 740 gct gaa att gag cag tcg gca tcc ggc tgt aca gta cga tcg gcc tcg      2352
Ala Glu Ile Glu Gln Ser Ala Ser Gly Cys Thr Val Arg Ser Ala Ser
745                 750                 755                 760 ggc gcc gtg ttc cga agc aaa aag gtg gtg gtt tcg tta ccg aca acc      2400
Gly Ala Val Phe Arg Ser Lys Lys Val Val Val Ser Leu Pro Thr Thr
                765                 770                 775 ttg tat ccc acc ttg aca ttt tca cca cct ctt ccc gcc gag aag caa      2448
Leu Tyr Pro Thr Leu Thr Phe Ser Pro Pro Leu Pro Ala Glu Lys Gln
            780                 785                 790 gca ttg gcg gaa aat tct atc ctg ggc tac tat agc aag ata gtc ttc      2496
Ala Leu Ala Glu Asn Ser Ile Leu Gly Tyr Tyr Ser Lys Ile Val Phe
        795                 800                 805 gta tgg gac aag ccg tgg tgg cgc gaa caa ggc ttc tcg ggc gtc ctc      2544
Val Trp Asp Lys Pro Trp Trp Arg Glu Gln Gly Phe Ser Gly Val Leu
    810                 815                 820 caa tcg agc tgt gac ccc atc tca ttt gcc aga gat acc agc atc gac      2592
Gln Ser Ser Cys Asp Pro Ile Ser Phe Ala Arg Asp Thr Ser Ile Asp
825                 830                 835                 840 gtc gat cga caa tgg tcc att acc tgt ttc atg gtc gga gac ccg gga      2640
Val Asp Arg Gln Trp Ser Ile Thr Cys Phe Met Val Gly Asp Pro Gly
                845                 850                 855 cgg aag tgg tcc caa cag tcc aag cag gta cga caa aag tct gtc tgg      2688
Arg Lys Trp Ser Gln Gln Ser Lys Gln Val Arg Gln Lys Ser Val Trp
            860                 865                 870 gac caa ctc cgc gca gcc tac gag aac gcc ggg gcc caa gtc cca gag      2736
Asp Gln Leu Arg Ala Ala Tyr Glu Asn Ala Gly Ala Gln Val Pro Glu
        875                 880                 885 ccg gcc aac gtg ctc gaa atc gag tgg tcg aag cag cag tat ttc caa      2784
Pro Ala Asn Val Leu Glu Ile Glu Trp Ser Lys Gln Gln Tyr Phe Gln
    890                 895                 900 gga gct ccg agc gcc gtc tat ggg ctg aac gat ctc atc aca ctg ggt      2832
Gly Ala Pro Ser Ala Val Tyr Gly Leu Asn Asp Leu Ile Thr Leu Gly
905                 910                 915                 920 tcg gcg ctc aga acg ccg ttc aag agt gtt cat ttc gtt gga acg gag      2880
Ser Ala Leu Arg Thr Pro Phe Lys Ser Val His Phe Val Gly Thr Glu
                925                 930                 935 acg tct tta gtt tgg aaa ggg tat atg gaa ggg gcc ata cga tcg ggt      2928
Thr Ser Leu Val Trp Lys Gly Tyr Met Glu Gly Ala Ile Arg Ser Gly
            940                 945                 950 caa cga ggt gct gca gaa gtt gtg gct agc ctg gtg cca gca gca tag      2976
Gln Arg Gly Ala Ala Glu Val Val Ala Ser Leu Val Pro Ala Ala
        955                 960                 965
```

<210> SEQ ID NO 27
<211> LENGTH: 991
<212> TYPE: PRT
<213> ORGANISM: Unknown
<220> FEATURE:
<223> OTHER INFORMATION: Barley alpha amylase signal sequence:BEST1
    mature:artificial spacer:K:trAPAO
<220> FEATURE:

```
<221> NAME/KEY: misc_feature
<222> LOCATION: (1546)..(1584)
<223> OTHER INFORMATION: spacer sequence
<220> FEATURE:
<221> NAME/KEY: misc_feature
<222> LOCATION: (1585)..(2973)
<223> OTHER INFORMATION: K:trAPAO
<220> FEATURE:
<221> NAME/KEY: misc_feature
<222> LOCATION: (1585)..(1587)
<223> OTHER INFORMATION: Extra lysine

<400> SEQUENCE: 27
```

Met Ala Asn Lys His Leu Ser Leu Ser Leu Phe Leu Val Leu Leu Gly
                -20                 -15                 -10

Leu Ser Ala Ser Leu Ala Ser Gly Thr Asp Phe Pro Val Arg Arg Thr
             -5              -1   1               5

Asp Leu Gly Gln Val Gln Gly Leu Ala Gly Asp Val Met Ser Phe Arg
         10              15              20

Gly Ile Pro Tyr Ala Ala Pro Pro Val Gly Gly Leu Arg Trp Lys Pro
25               30              35                      40

Pro Gln His Ala Arg Pro Trp Ala Gly Val Arg Pro Ala Thr Gln Phe
                 45              50                  55

Gly Ser Asp Cys Phe Gly Ala Ala Tyr Leu Arg Lys Gly Ser Leu Ala
             60                  65              70

Pro Gly Val Ser Glu Asp Cys Leu Tyr Leu Asn Val Trp Ala Pro Ser
             75              80                  85

Gly Ala Lys Pro Gly Gln Tyr Pro Val Met Val Trp Val Tyr Gly Gly
90               95                  100

Gly Phe Ala Gly Gly Thr Ala Ala Met Pro Tyr Tyr Asp Gly Glu Ala
105              110                 115                     120

Leu Ala Arg Gln Gly Val Val Val Thr Phe Asn Tyr Arg Thr Asn
                 125             130                 135

Ile Leu Gly Phe Phe Ala His Pro Gly Leu Ser Arg Glu Ser Pro Thr
             140                 145             150

Gly Thr Ser Gly Asn Tyr Gly Leu Leu Asp Ile Leu Ala Ala Leu Arg
             155             160             165

Trp Val Gln Ser Asn Ala Arg Ala Phe Gly Gly Asp Pro Gly Arg Val
170                 175                 180

Thr Val Phe Gly Glu Ser Ala Gly Ala Ser Ala Ile Gly Leu Leu Leu
185                 190             195                     200

Thr Ser Pro Leu Ser Lys Gly Leu Phe Arg Gly Ala Ile Leu Glu Ser
             205             210             215

Pro Gly Leu Thr Arg Pro Leu Ala Thr Leu Ala Asp Ser Ala Ala Ser
             220             225             230

Gly Glu Arg Leu Asp Ala Asp Leu Ser Arg Leu Arg Ser Thr Asp Pro
             235             240             245

Ala Thr Leu Met Ala Arg Ala Asp Ala Ala Arg Pro Ala Ser Arg Asp
250                 255             260

Leu Arg Arg Pro Arg Pro Thr Gly Pro Ile Val Asp Gly His Val Leu
265                 270             275                     280

Pro Gln Thr Asp Ser Ala Ala Ile Ala Ala Gly Gln Leu Ala Pro Val
                 285             290                 295

Arg Val Leu Ile Gly Thr Asn Ala Asp Glu Gly Arg Ala Phe Leu Gly
                 300             305                 310

Arg Ala Pro Met Glu Thr Pro Ala Asp Tyr Gln Ala Tyr Leu Glu Ala
                 315             320             325

```
Gln Phe Gly Asp Gln Ala Ala Ala Val Ala Ala Cys Tyr Pro Leu Asp
        330                 335                 340
Gly Arg Ala Thr Pro Lys Glu Met Val Ala Arg Ile Phe Gly Asp Asn
345                 350                 355                 360
Gln Phe Asn Arg Gly Val Ser Ala Phe Ser Glu Ala Leu Val Arg Gln
                365                 370                 375
Gly Ala Pro Val Trp Arg Tyr Gln Phe Asn Gly Asn Thr Glu Gly Gly
            380                 385                 390
Arg Ala Pro Ala Thr His Gly Ala Glu Ile Pro Tyr Val Phe Gly Val
        395                 400                 405
Phe Lys Leu Asp Glu Leu Gly Leu Phe Asp Trp Pro Pro Glu Gly Pro
    410                 415                 420
Thr Pro Ala Asp Arg Ala Leu Gly Gln Leu Met Ser Ser Ala Trp Val
425                 430                 435                 440
Arg Phe Ala Lys Asn Gly Asp Pro Ala Gly Asp Ala Leu Thr Trp Pro
                445                 450                 455
Ala Tyr Ser Thr Gly Lys Ser Thr Met Thr Phe Gly Pro Glu Gly Arg
            460                 465                 470
Ala Ala Val Val Ser Pro Gly Pro Ser Ile Pro Pro Cys Ala Asp Gly
        475                 480                 485
Ala Lys Ala Gly Gly Gly Ser Gly Gly Ser Gly Gly Gly Ser
490                 495                 500
Lys Asp Asn Val Ala Asp Val Val Val Gly Ala Gly Leu Ser Gly
505                 510                 515                 520
Leu Glu Thr Ala Arg Lys Val Gln Ala Ala Gly Leu Ser Cys Leu Val
                525                 530                 535
Leu Glu Ala Met Asp Arg Val Gly Gly Lys Thr Leu Ser Val Gln Ser
            540                 545                 550
Gly Pro Gly Arg Thr Thr Ile Asn Asp Leu Gly Ala Ala Trp Ile Asn
        555                 560                 565
Asp Ser Asn Gln Ser Glu Val Ser Arg Leu Phe Glu Arg Phe His Leu
570                 575                 580
Glu Gly Glu Leu Gln Arg Thr Thr Gly Asn Ser Ile His Gln Ala Gln
585                 590                 595                 600
Asp Gly Thr Thr Thr Ala Pro Tyr Gly Asp Ser Leu Leu Ser Glu
                605                 610                 615
Glu Val Ala Ser Ala Leu Ala Glu Leu Leu Pro Val Trp Ser Gln Leu
            620                 625                 630
Ile Glu Glu His Ser Leu Gln Asp Leu Lys Ala Ser Pro Gln Ala Lys
        635                 640                 645
Arg Leu Asp Ser Val Ser Phe Ala His Tyr Cys Glu Lys Glu Leu Asn
650                 655                 660
Leu Pro Ala Val Leu Gly Val Ala Asn Gln Ile Thr Arg Ala Leu Leu
665                 670                 675                 680
Gly Val Glu Ala His Glu Ile Ser Met Leu Phe Leu Thr Asp Tyr Ile
                685                 690                 695
Lys Ser Ala Thr Gly Leu Ser Asn Ile Phe Ser Asp Lys Lys Asp Gly
            700                 705                 710
Gly Gln Tyr Met Arg Cys Lys Thr Gly Met Gln Ser Ile Cys His Ala
        715                 720                 725
Met Ser Lys Glu Leu Val Pro Gly Ser Val His Leu Asn Thr Pro Val
730                 735                 740
```

```
Ala Glu Ile Glu Gln Ser Ala Ser Gly Cys Thr Val Arg Ser Ala Ser
745                 750                 755                 760

Gly Ala Val Phe Arg Ser Lys Lys Val Val Ser Leu Pro Thr Thr
            765                 770                 775

Leu Tyr Pro Thr Leu Thr Phe Ser Pro Pro Leu Pro Ala Glu Lys Gln
            780                 785                 790

Ala Leu Ala Glu Asn Ser Ile Leu Gly Tyr Tyr Ser Lys Ile Val Phe
            795                 800                 805

Val Trp Asp Lys Pro Trp Trp Arg Glu Gln Gly Phe Ser Gly Val Leu
810                 815                 820

Gln Ser Ser Cys Asp Pro Ile Ser Phe Ala Arg Asp Thr Ser Ile Asp
825                 830                 835                 840

Val Asp Arg Gln Trp Ser Ile Thr Cys Phe Met Val Gly Asp Pro Gly
            845                 850                 855

Arg Lys Trp Ser Gln Gln Ser Lys Gln Val Arg Gln Lys Ser Val Trp
            860                 865                 870

Asp Gln Leu Arg Ala Ala Tyr Glu Asn Ala Gly Ala Gln Val Pro Glu
            875                 880                 885

Pro Ala Asn Val Leu Glu Ile Glu Trp Ser Lys Gln Gln Tyr Phe Gln
890                 895                 900

Gly Ala Pro Ser Ala Val Tyr Gly Leu Asn Asp Leu Ile Thr Leu Gly
905                 910                 915                 920

Ser Ala Leu Arg Thr Pro Phe Lys Ser Val His Phe Val Gly Thr Glu
            925                 930                 935

Thr Ser Leu Val Trp Lys Gly Tyr Met Glu Gly Ala Ile Arg Ser Gly
            940                 945                 950

Gln Arg Gly Ala Ala Glu Val Val Ala Ser Leu Val Pro Ala Ala
            955                 960                 965
```

<210> SEQ ID NO 28
<211> LENGTH: 3618
<212> TYPE: DNA
<213> ORGANISM: Unknown
<220> FEATURE:
<223> OTHER INFORMATION: gst:esp1:sp:K:trAPAO
<220> FEATURE:
<221> NAME/KEY: CDS
<222> LOCATION: (1)..(3615)
<223> OTHER INFORMATION:
<220> FEATURE:
<221> NAME/KEY: misc_feature
<222> LOCATION: (1)..(687)
<223> OTHER INFORMATION: gst + polylinker
<220> FEATURE:
<221> NAME/KEY: mat_peptide
<222> LOCATION: (688)..()
<223> OTHER INFORMATION: esp1 mat
<220> FEATURE:
<221> NAME/KEY: misc_feature
<222> LOCATION: (2191)..(2226)
<223> OTHER INFORMATION: spacer sequence
<220> FEATURE:
<221> NAME/KEY: misc_feature
<222> LOCATION: (2227)..(3615)
<223> OTHER INFORMATION: K:trAPAO
<220> FEATURE:
<221> NAME/KEY: misc_feature
<222> LOCATION: (2227)..(2229)
<223> OTHER INFORMATION: extra lysine

<400> SEQUENCE: 28

```
atg tcc cct ata cta  ggt tat tgg aaa att  aag ggc ctt gtg caa     45
Met Ser Pro Ile Leu  Gly Tyr Trp Lys Ile  Lys Gly Leu Val Gln
            -225                -220                -215
```

```
ccc act cga ctt ctt ttg gaa tat ctt gaa gaa aaa tat gaa gag        90
Pro Thr Arg Leu Leu Leu Glu Tyr Leu Glu Glu Lys Tyr Glu Glu
            -210             -205            -200 cat ttg tat gag cgc gat gaa ggt gat aaa tgg cga aac aaa aag       135
His Leu Tyr Glu Arg Asp Glu Gly Asp Lys Trp Arg Asn Lys Lys
            -195             -190            -185 ttt gaa ttg ggt ttg gag ttt ccc aat ctt cct tat tat att gat       180
Phe Glu Leu Gly Leu Glu Phe Pro Asn Leu Pro Tyr Tyr Ile Asp
            -180             -175            -170 ggt gat gtt aaa tta aca cag tct atg gcc atc ata cgt tat ata       225
Gly Asp Val Lys Leu Thr Gln Ser Met Ala Ile Ile Arg Tyr Ile
            -165             -160            -155 gct gac aag cac aac atg ttg ggt ggt tgt cca aaa gag cgt gca       270
Ala Asp Lys His Asn Met Leu Gly Gly Cys Pro Lys Glu Arg Ala
            -150             -145            -140 gag att tca atg ctt gaa gga gcg gtt ttg gat att aga tac ggt       315
Glu Ile Ser Met Leu Glu Gly Ala Val Leu Asp Ile Arg Tyr Gly
            -135             -130            -125 gtt tcg aga att gca tat agt aaa gac ttt gaa act ctc aaa gtt       360
Val Ser Arg Ile Ala Tyr Ser Lys Asp Phe Glu Thr Leu Lys Val
            -120             -115            -110 gat ttt ctt agc aag cta cct gaa atg ctg aaa atg ttc gaa gat cgt   408
Asp Phe Leu Ser Lys Leu Pro Glu Met Leu Lys Met Phe Glu Asp Arg
            -105             -100             -95 tta tgt cat aaa aca tat tta aat ggt gat cat gta acc cat cct gac   456
Leu Cys His Lys Thr Tyr Leu Asn Gly Asp His Val Thr His Pro Asp
             -90              -85              -80 ttc atg ttg tat gac gct ctt gat gtt gtt tta tac atg gac cca atg   504
Phe Met Leu Tyr Asp Ala Leu Asp Val Val Leu Tyr Met Asp Pro Met
             -75              -70              -65 tgc ctg gat gcg ttc cca aaa tta gtt tgt ttt aaa aaa cgt att gaa   552
Cys Leu Asp Ala Phe Pro Lys Leu Val Cys Phe Lys Lys Arg Ile Glu
             -60              -55              -50 gct atc cca caa att gat aag tac ttg aaa tcc agc aag tat ata gca   600
Ala Ile Pro Gln Ile Asp Lys Tyr Leu Lys Ser Ser Lys Tyr Ile Ala
 -45              -40              -35              -30 tgg cct ttg cag ggc tgg caa gcc acg ttt ggt ggt ggc gac cat cct   648
Trp Pro Leu Gln Gly Trp Gln Ala Thr Phe Gly Gly Gly Asp His Pro
             -25              -20              -15 cca aaa tcg gat ctg gtt ccg cgt gga tcc ccg gaa ttc gct cct act   696
Pro Lys Ser Asp Leu Val Pro Arg Gly Ser Pro Glu Phe Ala Pro Thr
             -10               -5               -1   1 gtc aag att gat gct ggg atg gtg gtc ggc acg act act gtc ccc       744
Val Lys Ile Asp Ala Gly Met Val Val Gly Thr Thr Thr Val Pro
  5               10               15 ggc acc act gcg acc gtc agc gag ttc ttg ggc gtt cct ttt gcc gcc   792
Gly Thr Thr Ala Thr Val Ser Glu Phe Leu Gly Val Pro Phe Ala Ala
 20               25               30               35 tct ccg aca cga ttt gcg cct cct act cgt ccc gtg cct tgg tca acg   840
Ser Pro Thr Arg Phe Ala Pro Pro Thr Arg Pro Val Pro Trp Ser Thr
                  40               45               50 cct ttg caa gcc act gca tat ggt cca gca tgc cct caa caa ttc aat   888
Pro Leu Gln Ala Thr Ala Tyr Gly Pro Ala Cys Pro Gln Gln Phe Asn
                 55               60               65 tac ccc gaa gaa ctc cgt gag att acg atg gcc tgg ttc aat aca ccg   936
Tyr Pro Glu Glu Leu Arg Glu Ile Thr Met Ala Trp Phe Asn Thr Pro
             70               75               80 ccc ccg tca gct ggt gaa agt gag gac tgc ctg aac ctc aac atc tac   984
Pro Pro Ser Ala Gly Glu Ser Glu Asp Cys Leu Asn Leu Asn Ile Tyr
```

-continued

```
                85                      90                         95
gtc cca gga act gag aac aca aac aaa gcc gtc atg gtt tgg ata tac      1032
Val Pro Gly Thr Glu Asn Thr Asn Lys Ala Val Met Val Trp Ile Tyr
100                 105                 110                 115 ggt gga gcg ctg gaa tat ggt tgg aat tca ttc cac ctt tac gac ggg      1080
Gly Gly Ala Leu Glu Tyr Gly Trp Asn Ser Phe His Leu Tyr Asp Gly
            120                 125                 130 gct agt ttc gca gcc aat cag gat gtc atc gcc gtg acc atc aac tac      1128
Ala Ser Phe Ala Ala Asn Gln Asp Val Ile Ala Val Thr Ile Asn Tyr
                135                 140                 145 aga acg aac att ctg ggg ttc cct gct gcc cct cag ctt cca ata aca      1176
Arg Thr Asn Ile Leu Gly Phe Pro Ala Ala Pro Gln Leu Pro Ile Thr
            150                 155                 160 cag cga aat ctg ggg ttc cta gac caa agg ttt gct ttg gat tgg gta      1224
Gln Arg Asn Leu Gly Phe Leu Asp Gln Arg Phe Ala Leu Asp Trp Val
165                 170                 175 cag cgg aac atc gca gcc ttt ggc ggt gat cct cga aag gtc aca ata      1272
Gln Arg Asn Ile Ala Ala Phe Gly Gly Asp Pro Arg Lys Val Thr Ile
180                 185                 190                 195 ttt ggg cag agt gcg ggg ggc aga agt gtc gac gtc ctc ttg acg tct      1320
Phe Gly Gln Ser Ala Gly Gly Arg Ser Val Asp Val Leu Leu Thr Ser
                200                 205                 210 atg cca cac aac cca ccc ttc cga gca gca atc atg gag tcc ggt gtg      1368
Met Pro His Asn Pro Pro Phe Arg Ala Ala Ile Met Glu Ser Gly Val
            215                 220                 225 gct aac tac aac ttc ccc aag gga gat ttg tcc gaa cct tgg aac acc      1416
Ala Asn Tyr Asn Phe Pro Lys Gly Asp Leu Ser Glu Pro Trp Asn Thr
                230                 235                 240 act gtt caa gct ctc aac tgt acc acc agt atc gac atc ttg agt tgt      1464
Thr Val Gln Ala Leu Asn Cys Thr Thr Ser Ile Asp Ile Leu Ser Cys
245                 250                 255 atg aga aga gtc gat ctc gcc act ctg atg aac acg atc gag caa ctc      1512
Met Arg Arg Val Asp Leu Ala Thr Leu Met Asn Thr Ile Glu Gln Leu
260                 265                 270                 275 gga ctt ggg ttt gag tac acg ttg gac aac gta acg gct gtg tac cgt      1560
Gly Leu Gly Phe Glu Tyr Thr Leu Asp Asn Val Thr Ala Val Tyr Arg
                280                 285                 290 tct gaa acg gct cgc acg act ggt gac att gct cgt gta cct gtt ctc      1608
Ser Glu Thr Ala Arg Thr Thr Gly Asp Ile Ala Arg Val Pro Val Leu
            295                 300                 305 gtc ggg acg gtg gcc aac gac gga ctt ctc ttt gtc ctc ggg gag aat      1656
Val Gly Thr Val Ala Asn Asp Gly Leu Leu Phe Val Leu Gly Glu Asn
            310                 315                 320 gac acc caa gca tat ctc gag gag gca atc ccg aat cag ccc gac ctt      1704
Asp Thr Gln Ala Tyr Leu Glu Glu Ala Ile Pro Asn Gln Pro Asp Leu
325                 330                 335 tac cag act ctc ctt gga gca tat ccc att gga tcc cca ggg atc gga      1752
Tyr Gln Thr Leu Leu Gly Ala Tyr Pro Ile Gly Ser Pro Gly Ile Gly
340                 345                 350                 355 tcg cct caa gat cag att gcc gcc att gag acc gag gta aga ttc cag      1800
Ser Pro Gln Asp Gln Ile Ala Ala Ile Glu Thr Glu Val Arg Phe Gln
                360                 365                 370 tgt cct tct gcc atc gtg gct cag gac tcc cgg aat cgg ggt atc cct      1848
Cys Pro Ser Ala Ile Val Ala Gln Asp Ser Arg Asn Arg Gly Ile Pro
            375                 380                 385 tct tgg cgc tac tac tac aat gcg acc ttt gag aat ctg gag ctt ttc      1896
Ser Trp Arg Tyr Tyr Tyr Asn Ala Thr Phe Glu Asn Leu Glu Leu Phe
            390                 395                 400 cct ggg tcc gaa gtg tac cac agc tct gaa gtc ggg atg gtg ttt ggc      1944
```

```
                                                                               -continued Pro Gly Ser Glu Val Tyr His Ser Ser Glu Val Gly Met Val Phe Gly
    405                 410                 415 acg tat cct gtc gca agt gcg acc gcc ttg gag gcc cag acg agc aaa              1992
Thr Tyr Pro Val Ala Ser Ala Thr Ala Leu Glu Ala Gln Thr Ser Lys
420                 425                 430                 435 tac atg cag ggt gcc tgg gcg gcc ttt gcc aaa aac ccc atg aat ggg              2040
Tyr Met Gln Gly Ala Trp Ala Ala Phe Ala Lys Asn Pro Met Asn Gly
                440                 445                 450 cct ggg tgg aaa caa gtg ccg aat gtc gcg gcg ctt ggc tca cca ggc              2088
Pro Gly Trp Lys Gln Val Pro Asn Val Ala Ala Leu Gly Ser Pro Gly
            455                 460                 465 aaa gcc atc cag gtt gac gtc tct cca gcg aca ata gac caa cga tgt              2136
Lys Ala Ile Gln Val Asp Val Ser Pro Ala Thr Ile Asp Gln Arg Cys
        470                 475                 480 gcc ttg tac acg cgt tat tat act gag ttg ggc aca atc gcg ccg agg              2184
Ala Leu Tyr Thr Arg Tyr Tyr Thr Glu Leu Gly Thr Ile Ala Pro Arg
    485                 490                 495 aca ttt ggc gga ggc agc ggc gga ggc agc ggc gga ggc agc aaa gac              2232
Thr Phe Gly Gly Gly Ser Gly Gly Gly Ser Gly Gly Gly Ser Lys Asp
500                 505                 510                 515 aac gtt gcg gac gtg gta gtg gtg ggc gct ggc ttg agc ggt ttg gag              2280
Asn Val Ala Asp Val Val Val Val Gly Ala Gly Leu Ser Gly Leu Glu
                520                 525                 530 acg gca cgc aaa gtc cag gcc gcc ggt ctg tcc tgc ctc gtt ctt gag              2328
Thr Ala Arg Lys Val Gln Ala Ala Gly Leu Ser Cys Leu Val Leu Glu
            535                 540                 545 gcg atg gat cgt gta ggg gga aag act ctg agc gta caa tcg ggt ccc              2376
Ala Met Asp Arg Val Gly Gly Lys Thr Leu Ser Val Gln Ser Gly Pro
        550                 555                 560 ggc agg acg act atc aac gac ctc ggc gct gcg tgg atc aat gac agc              2424
Gly Arg Thr Thr Ile Asn Asp Leu Gly Ala Ala Trp Ile Asn Asp Ser
    565                 570                 575 aac caa agc gaa gta tcc aga ttg ttt gaa aga ttt cat ttg gag ggc              2472
Asn Gln Ser Glu Val Ser Arg Leu Phe Glu Arg Phe His Leu Glu Gly
580                 585                 590                 595 gag ctc cag agg acg act gga aat tca atc cat caa gca caa gac ggt              2520
Glu Leu Gln Arg Thr Thr Gly Asn Ser Ile His Gln Ala Gln Asp Gly
                600                 605                 610 aca acc act aca gct cct tat ggt gac tcc ttg ctg agc gag gag gtt              2568
Thr Thr Thr Thr Ala Pro Tyr Gly Asp Ser Leu Leu Ser Glu Glu Val
            615                 620                 625 gca agt gca ctt gcg gaa ctc ctc ccc gta tgg tct cag ctg atc gaa              2616
Ala Ser Ala Leu Ala Glu Leu Leu Pro Val Trp Ser Gln Leu Ile Glu
        630                 635                 640 gag cat agc ctt caa gac ctc aag gcg agc cct cag gcg aag cgg ctc              2664
Glu His Ser Leu Gln Asp Leu Lys Ala Ser Pro Gln Ala Lys Arg Leu
    645                 650                 655 gac agt gtg agc ttc gcg cac tac tgt gag aag gaa cta aac ttg cct              2712
Asp Ser Val Ser Phe Ala His Tyr Cys Glu Lys Glu Leu Asn Leu Pro
660                 665                 670                 675 gct gtt ctc ggc gta gca aac cag atc aca cgc gct ctg ctc ggt gtg              2760
Ala Val Leu Gly Val Ala Asn Gln Ile Thr Arg Ala Leu Leu Gly Val
                680                 685                 690 gaa gcc cac gag atc agc atg ctt ttt ctc acc gac tac atc aag agt              2808
Glu Ala His Glu Ile Ser Met Leu Phe Leu Thr Asp Tyr Ile Lys Ser
            695                 700                 705 gcc acc ggt ctc agt aat att ttc tcg gac aag aaa gac ggc ggg cag              2856
Ala Thr Gly Leu Ser Asn Ile Phe Ser Asp Lys Lys Asp Gly Gly Gln
        710                 715                 720
```

```
tat atg cga tgc aaa aca ggt atg cag tcg att tgc cat gcc atg tca    2904
Tyr Met Arg Cys Lys Thr Gly Met Gln Ser Ile Cys His Ala Met Ser
            725                 730                 735 aag gaa ctt gtt cca ggc tca gtg cac ctc aac acc ccc gtc gct gaa    2952
Lys Glu Leu Val Pro Gly Ser Val His Leu Asn Thr Pro Val Ala Glu
740                 745                 750                 755 att gag cag tcg gca tcc ggc tgt aca gta cga tcg gcc tcg ggc gcc    3000
Ile Glu Gln Ser Ala Ser Gly Cys Thr Val Arg Ser Ala Ser Gly Ala
                760                 765                 770 gtg ttc cga agc aaa aag gtg gtg gtt tcg tta ccg aca acc ttg tat    3048
Val Phe Arg Ser Lys Lys Val Val Val Ser Leu Pro Thr Thr Leu Tyr
            775                 780                 785 ccc acc ttg aca ttt tca cca cct ctt ccc gcc gag aag caa gca ttg    3096
Pro Thr Leu Thr Phe Ser Pro Pro Leu Pro Ala Glu Lys Gln Ala Leu
        790                 795                 800 gcg gaa aat tct atc ctg ggc tac tat agc aag ata gtc ttc gta tgg    3144
Ala Glu Asn Ser Ile Leu Gly Tyr Tyr Ser Lys Ile Val Phe Val Trp
    805                 810                 815 gac aag ccg tgg tgg cgc gaa caa ggc ttc tcg ggc gtc ctc caa tcg    3192
Asp Lys Pro Trp Trp Arg Glu Gln Gly Phe Ser Gly Val Leu Gln Ser
820                 825                 830                 835 agc tgt gac ccc atc tca ttt gcc aga gat acc agc atc gac gtc gat    3240
Ser Cys Asp Pro Ile Ser Phe Ala Arg Asp Thr Ser Ile Asp Val Asp
                840                 845                 850 cga caa tgg tcc att acc tgt ttc atg gtc gga gac ccg gga cgg aag    3288
Arg Gln Trp Ser Ile Thr Cys Phe Met Val Gly Asp Pro Gly Arg Lys
            855                 860                 865 tgg tcc caa cag tcc aag cag gta cga caa aag tct gtc tgg gac caa    3336
Trp Ser Gln Gln Ser Lys Gln Val Arg Gln Lys Ser Val Trp Asp Gln
        870                 875                 880 ctc cgc gca gcc tac gag aac gcc ggg gcc caa gtc cca gag ccg gcc    3384
Leu Arg Ala Ala Tyr Glu Asn Ala Gly Ala Gln Val Pro Glu Pro Ala
    885                 890                 895 aac gtg ctc gaa atc gag tgg tcg aag cag cag tat ttc caa gga gct    3432
Asn Val Leu Glu Ile Glu Trp Ser Lys Gln Gln Tyr Phe Gln Gly Ala
900                 905                 910                 915 ccg agc gcc gtc tat ggg ctg aac gat ctc atc aca ctg ggt tcg gcg    3480
Pro Ser Ala Val Tyr Gly Leu Asn Asp Leu Ile Thr Leu Gly Ser Ala
                920                 925                 930 ctc aga acg ccg ttc aag agt gtt cat ttc gtt gga acg gag acg tct    3528
Leu Arg Thr Pro Phe Lys Ser Val His Phe Val Gly Thr Glu Thr Ser
            935                 940                 945 tta gtt tgg aaa ggg tat atg gaa ggg gcc ata cga tcg ggt caa cga    3576
Leu Val Trp Lys Gly Tyr Met Glu Gly Ala Ile Arg Ser Gly Gln Arg
        950                 955                 960 ggt gct gca gaa gtt gtg gct agc ctg gtg cca gca gca tag            3618
Gly Ala Ala Glu Val Val Ala Ser Leu Val Pro Ala Ala
    965                 970                 975

<210> SEQ ID NO 29
<211> LENGTH: 1205
<212> TYPE: PRT
<213> ORGANISM: Unknown
<220> FEATURE:
<223> OTHER INFORMATION: gst:esp1:sp:K:trAPAO
<220> FEATURE:
<221> NAME/KEY: misc_feature
<222> LOCATION: (1)..(687)
<223> OTHER INFORMATION: gst + polylinker
<220> FEATURE:
<221> NAME/KEY: misc_feature
<222> LOCATION: (2191)..(2226)
<223> OTHER INFORMATION: spacer sequence
```

```
<220> FEATURE:
<221> NAME/KEY: misc_feature
<222> LOCATION: (2227)..(3615)
<223> OTHER INFORMATION: K:trAPAO
<220> FEATURE:
<221> NAME/KEY: misc_feature
<222> LOCATION: (2227)..(2229)
<223> OTHER INFORMATION: extra lysine

<400> SEQUENCE: 29
```

| | | | | | | | | | | | |
|---|---|---|---|---|---|---|---|---|---|---|---|
|Met|Ser|Pro|Ile|Leu|Gly|Tyr|Trp|Lys|Ile|Lys|Gly|Leu|Val|Gln
| | | |-225| | | |-220| | | |-215

Pro Thr Arg Leu Leu  Leu Glu Tyr Leu Glu  Glu Lys Tyr Glu Glu
             -210             -205             -200

His Leu Tyr Glu Arg  Asp Glu Gly Asp Lys  Trp Arg Asn Lys Lys
             -195             -190             -185

Phe Glu Leu Gly Leu  Glu Phe Pro Asn Leu  Pro Tyr Tyr Ile Asp
             -180             -175             -170

Gly Asp Val Lys Leu  Thr Gln Ser Met Ala  Ile Ile Arg Tyr Ile
             -165             -160             -155

Ala Asp Lys His Asn  Met Leu Gly Gly Cys  Pro Lys Glu Arg Ala
             -150             -145             -140

Glu Ile Ser Met Leu  Glu Gly Ala Val Leu  Asp Ile Arg Tyr Gly
             -135             -130             -125

Val Ser Arg Ile Ala  Tyr Ser Lys Asp Phe  Glu Thr Leu Lys Val
             -120             -115             -110

Asp Phe Leu Ser Lys  Leu Pro Glu Met Leu  Lys Met Phe Glu Asp Arg
             -105             -100                  -95

Leu Cys His Lys Thr  Tyr Leu Asn Gly Asp  His Val Thr His Pro Asp
              -90              -85                 -80

Phe Met Leu Tyr Asp  Ala Leu Asp Val Val  Leu Tyr Met Asp Pro Met
              -75              -70                 -65

Cys Leu Asp Ala Phe  Pro Lys Leu Val Cys  Phe Lys Lys Arg Ile Glu
              -60              -55                 -50

Ala Ile Pro Gln Ile  Asp Lys Tyr Leu Lys  Ser Ser Lys Tyr Ile Ala
-45                   -40                  -35                  -30

Trp Pro Leu Gln Gly  Trp Gln Ala Thr Phe  Gly Gly Asp His Pro
                -25                  -20                  -15

Pro Lys Ser Asp Leu  Val Pro Arg Gly Ser  Pro Glu Phe Ala Pro Thr
                -10                   -5                   -1   1

Val Lys Ile Asp Ala  Gly Met Val Gly Thr  Thr Thr Val Pro
 5                    10                  15

Gly Thr Thr Ala Thr  Val Ser Glu Phe Leu  Gly Val Pro Phe Ala Ala
 20                   25                  30                    35

Ser Pro Thr Arg Phe  Ala Pro Pro Thr Arg  Pro Val Pro Trp Ser Thr
              40                   45                   50

Pro Leu Gln Ala Thr  Ala Tyr Gly Pro Ala  Cys Pro Gln Gln Phe Asn
              55                   60                   65

Tyr Pro Glu Glu Leu  Arg Glu Ile Thr Met  Ala Trp Phe Asn Thr Pro
              70                   75                   80

Pro Pro Ser Ala Gly  Glu Ser Glu Asp Cys  Leu Asn Leu Asn Ile Tyr
              85                   90                   95

Val Pro Gly Thr Glu  Asn Thr Asn Lys Ala  Val Met Val Trp Ile Tyr
100                   105                  110                  115

Gly Gly Ala Leu Glu  Tyr Gly Trp Asn Ser  Phe His Leu Tyr Asp Gly
                120                  125                  130

```
Ala Ser Phe Ala Ala Asn Gln Asp Val Ile Ala Val Thr Ile Asn Tyr
            135                 140                 145

Arg Thr Asn Ile Leu Gly Phe Pro Ala Pro Gln Leu Pro Ile Thr
        150                 155                 160

Gln Arg Asn Leu Gly Phe Leu Asp Gln Arg Phe Ala Leu Asp Trp Val
    165                 170                 175

Gln Arg Asn Ile Ala Ala Phe Gly Gly Asp Pro Arg Lys Val Thr Ile
180                 185                 190                 195

Phe Gly Gln Ser Ala Gly Gly Arg Ser Val Asp Val Leu Leu Thr Ser
                200                 205                 210

Met Pro His Asn Pro Pro Phe Arg Ala Ala Ile Met Glu Ser Gly Val
            215                 220                 225

Ala Asn Tyr Asn Phe Pro Lys Gly Asp Leu Ser Glu Pro Trp Asn Thr
        230                 235                 240

Thr Val Gln Ala Leu Asn Cys Thr Thr Ser Ile Asp Ile Leu Ser Cys
    245                 250                 255

Met Arg Arg Val Asp Leu Ala Thr Leu Met Asn Thr Ile Glu Gln Leu
260                 265                 270                 275

Gly Leu Gly Phe Glu Tyr Thr Leu Asp Asn Val Thr Ala Val Tyr Arg
                280                 285                 290

Ser Glu Thr Ala Arg Thr Thr Gly Asp Ile Ala Arg Val Pro Val Leu
            295                 300                 305

Val Gly Thr Val Ala Asn Asp Gly Leu Leu Phe Val Leu Gly Glu Asn
        310                 315                 320

Asp Thr Gln Ala Tyr Leu Glu Glu Ala Ile Pro Asn Gln Pro Asp Leu
    325                 330                 335

Tyr Gln Thr Leu Leu Gly Ala Tyr Pro Ile Gly Ser Pro Gly Ile Gly
340                 345                 350                 355

Ser Pro Gln Asp Gln Ile Ala Ala Ile Glu Thr Glu Val Arg Phe Gln
                360                 365                 370

Cys Pro Ser Ala Ile Val Ala Gln Asp Ser Arg Asn Arg Gly Ile Pro
            375                 380                 385

Ser Trp Arg Tyr Tyr Tyr Asn Ala Thr Phe Glu Asn Leu Glu Leu Phe
        390                 395                 400

Pro Gly Ser Glu Val Tyr His Ser Ser Glu Val Gly Met Val Phe Gly
    405                 410                 415

Thr Tyr Pro Val Ala Ser Ala Thr Ala Leu Glu Ala Gln Thr Ser Lys
420                 425                 430                 435

Tyr Met Gln Gly Ala Trp Ala Ala Phe Ala Lys Asn Pro Met Asn Gly
                440                 445                 450

Pro Gly Trp Lys Gln Val Pro Asn Val Ala Ala Leu Gly Ser Pro Gly
            455                 460                 465

Lys Ala Ile Gln Val Asp Val Ser Pro Ala Thr Ile Asp Gln Arg Cys
        470                 475                 480

Ala Leu Tyr Thr Arg Tyr Tyr Thr Glu Leu Gly Thr Ile Ala Pro Arg
    485                 490                 495

Thr Phe Gly Gly Gly Ser Gly Gly Ser Gly Gly Ser Lys Asp
500                 505                 510                 515

Asn Val Ala Asp Val Val Val Gly Ala Gly Leu Ser Gly Leu
                520                 525                 530

Thr Ala Arg Lys Val Gln Ala Ala Gly Leu Ser Cys Leu Val Leu Glu
            535                 540                 545
```

-continued

```
Ala Met Asp Arg Val Gly Gly Lys Thr Leu Ser Val Gln Ser Gly Pro
            550                 555                 560
Gly Arg Thr Thr Ile Asn Asp Leu Gly Ala Ala Trp Ile Asn Asp Ser
            565                 570                 575
Asn Gln Ser Glu Val Ser Arg Leu Phe Glu Arg Phe His Leu Glu Gly
580                 585                 590                 595
Glu Leu Gln Arg Thr Thr Gly Asn Ser Ile His Gln Ala Gln Asp Gly
                600                 605                 610
Thr Thr Thr Thr Ala Pro Tyr Gly Asp Ser Leu Leu Ser Glu Glu Val
                615                 620                 625
Ala Ser Ala Leu Ala Glu Leu Leu Pro Val Trp Ser Gln Leu Ile Glu
            630                 635                 640
Glu His Ser Leu Gln Asp Leu Lys Ala Ser Pro Gln Ala Lys Arg Leu
            645                 650                 655
Asp Ser Val Ser Phe Ala His Tyr Cys Glu Lys Glu Leu Asn Leu Pro
660                 665                 670                 675
Ala Val Leu Gly Val Ala Asn Gln Ile Thr Arg Ala Leu Leu Gly Val
                680                 685                 690
Glu Ala His Glu Ile Ser Met Leu Phe Leu Thr Asp Tyr Ile Lys Ser
            695                 700                 705
Ala Thr Gly Leu Ser Asn Ile Phe Ser Asp Lys Asp Gly Gly Gln
            710                 715                 720
Tyr Met Arg Cys Lys Thr Gly Met Gln Ser Ile Cys His Ala Met Ser
            725                 730                 735
Lys Glu Leu Val Pro Gly Ser Val His Leu Asn Thr Pro Val Ala Glu
740                 745                 750                 755
Ile Glu Gln Ser Ala Ser Gly Cys Thr Val Arg Ser Ala Ser Gly Ala
                760                 765                 770
Val Phe Arg Ser Lys Lys Val Val Ser Leu Pro Thr Thr Leu Tyr
            775                 780                 785
Pro Thr Leu Thr Phe Ser Pro Pro Leu Pro Ala Glu Lys Gln Ala Leu
            790                 795                 800
Ala Glu Asn Ser Ile Leu Gly Tyr Tyr Ser Lys Ile Val Phe Val Trp
            805                 810                 815
Asp Lys Pro Trp Trp Arg Glu Gln Gly Phe Ser Gly Val Leu Gln Ser
820                 825                 830                 835
Ser Cys Asp Pro Ile Ser Phe Ala Arg Asp Thr Ser Ile Asp Val Asp
                840                 845                 850
Arg Gln Trp Ser Ile Thr Cys Phe Met Val Gly Asp Pro Gly Arg Lys
            855                 860                 865
Trp Ser Gln Gln Ser Lys Gln Val Arg Gln Lys Ser Val Trp Asp Gln
            870                 875                 880
Leu Arg Ala Ala Tyr Glu Asn Ala Gly Ala Gln Val Pro Glu Pro Ala
            885                 890                 895
Asn Val Leu Glu Ile Glu Trp Ser Lys Gln Gln Tyr Phe Gln Gly Ala
900                 905                 910                 915
Pro Ser Ala Val Tyr Gly Leu Asn Asp Leu Ile Thr Leu Gly Ser Ala
                920                 925                 930
Leu Arg Thr Pro Phe Lys Ser Val His Phe Val Gly Thr Glu Thr Ser
            935                 940                 945
Leu Val Trp Lys Gly Tyr Met Glu Gly Ala Ile Arg Ser Gly Gln Arg
            950                 955                 960
Gly Ala Ala Glu Val Val Ala Ser Leu Val Pro Ala Ala
```

-continued

```
          965                 970                 975
```

<210> SEQ ID NO 30
<211> LENGTH: 3591
<212> TYPE: DNA
<213> ORGANISM: Unknown
<220> FEATURE:
<223> OTHER INFORMATION: Open reading frame of BEST1:K:trAPAO fusion for
      bacterial exression vector pGEX-4T-1
<220> FEATURE:
<221> NAME/KEY: misc_feature
<222> LOCATION: (1)..(687)
<223> OTHER INFORMATION: gst + polylinker
<220> FEATURE:
<221> NAME/KEY: mat_peptide
<222> LOCATION: (688)..()
<223> OTHER INFORMATION: BEST1 mature
<220> FEATURE:
<221> NAME/KEY: misc_feature
<222> LOCATION: (2164)..(2199)
<223> OTHER INFORMATION: spacer sequence
<220> FEATURE:
<221> NAME/KEY: misc_feature
<222> LOCATION: (2200)..(3588)
<223> OTHER INFORMATION: K:trAPAO
<220> FEATURE:
<221> NAME/KEY: CDS
<222> LOCATION: (1)..(3588)
<223> OTHER INFORMATION:
<220> FEATURE:
<221> NAME/KEY: misc_feature
<222> LOCATION: (2200)..(2202)
<223> OTHER INFORMATION: extra lysine

<400> SEQUENCE: 30

```
atg tcc cct ata cta ggt tat tgg aaa att aag ggc ctt gtg caa        45
Met Ser Pro Ile Leu Gly Tyr Trp Lys Ile Lys Gly Leu Val Gln
            -225                -220                -215 ccc act cga ctt ctt ttg gaa tat ctt gaa gaa aaa tat gaa gag        90
Pro Thr Arg Leu Leu Leu Glu Tyr Leu Glu Glu Lys Tyr Glu Glu
            -210                -205                -200 cat ttg tat gag cgc gat gaa ggt gat aaa tgg cga aac aaa aag      135
His Leu Tyr Glu Arg Asp Glu Gly Asp Lys Trp Arg Asn Lys Lys
            -195                -190                -185 ttt gaa ttg ggt ttg gag ttt ccc aat ctt cct tat tat att gat      180
Phe Glu Leu Gly Leu Glu Phe Pro Asn Leu Pro Tyr Tyr Ile Asp
            -180                -175                -170 ggt gat gtt aaa tta aca cag tct atg gcc atc ata cgt tat ata      225
Gly Asp Val Lys Leu Thr Gln Ser Met Ala Ile Ile Arg Tyr Ile
            -165                -160                -155 gct gac aag cac aac atg ttg ggt ggt tgt cca aaa gag cgt gca      270
Ala Asp Lys His Asn Met Leu Gly Gly Cys Pro Lys Glu Arg Ala
            -150                -145                -140 gag att tca atg ctt gaa gga gcg gtt ttg gat att aga tac ggt      315
Glu Ile Ser Met Leu Glu Gly Ala Val Leu Asp Ile Arg Tyr Gly
            -135                -130                -125 gtt tcg aga att gca tat agt aaa gac ttt gaa act ctc aaa gtt      360
Val Ser Arg Ile Ala Tyr Ser Lys Asp Phe Glu Thr Leu Lys Val
            -120                -115                -110 gat ttt ctt agc aag cta cct gaa atg ctg aaa atg ttc gaa gat cgt  408
Asp Phe Leu Ser Lys Leu Pro Glu Met Leu Lys Met Phe Glu Asp Arg
            -105                -100                 -95 tta tgt cat aaa aca tat tta aat ggt gat cat gta acc cat cct gac  456
Leu Cys His Lys Thr Tyr Leu Asn Gly Asp His Val Thr His Pro Asp
             -90                 -85                 -80 ttc atg ttg tat gac gct ctt gat gtt gtt tta tac atg gac cca atg  504
Phe Met Leu Tyr Asp Ala Leu Asp Val Val Leu Tyr Met Asp Pro Met
```

```
                -75                 -70                 -65
tgc ctg gat gcg ttc cca aaa tta gtt tgt ttt aaa aaa cgt att gaa       552
Cys Leu Asp Ala Phe Pro Lys Leu Val Cys Phe Lys Lys Arg Ile Glu
    -60                 -55                 -50 gct atc cca caa att gat aag tac ttg aaa tcc agc aag tat ata gca       600
Ala Ile Pro Gln Ile Asp Lys Tyr Leu Lys Ser Ser Lys Tyr Ile Ala
-45                 -40                 -35                 -30 tgg cct ttg cag ggc tgg caa gcc acg ttt ggt ggt ggc gac cat cct       648
Trp Pro Leu Gln Gly Trp Gln Ala Thr Phe Gly Gly Gly Asp His Pro
                -25                 -20                 -15 cca aaa tcg gat ctg gtt ccg cgt gga tcc ccg gaa ttc acg gat ttt       696
Pro Lys Ser Asp Leu Val Pro Arg Gly Ser Pro Glu Phe Thr Asp Phe
            -10                  -5                  -1   1 ccg gtc cgc agg acc gat ctg ggc cag gtt cag gga ctg gcc ggg gac       744
Pro Val Arg Arg Thr Asp Leu Gly Gln Val Gln Gly Leu Ala Gly Asp
    5                   10                  15 gtg atg agc ttt cgc gga ata ccc tat gca gcg ccg ccg gtg ggc ggg       792
Val Met Ser Phe Arg Gly Ile Pro Tyr Ala Ala Pro Pro Val Gly Gly
20                  25                  30                  35 ctg cgt tgg aag ccg ccc caa cac gcc cgg ccc tgg gcg ggc gtt cgc       840
Leu Arg Trp Lys Pro Pro Gln His Ala Arg Pro Trp Ala Gly Val Arg
                40                  45                  50 ccc gcc acc caa ttt ggc tcc gac tgc ttc ggc gcg gcc tat ctt cgc       888
Pro Ala Thr Gln Phe Gly Ser Asp Cys Phe Gly Ala Ala Tyr Leu Arg
            55                  60                  65 aaa ggc agc ctc gcc ccc ggc gtg agc gag gac tgt ctt tac ctc aac       936
Lys Gly Ser Leu Ala Pro Gly Val Ser Glu Asp Cys Leu Tyr Leu Asn
        70                  75                  80 gta tgg gcg ccg tca ggc gct aaa ccc ggc cag tac ccc gtc atg gtc       984
Val Trp Ala Pro Ser Gly Ala Lys Pro Gly Gln Tyr Pro Val Met Val
85                  90                  95 tgg gtc tac ggc ggc ttc gcc ggc ggc acg gcc gcc atg ccc tac            1032
Trp Val Tyr Gly Gly Phe Ala Gly Gly Thr Ala Ala Met Pro Tyr
100                 105                 110                 115 tac gac ggc gag gcg ctt gcg cga cag ggc gtc gtc gtg gtg acg ttt       1080
Tyr Asp Gly Glu Ala Leu Ala Arg Gln Gly Val Val Val Val Thr Phe
                120                 125                 130 aac tat cgg acg aac atc ctg ggc ttt ttc gcc cat cct ggt ctc tcg       1128
Asn Tyr Arg Thr Asn Ile Leu Gly Phe Phe Ala His Pro Gly Leu Ser
            135                 140                 145 cgc gag agc ccc acc gga act tcg ggc aac tac ggc cta ctc gac att       1176
Arg Glu Ser Pro Thr Gly Thr Ser Gly Asn Tyr Gly Leu Leu Asp Ile
        150                 155                 160 ctc gcc gct ctt cgg tgg gtg cag agc aac gcc cgc gcc ttc gga ggg       1224
Leu Ala Ala Leu Arg Trp Val Gln Ser Asn Ala Arg Ala Phe Gly Gly
    165                 170                 175 gac ccc ggc cga gtg acg gtc ttt ggt gaa tcg gcc gga gcg agc gcg       1272
Asp Pro Gly Arg Val Thr Val Phe Gly Glu Ser Ala Gly Ala Ser Ala
180                 185                 190                 195 atc gga ctt ctg ctc acc tcg ccg ctg agc aag ggt ctc ttc cgt ggc       1320
Ile Gly Leu Leu Leu Thr Ser Pro Leu Ser Lys Gly Leu Phe Arg Gly
                200                 205                 210 gct atc ctc gaa agt cca ggg ctg acg cga ccg ctc gcg acg ctc gcc       1368
Ala Ile Leu Glu Ser Pro Gly Leu Thr Arg Pro Leu Ala Thr Leu Ala
            215                 220                 225 gac agc gcc gcc tcg ggc gag cgc ctc gac gcc gat ctt tcg cga ctg       1416
Asp Ser Ala Ala Ser Gly Glu Arg Leu Asp Ala Asp Leu Ser Arg Leu
        230                 235                 240 cgc tcg acc gac cca gcc acc ctg atg gcg cgc gcc gac gcg gcc cgc       1464
```

-continued

```
                Arg Ser Thr Asp Pro Ala Thr Leu Met Ala Arg Ala Asp Ala Ala Arg
                    245                 250                 255 ccg gca tcg cgg gac ctg cgc agg ccg cgt ccg acc gga ccg atc gtc       1512
Pro Ala Ser Arg Asp Leu Arg Arg Pro Arg Pro Thr Gly Pro Ile Val
260                 265                 270                 275 gat ggc cat gtg ctg ccg cag acc gac agc gcg gcg atc gcg gcg ggg       1560
Asp Gly His Val Leu Pro Gln Thr Asp Ser Ala Ala Ile Ala Ala Gly
                280                 285                 290 cag ctg gcg ccg gtt cgg gtc ctg atc gga acc aat gcc gac gaa ggc       1608
Gln Leu Ala Pro Val Arg Val Leu Ile Gly Thr Asn Ala Asp Glu Gly
                295                 300                 305 cgc gcc ttc ctc ggg cgc gcg ccg atg gag acg cca gcg gac tac caa       1656
Arg Ala Phe Leu Gly Arg Ala Pro Met Glu Thr Pro Ala Asp Tyr Gln
                310                 315                 320 gcc tat ctg gag gcg cag ttt ggc gac caa gcc gcc gcc gtg gcg gcg       1704
Ala Tyr Leu Glu Ala Gln Phe Gly Asp Gln Ala Ala Ala Val Ala Ala
325                 330                 335 tgc tat ccc ctc gac ggc cgg gcc acg ccc aag gaa atg gtc gcg cgc       1752
Cys Tyr Pro Leu Asp Gly Arg Ala Thr Pro Lys Glu Met Val Ala Arg
340                 345                 350                 355 atc ttc ggc gac aat cag ttc aat cgg ggg gtc tcg gcc ttc tcg gaa       1800
Ile Phe Gly Asp Asn Gln Phe Asn Arg Gly Val Ser Ala Phe Ser Glu
                360                 365                 370 gcg ctt gtg cgc cag ggc gcg ccc gtg tgg cgt tat cag ttc aac ggt       1848
Ala Leu Val Arg Gln Gly Ala Pro Val Trp Arg Tyr Gln Phe Asn Gly
                375                 380                 385 aat acc gag ggt gga aga gcg ccg gct acc cac gga gcc gaa att ccc       1896
Asn Thr Glu Gly Gly Arg Ala Pro Ala Thr His Gly Ala Glu Ile Pro
                390                 395                 400 tac gtt ttc ggg gtg ttc aag ctc gac gag ttg ggt ctg ttc gat tgg       1944
Tyr Val Phe Gly Val Phe Lys Leu Asp Glu Leu Gly Leu Phe Asp Trp
405                 410                 415 ccg ccc gag ggg ccc acg ccc gcc gac cgt gcg ctg ggc caa ctg atg       1992
Pro Pro Glu Gly Pro Thr Pro Ala Asp Arg Ala Leu Gly Gln Leu Met
420                 425                 430                 435 tcc tcc gcc tgg gtc cgg ttc gcc aag aat ggc gac ccc gcc ggg gac       2040
Ser Ser Ala Trp Val Arg Phe Ala Lys Asn Gly Asp Pro Ala Gly Asp
                440                 445                 450 gcc ctt acc tgg cct gcc tat tct acg ggc aag tcg acc atg aca ttc       2088
Ala Leu Thr Trp Pro Ala Tyr Ser Thr Gly Lys Ser Thr Met Thr Phe
                455                 460                 465 ggt ccc gag ggc cgc gcg gcg gtg gtg tcg ccc gga cct tcc atc ccc       2136
Gly Pro Glu Gly Arg Ala Ala Val Val Ser Pro Gly Pro Ser Ile Pro
                470                 475                 480 cct tgc gcg gat ggc gcc aag gcg ggg ggc gga ggc agc ggc gga ggc       2184
Pro Cys Ala Asp Gly Ala Lys Ala Gly Gly Gly Ser Gly Gly Gly
485                 490                 495 agc ggc gga ggc agc aaa gac aac gtt gcg gac gtg gta gtg gtg ggc       2232
Ser Gly Gly Gly Ser Lys Asp Asn Val Ala Asp Val Val Val Val Gly
500                 505                 510                 515 gct ggc ttg agc ggt ttg gag acg gca cgc aaa gtc cag gcc gcc ggt       2280
Ala Gly Leu Ser Gly Leu Glu Thr Ala Arg Lys Val Gln Ala Ala Gly
                520                 525                 530 ctg tcc tgc ctc gtt ctt gag gcg atg gat cgt gta ggg gga aag act       2328
Leu Ser Cys Leu Val Leu Glu Ala Met Asp Arg Val Gly Gly Lys Thr
                535                 540                 545 ctg agc gta caa tcg ggt ccc ggc agg acg act atc aac gac ctc ggc       2376
Leu Ser Val Gln Ser Gly Pro Gly Arg Thr Thr Ile Asn Asp Leu Gly
                550                 555                 560
```

```
gct gcg tgg atc aat gac agc aac caa agc gaa gta tcc aga ttg ttt    2424
Ala Ala Trp Ile Asn Asp Ser Asn Gln Ser Glu Val Ser Arg Leu Phe
565                 570                 575 gaa aga ttt cat ttg gag ggc gag ctc cag agg acg act gga aat tca    2472
Glu Arg Phe His Leu Glu Gly Glu Leu Gln Arg Thr Thr Gly Asn Ser
580                 585                 590                 595 atc cat caa gca caa gac ggt aca acc act aca gct cct tat ggt gac    2520
Ile His Gln Ala Gln Asp Gly Thr Thr Thr Thr Ala Pro Tyr Gly Asp
                600                 605                 610 tcc ttg ctg agc gag gag gtt gca agt gca ctt gcg gaa ctc ctc ccc    2568
Ser Leu Leu Ser Glu Glu Val Ala Ser Ala Leu Ala Glu Leu Leu Pro
            615                 620                 625 gta tgg tct cag ctg atc gaa gag cat agc ctt caa gac ctc aag gcg    2616
Val Trp Ser Gln Leu Ile Glu Glu His Ser Leu Gln Asp Leu Lys Ala
        630                 635                 640 agc cct cag gcg aag cgg ctc gac agt gtg agc ttc gcg cac tac tgt    2664
Ser Pro Gln Ala Lys Arg Leu Asp Ser Val Ser Phe Ala His Tyr Cys
    645                 650                 655 gag aag gaa cta aac ttg cct gct gtt ctc ggc gta gca aac cag atc    2712
Glu Lys Glu Leu Asn Leu Pro Ala Val Leu Gly Val Ala Asn Gln Ile
660                 665                 670                 675 aca cgc gct ctg ctc ggt gtg gaa gcc cac gag atc agc atg ctt ttt    2760
Thr Arg Ala Leu Leu Gly Val Glu Ala His Glu Ile Ser Met Leu Phe
                680                 685                 690 ctc acc gac tac atc aag agt gcc acc ggt ctc agt aat att ttc tcg    2808
Leu Thr Asp Tyr Ile Lys Ser Ala Thr Gly Leu Ser Asn Ile Phe Ser
            695                 700                 705 gac aag aaa gac ggc ggg cag tat atg cga tgc aaa aca ggt atg cag    2856
Asp Lys Lys Asp Gly Gly Gln Tyr Met Arg Cys Lys Thr Gly Met Gln
        710                 715                 720 tcg att tgc cat gcc atg tca aag gaa ctt gtt cca ggc tca gtg cac    2904
Ser Ile Cys His Ala Met Ser Lys Glu Leu Val Pro Gly Ser Val His
    725                 730                 735 ctc aac acc ccc gtc gct gaa att gag cag tcg gca tcc ggc tgt aca    2952
Leu Asn Thr Pro Val Ala Glu Ile Glu Gln Ser Ala Ser Gly Cys Thr
740                 745                 750                 755 gta cga tcg gcc tcg ggc gcc gtg ttc cga agc aaa aag gtg gtg gtt    3000
Val Arg Ser Ala Ser Gly Ala Val Phe Arg Ser Lys Lys Val Val Val
                760                 765                 770 tcg tta ccg aca acc ttg tat ccc acc ttg aca ttt tca cca cct ctt    3048
Ser Leu Pro Thr Thr Leu Tyr Pro Thr Leu Thr Phe Ser Pro Pro Leu
            775                 780                 785 ccc gcc gag aag caa gca ttg gcg gaa aat tct atc ctg ggc tac tat    3096
Pro Ala Glu Lys Gln Ala Leu Ala Glu Asn Ser Ile Leu Gly Tyr Tyr
        790                 795                 800 agc aag ata gtc ttc gta tgg gac aag ccg tgg tgg cgc gaa caa ggc    3144
Ser Lys Ile Val Phe Val Trp Asp Lys Pro Trp Trp Arg Glu Gln Gly
    805                 810                 815 ttc tcg ggc gtc ctc caa tcg agc tgt gac ccc atc tca ttt gcc aga    3192
Phe Ser Gly Val Leu Gln Ser Ser Cys Asp Pro Ile Ser Phe Ala Arg
820                 825                 830                 835 gat acc agc atc gac gtc gat cga caa tgg tcc att acc tgt ttc atg    3240
Asp Thr Ser Ile Asp Val Asp Arg Gln Trp Ser Ile Thr Cys Phe Met
                840                 845                 850 gtc gga gac ccg gga cgg aag tgg tcc caa cag tcc aag cag gta cga    3288
Val Gly Asp Pro Gly Arg Lys Trp Ser Gln Gln Ser Lys Gln Val Arg
            855                 860                 865 caa aag tct gtc tgg gac caa ctc cgc gca gcc tac gag aac gcc ggg    3336
Gln Lys Ser Val Trp Asp Gln Leu Arg Ala Ala Tyr Glu Asn Ala Gly
        870                 875                 880
```

```
gcc caa gtc cca gag ccg gcc aac gtg ctc gaa atc gag tgg tcg aag      3384
Ala Gln Val Pro Glu Pro Ala Asn Val Leu Glu Ile Glu Trp Ser Lys
    885                 890                 895 cag cag tat ttc caa gga gct ccg agc gcc gtc tat ggg ctg aac gat      3432
Gln Gln Tyr Phe Gln Gly Ala Pro Ser Ala Val Tyr Gly Leu Asn Asp
900                 905                 910                 915 ctc atc aca ctg ggt tcg gcg ctc aga acg ccg ttc aag agt gtt cat      3480
Leu Ile Thr Leu Gly Ser Ala Leu Arg Thr Pro Phe Lys Ser Val His
            920                 925                 930 ttc gtt gga acg gag acg tct tta gtt tgg aaa ggg tat atg gaa ggg      3528
Phe Val Gly Thr Glu Thr Ser Leu Val Trp Lys Gly Tyr Met Glu Gly
        935                 940                 945 gcc ata cga tcg ggt caa cga ggt gct gca gaa gtt gtg gct agc ctg      3576
Ala Ile Arg Ser Gly Gln Arg Gly Ala Ala Glu Val Val Ala Ser Leu
    950                 955                 960 gtg cca gca gca tag                                                  3591
Val Pro Ala Ala
    965

<210> SEQ ID NO 31
<211> LENGTH: 1196
<212> TYPE: PRT
<213> ORGANISM: Unknown
<220> FEATURE:
<223> OTHER INFORMATION: Open reading frame of BEST1:K:trAPAO fusion for
      bacterial exression vector pGEX-4T-1
<220> FEATURE:
<221> NAME/KEY: misc_feature
<222> LOCATION: (1)..(687)
<223> OTHER INFORMATION: gst + polylinker
<220> FEATURE:
<221> NAME/KEY: misc_feature
<222> LOCATION: (2164)..(2199)
<223> OTHER INFORMATION: spacer sequence
<220> FEATURE:
<221> NAME/KEY: misc_feature
<222> LOCATION: (2200)..(3588)
<223> OTHER INFORMATION: K:trAPAO
<220> FEATURE:
<221> NAME/KEY: misc_feature
<222> LOCATION: (2200)..(2202)
<223> OTHER INFORMATION: extra lysine

<400> SEQUENCE: 31

Met Ser Pro Ile Leu  Gly Tyr Trp Lys Ile  Lys Gly Leu Val Gln
                -225                -220                -215

Pro Thr Arg Leu Leu  Leu Glu Tyr Leu Glu  Glu Lys Tyr Glu Glu
                -210                -205                -200

His Leu Tyr Glu Arg  Asp Glu Gly Asp Lys  Trp Arg Asn Lys Lys
                -195                -190                -185

Phe Glu Leu Gly Leu  Glu Phe Pro Asn Leu  Pro Tyr Tyr Ile Asp
                -180                -175                -170

Gly Asp Val Lys Leu  Thr Gln Ser Met Ala  Ile Ile Arg Tyr Ile
                -165                -160                -155

Ala Asp Lys His Asn  Met Leu Gly Gly Cys  Pro Lys Glu Arg Ala
                -150                -145                -140

Glu Ile Ser Met Leu  Glu Gly Ala Val Leu  Asp Ile Arg Tyr Gly
                -135                -130                -125

Val Ser Arg Ile Ala  Tyr Ser Lys Asp Phe  Glu Thr Leu Lys Val
                -120                -115                -110

Asp Phe Leu Ser Lys  Leu Pro Glu Met Leu  Lys Met Phe Glu Asp Arg
                -105                -100                 -95
```

-continued

```
Leu Cys His Lys Thr Tyr Leu Asn Gly Asp His Val Thr His Pro Asp
            -90              -85              -80

Phe Met Leu Tyr Asp Ala Leu Asp Val Val Leu Tyr Met Asp Pro Met
        -75              -70              -65

Cys Leu Asp Ala Phe Pro Lys Leu Val Cys Phe Lys Lys Arg Ile Glu
        -60              -55              -50

Ala Ile Pro Gln Ile Asp Lys Tyr Leu Lys Ser Ser Lys Tyr Ile Ala
-45                  -40              -35                  -30

Trp Pro Leu Gln Gly Trp Gln Ala Thr Phe Gly Gly Gly Asp His Pro
                -25              -20                  -15

Pro Lys Ser Asp Leu Val Pro Arg Gly Ser Pro Glu Phe Thr Asp Phe
            -10               -5              -1   1

Pro Val Arg Arg Thr Asp Leu Gly Gln Val Gln Gly Leu Ala Gly Asp
     5                10                  15

Val Met Ser Phe Arg Gly Ile Pro Tyr Ala Ala Pro Pro Val Gly Gly
 20              25              30                   35

Leu Arg Trp Lys Pro Pro Gln His Ala Arg Pro Trp Ala Gly Val Arg
                40              45              50

Pro Ala Thr Gln Phe Gly Ser Asp Cys Phe Gly Ala Ala Tyr Leu Arg
             55              60                  65

Lys Gly Ser Leu Ala Pro Gly Val Ser Glu Asp Cys Leu Tyr Leu Asn
             70              75              80

Val Trp Ala Pro Ser Gly Ala Lys Pro Gly Gln Tyr Pro Val Met Val
 85                  90              95

Trp Val Tyr Gly Gly Gly Phe Ala Gly Gly Thr Ala Ala Met Pro Tyr
100             105             110                 115

Tyr Asp Gly Glu Ala Leu Ala Arg Gln Gly Val Val Val Thr Phe
                120             125                 130

Asn Tyr Arg Thr Asn Ile Leu Gly Phe Phe Ala His Pro Gly Leu Ser
            135             140                 145

Arg Glu Ser Pro Thr Gly Thr Ser Gly Asn Tyr Gly Leu Leu Asp Ile
            150             155             160

Leu Ala Ala Leu Arg Trp Val Gln Ser Asn Ala Arg Ala Phe Gly Gly
165             170             175

Asp Pro Gly Arg Val Thr Val Phe Gly Glu Ser Ala Gly Ala Ser Ala
180             185             190                 195

Ile Gly Leu Leu Leu Thr Ser Pro Leu Ser Lys Gly Leu Phe Arg Gly
            200             205             210

Ala Ile Leu Glu Ser Pro Gly Leu Thr Arg Pro Leu Ala Thr Leu Ala
            215             220             225

Asp Ser Ala Ala Ser Gly Glu Arg Leu Asp Ala Asp Leu Ser Arg Leu
            230             235             240

Arg Ser Thr Asp Pro Ala Thr Leu Met Ala Arg Ala Asp Ala Ala Arg
245             250             255

Pro Ala Ser Arg Asp Leu Arg Arg Pro Arg Thr Gly Pro Ile Val
260             265             270             275

Asp Gly His Val Leu Pro Gln Thr Asp Ser Ala Ala Ile Ala Ala Gly
            280             285                 290

Gln Leu Ala Pro Val Arg Val Leu Ile Gly Thr Asn Ala Asp Glu Gly
            295             300             305

Arg Ala Phe Leu Gly Arg Ala Pro Met Glu Thr Pro Ala Asp Tyr Gln
            310             315             320

Ala Tyr Leu Glu Ala Gln Phe Gly Asp Gln Ala Ala Ala Val Ala Ala
```

-continued

```
                325                 330                 335
Cys Tyr Pro Leu Asp Gly Arg Ala Thr Pro Lys Glu Met Val Ala Arg
340                 345                 350                 355
Ile Phe Gly Asp Asn Gln Phe Asn Arg Gly Val Ser Ala Phe Ser Glu
                360                 365                 370
Ala Leu Val Arg Gln Gly Ala Pro Val Trp Arg Tyr Gln Phe Asn Gly
            375                 380                 385
Asn Thr Glu Gly Gly Arg Ala Pro Ala Thr His Gly Ala Glu Ile Pro
            390                 395                 400
Tyr Val Phe Gly Val Phe Lys Leu Asp Glu Leu Gly Leu Phe Asp Trp
            405                 410                 415
Pro Pro Glu Gly Pro Thr Pro Ala Asp Arg Ala Leu Gly Gln Leu Met
420                 425                 430                 435
Ser Ser Ala Trp Val Arg Phe Ala Lys Asn Gly Asp Pro Ala Gly Asp
                440                 445                 450
Ala Leu Thr Trp Pro Ala Tyr Ser Thr Gly Lys Ser Thr Met Thr Phe
            455                 460                 465
Gly Pro Glu Gly Arg Ala Ala Val Val Ser Pro Gly Pro Ser Ile Pro
            470                 475                 480
Pro Cys Ala Asp Gly Ala Lys Ala Gly Gly Gly Ser Gly Gly Gly
485                 490                 495
Ser Gly Gly Gly Ser Lys Asp Asn Val Ala Asp Val Val Val Gly
500                 505                 510                 515
Ala Gly Leu Ser Gly Leu Glu Thr Ala Arg Lys Val Gln Ala Ala Gly
                520                 525                 530
Leu Ser Cys Leu Val Leu Glu Ala Met Asp Arg Val Gly Gly Lys Thr
            535                 540                 545
Leu Ser Val Gln Ser Gly Pro Gly Arg Thr Thr Ile Asn Asp Leu Gly
            550                 555                 560
Ala Ala Trp Ile Asn Asp Ser Asn Gln Ser Glu Val Ser Arg Leu Phe
            565                 570                 575
Glu Arg Phe His Leu Glu Gly Glu Leu Gln Arg Thr Thr Gly Asn Ser
580                 585                 590                 595
Ile His Gln Ala Gln Asp Gly Thr Thr Thr Thr Ala Pro Tyr Gly Asp
                600                 605                 610
Ser Leu Leu Ser Glu Glu Val Ala Ser Ala Leu Ala Glu Leu Leu Pro
            615                 620                 625
Val Trp Ser Gln Leu Ile Glu Glu His Ser Leu Gln Asp Leu Lys Ala
            630                 635                 640
Ser Pro Gln Ala Lys Arg Leu Asp Ser Val Ser Phe Ala His Tyr Cys
            645                 650                 655
Glu Lys Glu Leu Asn Leu Pro Ala Val Leu Gly Val Ala Asn Gln Ile
660                 665                 670                 675
Thr Arg Ala Leu Leu Gly Val Glu Ala His Glu Ile Ser Met Leu Phe
            680                 685                 690
Leu Thr Asp Tyr Ile Lys Ser Ala Thr Gly Leu Ser Asn Ile Phe Ser
            695                 700                 705
Asp Lys Lys Asp Gly Gly Gln Tyr Met Arg Cys Lys Thr Gly Met Gln
            710                 715                 720
Ser Ile Cys His Ala Met Ser Lys Glu Leu Val Pro Gly Ser Val His
            725                 730                 735
Leu Asn Thr Pro Val Ala Glu Ile Glu Gln Ser Ala Ser Gly Cys Thr
740                 745                 750                 755
```

```
Val Arg Ser Ala Ser Gly Ala Val Phe Arg Ser Lys Lys Val Val Val
            760                 765                 770

Ser Leu Pro Thr Thr Leu Tyr Pro Thr Leu Thr Phe Ser Pro Pro Leu
            775                 780                 785

Pro Ala Glu Lys Gln Ala Leu Ala Glu Asn Ser Ile Leu Gly Tyr Tyr
            790                 795                 800

Ser Lys Ile Val Phe Val Trp Asp Lys Pro Trp Arg Glu Gln Gly
    805                 810                 815

Phe Ser Gly Val Leu Gln Ser Ser Cys Asp Pro Ile Ser Phe Ala Arg
820                 825                 830                 835

Asp Thr Ser Ile Asp Val Asp Arg Gln Trp Ser Ile Thr Cys Phe Met
            840                 845                 850

Val Gly Asp Pro Gly Arg Lys Trp Ser Gln Gln Ser Lys Gln Val Arg
            855                 860                 865

Gln Lys Ser Val Trp Asp Gln Leu Arg Ala Ala Tyr Glu Asn Ala Gly
            870                 875                 880

Ala Gln Val Pro Glu Pro Ala Asn Val Leu Glu Ile Glu Trp Ser Lys
            885                 890                 895

Gln Gln Tyr Phe Gln Gly Ala Pro Ser Ala Val Tyr Gly Leu Asn Asp
900                 905                 910                 915

Leu Ile Thr Leu Gly Ser Ala Leu Arg Thr Pro Phe Lys Ser Val His
            920                 925                 930

Phe Val Gly Thr Glu Thr Ser Leu Val Trp Lys Gly Tyr Met Glu Gly
            935                 940                 945

Ala Ile Arg Ser Gly Gln Arg Gly Ala Ala Glu Val Val Ala Ser Leu
            950                 955                 960

Val Pro Ala Ala
    965

<210> SEQ ID NO 32
<211> LENGTH: 1803
<212> TYPE: DNA
<213> ORGANISM: Unknown
<220> FEATURE:
<223> OTHER INFORMATION: Glyc(-) APAO coding sequence; mutation in
      putative glycosylation sites
<220> FEATURE:
<221> NAME/KEY: CDS
<222> LOCATION: (1)..(1803)
<223> OTHER INFORMATION:

<400> SEQUENCE: 32 atg gca ctt gca ccg agc tac atc aat ccc cca aac gtc gcc tcc cca    48
Met Ala Leu Ala Pro Ser Tyr Ile Asn Pro Pro Asn Val Ala Ser Pro
1               5                   10                  15 gca ggg tat tct cac gtc ggc gta ggc cca gac gga ggg agg tat gtg    96
Ala Gly Tyr Ser His Val Gly Val Gly Pro Asp Gly Gly Arg Tyr Val
                20                  25                  30 aca ata gct gga cag att gga caa gac gct tcg ggc gtg aca gac cct   144
Thr Ile Ala Gly Gln Ile Gly Gln Asp Ala Ser Gly Val Thr Asp Pro
            35                  40                  45 gcc tac gag aaa cag gtt gcc caa gca ttc gcc aat ctg cga gct tgc   192
Ala Tyr Glu Lys Gln Val Ala Gln Ala Phe Ala Asn Leu Arg Ala Cys
        50                  55                  60 ctt gct gca gtt gga gcc act tca aac gac gtc acc aag ctc aat tac   240
Leu Ala Ala Val Gly Ala Thr Ser Asn Asp Val Thr Lys Leu Asn Tyr
65                  70                  75                  80 tac atc gtc gac tac gcc ccg agc aaa ctc acc gca att gga gat ggg   288
```

```
                    Tyr Ile Val Asp Tyr Ala Pro Ser Lys Leu Thr Ala Ile Gly Asp Gly
                                     85                  90                  95 ctg aag gct acc ttt gcc ctt gac agg ctc cct cct tgc acg ctg gtg         336
Leu Lys Ala Thr Phe Ala Leu Asp Arg Leu Pro Pro Cys Thr Leu Val
            100                 105                 110 cca gtg tcg gcc ttg tct tca cct gaa tac ctc ttt gag gtt gat gcc         384
Pro Val Ser Ala Leu Ser Ser Pro Glu Tyr Leu Phe Glu Val Asp Ala
            115                 120                 125 acg gcg ctg gtg ccg gga cac acg acc cca gac aac gtt gcg gac gtg         432
Thr Ala Leu Val Pro Gly His Thr Thr Pro Asp Asn Val Ala Asp Val
130                 135                 140 gta gtg gtg ggc gct ggc ttg agc ggt ttg gag acg gca cgc aaa gtc         480
Val Val Val Gly Ala Gly Leu Ser Gly Leu Glu Thr Ala Arg Lys Val
145                 150                 155                 160 cag gcc gcc ggt ctg tcc tgc ctc gtt ctt gag gcg atg gat cgt gta         528
Gln Ala Ala Gly Leu Ser Cys Leu Val Leu Glu Ala Met Asp Arg Val
                165                 170                 175 ggg gga aag act ctg agc gta caa tcg ggt ccc ggc agg acg act atc         576
Gly Gly Lys Thr Leu Ser Val Gln Ser Gly Pro Gly Arg Thr Thr Ile
                180                 185                 190 aac gac ctc ggc gct gcg tgg atc aat gat agc aat cag gcc gaa gta         624
Asn Asp Leu Gly Ala Ala Trp Ile Asn Asp Ser Asn Gln Ala Glu Val
                195                 200                 205 tcc aga ttg ttt gaa aga ttt cat ttg gag ggc gag ctc cag agg acg         672
Ser Arg Leu Phe Glu Arg Phe His Leu Glu Gly Glu Leu Gln Arg Thr
210                 215                 220 act gga aat tca atc cat caa gca caa gac ggt aca acc act aca gct         720
Thr Gly Asn Ser Ile His Gln Ala Gln Asp Gly Thr Thr Thr Thr Ala
225                 230                 235                 240 cct tat ggt gac tcc ttg ctg agc gag gag gtt gca agt gca ctt gcg         768
Pro Tyr Gly Asp Ser Leu Leu Ser Glu Glu Val Ala Ser Ala Leu Ala
                245                 250                 255 gaa ctc ctc ccc gta tgg tct cag ctg atc gaa gag cat agc ctt caa         816
Glu Leu Leu Pro Val Trp Ser Gln Leu Ile Glu Glu His Ser Leu Gln
                260                 265                 270 gac ctc aag gcg agc cct cag gcg aag cgg ctc gac agt gtg agc ttc         864
Asp Leu Lys Ala Ser Pro Gln Ala Lys Arg Leu Asp Ser Val Ser Phe
            275                 280                 285 gcg cac tac tgt gag aag gaa cta aac ttg cct gct gtt ctc ggc gta         912
Ala His Tyr Cys Glu Lys Glu Leu Asn Leu Pro Ala Val Leu Gly Val
            290                 295                 300 gca aac cag atc aca cgc gct ctg ctc ggt gtg gaa gcc cac gag atc         960
Ala Asn Gln Ile Thr Arg Ala Leu Leu Gly Val Glu Ala His Glu Ile
305                 310                 315                 320 agc atg ctt ttt ctc acc gac tac atc aag agt gcc acc ggt ctc agt        1008
Ser Met Leu Phe Leu Thr Asp Tyr Ile Lys Ser Ala Thr Gly Leu Ser
                325                 330                 335 aat att ttc tcg gac aag aaa gac ggc ggg cag tat atg cga tgc aaa        1056
Asn Ile Phe Ser Asp Lys Lys Asp Gly Gly Gln Tyr Met Arg Cys Lys
                340                 345                 350 aca ggt atg cag tcg att tgc cat gcc atg tca aag gaa ctt gtt cca        1104
Thr Gly Met Gln Ser Ile Cys His Ala Met Ser Lys Glu Leu Val Pro
            355                 360                 365 ggc tca gtg cac ctc aac acc ccc gtc gct gaa att gag cag tcg gca        1152
Gly Ser Val His Leu Asn Thr Pro Val Ala Glu Ile Glu Gln Ser Ala
            370                 375                 380 tcc ggc tgt aca gta cga tcg gcc tcg ggc gcc gtg ttc cga agc aaa        1200
Ser Gly Cys Thr Val Arg Ser Ala Ser Gly Ala Val Phe Arg Ser Lys
385                 390                 395                 400
```

```
aag gtg gtg gtt tcg tta ccg aca acc ttg tat ccc acc ttg aca ttt      1248
Lys Val Val Val Ser Leu Pro Thr Thr Leu Tyr Pro Thr Leu Thr Phe
            405                 410                 415 tca cca cct ctt ccc gcc gag aag caa gca ttg gcg gaa aat tct atc      1296
Ser Pro Pro Leu Pro Ala Glu Lys Gln Ala Leu Ala Glu Asn Ser Ile
        420                 425                 430 ctg ggc tac tat agc aag ata gtc ttc gta tgg gac aag ccg tgg tgg      1344
Leu Gly Tyr Tyr Ser Lys Ile Val Phe Val Trp Asp Lys Pro Trp Trp
                435                 440                 445 cgc gaa caa ggc ttc tcg ggc gtc ctc caa tcg agc tgt gac ccc atc      1392
Arg Glu Gln Gly Phe Ser Gly Val Leu Gln Ser Ser Cys Asp Pro Ile
            450                 455                 460 tca ttt gcc aga gat acc agc atc gac gtc gat cga caa tgg tcc att      1440
Ser Phe Ala Arg Asp Thr Ser Ile Asp Val Asp Arg Gln Trp Ser Ile
465                 470                 475                 480 acc tgt ttc atg gtc gga gac ccg gga cgg aag tgg tcc caa cag tcc      1488
Thr Cys Phe Met Val Gly Asp Pro Gly Arg Lys Trp Ser Gln Gln Ser
                485                 490                 495 aag cag gta cga caa aag tct gtc tgg gac caa ctc cgc gca gcc tac      1536
Lys Gln Val Arg Gln Lys Ser Val Trp Asp Gln Leu Arg Ala Ala Tyr
            500                 505                 510 gag aac gcc ggg gcc caa gtc cca gag ccg gcc aac gtg ctc gaa atc      1584
Glu Asn Ala Gly Ala Gln Val Pro Glu Pro Ala Asn Val Leu Glu Ile
        515                 520                 525 gag tgg tcg aag cag cag tat ttc caa gga gct ccg agc gcc gtc tat      1632
Glu Trp Ser Lys Gln Gln Tyr Phe Gln Gly Ala Pro Ser Ala Val Tyr
    530                 535                 540 ggg ctg aac gat ctc atc aca ctg ggt tcg gcg ctc aga acg ccg ttc      1680
Gly Leu Asn Asp Leu Ile Thr Leu Gly Ser Ala Leu Arg Thr Pro Phe
545                 550                 555                 560 aag agt gtt cat ttc gtt gga acg gag acg tct tta gtt tgg aaa ggg      1728
Lys Ser Val His Phe Val Gly Thr Glu Thr Ser Leu Val Trp Lys Gly
                565                 570                 575 tat atg gaa ggg gcc ata cga tcg ggt caa cga ggt gct gca gaa gtt      1776
Tyr Met Glu Gly Ala Ile Arg Ser Gly Gln Arg Gly Ala Ala Glu Val
            580                 585                 590 gtg gct agc ctg gtg cca gca gca tag                                   1803
Val Ala Ser Leu Val Pro Ala Ala
        595                 600

<210> SEQ ID NO 33
<211> LENGTH: 600
<212> TYPE: PRT
<213> ORGANISM: Unknown
<220> FEATURE:
<223> OTHER INFORMATION: Glyc(-) APAO coding sequence; mutation in
      putative glycosylation sites

<400> SEQUENCE: 33

Met Ala Leu Ala Pro Ser Tyr Ile Asn Pro Pro Asn Val Ala Ser Pro
1               5                   10                  15

Ala Gly Tyr Ser His Val Gly Val Gly Pro Asp Gly Gly Arg Tyr Val
            20                  25                  30

Thr Ile Ala Gly Gln Ile Gly Gln Asp Ala Ser Gly Val Thr Asp Pro
        35                  40                  45

Ala Tyr Glu Lys Gln Val Ala Gln Ala Phe Ala Asn Leu Arg Ala Cys
    50                  55                  60

Leu Ala Ala Val Gly Ala Thr Ser Asn Asp Val Thr Lys Leu Asn Tyr
65                  70                  75                  80

Tyr Ile Val Asp Tyr Ala Pro Ser Lys Leu Thr Ala Ile Gly Asp Gly
```

```
                    85                  90                  95
Leu Lys Ala Thr Phe Ala Leu Asp Arg Leu Pro Pro Cys Thr Leu Val
                100                 105                 110
Pro Val Ser Ala Leu Ser Ser Pro Glu Tyr Leu Phe Glu Val Asp Ala
                115                 120                 125
Thr Ala Leu Val Pro Gly His Thr Thr Pro Asp Asn Val Ala Asp Val
                130                 135                 140
Val Val Val Gly Ala Gly Leu Ser Gly Leu Glu Thr Ala Arg Lys Val
145                 150                 155                 160
Gln Ala Ala Gly Leu Ser Cys Leu Val Leu Glu Ala Met Asp Arg Val
                165                 170                 175
Gly Gly Lys Thr Leu Ser Val Gln Ser Gly Pro Gly Arg Thr Thr Ile
                180                 185                 190
Asn Asp Leu Gly Ala Ala Trp Ile Asn Asp Ser Asn Gln Ala Glu Val
                195                 200                 205
Ser Arg Leu Phe Glu Arg Phe His Leu Glu Gly Glu Leu Gln Arg Thr
                210                 215                 220
Thr Gly Asn Ser Ile His Gln Ala Gln Asp Gly Thr Thr Thr Thr Ala
225                 230                 235                 240
Pro Tyr Gly Asp Ser Leu Leu Ser Glu Glu Val Ala Ser Ala Leu Ala
                245                 250                 255
Glu Leu Leu Pro Val Trp Ser Gln Leu Ile Glu Glu His Ser Leu Gln
                260                 265                 270
Asp Leu Lys Ala Ser Pro Gln Ala Lys Arg Leu Asp Ser Val Ser Phe
                275                 280                 285
Ala His Tyr Cys Glu Lys Glu Leu Asn Leu Pro Ala Val Leu Gly Val
                290                 295                 300
Ala Asn Gln Ile Thr Arg Ala Leu Leu Gly Val Glu Ala His Glu Ile
305                 310                 315                 320
Ser Met Leu Phe Leu Thr Asp Tyr Ile Lys Ser Ala Thr Gly Leu Ser
                325                 330                 335
Asn Ile Phe Ser Asp Lys Lys Asp Gly Gly Gln Tyr Met Arg Cys Lys
                340                 345                 350
Thr Gly Met Gln Ser Ile Cys His Ala Met Ser Lys Glu Leu Val Pro
                355                 360                 365
Gly Ser Val His Leu Asn Thr Pro Val Ala Glu Ile Glu Gln Ser Ala
                370                 375                 380
Ser Gly Cys Thr Val Arg Ser Ala Ser Gly Ala Val Phe Arg Ser Lys
385                 390                 395                 400
Lys Val Val Val Ser Leu Pro Thr Thr Leu Tyr Pro Thr Leu Thr Phe
                405                 410                 415
Ser Pro Pro Leu Pro Ala Glu Lys Gln Ala Leu Ala Glu Asn Ser Ile
                420                 425                 430
Leu Gly Tyr Tyr Ser Lys Ile Val Phe Val Trp Asp Lys Pro Trp Trp
                435                 440                 445
Arg Glu Gln Gly Phe Ser Gly Val Leu Gln Ser Ser Cys Asp Pro Ile
                450                 455                 460
Ser Phe Ala Arg Asp Thr Ser Ile Asp Val Asp Arg Gln Trp Ser Ile
465                 470                 475                 480
Thr Cys Phe Met Val Gly Asp Pro Gly Arg Lys Trp Ser Gln Gln Ser
                485                 490                 495
Lys Gln Val Arg Gln Lys Ser Val Trp Asp Gln Leu Arg Ala Ala Tyr
                500                 505                 510
```

```
Glu Asn Ala Gly Ala Gln Val Pro Glu Pro Ala Asn Val Leu Glu Ile
            515                 520                 525

Glu Trp Ser Lys Gln Gln Tyr Phe Gln Gly Ala Pro Ser Ala Val Tyr
        530                 535                 540

Gly Leu Asn Asp Leu Ile Thr Leu Gly Ser Ala Leu Arg Thr Pro Phe
545                 550                 555                 560

Lys Ser Val His Phe Val Gly Thr Glu Thr Ser Leu Val Trp Lys Gly
                565                 570                 575

Tyr Met Glu Gly Ala Ile Arg Ser Gly Gln Arg Gly Ala Ala Glu Val
            580                 585                 590

Val Ala Ser Leu Val Pro Ala Ala
            595                 600

<210> SEQ ID NO 34
<211> LENGTH: 37
<212> TYPE: DNA
<213> ORGANISM: Artificial Sequence
<220> FEATURE:
<223> OTHER INFORMATION: 37-mer oligonucleotide

<400> SEQUENCE: 34
ggggaattca tggcacttgc accgagctac atcaatc                              37

<210> SEQ ID NO 35
<211> LENGTH: 1929
<212> TYPE: DNA
<213> ORGANISM: Exophiala spinifera
<220> FEATURE:
<221> NAME/KEY: Intron
<222> LOCATION: (739)..(811)
<223> OTHER INFORMATION:
<220> FEATURE:
<221> NAME/KEY: Intron
<222> LOCATION: (1134)..(1186)
<223> OTHER INFORMATION:

<400> SEQUENCE: 35
atggcacttg caccgagcta catcaatccc caaacgtcg cctccccagc agggtattcc        60
cacatcggcg taggcccaaa cgaagcgagg tatgtgacaa tagctggaca gattggacaa      120
gacgctttgg gcgtgacaga cccagcctac gagaaacagg ttgcccaagc attcgccaat     180
ctgcgagctt gccttgctgc agttggagcc tcttcaaacg acgtcaccaa gctcaattac     240
tacatcgtcg actacgcccc gagcaaactc accgcaattg agatgggct gaagtctacc      300 tttgcccttg acaggctccc tccttgcacg ctggtgccag taccggcctt ggcttcacct     360
gaatacctct ttgaggttga tgccacgcg ctggtgccag acactcgac cccagacaac      420 gttgcggacg tggtagtggt gggcgctggc ttgagcggtt tggagacggc acgcaaagtc     480
caggccgccg gtctgtcctg cctcgttctt gaggcgatgg atcgtgtagg gggaaagact     540
ctgagcgtac aatcgggtcc cggcaggacg actatcaacg acctcggcgc tgcgtggatc     600
aatgacagca ccaaagcga agtatccaga ttgtttgaaa gatttcattt ggagggcgag     660
ctccagagga cgaccggaaa ttcaatccat caagcacaag acggtacaac cactacagct     720
ccttatggtg actccccggt aagcacaatc ccactttgtg atgagacctc tgtcgagtgt     780
agaatacagt cactgactcc acttcgtcca gctgagcgag gaggttgcaa gtgcacttgc     840
ggaactcctc cccgtatggt ctcagctgat cgaagagtat agccttgaag accccaaggc     900
gagccctcag gcgaagcggc tcgacagtgt gagcttcgcg cactactgtg agaaggacct     960
```

-continued

```
aaacttgcct gctgttctca gcgtggcaaa ccagatcaca cgcgctctgc tcggtgtgga      1020
agcccacgag atcagcatgc tttttctcac cgactacatc aagagtgcca ccggtctcag      1080
taatattgtc tcggacaaga aagacggcgg gcagtatatg cgatgcaaaa caggtgcgtg      1140
cggtgtcctc tcaggtaggg gactcgtttc ttagtggtca ttccaggtat gcagtcgatt      1200
tgccatgcca tgtcaaagga acttgttcca ggctcagtgc acctcaacac ccccgtcgct      1260
ggaattgagc agtcggcgtc cggctgtata gtacgatcgg cctcgggcgc cgtgttccga      1320
agcaaaaagg tggtggtttc gttaccgaca acattgtatc ccaccttgac attttcacca      1380
cctcttcccg ccgagaagca agcattggcg gaaaaatcta tcctcggcta ctatagcaag      1440
atagtcttcg tatgggacaa cccgtggtgg cgcgaacaag gcttctcggg cgtcctccaa      1500
tcgagctgtg accccatctc atttgccaga gataccagca tcgaagtcga tcggcaatgg      1560
tccattacct gtttcatggt cggagacccg ggacggaagt ggtcccaaca gtccaagcag      1620
gtacgacaaa agtctgtctg ggaccaactc cgcgcagcct acgagaacgc cggggcccaa      1680
gtcccagagc cggccaacgt gctcgaaatc gagtggtcga agcagcagta tttccaagga      1740
gctccgagcg ccgtctatgg gctgaacgat ctcatcacac tgggttcggc gctcagaacg      1800
ccgttcaagt gtgttcattt cgttggaacg gagacgtctt tagtttggaa agggtatatg      1860
gaagggccca tacgatcggg tcaacgaggt gctgcagaag ttgtggctag cctggtgcca      1920
gcagcatag                                                               1929
```

<210> SEQ ID NO 36
<211> LENGTH: 600
<212> TYPE: PRT
<213> ORGANISM: Exophilia spinifera

<400> SEQUENCE: 36

```
Met Ala Leu Ala Pro Ser Tyr Ile Asn Pro Asn Val Ala Ser Pro
1               5                   10                  15

Ala Gly Tyr Ser His Ile Gly Val Gly Pro Asn Glu Ala Arg Tyr Val
            20                  25                  30

Thr Ile Ala Gly Gln Ile Gly Gln Asp Ala Leu Gly Val Thr Asp Pro
        35                  40                  45

Ala Tyr Glu Lys Gln Val Ala Gln Ala Phe Ala Asn Leu Arg Ala Cys
    50                  55                  60

Leu Ala Ala Val Gly Ala Ser Ser Asn Asp Val Thr Lys Leu Asn Tyr
65                  70                  75                  80

Tyr Ile Val Asp Tyr Ala Pro Ser Lys Leu Thr Ala Ile Gly Asp Gly
                85                  90                  95

Leu Lys Ser Thr Phe Ala Leu Asp Arg Leu Pro Pro Cys Thr Leu Val
            100                 105                 110

Pro Val Pro Ala Leu Ala Ser Pro Glu Tyr Leu Phe Glu Val Asp Ala
        115                 120                 125

Thr Ala Leu Val Pro Gly His Ser Thr Pro Asp Asn Val Ala Asp Val
    130                 135                 140

Val Val Val Gly Ala Gly Leu Ser Gly Leu Glu Thr Ala Arg Lys Val
145                 150                 155                 160

Gln Ala Ala Gly Leu Ser Cys Leu Val Leu Glu Ala Met Asp Arg Val
                165                 170                 175

Gly Gly Lys Thr Leu Ser Val Gln Ser Gly Pro Gly Arg Thr Thr Ile
            180                 185                 190

Asn Asp Leu Gly Ala Ala Trp Ile Asn Asp Ser Asn Gln Ser Glu Val
```

```
            195                 200                 205
Ser Arg Leu Phe Glu Arg Phe His Leu Glu Gly Glu Leu Gln Arg Thr
    210                 215                 220

Thr Gly Asn Ser Ile His Gln Ala Gln Asp Gly Thr Thr Thr Thr Ala
225                 230                 235                 240

Pro Tyr Gly Asp Ser Pro Leu Ser Glu Glu Val Ala Ser Ala Leu Ala
                245                 250                 255

Glu Leu Leu Pro Val Trp Ser Gln Leu Ile Glu Glu Tyr Ser Leu Glu
            260                 265                 270

Asp Pro Lys Ala Ser Pro Gln Ala Lys Arg Leu Asp Ser Val Ser Phe
        275                 280                 285

Ala His Tyr Cys Glu Lys Asp Leu Asn Leu Pro Ala Val Leu Ser Val
    290                 295                 300

Ala Asn Gln Ile Thr Arg Ala Leu Leu Gly Val Glu Ala His Glu Ile
305                 310                 315                 320

Ser Met Leu Phe Leu Thr Asp Tyr Ile Lys Ser Ala Thr Gly Leu Ser
                325                 330                 335

Asn Ile Val Ser Asp Lys Lys Asp Gly Gln Tyr Met Arg Cys Lys
            340                 345                 350

Thr Gly Met Gln Ser Ile Cys His Ala Met Ser Lys Glu Leu Val Pro
        355                 360                 365

Gly Ser Val His Leu Asn Thr Pro Val Ala Gly Ile Glu Gln Ser Ala
    370                 375                 380

Ser Gly Cys Ile Val Arg Ser Ala Ser Gly Ala Val Phe Arg Ser Lys
385                 390                 395                 400

Lys Val Val Val Ser Leu Pro Thr Thr Leu Tyr Pro Thr Leu Thr Phe
                405                 410                 415

Ser Pro Pro Leu Pro Ala Glu Lys Gln Ala Leu Ala Glu Lys Ser Ile
            420                 425                 430

Leu Gly Tyr Tyr Ser Lys Ile Val Phe Val Trp Asp Asn Pro Trp Trp
        435                 440                 445

Arg Glu Gln Gly Phe Ser Gly Val Leu Gln Ser Ser Cys Asp Pro Ile
    450                 455                 460

Ser Phe Ala Arg Asp Thr Ser Ile Glu Val Asp Arg Gln Trp Ser Ile
465                 470                 475                 480

Thr Cys Phe Met Val Gly Asp Pro Gly Arg Lys Trp Ser Gln Gln Ser
                485                 490                 495

Lys Gln Val Arg Gln Lys Ser Val Trp Asp Gln Leu Arg Ala Ala Tyr
            500                 505                 510

Glu Asn Ala Gly Ala Gln Val Pro Glu Pro Ala Asn Val Leu Glu Ile
        515                 520                 525

Glu Trp Ser Lys Gln Gln Tyr Phe Gln Gly Ala Pro Ser Ala Val Tyr
    530                 535                 540

Gly Leu Asn Asp Leu Ile Thr Leu Gly Ser Ala Leu Arg Thr Pro Phe
545                 550                 555                 560

Lys Cys Val His Phe Val Gly Thr Glu Thr Ser Leu Val Trp Lys Gly
                565                 570                 575

Tyr Met Glu Gly Ala Ile Arg Ser Gly Gln Arg Gly Ala Ala Glu Val
            580                 585                 590

Val Ala Ser Leu Val Pro Ala Ala
        595                 600

<210> SEQ ID NO 37
```

<211> LENGTH: 1929
<212> TYPE: DNA
<213> ORGANISM: Exophiala spinifera
<220> FEATURE:
<221> NAME/KEY: Intron
<222> LOCATION: (739)..(811)
<223> OTHER INFORMATION:
<220> FEATURE:
<221> NAME/KEY: Intron
<222> LOCATION: (1134)..(1186)
<223> OTHER INFORMATION:

<400> SEQUENCE: 37

| | | | | | |
|---|---|---|---|---|---|
| atggcacttg | caccgagcta | catcaatccc | ccaaacgtcg | cctccccagc | agggtattcc | 60 |
| cacatcggcg | taggcccaaa | cgaagcgagg | tatgtgacaa | tagctggaca | gattggacaa | 120 |
| gacgctttgg | gcgtgacaga | cccagcctac | gagaaacagg | ttgcccaagc | attcgccaat | 180 |
| ctgcgagctt | gccttgctgc | agttggagcc | tcttcaaacg | acgtcaccaa | gctcaattac | 240 |
| tacatcgtcg | actacgcccc | gagcaaactc | accgcaattg | gagatgggct | gaagtctacc | 300 |
| tttgcccttg | acaggctccc | tccttgcacg | ctggtgccag | taccggcctt | ggcttcacct | 360 |
| gaatacctct | ttgaggttga | cgccacggcg | ctggtgccag | gacactcgac | cccagacaac | 420 |
| gttgcgacg | tggtagtggt | gggcgctggc | ttgagcggct | tggagacggc | acgcaaagtc | 480 |
| caggccgccg | gtctgtcctg | cctcgttctt | gaggcgatgg | atcgtgtagg | gggaaagact | 540 |
| ctgagcgtac | aatcgggtcc | cggcaggacg | actatcaacg | acctcggcgc | tgcgtggatc | 600 |
| aatgacagca | accaaagcga | agtatccaga | ttgtttgaaa | gatttcattt | ggagggcgag | 660 |
| ctccagagga | cgaccggaaa | ttcaatccat | caagcacaag | acggtacaac | cactacagct | 720 |
| ccttatggtg | actcccggt | aagcacaatc | ccactttgtg | atgagacctc | tgtcgagtgt | 780 |
| agaatacagt | cactgactcc | acttcgtcca | gctgagcgag | gaggttgcaa | gtgcacttgc | 840 |
| ggaactcctc | cccgtatggt | ctcagctgat | cgaagagtat | agccttgaag | accccaaggc | 900 |
| gagccctcag | gcgaagcggc | tcgacagtgt | gagcttcgcg | cactactgtg | agaaggacct | 960 |
| aaacttgcct | gctgttctca | gcgtggcaaa | ccagatcaca | cgcgctctgc | tcggtgtgga | 1020 |
| agcccacgag | atcagcatgc | tttttctcac | cgactacatc | aagagtgcca | ccggtctcag | 1080 |
| taatattgtc | tcggacaaga | aagacggcgg | gcagtatatg | cgatgcaaaa | caggtgcgtg | 1140 |
| cggtgtcctc | tcaggtaggg | gactcgtttc | ttagtggtca | ttccaggtat | gcagtcgatt | 1200 |
| tgccatgcca | tgtcaaagga | acttgttcca | ggctcagtgc | acctcaacac | ccccgtcgct | 1260 |
| ggaattgagc | agtcggcgtc | cggctgtata | gtacgatcgg | cctcgggcgc | cgtgttccga | 1320 |
| agcaaaaagg | tggtggtttc | gttaccgaca | acattgtatc | ccaccttgac | attttcacca | 1380 |
| cctcttcccg | ccgagaagca | agcattggcg | gaaaaatcta | tcctcggcta | ctatagcaag | 1440 |
| atagtcttcg | tatgggacaa | cccgtggtgg | cgcgaacaag | gcttctcggg | cgtcctccaa | 1500 |
| tcgagctgtg | accccatctc | atttgccaga | gataccagca | tcgaagtcga | tcggcaatgg | 1560 |
| tccattacct | gtttcatggt | cggagacccg | ggacggaagt | ggtcccaaca | gtccaagcag | 1620 |
| gtacgacaaa | agtctgtctg | ggaccaactc | cgcgcagcct | acgagaacgc | cggggcccaa | 1680 |
| gtccagagc | cggccaacgt | gctcgaaatc | gagtggtcga | agcagcagta | tttccaagga | 1740 |
| gctccgagcg | ccgtctatgg | gctgaacgat | ctcatcacac | tgggttcggc | gctcagaacg | 1800 |
| ccgttcaagt | gtgttcattt | cgttggaacg | gagacgtctt | tagtttggaa | agggtatatg | 1860 |
| gaaggggcca | tacgatcggg | tcaacgaggt | gctgcagaag | ttgtggctag | cctggtgcca | 1920 |
| gcagcatag | | | | | | 1929 |

<210> SEQ ID NO 38
<211> LENGTH: 600
<212> TYPE: PRT
<213> ORGANISM: Exophiala spinifera

<400> SEQUENCE: 38

```
Met Ala Leu Ala Pro Ser Tyr Ile Asn Pro Asn Val Ala Ser Pro
1               5                   10                  15

Ala Gly Tyr Ser His Ile Gly Val Gly Pro Asn Glu Ala Arg Tyr Val
            20                  25                  30

Thr Ile Ala Gly Gln Ile Gly Gln Asp Ala Leu Gly Val Thr Asp Pro
        35                  40                  45

Ala Tyr Glu Lys Gln Val Ala Gln Ala Phe Ala Asn Leu Arg Ala Cys
50                  55                  60

Leu Ala Ala Val Gly Ala Ser Ser Asn Asp Val Thr Lys Leu Asn Tyr
65                  70                  75                  80

Tyr Ile Val Asp Tyr Ala Pro Ser Lys Leu Thr Ala Ile Gly Asp Gly
                85                  90                  95

Leu Lys Ser Thr Phe Ala Leu Asp Arg Leu Pro Pro Cys Thr Leu Val
            100                 105                 110

Pro Val Pro Ala Leu Ala Ser Pro Glu Tyr Leu Phe Glu Val Asp Ala
        115                 120                 125

Thr Ala Leu Val Pro Gly His Ser Thr Pro Asp Asn Val Ala Asp Val
130                 135                 140

Val Val Val Gly Ala Gly Leu Ser Gly Leu Glu Thr Ala Arg Lys Val
145                 150                 155                 160

Gln Ala Ala Gly Leu Ser Cys Leu Val Leu Glu Ala Met Asp Arg Val
                165                 170                 175

Gly Gly Lys Thr Leu Ser Val Gln Ser Gly Pro Gly Arg Thr Thr Ile
            180                 185                 190

Asn Asp Leu Gly Ala Ala Trp Ile Asn Asp Ser Asn Gln Ser Glu Val
        195                 200                 205

Ser Arg Leu Phe Glu Arg Phe His Leu Glu Gly Glu Leu Gln Arg Thr
210                 215                 220

Thr Gly Asn Ser Ile His Gln Ala Gln Asp Gly Thr Thr Thr Thr Ala
225                 230                 235                 240

Pro Tyr Gly Asp Ser Pro Leu Ser Glu Glu Val Ala Ser Ala Leu Ala
                245                 250                 255

Glu Leu Leu Pro Val Trp Ser Gln Leu Ile Glu Glu Tyr Ser Leu Glu
            260                 265                 270

Asp Pro Lys Ala Ser Pro Gln Ala Lys Arg Leu Asp Ser Val Ser Phe
        275                 280                 285

Ala His Tyr Cys Glu Lys Asp Leu Asn Leu Pro Ala Val Leu Ser Val
290                 295                 300

Ala Asn Gln Ile Thr Arg Ala Leu Leu Gly Val Glu Ala His Glu Ile
305                 310                 315                 320

Ser Met Leu Phe Leu Thr Asp Tyr Ile Lys Ser Ala Thr Gly Leu Ser
                325                 330                 335

Asn Ile Val Ser Asp Lys Lys Asp Gly Gly Gln Tyr Met Arg Cys Lys
            340                 345                 350

Thr Gly Met Gln Ser Ile Cys His Ala Met Ser Lys Glu Leu Val Pro
        355                 360                 365

Gly Ser Val His Leu Asn Thr Pro Val Ala Gly Ile Glu Gln Ser Ala
```

Ser Gly Cys Ile Val Arg Ser Ala Ser Gly Ala Val Phe Arg Ser Lys
385                 390                 395                 400

Lys Val Val Val Ser Leu Pro Thr Thr Leu Tyr Pro Thr Leu Thr Phe
            405                 410                 415

Ser Pro Pro Leu Pro Ala Glu Lys Gln Ala Leu Ala Glu Lys Ser Ile
        420                 425                 430

Leu Gly Tyr Tyr Ser Lys Ile Val Phe Val Trp Asp Asn Pro Trp Trp
            435                 440                 445

Arg Glu Gln Gly Phe Ser Gly Val Leu Gln Ser Ser Cys Asp Pro Ile
    450                 455                 460

Ser Phe Ala Arg Asp Thr Ser Ile Glu Val Asp Arg Gln Trp Ser Ile
465                 470                 475                 480

Thr Cys Phe Met Val Gly Asp Pro Gly Arg Lys Trp Ser Gln Gln Ser
                485                 490                 495

Lys Gln Val Arg Gln Lys Ser Val Trp Asp Gln Leu Arg Ala Ala Tyr
            500                 505                 510

Glu Asn Ala Gly Ala Gln Val Pro Glu Pro Ala Asn Val Leu Glu Ile
        515                 520                 525

Glu Trp Ser Lys Gln Gln Tyr Phe Gln Gly Ala Pro Ser Ala Val Tyr
    530                 535                 540

Gly Leu Asn Asp Leu Ile Thr Leu Gly Ser Ala Leu Arg Thr Pro Phe
545                 550                 555                 560

Lys Cys Val His Phe Val Gly Thr Glu Thr Ser Leu Val Trp Lys Gly
                565                 570                 575

Tyr Met Glu Gly Ala Ile Arg Ser Gly Gln Arg Gly Ala Ala Glu Val
            580                 585                 590

Val Ala Ser Leu Val Pro Ala Ala
        595                 600

<210> SEQ ID NO 39
<211> LENGTH: 1930
<212> TYPE: DNA
<213> ORGANISM: Exophiala spinifera
<220> FEATURE:
<221> NAME/KEY: Intron
<222> LOCATION: (739)..(811)
<223> OTHER INFORMATION:
<220> FEATURE:
<221> NAME/KEY: Intron
<222> LOCATION: (1134)..(1187)
<223> OTHER INFORMATION:
<220> FEATURE:
<221> NAME/KEY: misc_feature
<222> LOCATION: (649)..(649)
<223> OTHER INFORMATION: n = A,T,C or G

<400> SEQUENCE: 39
atggcacttg caccgagcta catcaatccc ccaaacgtcg cctccccagc agggtattct     60
cacgtcggcg taggcccaga cggagggagg tatgtgacaa tagctggaca gattggacaa    120
gacgcttcgg gcgtgacaga ccctgcctac gagaaacagg ttgcccaagc attcgccaat    180
ctgcgagctt gccttgctgc agttggagcc acttcaaacg acgtcaccaa gctcaattac    240
tacatcgtcg actacgcccc gagcaaactc accgcaattg gagatgggct gaaggctacc    300
tttgcccttg acaggctccc tccttgcacg ctggtgccag tgtcggcctt gtcttcacct    360
gaatacctct ttgaggttga tgccacggcg ctggtgccgg acacacgac cccagacaac    420 gttgcggacg tggtagtggt gggcgctggc ttgagcggtt tggagacggc acgcaaagtc    480

-continued

```
caggccgccg gtctgtcctg cctcgttctt gaggcgatgg atcgtgtagg gggaaagact    540
ctgagcgtac aatcgggtcc cggcaggacg actatcaacg acctcggcgc tgcgtggatc    600
aatgacagca accaaagcga agtatccaga ttgtttgaaa gatttcatnt ggagggcgag    660
ctccagagga cgactggaaa ttcaatccat caagcacaag acgtacaac  cactacagct    720
ccttatggtg actccttggt aagcacaatc ccactttgtg atgagacctc tgtcgagtgt    780
agaatacagt cactgattcc acttcgtcca gctgagcgag gaggttgcaa gtgcacttgc    840
ggaactcctc cccgtatggt ctcagctgat cgaagagcat agccttcaag acctcaaggc    900
gagccctcag gcgaagcggc tcgacagtgt gagcttcgcg cactactgtg agaaggaact    960
aaacttgcct gctgttctcg gcgtagcaaa ccagatcaca cgcgctctgc tcggtgtgga   1020
agcccacgag atcagcatgc ttttcctcac cgactacatc aagagtgcca ccggtctcag   1080
taatattttc tcggacaaga aagacggcgg gcagtatatg cgatgcaaaa caggtgcgtg   1140
tggtgtcgtc tcaggtgggg gactcgtttc tcaagtggtc atttcaggta tgcagtcgat   1200
ttgccatgcc atgtcaaagg aacttgttcc aggctcagtg cacctcaaca cccccgtcgc   1260
tgaaattgag cagtcggcat ccggctgtac agtacgatcg gcctcgggcg ccgtgttccg   1320
aagcaaaaag gtggtggttt cgttaccgac aaccttgtat cccaccttga cattttcacc   1380
acctctcccc gccgagaagc aagcattggc ggaaaattct atcctgggct actatagcaa   1440
gatagtcttc gtatgggaca gccgtggtg  gcgcgaacaa ggcttctcgg cgtcctcca    1500
atcgagctgt gaccccatct catttgccag agataccagc atcgacgtcg atcgacaatg   1560
gtccattacc tgtttcatgg tcggagaccc gggacggaag tggtcccaac agtccaagca   1620
ggtacgacaa aagtctgtct gggaccaact ccgcgcagcc tacgagaacg ccggggccca   1680
agtcccagag ccggccaacg tgctcgaaat cgagtggtcg aagcagcagt atttccaagg   1740
agctccgagc gccgtctatg gctgaacga  tctcatcaca ctgggttcgg cgctcagaac   1800
gccgttcaag agtgttcatt tcgttggaac ggagacgtct ttagtttgga aagggtatat   1860
ggaaggggcc atacgatcgg gtcaacgagg tgctgcagaa gttgtggcta gcctggtgcc   1920
agcagcatag                                                          1930
```

<210> SEQ ID NO 40
<211> LENGTH: 598
<212> TYPE: PRT
<213> ORGANISM: Exophiala spinifera
<220> FEATURE:
<221> NAME/KEY: MISC_FEATURE
<222> LOCATION: (216)..(216)
<223> OTHER INFORMATION: Xaa = any amino acid

<400> SEQUENCE: 40

```
Met Ala Leu Ala Pro Ser Tyr Ile Asn Pro Pro Asn Val Ala Ser Pro
  1               5                  10                  15

Ala Gly Tyr Ser His Val Gly Val Gly Pro Asp Gly Gly Arg Tyr Val
             20                  25                  30

Thr Ile Ala Gly Gln Ile Gly Gln Asp Ala Ser Gly Val Thr Asp Pro
         35                  40                  45

Ala Tyr Glu Lys Gln Val Ala Gln Ala Phe Ala Asn Leu Arg Ala Cys
     50                  55                  60

Leu Ala Ala Val Gly Ala Thr Ser Asn Asp Val Thr Lys Leu Asn Tyr
 65                  70                  75                  80

Tyr Ile Val Asp Tyr Ala Pro Ser Lys Leu Thr Ala Ile Gly Asp Gly
```

-continued

```
                    85                  90                  95
Leu Lys Ala Thr Phe Ala Leu Asp Arg Leu Pro Pro Cys Thr Leu Val
                100                 105                 110
Pro Val Ser Ala Leu Ser Ser Pro Glu Tyr Leu Phe Glu Val Asp Ala
            115                 120                 125
Thr Ala Leu Val Pro Gly His Thr Thr Pro Asp Asn Val Ala Asp Val
        130                 135                 140
Val Val Gly Ala Gly Leu Ser Gly Leu Glu Thr Ala Arg Lys Val Gln
145                 150                 155                 160
Ala Ala Gly Leu Ser Cys Leu Val Leu Glu Ala Met Asp Arg Val Gly
                165                 170                 175
Gly Lys Thr Leu Ser Val Gln Ser Gly Pro Gly Arg Thr Thr Ile Asn
                180                 185                 190
Asp Leu Gly Ala Ala Trp Ile Asn Asp Ser Asn Gln Ser Glu Val Ser
            195                 200                 205
Arg Leu Phe Glu Arg Phe His Xaa Glu Gly Glu Leu Gln Arg Thr Thr
        210                 215                 220
Gly Asn Ser Ile His Gln Ala Gln Asp Gly Thr Thr Thr Ala Pro
225                 230                 235                 240
Tyr Gly Asp Ser Leu Leu Ser Glu Glu Val Ala Ser Ala Leu Ala Glu
                245                 250                 255
Leu Leu Pro Val Trp Ser Gln Leu Ile Glu Glu His Ser Leu Gln Asp
                260                 265                 270
Leu Lys Ala Ser Pro Gln Ala Lys Arg Leu Asp Ser Val Ser Phe Ala
                275                 280                 285
His Tyr Cys Glu Lys Glu Leu Asn Leu Pro Ala Val Leu Gly Val Asn
                290                 295                 300
Gln Ile Thr Arg Ala Leu Leu Gly Val Glu Ala His Glu Ile Ser Met
305                 310                 315                 320
Leu Phe Leu Thr Asp Tyr Ile Lys Ser Ala Thr Gly Leu Ser Asn Ile
                325                 330                 335
Phe Ser Asp Lys Lys Asp Gly Gly Gln Tyr Met Arg Cys Lys Thr Gly
                340                 345                 350
Met Gln Ser Ile Cys His Ala Met Ser Lys Glu Leu Val Pro Gly Ser
            355                 360                 365
Val His Leu Asn Thr Pro Val Ala Glu Ile Glu Gln Ser Ala Ser Gly
        370                 375                 380
Cys Thr Val Arg Ser Ala Ser Gly Ala Val Phe Arg Ser Lys Lys Val
385                 390                 395                 400
Val Val Ser Leu Pro Thr Thr Leu Tyr Pro Thr Leu Thr Phe Ser Pro
                405                 410                 415
Pro Leu Pro Ala Glu Lys Gln Ala Leu Ala Glu Asn Ser Ile Leu Gly
                420                 425                 430
Tyr Tyr Ser Lys Ile Val Phe Val Trp Asp Lys Pro Trp Trp Arg Glu
            435                 440                 445
Gln Gly Phe Ser Gly Val Leu Gln Ser Ser Cys Asp Pro Ile Ser Phe
        450                 455                 460
Ala Arg Asp Thr Ser Ile Asp Val Asp Arg Gln Trp Ser Ile Thr Cys
465                 470                 475                 480
Phe Met Val Gly Asp Pro Gly Arg Lys Trp Ser Gln Ser Lys Gln
                485                 490                 495
Val Arg Gln Lys Ser Val Trp Asp Gln Leu Arg Ala Ala Tyr Glu Asn
                500                 505                 510
```

```
Ala Gly Ala Gln Val Pro Glu Pro Ala Asn Val Leu Glu Ile Glu Trp
            515                 520                 525
Ser Lys Gln Gln Tyr Phe Gln Gly Ala Pro Ser Ala Val Tyr Gly Leu
        530                 535                 540
Asn Asp Leu Ile Thr Leu Gly Ser Ala Leu Arg Thr Pro Phe Lys Ser
545                 550                 555                 560
Val His Phe Val Gly Thr Glu Thr Ser Leu Val Trp Lys Gly Tyr Met
                565                 570                 575
Glu Gly Ala Ile Arg Ser Gly Gln Arg Gly Ala Ala Glu Val Val Ala
            580                 585                 590
Ser Leu Val Pro Ala Ala
        595

<210> SEQ ID NO 41
<211> LENGTH: 1928
<212> TYPE: DNA
<213> ORGANISM: Rhinocladiella atrovirens
<220> FEATURE:
<221> NAME/KEY: Intron
<222> LOCATION: (739)..(811)
<223> OTHER INFORMATION:
<220> FEATURE:
<221> NAME/KEY: Intron
<222> LOCATION: (1134)..(1185)
<223> OTHER INFORMATION:

<400> SEQUENCE: 41
atggcacttg caccgagcta catcaatccc caaacctcg cctccccagc agggtattcc        60
cacgtcggcg taggcccaaa cggagggagg tatgcgacaa tagctggaca gattggacaa       120
gacgcttcgg ccgtgacaga ccctgcctac gagaaacagg ttgcccaagc attcgccaac       180
ctgcgagctt gtcttgctgc agttggagcc acttcaaacg acattaccaa gctcaattac       240
tacatcgtcg actacaaccc gagcaaactc accgcaattg gagatgggct gaaggctacc       300
tttgcccttg acaggctccc tccttgcacg ctggtgccag tgccggccct ggcttcacct       360
gaatacccct ttgaggttga tgccacggcg ctggttccag acactcaac cccagacaat       420 gttgcggacg tggtcgtggt gggcgctggc ttgagcggtt tggagacggc acgcaaagtc       480
caggctgccg ggctgtcctg cctcgttctt gaggcgatgg atcgtgtggg gggaaagact       540
ctgagcgtac aatcgggtcc cggcaggacg gctatcaatg acctcggcgc tgcgtggatc       600
aatgacagca accaaagcga agtattcaaa ttatttgaaa gatttcattt ggagggcgag       660
ctccagagga cgaccggaaa ttcaatccat caagcacaag acggtacaac cactacagct       720
ccttatggtg attccctggt aagcacaatt ccatcttgtg atgagacctc tgtcgtgtgt       780
agaatacagt cgctgactcc acatcgtcca gctgagcgag gaggttgcaa gtgcactcgc       840
ggaactcctt cccgcatggt ctcagctgat cgaagagcat agtcttgaag accccaaggc       900
gagccctcaa gcgaagcagc tcgacagtgt gagcttcgca cactactgtg agaaggatct       960
aagcttgcct gctgttctcg gcgtggcaaa ccagatcaca cgcgctctgc tcggtgtgga      1020
agcccacgag atcagcatgc tttttctcac cgactacatc aagagtgcca ccggtctcag      1080
taatattgtc tcggataaga aagacggtgg gcagtatatg cgatgcaaaa caggtgcgtg      1140
tggtgttctc tcagtgggag actcgtttct tagtggtcat tccaggtatg cagtcgcttt      1200
gccatgccat gtcaaaggaa cttgttccag gctcagtgca cctcaacacc ccgtcgccg      1260 aaattgagca gtcggcatcc ggctgtacag tacgatcggc ctcgggcggc gtgttccgaa      1320
```

```
gtaaaaaggt ggtggtttcg ttaccgacaa ccttgtatcc caccttgata ttttcaccac    1380
ctcttcccgc cgagaagcaa gcattggctg aaaaatccat cctgggctac tatagcaaga    1440
tagtcttcgt atgggacaag ccgtggtggc gcgaacaagg cttctcgggc gtcctccaat    1500
cgagctgtga ccccatctca tttgccagag ataccagcat cgaagtcgat cggcaatggt    1560
ccattacctg tttcatggtc ggagacccgg gacggaagtg gtcccaacag tccaagcagg    1620
tacgacagaa gtctgtctgg aaccaactcc gcgcagccta cgagaacgcc ggggcccaag    1680
tcccagagcc ggccaacgtg ctcgagatcg agtggtcgaa gcagcagtat tccaaggag    1740 cgccgagcgt cgtctatggg ctgaactgtc tcaacacact gggttcggcg ctcagaacgc    1800
cgttcaaggg tgttcatttc gttggaacgg agacgtcttt ggtttggaaa gggtatatgg    1860 aagggccat acgatcgggt cagcgaggcg ctgcagaagt tgtggctagc ctggtgccag    1920
cagcatag                                                            1928
```

<210> SEQ ID NO 42
<211> LENGTH: 598
<212> TYPE: PRT
<213> ORGANISM: Rhinocladiella atrovirens

<400> SEQUENCE: 42

```
Met Ala Leu Ala Pro Ser Tyr Ile Asn Pro Pro Asn Leu Ala Ser Pro
 1               5                  10                  15

Ala Gly Tyr Ser His Val Gly Val Gly Pro Asn Gly Gly Arg Tyr Ala
                20                  25                  30

Thr Ile Ala Gly Gln Ile Gly Gln Asp Ala Ser Ala Val Thr Asp Pro
            35                  40                  45

Ala Tyr Glu Lys Gln Val Ala Gln Ala Phe Ala Asn Leu Arg Ala Cys
        50                  55                  60

Leu Ala Val Gly Ala Thr Ser Asn Asp Ile Thr Lys Leu Asn Tyr
 65                  70                  75                  80

Tyr Ile Val Asp Tyr Asn Pro Ser Lys Leu Thr Ala Ile Gly Asp Gly
                85                  90                  95

Leu Lys Ala Thr Phe Ala Leu Asp Arg Leu Pro Pro Cys Thr Leu Val
            100                 105                 110

Pro Val Pro Ala Leu Ala Ser Pro Glu Tyr Pro Phe Glu Val Asp Ala
        115                 120                 125

Thr Ala Leu Val Pro Gly His Ser Thr Pro Asp Asn Val Ala Asp Val
    130                 135                 140

Val Val Val Gly Ala Gly Leu Ser Gly Leu Glu Thr Ala Arg Lys Val
145                 150                 155                 160

Gln Ala Ala Gly Leu Ser Cys Leu Val Leu Glu Ala Met Asp Arg Val
                165                 170                 175

Gly Gly Lys Thr Leu Ser Val Gln Ser Gly Pro Gly Arg Thr Ala Ile
            180                 185                 190

Asn Asp Leu Gly Ala Ala Trp Ile Asn Asp Ser Asn Gln Ser Glu Val
        195                 200                 205

Phe Lys Leu Phe Glu Arg Leu Glu Gly Glu Leu Gln Arg Thr Thr Gly
    210                 215                 220

Asn Ser Ile His Gln Ala Gln Asp Gly Thr Thr Thr Ala Pro Tyr
225                 230                 235                 240

Gly Asp Ser Leu Leu Ser Glu Glu Val Ala Ser Ala Leu Ala Glu Leu
                245                 250                 255

Leu Pro Ala Trp Ser Gln Leu Ile Glu Glu His Ser Leu Glu Asp Pro
```

```
                      260                   265                    270
Lys Ala Ser Pro Gln Ala Lys Gln Leu Asp Ser Val Ser Phe Ala His
            275                   280                   285
Tyr Cys Glu Lys Asp Leu Ser Leu Pro Ala Val Leu Gly Val Ala Asn
290                   295                   300
Gln Ile Thr Arg Ala Leu Leu Gly Val Glu Ala His Glu Ile Ser Met
305                   310                   315                   320
Leu Phe Leu Thr Asp Tyr Ile Lys Ser Ala Thr Gly Leu Ser Asn Ile
                325                   330                   335
Val Ser Asp Lys Lys Asp Gly Gly Gln Tyr Met Arg Cys Lys Thr Gly
            340                   345                   350
Met Gln Ser Leu Cys His Ala Met Ser Lys Glu Leu Val Pro Gly Ser
            355                   360                   365
Val His Leu Asn Thr Pro Val Ala Glu Ile Glu Gln Ser Ala Ser Gly
            370                   375                   380
Cys Thr Val Arg Ser Ala Ser Gly Gly Val Phe Arg Ser Lys Lys Val
385                   390                   395                   400
Val Val Ser Leu Pro Thr Thr Leu Tyr Pro Thr Leu Ile Phe Ser Pro
                405                   410                   415
Pro Leu Pro Ala Glu Lys Gln Ala Leu Ala Glu Lys Ser Ile Leu Gly
            420                   425                   430
Tyr Tyr Ser Lys Ile Val Phe Val Trp Asp Lys Pro Trp Arg Glu
            435                   440                   445
Gln Gly Phe Ser Gly Val Leu Gln Ser Ser Cys Asp Pro Ile Ser Phe
            450                   455                   460
Ala Arg Asp Thr Ser Ile Glu Val Asp Arg Gln Trp Ser Ile Thr Cys
465                   470                   475                   480
Phe Met Val Gly Asp Pro Gly Arg Lys Trp Ser Gln Ser Lys Gln
                485                   490                   495
Val Arg Gln Lys Ser Val Trp Asn Gln Leu Arg Ala Ala Tyr Glu Asn
            500                   505                   510
Ala Gly Ala Gln Val Pro Glu Pro Ala Asn Val Leu Glu Ile Glu Trp
            515                   520                   525
Ser Lys Gln Gln Tyr Phe Gln Gly Ala Pro Ser Val Val Tyr Gly Leu
            530                   535                   540
Asn Cys Leu Asn Thr Leu Gly Ser Ala Leu Arg Thr Pro Phe Lys Gly
545                   550                   555                   560
Val His Phe Val Gly Thr Glu Thr Ser Leu Val Trp Lys Gly Tyr Met
                565                   570                   575
Glu Gly Ala Ile Arg Ser Gly Gln Arg Gly Ala Ala Glu Val Val Ala
            580                   585                   590
Ser Leu Val Pro Ala Ala
            595

<210> SEQ ID NO 43
<211> LENGTH: 1928
<212> TYPE: DNA
<213> ORGANISM: Rhinocladiella atrovirens
<220> FEATURE:
<221> NAME/KEY: Intron
<222> LOCATION: (739)..(811)
<223> OTHER INFORMATION:
<220> FEATURE:
<221> NAME/KEY: Intron
<222> LOCATION: (1134)..(1186)
<223> OTHER INFORMATION:
```

<400> SEQUENCE: 43

```
atggcacttg caccgagcta catcaatccc caaacctcg cctccccagc agggtattcc      60
tacgtcggcg taggcccaaa cggagggagg tatgtgacaa tagctggaca gattggacaa     120
gacgcttcgg ccgtgacaga ccctgcctac gagaaacagg ttgcccaagc attcgccaac    180
ctgcgagctt gtcttgctgc agttggagcc acttcaaacg acattaccaa gctcaattac    240
tacatcgtcg actacaaccc gagcaaactc accgcaattg agatgggct gaaggctacc     300
tttgcccttg acaggctccc tccttgcacg ctggtgccag tgccggccct ggcttcacct    360
gaatacctct ttgaggttga tgccacggcg ctggttccag acactcaac cccagacaat     420
gttgcggacg tggtcgtggt gggcgctggc ttgagcggtt tggagacggc acgcaaagtc    480
caggctgccg ggctgtcctg cctcgttctt gaggcgatgg atcgtgtggg gggaaagact    540
ctgagcgtac aatcgggtcc cggcaggacg actatcaatg acctcggcgc tgcgtggatc    600
aatgacagca accaaagcga agtattcaaa ttatttgaaa gatttcattt ggagggcgag    660
ctccagagga cgaccggaaa ttcaatccat caagcacaag acgtacaac cactacagct     720
ccttatggtg attccctggt aagcacaatt ccatcttgtg atgagacctc tgtcgtgtgt    780
agaatacagt cgctgactcc acatcgtcca gctgagcgag gaggttgcaa gtgcactcgc    840
ggaactcctt cccgcatggt ctcagctgat cgaagagcat agtcttgaag accccaaggc    900
gagccctcaa gcgaagcagc tcgacagtgt gagcttcgca cactactgtg agaaggatct    960
aaacttgcct gctgttctcg gcgtggcaaa ccagatcaca cgcgctctgc tcggtgtgga   1020
agcccacgag atcagcatgt tttttctcac cgactacatc aagagtgcca ccggtctcag   1080
taatattgtc tcggataaga aagacggtgg gcagtatatg cgatgcaaaa caggtgcgtg   1140
tggtgttctc tcagtgggag actcgtttct tagtggtcat tccaggtatg cagtcgcttt   1200
gccatgccat gtcaaaggaa cttgttccag gctcagtgca cctcaacacc ccgtcgccg    1260
aaattgagca gtcggcatcc ggctgtacag tacgatcggc tcgggcggc gtgttccgaa    1320
gtaaaaaggt ggtggtttcg ttaccgacaa ccttgtatcc caccttgata ttttcaccac    1380
ctcttcccgc cgagaagcaa gcattggctg aaaaatccat cctgggctac tatagcaaga   1440
tagtcttcgt atgggacaag ccgtggtggc gcgaacaagg cttctcgggc gtcctccaat   1500
cgagctgtga ccccatctca tttgccagag ataccagcat cgaagtcgat cggcaatggt   1560
ccattacctg tttcatggtc ggagacccgg gacggaagtg gtcccaacag tccaagcagg   1620
tacgacagaa gtctgtctgg aaccaactcc gcgcagccta cgagaacgcc ggggcccaag   1680
tcccagagcc ggccaacgtg ctcgagatcg agtggtcgaa gcagcagtat ttccaaggag   1740
cgccgagcgc cgtctatggg ctgaactgtc tcaacacact gggttcggcg ctcagaacgc   1800
cgttcaaggg tgttcatttc gttggaacgg agacgtcttt ggtttggaaa gggtatatgg   1860
aagggggccat acgatcgggt cagcgaggcg ctgcagaagt tgtggctagc ctggtgccag   1920
cagcatag                                                          1928
```

<210> SEQ ID NO 44
<211> LENGTH: 591
<212> TYPE: PRT
<213> ORGANISM: Rhinocladiella atrovirens

<400> SEQUENCE: 44

```
Met Ala Leu Ala Pro Ser Tyr Ile Asn Pro Pro Asn Leu Ala Ser Pro
 1               5                  10                  15
```

-continued

```
Ala Gly Tyr Ser Tyr Val Gly Val Gly Pro Asn Gly Gly Arg Tyr Val
             20                  25                  30

Thr Ile Ala Gly Gln Ile Gly Gln Asp Ala Ser Ala Val Thr Asp Pro
         35                  40                  45

Ala Tyr Glu Lys Gln Val Ala Gln Ala Phe Ala Asn Leu Arg Ala Cys
 50                  55                  60

Leu Ala Ala Val Gly Ala Thr Ser Asn Asp Ile Thr Lys Leu Asn Tyr
 65                  70                  75                  80

Tyr Ile Val Asp Tyr Asn Pro Ser Lys Leu Thr Ala Ile Gly Asp Gly
                 85                  90                  95

Leu Lys Ala Thr Phe Ala Leu Asp Arg Leu Pro Pro Cys Thr Leu Val
             100                 105                 110

Pro Val Pro Ala Leu Ala Ser Pro Glu Tyr Leu Phe Glu Val Asp Ala
             115                 120                 125

Thr Ala Leu Val Pro Gly His Ser Thr Pro Asp Asn Val Ala Asp Val
 130                 135                 140

Val Val Val Gly Ala Gly Leu Ser Gly Leu Glu Thr Ala Arg Lys Val
145                 150                 155                 160

Gln Ala Ala Gly Leu Ser Cys Leu Val Leu Glu Ala Met Asp Arg Val
                 165                 170                 175

Gly Gly Lys Thr Leu Ser Val Gln Ser Gly Gly Arg Thr Thr Ile Asn
             180                 185                 190

Asp Leu Gly Ala Ala Trp Ile Asn Asp Ser Asn Gln Ser Glu Val Lys
         195                 200                 205

Leu Phe Glu Arg Phe His Leu Glu Gly Glu Leu Gln Arg Thr Thr Gly
210                 215                 220

Asn Ser Ile His Gln Ala Gln Asp Gly Thr Thr Thr Ala Pro Tyr
225                 230                 235                 240

Gly Ser Leu Leu Ser Glu Glu Val Ala Ser Ala Leu Ala Glu Leu Leu
                 245                 250                 255

Pro Ala Ser Gln Leu Ile Glu Glu His Ser Leu Glu Asp Pro Lys Ala
             260                 265                 270

Ser Pro Gln Ala Lys Gln Leu Asp Ser Val Ser Phe Ala His Tyr Cys
         275                 280                 285

Glu Lys Leu Asn Leu Ala Val Leu Gly Val Ala Asn Gln Ile Thr Arg
290                 295                 300

Ala Leu Leu Gly Val Glu Ala His Glu Ile Ser Met Phe Phe Leu Thr
305                 310                 315                 320

Asp Tyr Ile Lys Ser Ala Thr Gly Leu Ser Asn Ile Val Ser Asp Lys
                 325                 330                 335

Lys Asp Gly Gly Gln Tyr Met Arg Cys Lys Thr Gly Met Gln Ser Leu
             340                 345                 350

Cys His Ala Met Ser Lys Glu Leu Val Pro Gly Ser Val His Leu Asn
         355                 360                 365

Thr Pro Val Ala Glu Ile Glu Gln Ser Ala Ser Gly Cys Thr Val Arg
370                 375                 380

Ser Ala Ser Gly Gly Val Phe Arg Ser Lys Lys Val Val Leu Pro Thr
385                 390                 395                 400

Leu Tyr Pro Thr Leu Ile Phe Ser Pro Pro Leu Pro Ala Glu Lys Gln
                 405                 410                 415

Ala Leu Ala Glu Lys Ser Ile Leu Gly Tyr Tyr Ser Lys Ile Val Phe
             420                 425                 430

Val Trp Asp Lys Pro Trp Trp Arg Glu Gln Gly Phe Ser Gly Val Leu
```

-continued

```
                   435                 440                 445
Gln Ser Ser Cys Asp Pro Ile Ser Phe Ala Arg Asp Thr Ser Ile Glu
            450                 455                 460
Val Asp Arg Gln Trp Ser Ile Thr Cys Phe Met Val Gly Asp Pro Gly
465                 470                 475                 480
Arg Lys Trp Ser Gln Gln Ser Lys Gln Val Arg Gln Lys Ser Val Trp
                485                 490                 495
Asn Gln Leu Arg Ala Ala Tyr Glu Asn Ala Gly Ala Gln Val Pro Glu
            500                 505                 510
Pro Ala Asn Val Leu Glu Ile Glu Trp Ser Lys Gln Gln Tyr Phe Gln
            515                 520                 525
Gly Ala Pro Ser Ala Val Tyr Gly Leu Asn Cys Leu Asn Thr Leu Gly
            530                 535                 540
Ser Ala Leu Arg Thr Pro Phe Lys Gly Val His Phe Val Gly Thr Glu
545                 550                 555                 560
Thr Ser Leu Val Trp Lys Gly Tyr Met Glu Gly Ala Ile Arg Ser Gly
                565                 570                 575
Gln Arg Gly Ala Ala Glu Val Val Ala Ser Leu Val Pro Ala Ala
            580                 585                 590
```

<210> SEQ ID NO 45
<211> LENGTH: 1928
<212> TYPE: DNA
<213> ORGANISM: Rhinocladiella atrovirens
<220> FEATURE:
<221> NAME/KEY: Intron
<222> LOCATION: (739)..(811)
<223> OTHER INFORMATION:
<220> FEATURE:
<221> NAME/KEY: Intron
<222> LOCATION: (1134)..(1185)
<223> OTHER INFORMATION:

<400> SEQUENCE: 45

| | | | | | |
|---|---|---|---|---|---|
| atggcacttg | caccgagcta | catcaatccc | ccaaacctcg | cctccccagc | agggtattcc | 60 |
| cacgtcggcg | taggcccaaa | cggagggagg | tatgtgacaa | tagctggaca | gattggacaa | 120 |
| gacgcttcgg | ccgtgacaga | ccctgcctac | gagaaacagg | ttgcccaagc | attcgccaac | 180 |
| ctgcgagctt | gtcttgctgc | agttggagcc | acttcaaacg | acattaccaa | gctcaattac | 240 |
| tacatcgtcg | actacaaccc | gagcaaactc | accgcaattg | agatgggct | gaaggctacc | 300 |
| tttgcccttg | acaggctccc | tccttgcacg | ctggtgccag | tgccggccct | ggcttcacct | 360 |
| gaatacctct | tgaggttga | tgctacggcg | ctggttccag | acactcaac | cccagacaat | 420 |
| gttgcggacg | tggtcgtggt | gggcgctggc | ttgagcggtt | tggagacggc | acgcaaagtc | 480 |
| caggctgccg | ggctgtcctg | cctcgttctt | gaggcgatgg | atcgtgtggg | gggaaagact | 540 |
| ctgagcgtac | aatcgggtcc | cggcaggacg | actatcaatg | acctcggcgc | tgcgtggatc | 600 |
| aatgacagca | accaaagcga | agtattcaaa | ttatttgaaa | gatttcattt | ggagggcgag | 660 |
| ctccagagga | cgaccggaaa | ttcaatccat | caagcacaag | acgtacaac | cactacagct | 720 |
| ccttatggtg | attccctggt | aggcacaatt | ccatcttgtg | atgagacctc | tgtcgtgtgt | 780 |
| agaatacagt | cgctgactcc | acatcgtcca | gctgagcgag | gaggttgcaa | gtgcactcgc | 840 |
| ggaactcctt | cccgcatggc | ctcagctgat | cgaagagcat | agtcttgaag | accccaaggc | 900 |
| gagccctcaa | gcgaagcagc | tcgacagtgt | gagcttcgca | cactactgtg | agaaggatct | 960 |
| aaacttgcct | gctgttctcg | gcgtggcaaa | ccagatcaca | cgcgctctgc | tcggtgtgga | 1020 |

-continued

```
agcccacgag atcagcatgc tttttctcac cgactacatc aagagtgcca ccggtctcag    1080
taatattgtc tcggataaga aagacggtgg gcagtatatg cgatgcaaaa caggtgcgtg    1140
tggtgttctc tcagtgggag actcgtttct tagtggtcat tccaggtatg cagtcgcttt    1200
gccatgccat gtcaaaggaa cttgttccag gctcagtgca cctcaacacc cccgtcgccg    1260
aaattgagca gtcggcatcc ggctgtacag tacgatcggc ctcgggcggc gtgttccgaa    1320
gtaaaaaggt ggtggtttcg ttaccgacaa ccttgtatcc caccttgata ttttcaccac    1380
ctcttcccgc cgagaagcaa gcattggctg aaaaatccat cctgggctac tatagcaaga    1440
tagtcttcgt atgggacaag ctgtggtggc gcgaacaagg cttctcgggc gtcctccaat    1500
cgagctgtga ccccatctca tttgccagag ataccagcat cgaagtcgat cggcaatggt    1560
ccattacctg tttcatggtc ggagacccgg gacggaagtg gtcccaacag tccaagcagg    1620
tacgacagaa gtctgtctgg aaccaactcc gcgcagccta cgagaacgcc ggggcccaag    1680
tcccagagcc ggccaacgtg ctcgagatcg agtggtcgaa gcagcagtat ttccaaggag    1740
cgccgagcgc cgtctatggg ctgaactgtc tcaacacact gggttcggcg ctcagaacgc    1800
cgttcaaggg tgttcatttc gttggaacgg agacgtcttt ggtttggaaa gggtatatgg    1860
aagggcccat acgatcgggt cagcgaggcg ctgcagaagt tgtgcctagc ctggtgccag    1920
cagcatag                                                              1928
```

<210> SEQ ID NO 46
<211> LENGTH: 591
<212> TYPE: PRT
<213> ORGANISM: Rhinocladiella atrovirens

<400> SEQUENCE: 46

```
Met Ala Leu Ala Pro Ser Tyr Ile Asn Pro Pro Asn Ala Ser Pro Ala
1               5                   10                  15

Gly Tyr Ser His Val Gly Val Gly Pro Asn Gly Gly Arg Tyr Val Thr
            20                  25                  30

Ile Ala Gly Gln Ile Gly Gln Asp Ala Ser Ala Val Thr Asp Pro Ala
        35                  40                  45

Tyr Glu Lys Gln Val Ala Gln Ala Phe Ala Asn Leu Arg Ala Cys Leu
    50                  55                  60

Ala Ala Val Gly Ala Thr Ser Asn Asp Ile Thr Lys Leu Asn Tyr Tyr
65                  70                  75                  80

Ile Val Asp Tyr Asn Pro Ser Lys Leu Thr Ala Ile Gly Asp Gly Leu
                85                  90                  95

Lys Ala Thr Phe Ala Leu Asp Arg Leu Pro Pro Cys Thr Leu Val Pro
            100                 105                 110

Val Pro Ala Leu Ala Ser Pro Glu Tyr Leu Phe Glu Val Asp Ala Thr
        115                 120                 125

Ala Leu Val Pro Gly His Ser Thr Pro Asp Asn Val Ala Asp Val Val
    130                 135                 140

Val Val Gly Ala Gly Leu Ser Gly Leu Glu Thr Ala Arg Lys Val Gln
145                 150                 155                 160

Ala Ala Gly Leu Ser Cys Leu Val Leu Glu Ala Met Asp Arg Val Gly
                165                 170                 175

Gly Lys Thr Leu Ser Val Gln Ser Gly Pro Gly Arg Thr Thr Ile Asn
            180                 185                 190

Asp Leu Gly Ala Ala Trp Ile Asn Asp Ser Asn Gln Ser Glu Val Phe
        195                 200                 205
```

```
Lys Leu Phe Glu Arg Phe His Leu Gly Glu Leu Gln Arg Thr Thr
    210                 215                 220

Gly Asn Ser Ile His Gln Ala Gln Asp Gly Thr Thr Thr Ala Pro
225                 230                 235                 240

Tyr Gly Asp Ser Leu Leu Ser Glu Val Ala Ser Ala Leu Ala Glu
                245                 250                 255

Leu Leu Pro Ala Trp Ser Gln Leu Ile Glu His Ser Leu Glu Asp
            260                 265                 270

Pro Lys Ala Ser Pro Gln Ala Lys Gln Leu Asp Ser Val Ser Phe Ala
        275                 280                 285

His Tyr Cys Glu Lys Asp Leu Asn Leu Pro Ala Val Leu Gly Val Ala
    290                 295                 300

Asn Gln Ile Thr Arg Ala Leu Leu Gly Val Glu Ala His Glu Ile Ser
305                 310                 315                 320

Met Leu Phe Leu Thr Asp Tyr Ile Lys Ser Ala Thr Gly Leu Ser Asn
                325                 330                 335

Ile Val Ser Asp Lys Lys Asp Gly Gly Gln Tyr Met Arg Cys Lys Thr
            340                 345                 350

Gly Met Gln Ser Leu Cys His Ala Met Ser Lys Glu Leu Val Pro Gly
        355                 360                 365

Ser Val His Leu Asn Thr Pro Val Ala Glu Ile Glu Gln Ser Ala Ser
    370                 375                 380

Gly Cys Thr Val Arg Ser Ala Ser Gly Val Phe Arg Ser Lys Lys
385                 390                 395                 400

Val Ser Leu Pro Thr Thr Leu Tyr Pro Thr Leu Ile Phe Ser Pro Leu
                405                 410                 415

Pro Ala Glu Lys Gln Ala Leu Ala Glu Lys Ser Ile Gly Tyr Tyr Ser
            420                 425                 430

Lys Ile Val Phe Val Asp Lys Leu Trp Trp Arg Glu Gln Gly Phe Ser
        435                 440                 445

Gly Val Leu Gln Ser Ser Cys Asp Pro Ile Ser Phe Ala Arg Asp Thr
450                 455                 460

Ser Ile Glu Val Asp Arg Gln Ser Ile Thr Cys Phe Met Val Gly Asp
465                 470                 475                 480

Pro Arg Lys Trp Ser Gln Gln Ser Lys Gln Val Arg Gln Lys Ser Val
                485                 490                 495

Trp Asn Gln Leu Arg Ala Ala Tyr Glu Asn Ala Gly Ala Gln Val Pro
            500                 505                 510

Glu Pro Ala Asn Val Leu Glu Ile Glu Trp Ser Lys Gln Gln Tyr Phe
        515                 520                 525

Gln Ala Pro Ser Ala Val Tyr Gly Leu Asn Cys Leu Asn Thr Leu Gly
    530                 535                 540

Ser Ala Leu Arg Thr Pro Phe Lys Gly Val His Phe Val Gly Thr Glu
545                 550                 555                 560

Thr Ser Leu Val Trp Lys Gly Tyr Met Glu Gly Ala Ile Arg Ser Gly
                565                 570                 575

Gln Arg Gly Ala Ala Glu Val Val Pro Ser Leu Val Pro Ala Ala
            580                 585                 590
```

<210> SEQ ID NO 47
<211> LENGTH: 600
<212> TYPE: PRT
<213> ORGANISM: Exophiala spinifera

<400> SEQUENCE: 47

-continued

```
Met Ala Leu Ala Pro Ser Tyr Ile Asn Pro Asn Val Ala Ser Pro
 1               5                  10                  15

Ala Gly Tyr Ser His Val Gly Val Gly Pro Asp Gly Gly Arg Tyr Val
                20                  25                  30

Thr Ile Ala Gly Gln Ile Gly Gln Asp Ala Ser Gly Val Thr Asp Pro
                35                  40                  45

Ala Tyr Glu Lys Gln Val Ala Gln Ala Phe Ala Asn Leu Arg Ala Cys
        50                  55                  60

Leu Ala Ala Val Gly Ala Thr Ser Asn Asp Val Thr Lys Leu Asn Tyr
 65                  70                  75                  80

Tyr Ile Val Asp Tyr Ala Pro Ser Lys Leu Thr Ala Ile Gly Asp Gly
                    85                  90                  95

Leu Lys Ala Thr Phe Ala Leu Asp Arg Leu Pro Pro Cys Thr Leu Val
            100                 105                 110

Pro Val Ser Ala Leu Ser Ser Pro Glu Tyr Leu Phe Glu Val Asp Ala
            115                 120                 125

Thr Ala Leu Val Pro Gly His Thr Thr Pro Asp Asn Val Ala Asp Val
            130                 135                 140

Val Val Val Gly Ala Gly Leu Ser Gly Leu Glu Thr Ala Arg Lys Val
145                 150                 155                 160

Gln Ala Ala Gly Leu Ser Cys Leu Val Leu Glu Ala Met Asp Arg Val
                165                 170                 175

Gly Gly Lys Thr Leu Ser Val Gln Ser Gly Pro Gly Arg Thr Thr Ile
                180                 185                 190

Asn Asp Leu Gly Ala Ala Trp Ile Asn Asp Ser Asn Gln Ser Glu Val
            195                 200                 205

Ser Arg Leu Phe Glu Arg Phe His Leu Glu Gly Glu Leu Gln Arg Thr
            210                 215                 220

Thr Gly Asn Ser Ile His Gln Ala Gln Asp Gly Thr Thr Thr Thr Ala
225                 230                 235                 240

Pro Tyr Gly Asp Ser Leu Leu Ser Glu Glu Val Ala Ser Ala Leu Ala
                    245                 250                 255

Glu Leu Leu Pro Val Trp Ser Gln Leu Ile Glu Glu His Ser Leu Gln
                260                 265                 270

Asp Leu Lys Ala Ser Pro Gln Ala Lys Arg Leu Asp Ser Val Ser Phe
            275                 280                 285

Ala His Tyr Cys Glu Lys Glu Leu Asn Leu Pro Ala Val Leu Gly Val
            290                 295                 300

Ala Asn Gln Ile Thr Arg Ala Leu Leu Gly Val Glu Ala His Glu Ile
305                 310                 315                 320

Ser Met Leu Phe Leu Thr Asp Tyr Ile Lys Ser Ala Thr Gly Leu Ser
                    325                 330                 335

Asn Ile Phe Ser Asp Lys Lys Asp Gly Gly Gln Tyr Met Arg Cys Lys
                340                 345                 350

Thr Gly Met Gln Ser Ile Cys His Ala Met Ser Lys Glu Leu Val Pro
            355                 360                 365

Gly Ser Val His Leu Asn Thr Pro Val Ala Glu Ile Glu Gln Ser Ala
        370                 375                 380

Ser Gly Cys Thr Val Arg Ser Ala Ser Gly Ala Val Phe Arg Ser Lys
385                 390                 395                 400

Lys Val Val Val Ser Leu Pro Thr Thr Leu Tyr Pro Thr Leu Thr Phe
                    405                 410                 415
```

```
Ser Pro Pro Leu Pro Ala Glu Lys Gln Ala Leu Ala Glu Asn Ser Ile
            420                 425                 430

Leu Gly Tyr Tyr Ser Lys Ile Val Phe Val Trp Asp Lys Pro Trp Trp
                435                 440                 445

Arg Glu Gln Gly Phe Ser Gly Val Leu Gln Ser Ser Cys Asp Pro Ile
        450                 455                 460

Ser Phe Ala Arg Asp Thr Ser Ile Asp Val Asp Arg Gln Trp Ser Ile
465                 470                 475                 480

Thr Cys Phe Met Val Gly Asp Pro Gly Arg Lys Trp Ser Gln Gln Ser
                485                 490                 495

Lys Gln Val Arg Gln Lys Ser Val Trp Asp Gln Leu Arg Ala Ala Tyr
            500                 505                 510

Glu Asn Ala Gly Ala Gln Val Pro Glu Pro Ala Asn Val Leu Glu Ile
            515                 520                 525

Glu Trp Ser Lys Gln Gln Tyr Phe Gln Gly Ala Pro Ser Ala Val Tyr
            530                 535                 540

Gly Leu Asn Asp Leu Ile Thr Leu Gly Ser Ala Leu Arg Thr Pro Phe
545                 550                 555                 560

Lys Ser Val His Phe Val Gly Thr Glu Thr Ser Leu Val Trp Lys Gly
                565                 570                 575

Tyr Met Glu Gly Ala Ile Arg Ser Gly Gln Arg Gly Ala Ala Glu Val
                580                 585                 590

Val Ala Ser Leu Val Pro Ala Ala
            595                 600

<210> SEQ ID NO 48
<211> LENGTH: 1392
<212> TYPE: DNA
<213> ORGANISM: Unknown
<220> FEATURE:
<223> OTHER INFORMATION: Cys (-) APAO; removal of cysteine 461
<220> FEATURE:
<221> NAME/KEY: CDS
<222> LOCATION: (1)..(1392)
<223> OTHER INFORMATION:

<400> SEQUENCE: 48 aaa gac aac gtt gcg gac gtg gta gtg gtg ggc gct ggc ttg agc ggt       48
Lys Asp Asn Val Ala Asp Val Val Val Val Gly Ala Gly Leu Ser Gly
1               5                   10                  15 ttg gag acg gca cgc aaa gtc cag gcc gcc ggt ctg tcc tgc ctc gtt       96
Leu Glu Thr Ala Arg Lys Val Gln Ala Ala Gly Leu Ser Cys Leu Val
                20                  25                  30 ctt gag gcg atg gat cgt gta ggg gga aag act ctg agc gta caa tcg      144
Leu Glu Ala Met Asp Arg Val Gly Gly Lys Thr Leu Ser Val Gln Ser
            35                  40                  45 ggt ccc ggc agg acg act atc aac gac ctc ggc gct gcg tgg atc aat      192
Gly Pro Gly Arg Thr Thr Ile Asn Asp Leu Gly Ala Ala Trp Ile Asn
        50                  55                  60 gac agc aac caa agc gaa gta tcc aga ttg ttt gaa aga ttt cat ttg      240
Asp Ser Asn Gln Ser Glu Val Ser Arg Leu Phe Glu Arg Phe His Leu
65                  70                  75                  80 gag ggc gag ctc cag agg acg act gga aat tca atc cat caa gca caa      288
Glu Gly Glu Leu Gln Arg Thr Thr Gly Asn Ser Ile His Gln Ala Gln
                85                  90                  95 gac ggt aca acc act aca gct cct tat ggt gac tcc ttg ctg agc gag      336
Asp Gly Thr Thr Thr Thr Ala Pro Tyr Gly Asp Ser Leu Leu Ser Glu
                100                 105                 110 gag gtt gca agt gca ctt gcg gaa ctc ctc ccc gta tgg tct cag ctg      384
```

```
Glu Val Ala Ser Ala Leu Ala Glu Leu Leu Pro Val Trp Ser Gln Leu
            115                 120                 125 atc gaa gag cat agc ctt caa gac ctc aag gcg agc cct cag gcg aag          432
Ile Glu Glu His Ser Leu Gln Asp Leu Lys Ala Ser Pro Gln Ala Lys
        130                 135                 140 cgg ctc gac agt gtg agc ttc gcg cac tac tgt gag aag gaa cta aac          480
Arg Leu Asp Ser Val Ser Phe Ala His Tyr Cys Glu Lys Glu Leu Asn
145                 150                 155                 160 ttg cct gct gtt ctc ggc gta gca aac cag atc aca cgc gct ctg ctc          528
Leu Pro Ala Val Leu Gly Val Ala Asn Gln Ile Thr Arg Ala Leu Leu
                165                 170                 175 ggt gtg gaa gcc cac gag atc agc atg ctt ttt ctc acc gac tac atc          576
Gly Val Glu Ala His Glu Ile Ser Met Leu Phe Leu Thr Asp Tyr Ile
            180                 185                 190 aag agt gcc acc ggt ctc agt aat att ttc tcg gac aag aaa gac ggc          624
Lys Ser Ala Thr Gly Leu Ser Asn Ile Phe Ser Asp Lys Lys Asp Gly
        195                 200                 205 ggg cag tat atg cga tgc aaa aca ggt atg cag tcg att tgc cat gcc          672
Gly Gln Tyr Met Arg Cys Lys Thr Gly Met Gln Ser Ile Cys His Ala
    210                 215                 220 atg tca aag gaa ctt gtt cca ggc tca gtg cac ctc aac acc ccc gtc          720
Met Ser Lys Glu Leu Val Pro Gly Ser Val His Leu Asn Thr Pro Val
225                 230                 235                 240 gct gaa att gag cag tcg gca tcc ggc tgt aca gta cga tcg gcc tcg          768
Ala Glu Ile Glu Gln Ser Ala Ser Gly Cys Thr Val Arg Ser Ala Ser
                245                 250                 255 ggc gcc gtg ttc cga agc aaa aag gtg gtg gtt tcg tta ccg aca acc          816
Gly Ala Val Phe Arg Ser Lys Lys Val Val Val Ser Leu Pro Thr Thr
            260                 265                 270 ttg tat ccc acc ttg aca ttt tca cca cct ctt ccc gcc gag aag caa          864
Leu Tyr Pro Thr Leu Thr Phe Ser Pro Pro Leu Pro Ala Glu Lys Gln
        275                 280                 285 gca ttg gcg gaa aat tct atc ctg ggc tac tat agc aag ata gtc ttc          912
Ala Leu Ala Glu Asn Ser Ile Leu Gly Tyr Tyr Ser Lys Ile Val Phe
    290                 295                 300 gta tgg gac aag ccg tgg tgg cgc gaa caa ggc ttc tcg ggc gtc ctc          960
Val Trp Asp Lys Pro Trp Trp Arg Glu Gln Gly Phe Ser Gly Val Leu
305                 310                 315                 320 caa tcg agc tcc gac ccc atc tca ttt gcc aga gat acc agc atc gac         1008
Gln Ser Ser Ser Asp Pro Ile Ser Phe Ala Arg Asp Thr Ser Ile Asp
                325                 330                 335 gtc gat cga caa tgg tcc att acc tgt ttc atg gtc gga gac ccg gga         1056
Val Asp Arg Gln Trp Ser Ile Thr Cys Phe Met Val Gly Asp Pro Gly
            340                 345                 350 cgg aag tgg tcc caa cag tcc aag cag gta cga caa aag tct gtc tgg         1104
Arg Lys Trp Ser Gln Gln Ser Lys Gln Val Arg Gln Lys Ser Val Trp
        355                 360                 365 gac caa ctc cgc gca gcc tac gag aac gcc ggg gcc caa gtc cca gag         1152
Asp Gln Leu Arg Ala Ala Tyr Glu Asn Ala Gly Ala Gln Val Pro Glu
    370                 375                 380 ccg gcc aac gtg ctc gaa atc gag tgg tcg aag cag cag tat ttc caa         1200
Pro Ala Asn Val Leu Glu Ile Glu Trp Ser Lys Gln Gln Tyr Phe Gln
385                 390                 395                 400 gga gct ccg agc gcc gtc tat ggg ctg aac gat ctc atc aca ctg ggt         1248
Gly Ala Pro Ser Ala Val Tyr Gly Leu Asn Asp Leu Ile Thr Leu Gly
                405                 410                 415 tcg gcg ctc aga acg ccg ttc aag agt gtt cat ttc gtt gga acg gag         1296
Ser Ala Leu Arg Thr Pro Phe Lys Ser Val His Phe Val Gly Thr Glu
            420                 425                 430
```

```
acg tct tta gtt tgg aaa ggg tat atg gaa ggg gcc ata cga tcg ggt    1344
Thr Ser Leu Val Trp Lys Gly Tyr Met Glu Gly Ala Ile Arg Ser Gly
        435                 440                 445 caa cga ggt gct gca gaa gtt gtg gct agc ctg gtg cca gca gca tag    1392
Gln Arg Gly Ala Ala Glu Val Val Ala Ser Leu Val Pro Ala Ala
    450                 455                 460
```

<210> SEQ ID NO 49
<211> LENGTH: 463
<212> TYPE: PRT
<213> ORGANISM: Unknown
<220> FEATURE:
<223> OTHER INFORMATION: Cys (-) APAO; removal of cysteine 461

<400> SEQUENCE: 49

```
Lys Asp Asn Val Ala Asp Val Val Val Gly Ala Gly Leu Ser Gly
1               5                   10                  15

Leu Glu Thr Ala Arg Lys Val Gln Ala Ala Gly Leu Ser Cys Leu Val
            20                  25                  30

Leu Glu Ala Met Asp Arg Val Gly Gly Lys Thr Leu Ser Val Gln Ser
            35                  40                  45

Gly Pro Gly Arg Thr Thr Ile Asn Asp Leu Gly Ala Ala Trp Ile Asn
    50                  55                  60

Asp Ser Asn Gln Ser Glu Val Ser Arg Leu Phe Glu Arg Phe His Leu
65                  70                  75                  80

Glu Gly Glu Leu Gln Arg Thr Thr Gly Asn Ser Ile His Gln Ala Gln
                85                  90                  95

Asp Gly Thr Thr Thr Thr Ala Pro Tyr Gly Asp Ser Leu Leu Ser Glu
            100                 105                 110

Glu Val Ala Ser Ala Leu Ala Glu Leu Leu Pro Val Trp Ser Gln Leu
            115                 120                 125

Ile Glu Glu His Ser Leu Gln Asp Leu Lys Ala Ser Pro Gln Ala Lys
        130                 135                 140

Arg Leu Asp Ser Val Ser Phe Ala His Tyr Cys Glu Lys Glu Leu Asn
145                 150                 155                 160

Leu Pro Ala Val Leu Gly Val Ala Asn Gln Ile Thr Arg Ala Leu Leu
                165                 170                 175

Gly Val Glu Ala His Glu Ile Ser Met Leu Phe Leu Thr Asp Tyr Ile
            180                 185                 190

Lys Ser Ala Thr Gly Leu Ser Asn Ile Phe Ser Asp Lys Lys Asp Gly
        195                 200                 205

Gly Gln Tyr Met Arg Cys Lys Thr Gly Met Gln Ser Ile Cys His Ala
    210                 215                 220

Met Ser Lys Glu Leu Val Pro Gly Ser Val His Leu Asn Thr Pro Val
225                 230                 235                 240

Ala Glu Ile Glu Gln Ser Ala Ser Gly Cys Thr Val Arg Ser Ala Ser
                245                 250                 255

Gly Ala Val Phe Arg Ser Lys Lys Val Val Ser Leu Pro Thr Thr
            260                 265                 270

Leu Tyr Pro Thr Leu Thr Phe Ser Pro Pro Leu Pro Ala Glu Lys Gln
        275                 280                 285

Ala Leu Ala Glu Asn Ser Ile Leu Gly Tyr Tyr Ser Lys Ile Val Phe
    290                 295                 300

Val Trp Asp Lys Pro Trp Trp Arg Glu Gln Gly Phe Ser Gly Val Leu
305                 310                 315                 320

Gln Ser Ser Ser Asp Pro Ile Ser Phe Ala Arg Asp Thr Ser Ile Asp
```

-continued

|  |  |  | 325 |  |  |  | 330 |  |  |  | 335 |  |  |
|---|---|---|---|---|---|---|---|---|---|---|---|---|---|
| Val | Asp | Arg | Gln | Trp | Ser | Ile | Thr | Cys | Phe | Met | Val | Gly | Asp | Pro | Gly |
|  |  |  | 340 |  |  |  | 345 |  |  |  | 350 |  |  |

Val Asp Arg Gln Trp Ser Ile Thr Cys Phe Met Val Gly Asp Pro Gly
                340                 345                 350

Arg Lys Trp Ser Gln Gln Ser Lys Gln Val Arg Gln Lys Ser Val Trp
            355                 360                 365

Asp Gln Leu Arg Ala Ala Tyr Glu Asn Ala Gly Ala Gln Val Pro Glu
        370                 375                 380

Pro Ala Asn Val Leu Glu Ile Glu Trp Ser Lys Gln Gln Tyr Phe Gln
385                 390                 395                 400

Gly Ala Pro Ser Ala Val Tyr Gly Leu Asn Asp Leu Ile Thr Leu Gly
                405                 410                 415

Ser Ala Leu Arg Thr Pro Phe Lys Ser Val His Phe Val Gly Thr Glu
                420                 425                 430

Thr Ser Leu Val Trp Lys Gly Tyr Met Glu Gly Ala Ile Arg Ser Gly
            435                 440                 445

Gln Arg Gly Ala Ala Glu Val Val Ala Ser Leu Val Pro Ala Ala
            450                 455                 460

<210> SEQ ID NO 50
<211> LENGTH: 1392
<212> TYPE: DNA
<213> ORGANISM: Unknown
<220> FEATURE:
<223> OTHER INFORMATION: Cys (-) APAO; removal of cysteines 359 and 461
<220> FEATURE:
<221> NAME/KEY: CDS
<222> LOCATION: (1)..(1392)
<223> OTHER INFORMATION:

<400> SEQUENCE: 50

```
aaa gac aac gtt gcg gac gtg gta gtg gtg ggc gct ggc ttg agc ggt        48
Lys Asp Asn Val Ala Asp Val Val Val Val Gly Ala Gly Leu Ser Gly
1               5                   10                  15 ttg gag acg gca cgc aaa gtc cag gcc gcc ggt ctg tcc tgc ctc gtt        96
Leu Glu Thr Ala Arg Lys Val Gln Ala Ala Gly Leu Ser Cys Leu Val
            20                  25                  30 ctt gag gcg atg gat cgt gta ggg gga aag act ctg agc gta caa tcg       144
Leu Glu Ala Met Asp Arg Val Gly Gly Lys Thr Leu Ser Val Gln Ser
        35                  40                  45 ggt ccc ggc agg acg act atc aac gac ctc ggc gct gcg tgg atc aat       192
Gly Pro Gly Arg Thr Thr Ile Asn Asp Leu Gly Ala Ala Trp Ile Asn
    50                  55                  60 gac agc aac caa agc gaa gta tcc aga ttg ttt gaa aga ttt cat ttg       240
Asp Ser Asn Gln Ser Glu Val Ser Arg Leu Phe Glu Arg Phe His Leu
65                  70                  75                  80 gag ggc gag ctc cag agg acg act gga aat tca atc cat caa gca caa       288
Glu Gly Glu Leu Gln Arg Thr Thr Gly Asn Ser Ile His Gln Ala Gln
                85                  90                  95 gac ggt aca acc act aca gct cct tat ggt gac tcc ttg ctg agc gag       336
Asp Gly Thr Thr Thr Thr Ala Pro Tyr Gly Asp Ser Leu Leu Ser Glu
            100                 105                 110 gag gtt gca agt gca ctt gcg gaa ctc ctc ccc gta tgg tct cag ctg       384
Glu Val Ala Ser Ala Leu Ala Glu Leu Leu Pro Val Trp Ser Gln Leu
        115                 120                 125 atc gaa gag cat agc ctt caa gac ctc aag gcg agc cct cag gcg aag       432
Ile Glu Glu His Ser Leu Gln Asp Leu Lys Ala Ser Pro Gln Ala Lys
    130                 135                 140 cgg ctc gac agt gtg agc ttc gcg cac tac tgt gag aag gaa cta aac       480
Arg Leu Asp Ser Val Ser Phe Ala His Tyr Cys Glu Lys Glu Leu Asn
145                 150                 155                 160
```

-continued

```
ttg cct gct gtt ctc ggc gta gca aac cag atc aca cgc gct ctg ctc    528
Leu Pro Ala Val Leu Gly Val Ala Asn Gln Ile Thr Arg Ala Leu Leu
            165                 170                 175 ggt gtg gaa gcc cac gag atc agc atg ctt ttt ctc acc gac tac atc    576
Gly Val Glu Ala His Glu Ile Ser Met Leu Phe Leu Thr Asp Tyr Ile
        180                 185                 190 aag agt gcc acc ggt ctc agt aat att ttc tcg gac aag aaa gac ggc    624
Lys Ser Ala Thr Gly Leu Ser Asn Ile Phe Ser Asp Lys Lys Asp Gly
    195                 200                 205 ggg cag tat atg cga tgc aaa aca ggt atg cag tcg att tcg cat gcc    672
Gly Gln Tyr Met Arg Cys Lys Thr Gly Met Gln Ser Ile Ser His Ala
210                 215                 220 atg tca aag gaa ctt gtt cca ggc tca gtg cac ctc aac acc ccc gtc    720
Met Ser Lys Glu Leu Val Pro Gly Ser Val His Leu Asn Thr Pro Val
225                 230                 235                 240 gct gaa att gag cag tcg gca tcc ggc tgt aca gta cga tcg gcc tcg    768
Ala Glu Ile Glu Gln Ser Ala Ser Gly Cys Thr Val Arg Ser Ala Ser
                245                 250                 255 ggc gcc gtg ttc cga agc aaa aag gtg gtg gtt tcg tta ccg aca acc    816
Gly Ala Val Phe Arg Ser Lys Lys Val Val Val Ser Leu Pro Thr Thr
            260                 265                 270 ttg tat ccc acc ttg aca ttt tca cca cct ctt ccc gcc gag aag caa    864
Leu Tyr Pro Thr Leu Thr Phe Ser Pro Pro Leu Pro Ala Glu Lys Gln
        275                 280                 285 gca ttg gcg gaa aat tct atc ctg ggc tac tat agc aag ata gtc ttc    912
Ala Leu Ala Glu Asn Ser Ile Leu Gly Tyr Tyr Ser Lys Ile Val Phe
    290                 295                 300 gta tgg gac aag ccg tgg tgg cgc gaa caa ggc ttc tcg ggc gtc ctc    960
Val Trp Asp Lys Pro Trp Trp Arg Glu Gln Gly Phe Ser Gly Val Leu
305                 310                 315                 320 caa tcg agc tcc gac ccc atc tca ttt gcc aga gat acc agc atc gac   1008
Gln Ser Ser Ser Asp Pro Ile Ser Phe Ala Arg Asp Thr Ser Ile Asp
                325                 330                 335 gtc gat cga caa tgg tcc att acc tgt ttc atg gtc gga gac ccg gga   1056
Val Asp Arg Gln Trp Ser Ile Thr Cys Phe Met Val Gly Asp Pro Gly
            340                 345                 350 cgg aag tgg tcc caa cag tcc aag cag gta cga caa aag tct gtc tgg   1104
Arg Lys Trp Ser Gln Gln Ser Lys Gln Val Arg Gln Lys Ser Val Trp
        355                 360                 365 gac caa ctc cgc gca gcc tac gag aac gcc ggg gcc caa gtc cca gag   1152
Asp Gln Leu Arg Ala Ala Tyr Glu Asn Ala Gly Ala Gln Val Pro Glu
    370                 375                 380 ccg gcc aac gtg ctc gaa atc gag tgg tcg aag cag cag tat ttc caa   1200
Pro Ala Asn Val Leu Glu Ile Glu Trp Ser Lys Gln Gln Tyr Phe Gln
385                 390                 395                 400 gga gct ccg agc gcc gtc tat ggg ctg aac gat ctc atc aca ctg ggt   1248
Gly Ala Pro Ser Ala Val Tyr Gly Leu Asn Asp Leu Ile Thr Leu Gly
                405                 410                 415 tcg gcg ctc aga acg ccg ttc aag agt gtt cat ttc gtt gga acg gag   1296
Ser Ala Leu Arg Thr Pro Phe Lys Ser Val His Phe Val Gly Thr Glu
            420                 425                 430 acg tct tta gtt tgg aaa ggg tat atg gaa ggg gcc ata cga tcg ggt   1344
Thr Ser Leu Val Trp Lys Gly Tyr Met Glu Gly Ala Ile Arg Ser Gly
        435                 440                 445 caa cga ggt gct gca gaa gtt gtg gct agc ctg gtg cca gca gca tag   1392
Gln Arg Gly Ala Ala Glu Val Val Ala Ser Leu Val Pro Ala Ala
    450                 455                 460
```

<210> SEQ ID NO 51

```
<211> LENGTH: 463
<212> TYPE: PRT
<213> ORGANISM: Unknown
<220> FEATURE:
<223> OTHER INFORMATION: Cys (-) APAO; removal of cysteines 359 and 461

<400> SEQUENCE: 51
```

| | | | | | | | | | | | | | | | |
|---|---|---|---|---|---|---|---|---|---|---|---|---|---|---|---|
| Lys | Asp | Asn | Val | Ala | Asp | Val | Val | Gly | Ala | Gly | Leu | Ser | Gly | | |
| 1 | | | | 5 | | | | | 10 | | | | | 15 | |
| Leu | Glu | Thr | Ala | Arg | Lys | Val | Gln | Ala | Ala | Gly | Leu | Ser | Cys | Leu | Val |
| | | | 20 | | | | | 25 | | | | | 30 | | |
| Leu | Glu | Ala | Met | Asp | Arg | Val | Gly | Lys | Thr | Leu | Ser | Val | Gln | Ser | |
| | | 35 | | | | | 40 | | | | | 45 | | | |
| Gly | Pro | Gly | Arg | Thr | Thr | Ile | Asn | Asp | Leu | Gly | Ala | Ala | Trp | Ile | Asn |
| | 50 | | | | | 55 | | | | | 60 | | | | |
| Asp | Ser | Asn | Gln | Ser | Glu | Val | Ser | Arg | Leu | Phe | Glu | Arg | Phe | His | Leu |
| 65 | | | | | 70 | | | | | 75 | | | | | 80 |
| Glu | Gly | Glu | Leu | Gln | Arg | Thr | Thr | Gly | Asn | Ser | Ile | His | Gln | Ala | Gln |
| | | | | 85 | | | | | 90 | | | | | 95 | |
| Asp | Gly | Thr | Thr | Thr | Thr | Ala | Pro | Tyr | Gly | Asp | Ser | Leu | Leu | Ser | Glu |
| | | | 100 | | | | | 105 | | | | | 110 | | |
| Glu | Val | Ala | Ser | Ala | Leu | Ala | Glu | Leu | Leu | Pro | Val | Trp | Ser | Gln | Leu |
| | | | 115 | | | | | 120 | | | | | 125 | | |
| Ile | Glu | Glu | His | Ser | Leu | Gln | Asp | Leu | Lys | Ala | Ser | Pro | Gln | Ala | Lys |
| 130 | | | | | 135 | | | | | 140 | | | | | |
| Arg | Leu | Asp | Ser | Val | Ser | Phe | Ala | His | Tyr | Cys | Glu | Lys | Glu | Leu | Asn |
| 145 | | | | | 150 | | | | | 155 | | | | | 160 |
| Leu | Pro | Ala | Val | Leu | Gly | Val | Ala | Asn | Gln | Ile | Thr | Arg | Ala | Leu | Leu |
| | | | | 165 | | | | | 170 | | | | | 175 | |
| Gly | Val | Glu | Ala | His | Glu | Ile | Ser | Met | Leu | Phe | Leu | Thr | Asp | Tyr | Ile |
| | | | 180 | | | | | 185 | | | | | 190 | | |
| Lys | Ser | Ala | Thr | Gly | Leu | Ser | Asn | Ile | Phe | Ser | Asp | Lys | Lys | Asp | Gly |
| | | | 195 | | | | | 200 | | | | | 205 | | |
| Gly | Gln | Tyr | Met | Arg | Cys | Lys | Thr | Gly | Met | Gln | Ser | Ile | Ser | His | Ala |
| | 210 | | | | | 215 | | | | | 220 | | | | |
| Met | Ser | Lys | Glu | Leu | Val | Pro | Gly | Ser | Val | His | Leu | Asn | Thr | Pro | Val |
| 225 | | | | | 230 | | | | | 235 | | | | | 240 |
| Ala | Glu | Ile | Glu | Gln | Ser | Ala | Ser | Gly | Cys | Thr | Val | Arg | Ser | Ala | Ser |
| | | | | 245 | | | | | 250 | | | | | 255 | |
| Gly | Ala | Val | Phe | Arg | Ser | Lys | Lys | Val | Val | Ser | Leu | Pro | Thr | Thr | |
| | | | 260 | | | | | 265 | | | | | 270 | | |
| Leu | Tyr | Pro | Thr | Leu | Thr | Phe | Ser | Pro | Pro | Leu | Pro | Ala | Glu | Lys | Gln |
| | | 275 | | | | | 280 | | | | | 285 | | | |
| Ala | Leu | Ala | Glu | Asn | Ser | Ile | Leu | Gly | Tyr | Tyr | Ser | Lys | Ile | Val | Phe |
| | 290 | | | | | 295 | | | | | 300 | | | | |
| Val | Trp | Asp | Lys | Pro | Trp | Trp | Arg | Glu | Gln | Gly | Phe | Ser | Gly | Val | Leu |
| 305 | | | | | 310 | | | | | 315 | | | | | 320 |
| Gln | Ser | Ser | Ser | Asp | Pro | Ile | Ser | Phe | Ala | Arg | Asp | Thr | Ser | Ile | Asp |
| | | | | 325 | | | | | 330 | | | | | 335 | |
| Val | Asp | Arg | Gln | Trp | Ser | Ile | Thr | Cys | Phe | Met | Val | Gly | Asp | Pro | Gly |
| | | | 340 | | | | | 345 | | | | | 350 | | |
| Arg | Lys | Trp | Ser | Gln | Gln | Ser | Lys | Gln | Val | Arg | Gln | Lys | Ser | Val | Trp |
| | | 355 | | | | | 360 | | | | | 365 | | | |
| Asp | Gln | Leu | Arg | Ala | Ala | Tyr | Glu | Asn | Ala | Gly | Ala | Gln | Val | Pro | Glu |
| | 370 | | | | | 375 | | | | | 380 | | | | |

```
Pro Ala Asn Val Leu Glu Ile Glu Trp Ser Lys Gln Gln Tyr Phe Gln
385                 390                 395                 400

Gly Ala Pro Ser Ala Val Tyr Gly Leu Asn Asp Leu Ile Thr Leu Gly
            405                 410                 415

Ser Ala Leu Arg Thr Pro Phe Lys Ser Val His Phe Val Gly Thr Glu
            420                 425                 430

Thr Ser Leu Val Trp Lys Gly Tyr Met Glu Gly Ala Ile Arg Ser Gly
            435                 440                 445

Gln Arg Gly Ala Ala Glu Val Val Ala Ser Leu Val Pro Ala Ala
        450                 455                 460
```

<210> SEQ ID NO 52
<211> LENGTH: 1392
<212> TYPE: DNA
<213> ORGANISM: Unknown
<220> FEATURE:
<223> OTHER INFORMATION: Cys (-) APAO; removal of cysteines 169, 359, and 461
<220> FEATURE:
<221> NAME/KEY: CDS
<222> LOCATION: (1)..(1392)
<223> OTHER INFORMATION:

<400> SEQUENCE: 52

```
aaa gac aac gtt gcg gac gtg gta gtg gtg ggc gct ggc ttg agc ggt      48
Lys Asp Asn Val Ala Asp Val Val Val Val Gly Ala Gly Leu Ser Gly
1               5                   10                  15 ttg gag acg gca cgc aaa gtc cag gcc gcc ggt ctg agc tcc ctc gtt      96
Leu Glu Thr Ala Arg Lys Val Gln Ala Ala Gly Leu Ser Ser Leu Val
            20                  25                  30 ctt gag gcg atg gat cgt gta ggg gga aag act ctg agc gta caa tcg     144
Leu Glu Ala Met Asp Arg Val Gly Gly Lys Thr Leu Ser Val Gln Ser
        35                  40                  45 ggt ccc ggc agg acg act atc aac gac ctc ggc gct gcg tgg atc aat     192
Gly Pro Gly Arg Thr Thr Ile Asn Asp Leu Gly Ala Ala Trp Ile Asn
    50                  55                  60 gac agc aac caa agc gaa gta tcc aga ttg ttt gaa aga ttt cat ttg     240
Asp Ser Asn Gln Ser Glu Val Ser Arg Leu Phe Glu Arg Phe His Leu
65                  70                  75                  80 gag ggc gag ctc cag agg acg act gga aat tca atc cat caa gca caa     288
Glu Gly Glu Leu Gln Arg Thr Thr Gly Asn Ser Ile His Gln Ala Gln
                85                  90                  95 gac ggt aca acc act aca gct cct tat ggt gac tcc ttg ctg agc gag     336
Asp Gly Thr Thr Thr Thr Ala Pro Tyr Gly Asp Ser Leu Leu Ser Glu
            100                 105                 110 gag gtt gca agt gca ctt gcg gaa ctc ctc ccc gta tgg tct cag ctg     384
Glu Val Ala Ser Ala Leu Ala Glu Leu Leu Pro Val Trp Ser Gln Leu
        115                 120                 125 atc gaa gag cat agc ctt caa gac ctc aag gcg agc cct cag gcg aag     432
Ile Glu Glu His Ser Leu Gln Asp Leu Lys Ala Ser Pro Gln Ala Lys
    130                 135                 140 cgg ctc gac agt gtg agc ttc gcg cac tac tgt gag aag gaa cta aac     480
Arg Leu Asp Ser Val Ser Phe Ala His Tyr Cys Glu Lys Glu Leu Asn
145                 150                 155                 160 ttg cct gct gtt ctc ggc gta gca aac cag atc aca cgc gct ctg ctc     528
Leu Pro Ala Val Leu Gly Val Ala Asn Gln Ile Thr Arg Ala Leu Leu
                165                 170                 175 ggt gtg gaa gcc cac gag atc agc atg ctt ttt ctc acc gac tac atc     576
Gly Val Glu Ala His Glu Ile Ser Met Leu Phe Leu Thr Asp Tyr Ile
            180                 185                 190
```

-continued

| | | | | | | | | | | | | | |
|---|---|---|---|---|---|---|---|---|---|---|---|---|---|
| aag | agt | gcc | acc | ggt | ctc | agt | aat | att | ttc | tcg | gac | aag | aaa gac ggc | 624 |
| Lys | Ser | Ala | Thr | Gly | Leu | Ser | Asn | Ile | Phe | Ser | Asp | Lys | Lys Asp Gly |
| | | 195 | | | | 200 | | | | 205 | | | |
| ggg | cag | tat | atg | cga | tgc | aaa | aca | ggt | atg | cag | tcg | att | tcg cat gcc | 672 |
| Gly | Gln | Tyr | Met | Arg | Cys | Lys | Thr | Gly | Met | Gln | Ser | Ile | Ser His Ala |
| 210 | | | | | 215 | | | | | 220 | | | |
| atg | tca | aag | gaa | ctt | gtt | cca | ggc | tca | gtg | cac | ctc | aac | acc ccc gtc | 720 |
| Met | Ser | Lys | Glu | Leu | Val | Pro | Gly | Ser | Val | His | Leu | Asn | Thr Pro Val |
| 225 | | | | 230 | | | | | 235 | | | | 240 |
| gct | gaa | att | gag | cag | tcg | gca | tcc | ggc | tgt | aca | gta | cga | tcg gcc tcg | 768 |
| Ala | Glu | Ile | Glu | Gln | Ser | Ala | Ser | Gly | Cys | Thr | Val | Arg | Ser Ala Ser |
| | | | | 245 | | | | | 250 | | | | 255 |
| ggc | gcc | gtg | ttc | cga | agc | aaa | aag | gtg | gtg | gtt | tcg | tta | ccg aca acc | 816 |
| Gly | Ala | Val | Phe | Arg | Ser | Lys | Lys | Val | Val | Val | Ser | Leu | Pro Thr Thr |
| | | | 260 | | | | 265 | | | | | 270 | |
| ttg | tat | ccc | acc | ttg | aca | ttt | tca | cca | cct | ctt | ccc | gcc | gag aag caa | 864 |
| Leu | Tyr | Pro | Thr | Leu | Thr | Phe | Ser | Pro | Pro | Leu | Pro | Ala | Glu Lys Gln |
| | | 275 | | | | | 280 | | | | | 285 | |
| gca | ttg | gcg | gaa | aat | tct | atc | ctg | ggc | tac | tat | agc | aag | ata gtc ttc | 912 |
| Ala | Leu | Ala | Glu | Asn | Ser | Ile | Leu | Gly | Tyr | Tyr | Ser | Lys | Ile Val Phe |
| 290 | | | | | 295 | | | | | 300 | | | |
| gta | tgg | gac | aag | ccg | tgg | tgg | cgc | gaa | caa | ggc | ttc | tcg | ggc gtc ctc | 960 |
| Val | Trp | Asp | Lys | Pro | Trp | Trp | Arg | Glu | Gln | Gly | Phe | Ser | Gly Val Leu |
| 305 | | | | 310 | | | | | 315 | | | | 320 |
| caa | tcg | agc | tcc | gac | ccc | atc | tca | ttt | gcc | aga | gat | acc | agc atc gac | 1008 |
| Gln | Ser | Ser | Ser | Asp | Pro | Ile | Ser | Phe | Ala | Arg | Asp | Thr | Ser Ile Asp |
| | | | | 325 | | | | | 330 | | | | 335 |
| gtc | gat | cga | caa | tgg | tcc | att | acc | tgt | ttc | atg | gtc | gga | gac ccg gga | 1056 |
| Val | Asp | Arg | Gln | Trp | Ser | Ile | Thr | Cys | Phe | Met | Val | Gly | Asp Pro Gly |
| | | | 340 | | | | | 345 | | | | | 350 |
| cgg | aag | tgg | tcc | caa | cag | tcc | aag | cag | gta | cga | caa | aag | tct gtc tgg | 1104 |
| Arg | Lys | Trp | Ser | Gln | Gln | Ser | Lys | Gln | Val | Arg | Gln | Lys | Ser Val Trp |
| | | 355 | | | | | 360 | | | | | 365 | |
| gac | caa | ctc | cgc | gca | gcc | tac | gag | aac | gcc | ggg | gcc | caa | gtc cca gag | 1152 |
| Asp | Gln | Leu | Arg | Ala | Ala | Tyr | Glu | Asn | Ala | Gly | Ala | Gln | Val Pro Glu |
| 370 | | | | | 375 | | | | | 380 | | | |
| ccg | gcc | aac | gtg | ctc | gaa | atc | gag | tgg | tcg | aag | cag | cag | tat ttc caa | 1200 |
| Pro | Ala | Asn | Val | Leu | Glu | Ile | Glu | Trp | Ser | Lys | Gln | Gln | Tyr Phe Gln |
| 385 | | | | 390 | | | | | 395 | | | | 400 |
| gga | gct | ccg | agc | gcc | gtc | tat | ggg | ctg | aac | gat | ctc | atc | aca ctg ggt | 1248 |
| Gly | Ala | Pro | Ser | Ala | Val | Tyr | Gly | Leu | Asn | Asp | Leu | Ile | Thr Leu Gly |
| | | | 405 | | | | | 410 | | | | | 415 |
| tcg | gcg | ctc | aga | acg | ccg | ttc | aag | agt | gtt | cat | ttc | gtt | gga acg gag | 1296 |
| Ser | Ala | Leu | Arg | Thr | Pro | Phe | Lys | Ser | Val | His | Phe | Val | Gly Thr Glu |
| | | | 420 | | | | 425 | | | | | 430 | |
| acg | tct | tta | gtt | tgg | aaa | ggg | tat | atg | gaa | ggg | gcc | ata | cga tcg ggt | 1344 |
| Thr | Ser | Leu | Val | Trp | Lys | Gly | Tyr | Met | Glu | Gly | Ala | Ile | Arg Ser Gly |
| | | 435 | | | | | 440 | | | | | 445 | |
| caa | cga | ggt | gct | gca | gaa | gtt | gtg | gct | agc | ctg | gtg | cca | gca gca tag | 1392 |
| Gln | Arg | Gly | Ala | Ala | Glu | Val | Val | Ala | Ser | Leu | Val | Pro | Ala Ala |
| 450 | | | | | 455 | | | | | 460 | | | |

<210> SEQ ID NO 53
<211> LENGTH: 463
<212> TYPE: PRT
<213> ORGANISM: Unknown
<220> FEATURE:
<223> OTHER INFORMATION: Cys (-) APAO; removal of cysteines 169, 359, and 461

<400> SEQUENCE: 53

-continued

```
Lys Asp Asn Val Ala Asp Val Val Val Gly Ala Gly Leu Ser Gly
1               5                   10                  15

Leu Glu Thr Ala Arg Lys Val Gln Ala Ala Gly Leu Ser Ser Leu Val
            20                  25              30

Leu Glu Ala Met Asp Arg Val Gly Gly Lys Thr Leu Ser Val Gln Ser
        35                  40                  45

Gly Pro Gly Arg Thr Thr Ile Asn Asp Leu Gly Ala Ala Trp Ile Asn
    50                  55                  60

Asp Ser Asn Gln Ser Glu Val Ser Arg Leu Phe Glu Arg Phe His Leu
65              70                  75                  80

Glu Gly Glu Leu Gln Arg Thr Thr Gly Asn Ser Ile His Gln Ala Gln
                85                  90                  95

Asp Gly Thr Thr Thr Ala Pro Tyr Gly Asp Ser Leu Leu Ser Glu
            100                 105                 110

Glu Val Ala Ser Ala Leu Ala Glu Leu Leu Pro Val Trp Ser Gln Leu
            115                 120                 125

Ile Glu Glu His Ser Leu Gln Asp Leu Lys Ala Ser Pro Gln Ala Lys
    130                 135                 140

Arg Leu Asp Ser Val Ser Phe Ala His Tyr Cys Glu Lys Glu Leu Asn
145             150                 155                 160

Leu Pro Ala Val Leu Gly Val Ala Asn Gln Ile Thr Arg Ala Leu Leu
                165                 170                 175

Gly Val Glu Ala His Glu Ile Ser Met Leu Phe Leu Thr Asp Tyr Ile
            180                 185                 190

Lys Ser Ala Thr Gly Leu Ser Asn Ile Phe Ser Asp Lys Lys Asp Gly
    195                 200                 205

Gly Gln Tyr Met Arg Cys Lys Thr Gly Met Gln Ser Ile Ser His Ala
210                 215                 220

Met Ser Lys Glu Leu Val Pro Gly Ser Val His Leu Asn Thr Pro Val
225                 230                 235                 240

Ala Glu Ile Glu Gln Ser Ala Ser Gly Cys Thr Val Arg Ser Ala Ser
            245                 250                 255

Gly Ala Val Phe Arg Ser Lys Val Val Ser Leu Pro Thr Thr
            260                 265                 270

Leu Tyr Pro Thr Leu Thr Phe Ser Pro Pro Leu Pro Ala Glu Lys Gln
    275                 280                 285

Ala Leu Ala Glu Asn Ser Ile Leu Gly Tyr Tyr Ser Lys Ile Val Phe
    290                 295                 300

Val Trp Asp Lys Pro Trp Trp Arg Glu Gln Gly Phe Ser Gly Val Leu
305                 310                 315                 320

Gln Ser Ser Ser Asp Pro Ile Ser Phe Ala Arg Asp Thr Ser Ile Asp
                325                 330                 335

Val Asp Arg Gln Trp Ser Ile Thr Cys Phe Met Val Gly Asp Pro Gly
            340                 345                 350

Arg Lys Trp Ser Gln Gln Ser Lys Gln Val Arg Gln Lys Ser Val Trp
            355                 360                 365

Asp Gln Leu Arg Ala Ala Tyr Glu Asn Ala Gly Ala Gln Val Pro Glu
        370                 375                 380

Pro Ala Asn Val Leu Glu Ile Glu Trp Ser Lys Gln Gln Tyr Phe Gln
385                 390                 395                 400

Gly Ala Pro Ser Ala Val Tyr Gly Leu Asn Asp Leu Ile Thr Leu Gly
                405                 410                 415

Ser Ala Leu Arg Thr Pro Phe Lys Ser Val His Phe Val Gly Thr Glu
```

-continued

```
                420              425              430
Thr Ser Leu Val Trp Lys Gly Tyr Met Glu Gly Ala Ile Arg Ser Gly
        435              440              445
Gln Arg Gly Ala Ala Glu Val Val Ala Ser Leu Val Pro Ala Ala
    450              455              460

<210> SEQ ID NO 54
<211> LENGTH: 11
<212> TYPE: PRT
<213> ORGANISM: Exophiala spinifera

<400> SEQUENCE: 54

Asp Val Val Val Gly Ala Gly Leu Ser Gly
1               5                   10
```

AMINO POLYOL AMINE OXIDASE POLYNUCLEOTIDES AND RELATED POLYPEPTIDES AND METHODS OF USE

CROSS REFERENCE TO RELATED APPLICATION

This application is a continuation of U.S. application Ser. No. 09/352,159, filed Jul. 12, 1999, now U.S. Pat. No. 6,211,434, which claims benefit to of Ser. No. 60/135,391, filed May 21, 1999 and Ser. No. 60/092,936, filed Jul. 15, 1998. This application is also a continuation of Ser. No. 09/352,168, filed Jul. 12, 1999, now U.S. Pat. No. 6, 211,435, all of which are hereby incorporated by reference.

TECHNICAL FIELD

The present invention relates generally to the detection and isolation of fumonisin and AP1 degrading enzymes and to compositions and methods for the in vivo detoxification or degradation of fumonisin or its hydrolysis product AP1. This method has broad application in agricultural biotechnology and crop agriculture and in the improvement of food grain quality.

BACKGROUND OF THE INVENTION

Fungal diseases are common problems in crop agriculture. Many strides have been made against plant diseases as exemplified by the use of hybrid plants, pesticides and improved agricultural practices. However, as any grower or home gardener can attest, the problems of fungal plant disease continue to cause difficulties in plant cultivation. Thus, there is a continuing need for new methods and materials for solving the problems caused by fungal diseases of plants.

These problems can be met through a variety of approaches. For example, the infectious organisms can be controlled through the use of agents that are selectively biocidal for the pathogens. Another method is interference with the mechanism by which the pathogen invades the host crop plant. Yet another method, in the case of pathogens that cause crop losses, is interference with the mechanism by which the pathogen causes injury to the host crop plant. Still another method, in the case of pathogens that produce toxins that are undesirable to mammals or other animals that feed on the crop plants, is interference with toxin production, storage, or activity. This invention falls into the latter two categories.

Since their discovery and structural elucidation in 1988 (Bezuidenhout et al., Journal *Chem Soc, Chem Commun* 1988: 743–745 (1988)), fumonisins have been recognized as a potentially serious problem in maize-fed livestock. They are linked to several animal toxicoses including leukoencephalomalacia (Marasas, et al, *Onderstepoort Journal of Veterinary Research* 55: 197–204 (1988); Wilson, et at, *American Association of Veterinary Laboratory Diagnosticians: Abstracts 33rd Annual Meeting*, Denver, Colo., Oct. 7–9, 1990, Madison, Wis., USA) and porcine pulmonary edema (Colvin, et al., *Mycopathologia* 117: 79–82 (1992)). Fumonisins are also suspected carcinogens (Geary W (1971) *Coord Chem Rev* 7: 81; Gelderblom, et al., *Carcinogenesis* 12: 1247–1251 (1991); Gelderblom, et al, *Carcinogenesis* 13: 433–437 (1992)). Fusarium isolates in section Liseola produce fumonisins in culture at levels from 2 to >4000 ppm (Leslie, et al., *Phytopathology* 82: 341–345 (1992)). Isolates from maize (predominantly mating population A) are among the highest producers of fumonisin. (Leslie et al., supra).

Fumonisin levels detected in field-grown maize have fluctuated widely depending on location and growing season, but both preharvest and postharvest surveys of field maize have indicated that the potential for high levels of fumonisins exists (Murphy, et al., *J Agr Food Chem* 41: 263–266 (1993)). Surveys of food and feed products have also detected fumonisin (Holcomb, et al., *J Agr Food Chem* 41: 764–767 (1993); Hopmans, et al., *J Agr Food Chem* 41: 1655–1658 (1993); Sydenham, et al., *J Agr Food Chem* 39: 2014–2018 (1991)). The etiology of Fusarium ear mold is poorly understood, although physical damage to the ear and certain environmental conditions can contribute to its occurrence (Nelson, *Mycopathologia* 117: 29–36 (1992)). Fusarium can be isolated from most field grown maize, even when no visible mold is present. The relationship between seedling infection and stalk and ear diseases caused by Fusarium is not clear. Genetic resistance to visible kernel mold has been identified (Gendloff, et al., *Phytopathology* 76: 684–688 (1986); Holley, et al., *Plant Dis* 73: 578–580 (1989)), but the relationship to visible mold to fumonisin production has yet to be elucidated.

Fumonisins have been shown in in vitro mammalian cell studies to inhibit sphingolipid biosynthesis through inhibition of the enzyme sphingosine N-acetyl transferase, resulting in the accumulation of the precursor sphinganine (Norred, et al., *Mycopathologia* 117: 73–78 (1992); Wang, et al., Biol Chem 266: 14486 (1991); Yoo, et al., *Toxicol Appl Pharmacol* 114: 9–15 (1992); Nelson, et al., *Annu Rev Phytpathol* 31:233–252 (1993)). It is likely that inhibition of this pathway accounts for at least some of fumonisin's toxicity, and support for this comes from measures of sphinganine: sphingosine ratios in animals fed purified fumonisin (Wang, et al., *J Nutr* 122: 1706–1716 (1992)). Fumonisins also affect plant cell growth (Abbas, et al., *Weed Technol* 6: 548–552 (1992); Vanasch, et al., *Phytopathology* 82: 1330–1332 (1992); Vesonder, et al., *Arch Environ Contam Toxicol* 23: 464–467 (1992)). Kuti et al., (Abstract, Annual Meeting American Phytopathological Society, Memphis, Tenn.: APS Press 1993) reported on the ability of exogenously added fumonisins to accelerate disease development and increase sporulation of *Fusarium moniliforme* and *Fusarium oxysporum* on tomato.

Enzymes that degrade the fungal toxin fumonisin to its de-esterified form (e.g. AP1 from FB1) have been identified in U.S. Pat. No. 5,716,820, issued Feb. 10, 1998, U.S. Pat. No. 5,792,931 issued Aug. 11, 1998; and pending U.S. application Ser. Nos. 08/888,950 and 08/888,949, both filed Jul. 7, 1997, and all hereby incorporated by reference. It is understood that AP1 as used here designates the hydrolyzed form of any fumonisin, FB1, FB2, FB3, FB4, or any other AP1-like compounds, including synthetically produced AP1 like compounds, that contain a C-2 or C-1 amine group and one or more adjacent hydroxyl groups. Plants expressing a fumonisin esterase enzyme, infected by fumonisin producing fungus, and tested for fumonisin and AP1 were found to have low levels of fumonisin but high levels of AP1. AP1 is less toxic than fumonisins to plants and probably also to animals but contamination with AP1 is still a concern (Lamprecht, et al., *Phytopathology*, 84:383–391 (1991)). The preferred result would be complete detoxification of fumonisin to a non-toxic form. Therefore enzymes capable of degrading AP1 are necessary for the further detoxification of fumonisin.

The present invention provides newly discovered polynucleotides and related polypeptides of amino polyol amine oxidase (abbreviated APAO, formerly known as AP1 catabolase, U.S. Pat. No. 5,716,820, supra, U.S. Pat. No.

5,792,931 supra; pending U.S. application Ser. Nos. 08/888, 950 and 08/888,949, supra; trAPAO is the abbreviation for a truncated, but still functional APAO), capable of oxidatively deaminating the AP1 to a compound identified as the 2-oxo derivative of AP1 or its cyclic ketal form (abbreviated as 2-OP, formerly called AP1-N1, U.S. Pat. No. 5,716,820, and U.S. Pat. No. 5,792,931 supra; pending U.S. application Ser. Nos. 08/888,950 and 08/888,949, supra), isolated from *Exophiala spinifera*, ATCC 74269. The partially purified APAO enzyme from *Exophiala spinifera* has little or no activity on intact FB1, a form of fumonisin. However, recombinant APAO enzyme from *Exophiala spinifera*, expressed in *E. coli*, has significant but reduced activity on intact FB1 and other B-series fumonisins. APAO or trAPAO thus could potentially be used without fumonisin esterase since the amine group is the major target for detoxification. Alternatively, fumonisin esterase and APAO (or trAPAO) can be used together for degrading toxins.

APAO is a type of flavin amine oxidase (EC 1.4.3.4, enzyme class nomeclature, see *Enzyme Nomenclature* 1992, Recommendations of the Nomenclature Committee of the IUBMB on the Nomenclature and Classification of Enzymes, Academic Press, Inc. (1992)). Flavin amine oxidases are known in mammals as monoamine oxidases, where they participate in the conversion of amines involved in neuronal function. A prokaryotic flavin amine oxidase that deaminates putrescine has been described (Ishizuka et al., *J. Gen Microbiol.* 139:425–432 (1993)). A single fungal gene, from *Aspergillus niger* has been cloned (Schilling et al., *Mol Gen Genet.* 247:430–438 (1995)). It deaminates a variety of alkyl and aryl amines, but when tested for its ability to oxidize AP1, was found to not contain AP1 oxidizing activity.

The toxicity of fumonisins and their potential widespread occurrence in food and feed makes it imperative to find detoxification or elimination strategies to remove the compound from the food chain.

SUMMARY OF THE INVENTION

The present invention provides polynucleotides, related polypeptides, and all conservatively modified variants of newly discovered APAOs. The nucleotide sequences of the APAOs comprise the sequence shown in SEQ ID NOS: 35, 37, 39, 41, 43, and 45. For expression in a plant, the polynuclcotide of the present invention can be operably linked to a targeting sequence. It is an object of the present invention to provide transgenic plants comprising the nucleic acids of the present invention.

Therefore, in one aspect, the present invention relates to an isolated nucleic acid comprising a member selected from the group consisting of (a) a polynucleotide encoding a polypeptide of the present invention; (b) a polynucleotide comprising at least 20 contiguous bases of the polynucleotides of the present invention; (c) a polynucleotide having at least 50% sequence identity to the polynucleotides of the present invention; (d) a polynucleotide comprising at least 25 nucleotide in length which hybridizes under low stringency conditions to the polynucleotides of the present invention; and (e) a polynucleotide complementary to a polynucleotide of (a) through (e). The isolated nucleic acid can be DNA. The isolated nucleic acid can also be RNA.

In another aspect, the present invention relates to vectors comprising the polynucleotides of the present invention. Also the present invention relates to recombinant expression cassettes, comprising a nucleic acid of the present invention operably linked to a promoter.

In another aspect, the present invention is directed to a host cell into which has been introduced the recombinant expression cassette.

In yet another aspect, the present invention relates to a transgenic plant or plant cell comprising a recombinant expression cassette with a promoter operably linked to any of the isolated nucleic acids of the present invention. Preferred plants containing the recombinant expression cassette of the present invention include but are not limited to maize, soybean, sunflower, sorghum, canola, wheat, alfalfa, cotton, rice, barley, tomato, and millet. The present invention also provides transgenic seed from the transgenic plant.

In another aspect, the present invention relates to an isolated protein selected from the group consisting of (a) a polypeptide comprising at least 25 contiguous amino acids of SEQ ID NOS: 36, 38, 40, 42, 44, and 46; (b) a polypeptide comprising at least 55% sequence identity to SEQ ID NO: 36, 38, 40, 42, 44, and 46; (c) a polypeptide encoded by a nucleic acid of the present invention; (d) a polypeptide characterized by SEQ ID NO: 36, 38, 40, 42, 44, and 46; and (e) a conservatively modified variant of SEQ ID NO: 36, 38, 40, 42, 44, and 46.

Preferred embodiments of the subject invention include a host cell stably transformed by a polynucleotide construct as described above, and a method of producing a polypeptide of a recombinant gene comprising expressing a polynucleotide of the present invention in a recombinantly engineered cell and purifying the resulting polypeptide.

A number of expression systems using the said host cells could be used, such as but not limited to, microbial, bacterial, mammalian, insect, plant cells, yeast, or virus. In one embodiment the fumonisin degrading enzymes can be isolated and purified from the seeds or plant parts of a plant expressing the said enzyme.

Another embodiment of the subject invention comprises a method of reducing pathogenicity of a fungus producing fumonisin by transferring to a plant the nucleic acids of the present invention either by themselves or in combination with a nucleic acid coding for a fumonisin esterase.

This invention further provides methods of degrading fumonisin, a fumonisin degradative product, or a structurally related mycotoxin, comprising the step of reacting the mycotoxin with the degradative enzymes of the present invention. Additionally, fumonisins can be degraded to a less toxic form by application of both fumonisin esterase enzymes and APAO enzyme. Mycotoxins can be degraded in harvested grain, during the processing of harvested grain, in animal feed, or in plant tissue as, for example, during the use of the plant for silage or as a spray on grain, fruit or vegetables.

The polynucleotides of the present invention can also be used as a selectable marker for plant transformation. By transforming plant cells with an expression cassette containing the polynucleotide of the present invention and then placing the plant cells on media containing FB1, AP1 or a phytotoxic analog, only the plant cells expressing the polynucleotide of the present invention would survive.

Another embodiment of the present invention is the use of the enzyme fumonisin esterase and APAO by themselves or in combination as reagents for detecting fumonisin and structurally related toxins.

DETAILED DESCRIPTION OF THE INVENTION

Unless defined otherwise, all technical and scientific terms used herein have the same meaning as commonly understood by one of ordinary skill in the art to which this invention belongs. Unless mentioned otherwise, the techniques employed or contemplated herein are standard methodologies well known to one of ordinary skill in the art. The materials, methods and examples are illustrative only and not limiting. The following is presented by way of illustration and is not intended to limit the scope of the invention.

The practice of the present invention will employ, unless otherwise indicated, conventional techniques of botany, microbiology, tissue culture, molecular biology, chemistry, biochemistry and recombinant DNA technology, which are within the skill of the art. Such techniques are explained fully in the literature. See, e.g., J. H. Langenheim and K. V. Thimann, *Botany: Plant Biology and Its Relation to Human Affairs* (1982) John Wiley; *Cell Culture and Somatic Cell Genetics of Plants*, Vol. 1 (I. K. Vasil, ed. 1984); R. V. Stanier, J. L. Ingraham, M. L. Wheelis, and P. R. Painter, *The Microbial World*, (1986) 5th Ed., Prentice-Hall; O. D. Dhringra and J. B. Sinclair, *Basic Plant Pathology Methods*, (1985) CRC Press; Maniatis, Fritsch & Sambrook, *Molecular Cloning: A Laboratory Manual* (1982); *DNA Cloning*, Vols. I and II (D. N. Glover ed. 1985); *Oligonucleotide Synthesis* (M. J. Gait ed. 1984); *Nucleic Acid Hybridization* (B. D. Hames & S. J. Higgins eds. 1984); and the series *Methods in Enzymology* (S. Colowick and N. Kaplan, eds., Academic Press, Inc.).

Units, prefixes, and symbols may be denoted in their SI accepted form. Unless otherwise indicated, nucleic acids are written left to right in 5' to 3' orientation; amino acid sequences are written left to right in amino to carboxy orientation, respectively. Numeric ranges are inclusive of the numbers defining the range. Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes. The terms defined below are more fully defined by reference to the specification as a whole.

In describing the present invention, the following terms will be employed, and are intended to be defined as indicated below.

By "microbe" is meant any microorganism (including both eukaryotic and prokaryotic microorganisms), such as fungi, yeast, bacteria, actinomycetes, algae and protozoa, as well as other unicellular structures.

A "fumonisin-producing microbe" is any microbe capable of producing the mycotoxin fumonisin or analogs thereof. Such microbes are generally members of the fungal genus Fusarium, as well as recombinantly derived organisms, which have been genetically altered to enable them to produce fumonisin or analogs thereof By "degrading fumonisin" is meant any modification to fumonisin, AP1, or any derivative of fumonisin or AP1 which causes a decrease or loss in its toxic activity, such as degradation to less than 1%, 5%, 10%, or 50% of original toxicity, with less than 10% being preferred. Such a change can comprise cleavage of any of the various bonds, oxidation, reduction, the addition or deletion of a chemical moiety, or any other change that affects the activity of the molecule. In a preferred embodiment, the modification includes hydrolysis of the ester linkage in the molecule as a first step and then oxidative deamination. Furthermore, chemically altered fumonisin can be isolated from cultures of microbes that produce an enzyme of this invention, such as growing the organisms on media containing radioactively-labeled fumonisin, tracing the label, and isolating the degraded toxin for further study. The degraded fumonisin can be compared to the active compound for its phytotoxicity or mammalian toxicity in known sensitive species, such as porcines, rabbits, and equines or in cell or tissue culture assays. Such toxicity assays are known in the art. For example, in plants a whole leaf bioassay can be used in which solutions of the active and inactive compound are applied to the leaves of sensitive plants. The leaves may be treated in situ or, alternatively, excised leaves may be used. The relative toxicity of the compounds can be estimated by grading the ensuing damage to the plant tissues and by measuring the size of lesions formed within a given time period. Other known assays can be performed at the cellular level, employing standard tissue culture methodologies e.g., using cell suspension cultures.

By "fumonisin esterase" is meant any enzyme capable of hydrolysis of the ester linkage in fumonisin or a structurally similar molecule such as AAL toxin. Two examples of such enzymes are ESP1 and BEST1 found in U.S. Pat. No. 5,716,820, issued Feb. 10, 1998, U.S. Pat. No. 5,792,931 issued Aug. 11, 1998; and pending U.S. application Ser. Nos. 08/888,950 and 08/888,949, both filed Jul. 7, 1997.

By "structurally related mycotoxin" is meant any mycotoxin having a chemical structure related to a fumonisin or AP1 such as AAL toxin, fumonisin B1, fumonisin B2, fumonisin B3, fumonisin B4, fumonisin C1, fumonisin A1 and A2, and their analogs or hydrolyzed forms, as well as other mycotoxins having similar chemical structures, including synthetically made analogs that contain a C-2 or C-1 amine group and one or more adjacent hydroxyl groups, that would be expected to be degraded by the activity of an enzyme of the present invention. The present invention is the first flavin amine oxidase known to attack a primary amine not located at C-1 (i.e. C-2 of AP1) and resulting in a keto rather than an aldehydic product.

It is understood that "AP1" or "amino polyol" as used here is to designate the hydrolyzed form of any fumonisin, FB1, FB2, FB3, FB4, AAL, or any other AP1-like compound, including a compound made synthetically, that contains a C-2 or C-1 amine group and one or more adjacent hydroxyl groups.

By "amplified" is meant the construction of multiple copies of a nucleic acid sequence or multiple copies complementary to the nucleic acid sequence using at least one of the nucleic acid sequences as a template. Amplification systems include the polymerase chain reaction (PCR) system, ligase chain reaction (LCR) system, nucleic acid sequence based amplification (NASBA, Cangene, Mississauga, Ontario), Q-Beta Replicase systems, transcription-based amplification system (TAS), and strand displacement amplification (SDA). See, e.g., *Diagnostic Molecular Microbiology: Principles and Applications*, D. H. Persing et at., Ed., American Society for Microbiology, Washington, D.C. (1993). The product of amplification is termed an amplicon.

The term "conservatively modified variants" applies to both amino acid and nucleic acid sequences. With respect to particular nucleic acid sequences, conservatively modified variants refer to those nucleic acids that encode identical or conservatively modified variants of the amino acid sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations" and represent one species of conservatively modified variation. Every nucleic acid sequence herein that encodes a polypeptide also describes every possible silent variation of the nucleic acid. One of ordinary skill will recognize that each codon in a nucleic acid (except AUG, which is ordinarily the only codon for methionine, one exception is *Micrococcus rubens*, for which GTG is the methionine codon (Oshizuka, et al, *J Gen'l Microbiol*, 139:425–432 (1993)) can be modified to yield a functionally identical molecule. Accordingly, each silent variation of a nucleic acid, which encodes a polypeptide of the present invention, is implicit in each described polypeptide sequence and incorporated herein by reference.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" when the alteration results in the substitution of an amino acid with a chemically similar amino acid. Thus, any number of amino acid residues selected from the group of integers consisting of from 1 to 15 can be so altered. Thus, for example, 1, 2, 3, 4, 5, 7, or 10 alterations can be made. Conservatively modified variants typically provide similar biological activity as the unmodified polypeptide sequence from which they are derived. For example, substrate specificity, enzyme activity, or ligand/receptor binding is generally at least 30%, 40%, 50%, 60%, 70%, 80%, or 90%, preferably 60–90% of the native protein for it's native substrate. Conservative substitution tables providing functionally similar amino acids are well known in the art.

The following six groups each contain amino acids that are conservative substitutions for one another:
1) Alanine (A), Serine (S), Threonine (T);
2) Aspartic acid (D), Glutamic acid (E);
3) Asparagine A), Glutamine (Q);
4) Arginine (R), Lysine (K);
5) Isoleucine (I), Leucine (L), Methionine (M), Valine (V); and
6) Phenylalanine (F), Tyrosine (Y), Tryptophan (W).
See also, Creighton (1984) Proteins W. H. Freeman and Company.

As used herein, "consisting essentially of" means the inclusion of additional sequences to an object polynucleotide where the additional sequences do not selectively hybridize, under stringent hybridization conditions, to the same CDNA as the polynucleotide and where the hybridization conditions include a wash step in 0.1×SSC and 0.1% sodium dodecyl sulfate at 65° C.

By "encoding" or "encoded", with respect to a specified nucleic acid, is meant comprising the information for translation into the specified protein. A nucleic acid encoding a protein may comprise non-translated sequences (e.g., introns) within translated regions of the nucleic acid, or may lack such intervening non-translated sequences (e.g., as in cDNA). The information by which a protein is encoded is specified by the use of codons. Typically, the amino acid sequence is encoded by the nucleic acid using the "universal" genetic code. However, variants of the universal code, such as is present in some plant, animal, and fungal mitochondria, the bacterium *Mycoplasma capricolum* (*Proc. Natl. Acad. Sci.* (*USA*), 82: 2306–2309 (1985)), or the ciliate Macronucleus, may be used when the nucleic acid is expressed using these organisms.

When the nucleic acid is prepared or altered synthetically, advantage can be taken of known codon preferences of the intended host where the nucleic acid is to be expressed. For example, although nucleic acid sequences of the present invention may be expressed in both monocotyledonous and dicotyledonous plant species, sequences can be modified to account for the specific codon preferences and GC content preferences of monocotyledonous plants or dicotyledonous plants as these preferences have been shown to differ (Murray et al. *Nucl. Acids Res.* 17: 477–498 (1989) and herein incorporated by reference). Thus, the maize preferred codon for a particular amino acid might be derived from known gene sequences from maize. Maize codon usage for 28 genes from maize plants is listed in Table 4 of Murray et al., supra.

As used herein, "heterologous" in reference to a nucleic acid is a nucleic acid that originates from a foreign species, or, if from the same species, is substantially modified from its native form in composition and/or genomic locus by deliberate human intervention. For example, a promoter operably linked to a heterologous structural gene is from a species different from that from which the structural gene was derived, or, if from the same species, one or both are substantially modified from their original form. A heterologous protein may originate from a foreign species or, if from the same species, is substantially modified from its original form by deliberate human intervention.

By "host cell" or "recombinantly engineered cell" is meant a cell, which contains a vector and supports the replication and/or expression of the expression vector. Host cells may be prokaryotic cells such as *E. coli*, or eukaryotic cells such as yeast, Pichia, insect, plant, amphibian, or mammalian cells. Preferably, host cells are monocotyledonous or dicotyledonous plant cells, including but not limited to maize, sorghum, sunflower, soybean, wheat, alfalfa, rice, cotton, canola, barley, millet, and tomato. A particularly preferred monocotyledonous host cell is a maize host cell.

The term "hybridization complex" includes reference to a duplex nucleic acid structure formed by two single-stranded nucleic acid sequences selectively hybridized with each other.

The term "introduced" in the context of inserting a nucleic acid into a cell, means "transfection" or "transformation" or "transduction" and includes reference to the incorporation of a nucleic acid into a eukaryotic or prokaryotic cell where the nucleic acid may be incorporated into the genome of the cell (e.g., chromosome, plasmid, plastid or mitochondrial DNA), converted into an autonomous replicon, or transiently expressed (e.g., transfected mRNA).

The term "isolated" refers to material, such as a nucleic acid or a protein, which is substantially or essentially free from components which normally accompany or interact with it as found in its naturally occurring environment. The isolated material optionally comprises material not found with the material in its natural environment. Nucleic acids, which are "isolated", as defined herein, are also referred to as "heterologous" nucleic acids.

Unless otherwise stated, the term "APAO nucleic acid" means a nucleic acid comprising a polynucleotide ("APAO polynucleotide") encoding an APAO polypeptide. The term APAO, unless otherwise stated can encompass both APAO and the functional, truncated version of APAO designated trAPAO.

As used herein, "nucleic acid" includes reference to a deoxyribonucleotide or ribonucleotide polymer in either single- or double-stranded form, and unless otherwise limited, encompasses known analogues having the essential nature of natural nucleotides in that they hybridize to single-stranded nucleic acids in a manner similar to naturally occurring nucleotides (e.g., peptide nucleic acids).

By "nucleic acid library" is meant a collection of isolated DNA or RNA molecules, which comprise and substantially represent the entire transcribed fraction of a genome of a specified organism. Construction of exemplary nucleic acid libraries, such as genomic and cDNA libraries, is taught in standard molecular biology references such as Berger and Kimmel, *Guide to Molecular Cloning Techniques, Methods in Enzymology*, Vol. 152, Academic Press, Inc., San Diego, Calif. (Berger); Sambrook et al., *Molecular Cloning—A Laboratory Manual*, 2nd ed., Vol. 1–3 (1989); and *Current Protocols in Molecular Biology*, F. M. Ausubel et al., Eds., Current Protocols, a joint venture between Greene Publishing Associates, Inc. and John Wiley & Sons, Inc. (1994 Supplement).

As used herein "operably linked" includes reference to a functional linkage between a promoter and a second sequence, wherein the promoter sequence initiates and mediates transcription of the DNA sequence corresponding to the second sequence. Generally, operably linked means that the nucleic acid sequences being linked are contiguous and, where necessary to join two protein coding regions, contiguous and in the same reading frame.

As used herein, the term "plant" includes reference to whole plants, plant organs (e.g., leaves, stems, roots, etc.), seeds and plant cells and progeny of same. Plant cell, as used herein includes, without limitation, seeds suspension cultures, embryos, meristematic regions, callus tissue, leaves, roots, shoots, gametophytes, sporophytes, pollen, and microspores. The class of plants, which can be used in the methods of the invention, is generally as broad as the class of higher plants amenable to transformation techniques, including both monocotyledonous and dicotyledonous plants including species from the genera: Cucurbita, Rosa, Vitis, Juglans, Fragaria, Lotus, Medicago, Onobrychis, Trifolium, Trigonella, Vigna, Citrus, Linum, Geranium, Manihot, Daucus, Arabidopsis, Brassica, Raphanus, Sinapis, Atropa, Capsicum, Datura, Hyoscyamus, Lycopersicon, Nicotiana, Solanum, Petunia, Digitalis, Majorana, Ciahorium, Helianthus, Lactuca, Bromus, Asparagus, Antirrhinum, Heterocallis, Nemesis, Pelargonium, Panieum, Pennisetum, Ranunculus, Senecio, Salpiglossis, Cucumis, Browaalia, Glycine, Pisum, Phaseolus, Lolium, Oryza, Avena, Hordeum, Secale, Allium, and Triticum. A particularly preferred plant is *Zea mays*.

As used herein, "polynucleotide" includes reference to a deoxyribopolynucleotide, ribopolynucleotide, or analogs thereof that have the essential nature of a natural ribonucleotide in that they hybridize, under stringent hybridization conditions, to substantially the same nucleotide sequence as naturally occurring nucleotides and/or allow translation into the same amino acid(s) as the naturally occurring nucleotide (s). A polynucleotide can be full-length or a subsequence of a native or heterologous structural or regulatory gene. Unless otherwise indicated, the term includes reference to the specified sequence as well as the complementary sequence thereof. Thus, DNAs or RNAs with backbones modified for stability or for other reasons are "polynucleotides" as that term is intended herein. Moreover, DNAs or RNAs comprising unusual bases, such as inosine, or modified bases, such as tritylated bases, to name just two examples, are polynucleotides as the term is used herein. It will be appreciated that a great variety of modifications have been made to DNA and RNA that serve many useful purposes known to those of skill in the art. The term polynucleotide as it is employed herein embraces such chemically, enzymatically or metabolically modified forms of polynucleotides, as well as the chemical forms of DNA and RNA characteristic of viruses and cells, including inter alia, simple and complex cells.

The terms "polypeptide", "peptide" and "protein" are used interchangeably herein to refer to a polymer of amino acid residues. The terms apply to amino acid polymers in which one or more amino acid residue is an artificial chemical analogue of a corresponding naturally occurring amino acid, as well as to naturally occurring amino acid polymers.

As used herein "promoter" includes reference to a region of DNA upstream from the start of transcription and involved in recognition and binding of RNA polymerase and other proteins to initiate transcription. A "plant promoter" is a promoter capable of initiating transcription in plant cells. Exemplary plant promoters include, but are not limited to, those that are obtained from plants, plant viruses, and bacteria which comprise genes expressed in plant cells such Agrobacterium or Rhizobium. Examples are promoters that preferentially initiate transcription in certain tissues, such as leaves, roots, seeds, fibres, xylem vessels, tracheids, or sclerenchyma. Such promoters are referred to as "tissue preferred". A "cell type" specific promoter primarily drives expression in certain cell types in one or more organs, for example, vascular cells in roots or leaves. An "inducible" or "regulatable" promoter is a promoter, which is under environmental control. Examples of environmental conditions that may effect transcription by inducible promoters include anaerobic conditions or the presence of light. Another type of promoter is a developmentally regulated promoter, for example, a promoter that drives expression during pollen development. Tissue preferred, cell type specific, developmentally regulated, and inducible promoters constitute the class of "non-constitutive" promoters. A "constitutive" promoter is a promoter, which is active under most environmental conditions.

The term "APAO polypeptide or trAPAO polypeptide" refers to one or more amino acid sequences. The term is also inclusive of fragments, variants, homologs, alleles or precursors (e.g., preproproteins or proproteins) thereof. An "APAO or trAPAO protein" comprises an APAO or trAPAO polypeptide.

As used herein "recombinant" includes reference to a cell or vector, that has been modified by the introduction of a heterologous nucleic acid or that the cell is derived from a cell so modified. Thus, for example, recombinant cells express genes that are not found in identical form within the native (non-recombinant) form of the cell or express native genes that are otherwise abnormally expressed, under expressed or not expressed at all as a result of deliberate human intervention. The term "recombinant" as used herein does not encompass the alteration of the cell or vector by naturally occurring events (e.g., spontaneous mutation, natural transformation/transduction/transposition) such as those occurring without deliberate human intervention.

As used herein, a "recombinant expression cassette" is a nucleic acid construct, generated recombinantly or synthetically, with a series of specified nucleic acid elements, which permit transcription of a particular nucleic acid in a target cell. The recombinant expression cassette can be incorporated into a plasmid, chromosome, mitochondrial DNA, plastid DNA, virus, or nucleic acid fragment. Typically, the recombinant expression cassette portion of an expression vector includes, among other sequences, a nucleic acid to be transcribed, and a promoter.

The term "residue" or "amino acid residue" or "amino acid" are used interchangeably herein to refer to an amino acid that is incorporated into a protein, polypeptide, or peptide (collectively "protein"). The amino acid may be a naturally occurring amino acid and, unless otherwise limited, may encompass known analogs of natural amino acids that can function in a similar manner as naturally occurring amino acids.

The term "selectively hybridizes" includes reference to hybridization, under stringent hybridization conditions, of a nucleic acid sequence to a specified nucleic acid target sequence to a detectably greater degree (e.g., at least 2-fold over background) than its hybridization to non-target nucleic acid sequences and to the substantial exclusion of non-target nucleic acids. Selectively hybridizing sequences typically have about at least 40% sequence identity, preferably 60–90% sequence identity, and most preferably 100% sequence identity (i.e., complementary) with each other.

The terms "stringent conditions" or "stringent hybridization conditions" include reference to conditions under which a probe will hybridize to its target sequence, to a detectably greater degree than other sequences (e.g., at least 2-fold over background). Stringent conditions are sequence-dependent and will be different in different circumstances. By controlling the stringency of the hybridization and/or washing conditions, target sequences can be identified which can be up to 100% complementary to the probe (homologous probing). Alternatively, stringency conditions can be adjusted to allow some mismatching in sequences so that lower degrees of similarity are detected (heterologous probing). Optimally, the probe is approximately 500 nucleotides in length, but can vary greatly in length from less than 500 nucleotides to equal to the entire length of the target sequence.

Typically, stringent conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide or Denhardt's. Exemplary low stringency conditions include hybridization with a buffer solution of 30 to 35% formamide, 1 M NaCl, 1% SDS (sodium dodecyl sulphate) at 37° C., and a wash in 1× to 2×SSC (20X SSC=3.0 M NaCl/0.3 M trisodium citrate) at 50 to 55° C. Exemplary moderate stringency conditions include hybridization in 40 to 45% formamide, 1 M NaCl, 1% SDS at 37° C., and a wash in 0.5× to 1×SSC at 55 to 60° C. Exemplary high stringency conditions include hybridization in 50% formamide, 1 M NaCl, 1% SDS at 37° C., and a wash in 0.1×SSC at 60 to 65° C. Specificity is typically the function of post-hybridization washes, the critical factors being the ionic strength and temperature of the final wash solution. For DNA-DNA hybrids, the $T_m$ can be approximated from the equation of Meinkoth and Wahl, Anal. Biochem., 138:267–284 (1984): $T_m$=81.5° C.+16.6 (log M)+0.41 (%GC)−0.61 (% form)−500/L; where M is the molarity of monovalent cations, %GC is the percentage of guanosine and cytosine nucleotides in the DNA, % form is the percentage of formamide in the hybridization solution, and L is the length of the hybrid in base pairs. The $T_m$ is the temperature (under defined ionic strength and pH) at which 50% of a complementary target sequence hybridizes to a perfectly matched probe. $T_m$ is reduced by about 1° C. for each 1% of mismatching; thus, $T_m$, hybridization and/or wash conditions can be adjusted to hybridize to sequences of the desired identity. For example, if sequences with ≥90% identity are sought, the $T_m$ can be decreased 10° C. Generally, stringent conditions are selected to be about 5° C. lower than the thermal melting point ($T_m$) for the specific sequence and its complement at a defined ionic strength and pH. However, severely stringent conditions can utilize a hybridization and/or wash at 1, 2, 3, or 4° C. lower than the thermal melting point ($T_m$); moderately stringent conditions can utilize a hybridization and/or wash at 6, 7, 8, 9, or 10° C. lower than the thermal melting point ($T_m$); low stringency conditions can utilize a hybridization and/or wash at 11, 12, 13, 14,1 5, or 20° C. lower than the thermal melting point ($T_m$). Using the equation, hybridization and wash compositions, and desired $T_m$, those of ordinary skill will understand that variations in the stringency of hybridization and/or wash solutions are inherently described. If the desired degree of mismatching results in a $T_m$ of less than 45° C. (aqueous solution) or 32° C. (formamide solution) it is preferred to increase the SSC concentration so that a higher temperature can be used. An extensive guide to the hybridization of nucleic acids is found in Tijssen, Laboratory Techniques in Biochemistry and Molecular Biology—Hybridization with Nucleic Acid Probes, Part I, Chapter 2 "Overview of principles of hybridization and the strategy of nucleic acid probe assays", Elsevier, N.Y. (1993); and Current Protocols in Molecular Biology, Chapter 2, Ausubel, et al., Eds., Greene Publishing and Wiley-Interscience, New York (1995). Unless otherwise stated, in the present application high stringency is defined as hybridization in 4×SCC, 5× Denhardt's (5 g Ficoll, 5 g polyvinypyrrolidone, 5 g bovine serum albumin in 500 ml of water), 0.1 mg/ml boiled salmon sperm DNA, and 25 mM Na phosphate at 65° C., and a wash in 0.1×SSC, 0.1% SDS at 65° C.

As used herein, "transgenic plant" includes reference to a plant, which comprises within its genome a heterologous polynucleotide. Generally, the heterologous polynucleotide is stably integrated within the genome such that the polynucleotide is passed on to successive generations. The heterologous polynucleotide may be integrated into the genome alone or as part of a recombinant expression cassette. "Transgenic" is used herein to include any cell, cell line, callus, tissue, plant part or plant, the genotype of which has been altered by the presence of heterologous nucleic acid including those transgenics initially so altered as well as those created by sexual crosses or asexual propagation from the initial transgenic. The term "transgenic" as used herein does not encompass the alteration of the genome (chromosomal or extra-chromosomal) by conventional plant breeding methods or by naturally occurring events such as random cross-fertilization, non-recombinant viral infection, non-recombinant bacterial transformation, non-recombinant transposition, or spontaneous mutation.

As used herein, "vector" includes reference to a nucleic acid used in transfection of a host cell and into which can be inserted a polynucleotide. Vectors are often replicons. Expression vectors permit transcription of a nucleic acid inserted therein.

The following terms are used to describe the sequence relationships between two or more nucleic acids or polynucleotides or polypeptides: (a) "reference sequence", (b) "comparison window", (c) "sequence identity", (d) "percentage of sequence identity", and (e) "substantial identity".

(a) As used herein, "reference sequence" is a defined sequence used as a basis for sequence comparison. A reference sequence may be a subset or the entirety of a specified sequence; for example, as a segment of a full-length cDNA or gene sequence, or the complete cDNA or gene sequence.

(b) As used herein, "comparison window" means includes reference to a contiguous and specified segment of a polynucleotide sequence, wherein the polynucleotide sequence may be compared to a reference sequence and wherein the portion of the polynucleotide sequence in the comparison window may comprise additions or deletions (i.e., gaps) compared to the reference sequence (which does not comprise additions or deletions) for optimal alignment of the two sequences. Generally, the comparison window is at least 20 contiguous nucleotides in length, and optionally can be 30, 40, 50, 100, or longer. Those of skill in the art understand that to avoid a high similarity to a reference sequence due to inclusion of gaps in the polynucleotide sequence a gap penalty is typically introduced and is subtracted from the number of matches.

Methods of alignment of nucleotide and amino acid sequences for comparison are well known in the art. The local homology algorithm (Best Fit) of Smith and Waterman, Adv. Appl. Math may conduct optimal alignment of sequences for comparison 2: 482 (1981); by the homology alignment algorithm (GAP) of Needleman and Wunsch, J Mol. Biol. 48: 443 (1970); by the search for similarity method (Tfasta and Fasta) of Pearson and Lipman, Proc. Natl. Acad. Sci. 85: 2444 (1988); by computerized implementations of these algorithms, including, but not limited to: CLUSTAL in the PC/Gene program by Intelligenetics, Mountain View, Calif., GAP, BESTFIT, BLAST, FASTA, and TFASTA in the Wisconsin Genetics Software Package, Genetics Computer Group (GCG), 575 Science Dr., Madison, Wis., USA; the CLUSTAL program is well described by Higgins and Sharp, Gene 73: 237–244 (1988); Higgins and Sharp, CABIOS 5: 151–153 (1989); Corpet, et al., Nucleic Acids Research 16: 10881–90 (1988); Huang, et at, Computer Applications in the Biosciences 8: 155–65 (1992), and Pearson, et al., Methods in Molecular Biology 24: 307–331 (1994). The preferred program to use for optimal global alignment of multiple sequences is PileUp (Feng and Doolittle, Journal of Molecular Evolution, 25:351–360 (1987) which is similar to the method described by Higgins and Sharp, CABIOS, 5:151–153 (1989) and hereby incorporated by reference). The BLAST family of programs which can be used for database similarity searches includes: BLASTN for nucleotide query sequences against nucleotide database sequences; BLASTX for nucleotide query sequences against protein database sequences; BLASTP for protein query sequences against protein database sequences; TBLASTN for protein query sequences against nucleotide database sequences; and TBLASTX for nucleotide query sequences against nucleotide database sequences. See, Current Protocols in Molecular Biology, Chapter 19, Ausubel, et al., Eds., Greene Publishing and Wiley-Interscience, New York (1995).

GAP uses the algorithm of Needleman and Wunsch (J. Mol. Biol. 48: 443–453, 1970) to find the alignment of two complete sequences that maximizes the number of matches and minimizes the number of gaps. GAP considers all possible alignments and gap positions and creates the alignment with the largest number of matched bases and the fewest gaps. It allows for the provision of a gap creation penalty and a gap extension penalty in units of matched bases. GAP must make a profit of gap creation penalty number of matches for each gap it inserts. If a gap extension penalty greater than zero is chosen, GAP must, in addition, make a profit for each gap inserted of the length of the gap times the gap extension penalty. Default gap creation penalty values and gap extension penalty values in Version 10 of the Wisconsin Genetics Software Package are 8 and 2, respectively. The gap creation and gap extension penalties can be expressed as an integer selected from the group of integers consisting of from 0 to 100. Thus, for example, the gap creation and gap extension penalties can be 0, 1, 2, 3, 4, 5, 6, 7, 8, 9, 10, 15, 20, 30, 40, 50, or greater.

GAP presents one member of the family of best alignments. There may be many members of this family, but no other member has a better quality. GAP displays four figures of merit for alignments: Quality, Ratio, Identity, and Similarity. The Quality is the metric maximized in order to align the sequences. Ratio is the quality divided by the number of bases in the shorter segment. Percent Identity is the percent of the symbols that actually match. Percent Similarity is the percent of the symbols that are similar. Symbols that are across from gaps are ignored. A similarity is scored when the scoring matrix value for a pair of symbols is greater than or equal to 0.50, the similarity threshold. The scoring matrix used in Version 10 of the Wisconsin Genetics Software Package is BLOSUM62 (see Henikoff & Henikoff (1989) Proc. Natl. Acad. Sci. USA 89:10915).

Unless otherwise stated, sequence identity/similarity values provided herein refer to the value obtained using the BLAST 2.0 suite of programs using default parameters. Altschul et al., Nucleic Acids Res. 25:3389–3402 (1997).

As those of ordinary skill in the art will understand, BLAST searches assume that proteins can be modeled as random sequences. However, many real proteins comprise regions of nonrandom sequences, which may be homopolymeric tracts, short-period repeats, or regions enriched in one or more amino acids. Such low-complexity regions may be aligned between unrelated proteins even though other regions of the protein are entirely dissimilar. A number of low-complexity filter programs can be employed to reduce such low-complexity alignments. For example, the SEG (Wooten and Federhen, Comput. Chem., 17:149–163 (1993)) and XNU (Claverie and States, Comput. Chem., 17:191–201 (1993)) low-complexity filters can be employed alone or in combination.

(c) As used herein, "sequence identity" or "identity" in the context of two nucleic acid or polypeptide sequences includes reference to the residues in the two sequences, which are the same when aligned for maximum correspondence over a specified comparison window. When percentage of sequence identity is used in reference to proteins it is recognized that residue positions which are not identical often differ by conservative amino acid substitutions, where amino acid residues are substituted for other amino acid residues with similar chemical properties (e.g. charge or hydrophobicity) and therefore do not change the functional properties of the molecule. Where sequences differ in conservative substitutions, the percent sequence identity may be adjusted upwards to correct for the conservative nature of the substitution. Sequences, which differ by such conservative substitutions, arc said to have "sequence similarity" or "similarity". Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., according to the algorithm of Meyers and Miller, Computer Applic. Biol. Sci., 4: 11–17 (1988) e.g., as implemented in the program PC/GENE (Intelligenetics, Mountain View, Calif., USA).

(d) As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

(e) (i) The term "substantial identity" of polynucleotide sequences means that a polynucleotide comprises a sequence that has between 50–100% sequence identity, preferably at least 50% sequence identity, preferably at least 60% sequence identity, preferably at least 70%, more preferably at least 80%, more preferably at least 90% and most preferably at least 95%, compared to a reference sequence using one of the alignment programs described using standard parameters. One of skill will recognize that these values can be appropriately adjusted to determine corresponding identity of proteins encoded by two nucleotide sequences by taking into account codon degeneracy, amino acid similarity, reading frame positioning and the like. Substantial identity of amino acid sequences for these purposes normally means sequence identity of between 40–100%, preferably at least 55%, preferably at least 60%, more preferably at least 70%, 80%, 90%, and most preferably at least 95%.

Another indication that nucleotide sequences are substantially identical is if two molecules hybridize to each other under stringent conditions. The degeneracy of the genetic code allows for many amino acids substitutions that lead to variety in the nucleotide sequence that code for the same amino acid, hence it is possible that the DNA sequence could code for the same polypeptide but not hybridize to each other under stringent conditions. This may occur, e.g., when a copy of a nucleic acid is created using the maximum codon degeneracy permitted by the genetic code. One indication that two nucleic acid sequences are substantially identical is that the polypeptide, which the first nucleic acid encodes, is immunologically cross reactive with the polypeptide encoded by the second nucleic acid.

(e) (ii) The terms "substantial identity" in the context of a peptide indicates that a peptide comprises a sequence with between 55–100% sequence identity to a reference sequence preferably at least 55% sequence identity, preferably 60% preferably 70%, more preferably 80%, most preferably at least 90% or 95% sequence identity to the reference sequence over a specified comparison window. Preferably, optimal alignment is conducted using the homology alignment algorithm of Needleman and Wunsch, *J Mol. Biol.* 48: 443 (1970). An indication that two peptide sequences are substantially identical is that one peptide is immunologically reactive with antibodies raised against the second peptide. Thus, a peptide is substantially identical to a second peptide, for example, where the two peptides differ only by a conservative substitution. In addition, a peptide can be substantially identical to a second peptide when they differ by a non-conservative change if the epitope that the antibody recognizes is substantially identical. Peptides, which are "substantially similar" share sequences as, noted above except that residue positions, which are not identical, may differ by conservative amino acid changes.

Fumonisin Degrading Organisms

The present invention is based on the discovery of organisms with the ability to degrade the mycotoxin fumonisin. In a search for a biological means of detoxifying fumonisins, several dematiaceous hyphomycetes were isolated from field-grown maize kernels. The fungi were found to be capable of growing on fumonisins B1 or B2 (FB1 or FB2) as a sole carbon source, degrading it partially or completely in the process. One species, identified as *Exophiala spinifera*, a "black yeast", was recovered from maize seed from diverse locations in the southeastern and south central US. The enzyme-active strain of *Exophiala spinifera* (ATCC 74269) was deposited (see U.S. patent application Ser. No. 5,716,820, issued Feb. 10, 1998, U.S. Pat. No. 5,792,931 issued Aug. 11, 1998; and pending U.S. application Ser. Nos. 08/888,950 and 08/888,949, both filed Jul. 7, 1997). Other ernzyme-active strains of *Exophiala spinifera* were used to isolate APAO polynucleotides. Isolate ESP002 was isolated from palm trees (ATCC 26089) and isolate ESP003 was isolated from maize seed. Another fungus from which APAO polynucleotides were isolated was *Rhinocladiella afrovirens* (RAT 011).

Nucleic Acids

The present invention provides, inter alia, isolated nucleic acids of RNA, DNA, and analogs and/or chimeras thereof, comprising an APAO or trAPAO polynucleotide.

The present invention also includes polynucleotides optimized for expression in different organisms. For example, for expression of the polynucleotide in a maize plant, the sequence can be altered to account for specific codon preferences and to alter GC content as according to Murray et al, supra. Maize codon usage for 28 genes from maize plants is listed in Table 4 of Murray, et al., supra.

The APAO or trAPAO nucleic acids of the present invention comprise isolated APAO or trAPAO polynucleotides which, are inclusive of:

(a) a polynucleotide encoding an APAO or irAPAO polypeptide of the sequences shown in SEQ ID NOS: 36, 38, 40, 42, 44, and 46, and conservatively modified and polymorphic variants thereof;

(b) a polynucleotide which selectively hybridizes to a polynucleotide of (a) or (b);

(c) a polynucleotide having at least 50% sequence identity with polynucleotides of (a) or (b);

(d) complementary sequences of polynucleotides of (a), (b), or (c); and (e) a polynucleotide comprising at least 25 contiguous nucleotides from a polynucleotide of (a), (b), (c), or (d).

In addition, polynucleotides are presented that are a fusion of an APAO or trAPAO polynucleotide and the polynucleotide of a fumonisin esterase. The invention encompasses the sequences from Exophiala or Rhinocladiella as well as sequences having sequence similarity with such sequences. It is recognized that the sequences of the invention can be used to isolate corresponding sequences in other organisms. Methods such as PCR, hybridization, and the like can be used to identify sequences having substantial sequence similarity to the sequences of the invention. See, for example, Sambrook, et al., (1989) *Molecular Cloning: A*

*Laboratory Manual* (2d ed., Cold Spring Harbor Laboratory Press, Planview, N.Y.) and Innis et al., (1990) *PCR Protocols: Guide to Methods and Applications* (Academic Press, New York). Coding sequences isolated based on their sequence identity to the entire fumonisin degrading coding sequences set forth herein or to fragments thereof are encompassed by the present invention.

It is recognized that the sequences of the invention can be used to isolate similar sequences from other fumonisin degrading organisms. Likewise sequences from other fumonisin degrading organisms may be used in combination with the sequences of the present invention. See, for example, copending application entitled "Compositions and Methods for Fumonisin Detoxification", U.S. application Ser. No. 601092,953, filed concurrently herewith and herein incorporated by reference.

Plasmids containing the polynucleotide sequences of the invention were deposited with American Type Culture Collection (ATCC), Manassas, Va., and assigned Accession Nos. 98812, 98813, 98814, 98815, 98816, and PTA-32. These deposits will be maintained under the terms of the Budapest Treaty on the International Recognition of the Deposit of Microorganisms for the Purposes of Patent Procedure. These deposits were made merely as a convenience for those of skill in the art and are not an admission that a deposit is required under 35 U.S.C. § 112.

Construction of Nucleic Acids

The isolated nucleic acids of the present invention can be made using (a) standard recombinant methods, (b) synthetic techniques, or combinations thereof. In some embodiments, the polynucleotides of the present invention will be cloned, amplified, or otherwise constructed from a fungus or bacteria.

The nucleic acids may conveniently comprise sequences in addition to a polynucleotide of the present invention. For example, a multi-cloning site comprising one or more endonuclease restriction sites may be inserted into the nucleic acid to aid in isolation of the polynucleotide. Also, translatable sequences may be inserted to aid in the isolation of the translated polynucleotide of the present invention. For example, a hexa-histidine marker sequence provides a convenient means to purify the proteins of the present invention. The nucleic acid of the present invention—excluding the polynucleotide sequence—is optionally a vector, adapter, or linker for cloning and/or expression of a polynucleotide of the present invention. Additional sequences may be added to such cloning and/or expression sequences to optimize their function in cloning and/or expression, to aid in isolation of the polynucleotide, or to improve the introduction of the polynucleotide into a cell. Typically, the length of a nucleic acid of the present invention less the length of its polynucleotide of the present invention is less than 20 kilobase pairs, often less than 15 kb, and frequently less than 10 kb. Use of cloning vectors, expression vectors, adapters, and linkers is well known in the art. Exemplary nucleic acids include such vectors as: M13, lambda ZAP Express, lambda ZAPII, lambda gt10, lambda gt11, pBK-CMV, pBK-RSV, pBluescript II, lambda DASH II, lambda EMBL 3, lambda EMBL 4, pWE15, SuperCos 1, SurfZap, Uni-ZAP, pBC, pBS+/−, pSG5, pBK, pCR-Script, pET, pSPUTK, p3'SS, pGEM, pSK+/−, pGEX, pSPORTI and II, pOPRSVI CAT, pOP13 CAT, pXTI, pSG5, pPbac, pMbac, pMC1neo, pOG44, pOG45, pFRTβGAL, pNEOβGAL, pRS403, pRS404, pRS405, pRS406, pRS413, pRS414, pRS415, pRS416, lambda MOSSlox, and lambda MOSElox. Optional vectors for the present invention, include but are not limited to, lambda ZAP II, and pGEX. For a description of various nucleic acids see, for example, Stratagene Cloning Systems, Catalogs 1995, 1996, 1997 (La Jolla, Calif.); and, Amersham Life Sciences, Inc, Catalog '97 (Arlington Heights, Ill.).

Synthetic Methods for Constructing Nucleic Acids

The isolated nucleic acids of the present invention can also be prepared by direct chemical synthesis by methods such as the phosphotriester method of Narang et al., *Meth. Enzymol.* 68: 90–99 (1979); the phosphodiester method of Brown et al., *Meth. Enzymol.* 68: 109–151 (1979); the diethylphosphoramidite method of Beaucage et al., *Tetra. Lett.* 22: 1859–1862 (1981); the solid phase phosphoramidite triester method described by Beaucage and Caruthers, *Tetra. Letts.* 22(20): 1859–1862 (1981), e.g., using an automated synthesizer, e.g, as described in Needham-VanDevanter et al., *Nucleic Acids Res.*, 12: 6159–6168 (1984); and, the solid support method of U.S. Pat. No. 4,458,066. Chemical synthesis generally produces a single stranded oligonucleotide. This may be converted into double stranded DNA by hybridization with a complementary sequence, or by polymerization with a DNA polymerase using the single strand as a template. One of skill will recognize that while chemical synthesis of DNA is limited to sequences of about 100 bases, longer sequences may be obtained by the ligation of shorter sequences.

UTRs and Codon Preference

In general, translational efficiency has been found to be regulated by specific sequence elements in the 5' non-coding or untranslated region (5' UTR) of the RNA. Positive sequence motifs include translational initiation consensus sequences (Kozak, *Nucleic Acids Res.* 15:8125 (1987)) and the 5<G>7 methyl GpppG RNA cap structure (Drummond et al., *Nucleic Acids Res.* 13:7375 (1985)). Negative elements include stable intramolecular 5' UTR stem-loop structures (Muesing et al., *Cell* 48:691 (1987)) and AUG sequences or short open reading frames preceded by an appropriate AUG in the 5' UTR (Kozak, supra, Rao et al., *Mol. and Cell. Biol.* 8:284 (1988)). Accordingly, the present invention provides 5' and/or 3' UTR regions for modulation of translation of heterologous coding sequences.

Further, the polypeptide-encoding segments of the polynucleotides of the present invention can be modified to alter codon usage. Altered codon usage can be employed to alter translational efficiency and/or to optimize the coding sequence for expression in a desired host or to optimize the codon usage in a heterologous sequence for expression in maize. Codon usage in the coding regions of the polynucleotides of the present invention can be analyzed statistically using commercially available software packages such as "Codon Preference" available from the University of Wisconsin Genetics Computer Group (see Devereaux et al., *Nucleic Acids Res.* 12: 387–395 (1984)) or MacVector 4.1 (Eastman Kodak Co., New Haven, Conn.). Thus, the present invention provides a codon usage frequency characteristic of the coding region of at least one of the polynucleotides of the present invention. The number of polynucleotides (3 nucleotides per amino acid) that can be used to determine a codon usage frequency can be any integer from 3 to the number of polynucleotides of the present invention as provided herein. Optionally, the polynucleotides will be full-length sequences. An exemplary number of sequences for statistical analysis can be at least 1, 5, 10, 20, 50, or 100.

Sequence Shuffling

The present invention provides methods for sequence shuffling using polynucleotides of the present invention, and compositions resulting therefrom. Sequence shuffling is described in PCT publication No. 96/19256. See also, Zhang, J.-H., et al. *Proc. Nail. Acad. Sci. USA* 94:4504–4509 (1997) and Zhao, et al., *Nature Biotech* 16:258–261 (1998). Generally, sequence shuffling provides a means for generating libraries of polynucleotides having a desired characteristic, which can be selected or screened for. Libraries of recombinant polynucleotides are generated from a population of related sequence polynucleotides, which comprise sequence regions, which have substantial sequence identity and can be homologously recombined in vitro or in vivo. The population of sequence-recombined polynucleotides comprises a subpopulation of polynucleotides which possess desired or advantageous characteristics and which can be selected by a suitable selection or screening method. The characteristics can be any property or attribute capable of being selected for or detected in a screening system, and may include properties of: an encoded protein, a transcriptional element, a sequence controlling transcription, RNA processing, RNA stability, chromatin conformation, translation, or other expression property of a gene or transgene, a replicative element, a protein-binding element, or the like, such as any feature which confers a selectable or detectable property. In some embodiments, the selected characteristic will be an altered $K_m$ and/or $K_{cat}$ over the wild-type protein as provided herein. In other embodiments, a protein or polynucleotide generated from sequence shuffling will have a substrate binding affinity greater than the non-shuffled wild-type polynucleotide. In yet other embodiments, a protein or polynucleotide generated from sequence shuffling will have an altered pH optimum as compared to the non-shuffled wild-type polynuclcotide. The increase in such properties can be at least 110%, 120%, 130%, 140% or greater than 150% of the wild-type value.

Recombinant Expression Cassettes

The present invention further provides recombinant expression cassettes comprising a nucleic acid of the present invention. A nucleic acid sequence coding for the desired polynucleotide of the present invention, for example a cDNA or a genomic sequence encoding a polypeptide long enough to code for an active protein of the present invention, can be used to construct a recombinant expression cassette which can be introduced into the desired host cell. A recombinant expression cassette will typically comprise a polynucleotide of the present invention operably linked to transcriptional initiation regulatory sequences which will direct the transcription of the polynucleotide in the intended host cell, such as tissues of a transformed plant.

For example, plant expression vectors may include (1) a cloned plant gene under the transcriptional control of 5' and 3' regulatory sequences and (2) a dominant selectable marker. Such plant expression vectors may also contain, if desired, a promoter regulatory region (e.g., one conferring inducible or constitutive, environmentally- or developmentally-regulated, or cell- or tissue-specific/ selective expression), a transcription initiation start site, a ribosome binding site, an RNA processing signal, a transcription termination site, and/or a polyadenylation signal.

A plant promoter fragment can be employed which will direct expression of a polynucleotide of the present invention in all tissues of a regenerated plant. Such promoters are referred to herein as "constitutive" promoters and are active under most environmental conditions and states of development or cell differentiation. Examples of constitutive promoters include the 1'- or 2'-promoter derived from T-DNA of *Agrobacterium tumefaciens*, the Smas promoter, the cinnamyl alcohol dehydrogenase promoter (U.S. Pat. No. 5,683,439), the Nos promoter, the rubisco promoter, the GRP1-8 promoter, the 35S promoter from cauliflower mosaic virus (CaMV), as described in Odell et al., (1985), *Nature*, 313:810–812, rice actin (McElroy et al., (1990), *Plant Cell*, 163–171); ubiquitin (Christensen et al., (1992), *Plant Mol. Biol.* 12:619–632; and Christensen, et al., (1992), *Plant Mol. Biol.* 18:675–689); pEMU (Last, et al., (1991), *Theor. Appl. Genet.* 81:581–588); MAS (Velten et al., (1984), *EMBO J.* 3:2723–2730); and maize H3 histone (Lepetit et al., (1992), *Mol. Gen. Genet.* 231:276–285; and Atanassvoa et al., (1992), *Plant Journal* 2(3):291–300), the Rsyn7 as described in published PCT Application WO 97/44756, ALS promoter, as described in published PCT Application WO 96/30530, and other transcription initiation regions from various plant genes known to those of skill. For the present invention ubiquitin is the preferred promoter for expression in monocot plants.

Alternatively, the plant promoter can direct expression of a polynucleotide of the present invention in a specific tissue or may be otherwise under more precise environmental or developmental control. Such promoters are referred to here as "inducible" promoters. Environmental conditions that may effect transcription by inducible promoters include pathogen attack, anaerobic conditions, or the presence of light. Examples of inducible promoters are the Adh1 promoter, which is inducible by hypoxia or cold stress, the Hsp70 promoter, which is inducible by heat stress, and the PPDK promoter, which is inducible by light.

Examples of promoters under developmental control include promoters that initiate transcription only, or preferentially, in certain tissues, such as leaves, roots, fruit, seeds, or flowers. The operation of a promoter may also vary depending on its location in the genome. Thus, an inducible promoter may become fully or partially constitutive in certain locations.

If polypeptide expression is desired, it is generally desirable to include a polyadenylation region at the 3' end of a polynucleotide coding region. The polyadenylation region can be derived from a variety of plant genes, or from T-DNA. The 3' end sequence to be added can be derived from, for example, the nopaline synthase or octopine synthase genes, or alternatively from another plant gene, or less preferably from any other eukaryotic gene. Examples of such regulatory elements include, but are not limited to, 3' termination and/or polyadenylation regions such as those of the *Agrobacterium tumefaciens* nopaline synthase (nos) gene (Bevan et al., (1983), *Nucl. Acids Res.* 12:369–385); the potato proteinase inhibitor II (PINII) gene (Keil, et al., (1986), *Nucl. Acids Res.* 14:5641–5650; and An et al., (1989), *Plant Cell* 1:115–122); and the CaMV 19S gene (Mogen et al., (1990), *Plant Cell* 2:1261–1272).

An intron sequence can be added to the 5' untranslated region or the coding sequence of the partial coding sequence to increase the amount of the mature message that accumulates in the cytosol. Inclusion of a spliceable intron in the transcription unit in both plant and animal expression constructs has been shown to increase gene expression at both the mRNA and protein levels up to 1000-fold. Buchman and Berg, *Mol. Cell Biol.* 8: 4395–4405 (1988); Callis et al., *Genes Dev.* 1: 1183–1200 (1987). Such intron enhancement of gene expression is typically greatest when placed near the 5' end of the transcription unit. Use of maize introns Adh1-S intron 1, 2, and 6, the Bronze-1 intron are known in the art. See generally, *The Maize Handbook*, Chapter 116, Freeling and Walbot, Eds., Springer, New York (1994).

Plant signal sequences, including, but not limited to, signal-peptide encoding DNA/RNA sequences which target proteins to the extracellular matrix of the plant cell (Dratewka-Kos, et al., (1989), *J. Biol. Chem.* 264:4896–4900), the *Nicotiana plumbaginifolia* extension gene (DeLoose, et al., (1991), *Gene* 99:95–100), signal peptides which target proteins to the vacuole like the sweet potato sporamin gene (Matsuka, et al., (1991), *PNAS* 88:834) and the barley lectin gene (Wilkins, et al., (1 990), *Plant Cell*, 2:301–313), signal peptides which cause proteins to be secreted such as that of PRIb (Lind, et al., (1992), *Plant Mol. Biol.* 18:47–53), or the barley alpha amylase (BAA) (Rahmatullah, et al., *Plant Mot. Biol.* 12:119 (1989)) and hereby incorporated by reference), or from the present invention the signal peptide from the ESP1 or BEST1 gene, or signal peptides which target proteins to the plastids such as that of rapeseed enoyl-Acp reductase (Verwaert, et al., (1994), *Plant Mol. Biol.* 26:189–202) are useful in the invention. The barley alpha amylase signal sequence fused to the trAPAO or APAO polynucleotide is the preferred construct for expression in maize for the present invention.

The vector comprising the sequences from a polynucleotide of the present invention will typically comprise a marker gene, which confers a selectable phenotype on plant cells. Usually, the selectable marker gene will encode antibiotic resistance, with suitable genes including genes coding for resistance to the antibiotic spectinomycin (e.g., the aada gene), the streptomycin phosphotransferase (SPT) gene coding for streptomycin resistance, the neomycin phosphotransferase (NPTII) gene encoding kanamycin or geneticin resistance, the hygromycin phosphotransferase (HPT) gene coding for hygromycin resistance, genes coding for resistance to herbicides which act to inhibit the action of acetolactate synthase (ALS), in particular the sulfonylurea-type herbicides (e.g., the acetolactate synthase (ALS) gene containing mutations leading to such resistance in particular the S4 and/or Hra mutations), genes coding for resistance to herbicides which act to inhibit action of glutamine synthase, such as phosphinothricin or basta (e.g., the bar gene), or other such genes known in the art. The bar gene encodes resistance to the herbicide basta, and the ALS gene encodes resistance to the herbicide chlorsulfuron.

Alternatively, the invention, itself, could be used as a method for selection of transformants, in other words as a selectable marker. An APAO or trAPAO polynucleotide operably linked to a promoter and then transformed into a plant cell by any of the methods described in the present application would express the degradative enzyme. When the plant cells are placed in the presence of fumonisin, AP1, or a phytotoxic analog in culture only the transformed cells would be able to grow. In another embodiment, the plant cell could be transformed with both a polynucleotide for APAO and a polynucleotide for fumonisin esterase. The selective agent in this case could be either AP1 or fumonisin or any structural analog. Thus, growth of plant cells in the presence of a mycotoxin favors the survival of plant cells that have been transformed to express the coding sequence that codes for one of the enzymes of this invention and degrades the toxin. When the APAO or trAPAO cassette with or without the fumonisin esterase polynucleotide, is co-transformed with another gene of interest and then placed in the presence of fumonisin, AP1 or a phytotoxic analog, this invention would allow for selection of only those plant cells that contain the gene of interest. In the past antibiotic resistance genes have been used as selectable markers. Given the current concerns by consumers and environmentalist over use of antibiotic genes and the possibility of resistant microorganisms arising due to this use, a non-antibiotic resistant selectable marker system such as the present invention, fulfills this very important need.

Typical vectors useful for expression of genes in higher plants are well known in the art and include vectors derived from the tumor-inducing (Ti) plasmid of *Agrobacterium tumefaciens* described by Rogers et al., Meth. In Enzymol., 153:253–277 (1987). These vectors are plant integrating vectors in that on transformation, the vectors integrate a portion of vector DNA into the genome of the host plant. Exemplary *A. tumefaciens* vectors useful herein are plasmids pKYLX6 and pKYLX7 of Schardl et al., *Gene*, 61:1–11 (1987) and Berger el al., Proc. Natl. Acad. Sci. U.S.A., 86:8402–8406 (1989). Another useful vector herein is plasmid pB1101.2 that is available from CLONTECH Laboratories, Inc. (Palo Alto, Calif.).

Expression of Proteins in Host Cells

Using the nucleic acids of the present invention, one may express a protein of the present invention in a recombinantly engineered cell such as bacteria, yeast, insect, mammalian, or preferably plant cells. The cells produce the protein in a non-natural condition (e.g., in quantity, composition, location, and/or time), because they have been genetically altered through human intervention to do so.

It is expected that those of skill in the art are knowledgeable in the numerous expression systems available for expression-of a nucleic acid encoding a protein of the present invention. No attempt to describe in detail the various methods known for the expression of proteins in prokaryotes or eukaryotes will be made.

In brief summary, the expression of isolated nucleic acids encoding a protein of the present invention will typically be achieved by operably linking, for example, the DNA or CDNA to a promoter (which is either constitutive or inducible), followed by incorporation into an expression vector. The vectors can be suitable for replication and integration in either prokaryotes or eukaryotes. Typical expression vectors contain transcription and translation terminators, initiation sequences, and promoters useful for regulation of the expression of the DNA encoding a protein of the present invention. To obtain high level expression of a cloned gene, it is desirable to construct expression vectors which contain, at the minimum, a strong promoter, such as ubiquitin, to direct transcription, a ribosome binding site for translational initiation, and a transcription/translation terminator. Constitutive promoters are classified as providing for a range of constitutive expression. Thus, some are weak constitutive promoters, and others are strong constitutive promoters. Generally, by "weak promoter" is intended a promoter that drives expression of a coding sequence at a low level. By "low level" is intended at levels of about 1/10,000 transcripts to about 1/100,000 transcripts to about 1/500,000 transcripts. Conversely, a "strong promoter" drives expression of a coding sequence at a "high level", or about 1/10 transcripts to about 1/100 transcripts to about 1/1,000 transcripts.

One of skill would recognize that modifications could be made to a protein of the present invention without diminishing its biological activity. Some modifications may be made to facilitate the cloning, expression, or incorporation of the targeting molecule into a fusion protein. Such modifications are well known to those of skill in the art and include, for example, a methionine added at the amino terminus to provide an initiation site, or additional amino acids (e.g., poly His) placed on either terminus to create conveniently located restriction sites or termination codons or purification sequences.

A. Expression in Prokaryotes

Prokaryotic cells may be used as hosts for expression. Prokaryotes most frequently are represented by various strains of E. coli; however, other microbial strains may also be used. Commonly used prokaryotic control sequences which are defined herein to include promoters for transcription initiation, optionally with an operator, along with ribosome binding site sequences, include such commonly used promoters as the beta lactamase (penicillinase) and lactose (lac) promoter systems (Chang et al., Nature 198:1056 (1977)), the tryptophan (trp) promoter system (Goeddel et al., Nucleic Acids Res. 8:4057 (1980)) and the lambda derived P L promoter and N-gene ribosome binding site (Shimatake et al., Nature 292:128 (1981)). The inclusion of selection markers in DNA vectors transfected in E. coli is also useful. Examples of such markers include genes specifying resistance to ampicillin, tetracycline, or chloramphenicol.

The vector is selected to allow introduction of the gene of interest into the appropriate host cell. Bacterial vectors are typically of plasmid or phage origin. Appropriate bacterial cells are infected with phage vector particles or transfected with naked phage vector DNA. If a plasmid vector is used, the bacterial cells are transfected with the plasmid vector DNA. Expression systems for expressing a protein of the present invention are available using Bacillus sp. and Salmonella (Palva, et al., Gene 22: 229–235 (1983); Mosbach, et al., Nature 302: 543–545 (1983)). The pGEX-4T-1 plasmid vector from Pharmacia is the preferred E. coli expression vector for the present invention.

B. Expression in Eukaryotes

A variety of eukaryotic expression systems such as yeast, insect cell lines, plant and mammalian cells, are known to those of skill in the art. As explained briefly below, the present invention can be expressed in these eukaryotic systems. In some embodiments, transformed/transfected plant cells, as discussed infra, are employed as expression systems for production of the proteins of the instant invention.

Synthesis of heterologous proteins in yeast is well known. Sherman, F., et al., *Methods in Yeast Genetics*, Cold Spring Harbor Laboratory (1982) is a well recognized work describing the various methods available to produce the protein in yeast. Two widely utilized yeasts for production of eukaryotic proteins are *Saccharomyces cerevisiae* and *Pichia pastoris*. Vectors, strains, and protocols for expression in Saccharomyces and Pichia are known in the art and available from commercial suppliers (e.g., Invitrogen). Suitable vectors usually have expression control sequences, such as promoters, including 3-phosphoglycerate kinase or alcohol oxidase, and an origin of replication, termination sequences and the like as desired.

A protein of the present invention, once expressed, can be isolated from yeast by lysing the cells and applying standard protein isolation techniques to the lysates or the pellets. The monitoring of the purification process can be accomplished by using Western blot techniques or radioimmunoassay of other standard immunoassay techniques.

The sequences encoding proteins of the present invention can also be ligated to various expression vectors for use in transfecting cell cultures of, for instance, mammalian, insect, or plant origin. Mammalian cell systems often will be in the form of monolayers of cells although mammalian cell suspensions may also be used. A number of suitable host cell lines capable of expressing intact proteins have been developed in the art, and include the HEK293, BHK21, and CHO cell lines. Expression vectors for these cells can include expression control sequences, such as an origin of replication, a promoter (e.g., the CMV promoter, a HSV tk promoter or pgk (phosphoglycerate kinase) promoter), an enhancer (Queen et al., *Immunol. Rev.* 89: 49 (1986)), and necessary processing information sites, such as ribosome binding sites, RNA splice sites, polyadenylation sites (e.g., an SV40 large T Ag poly A addition site), and transcriptional terminator sequences. Other animal cells useful for production of proteins of the present invention are available, for instance, from the American Type Culture Collection Catalogue of Cell Lines and Hybridomas (7th edition, 1992).

Appropriate vectors for expressing proteins of the present invention in insect cells are usually derived from the SF9 baculovirus. Suitable insect cell lines include mosquito larvae, silkworm, armyworm, moth, and Drosophila cell lines such as a Schneider cell line (See Schneider, *J Embryol. Exp. Morphol.* 27: 353–365 (1987).

As with yeast, when higher animal or plant host cells are employed, polyadenylation or transcription terminator sequences are typically incorporated into the vector. An example of a terminator sequence is the polyadenlyation sequence from the bovine growth hormone gene. Sequences for accurate splicing of the transcript may also be included. An example of a splicing sequence is the VP1 intron from SV40 (Sprague, et al., *J. Virol.* 45: 773–781 (1983)). Additionally, gene sequences to control replication in the host cell may be incorporated into the vector such as those found in bovine papilloma virus type-vectors. Saveria-Campo, M., Bovine Papilloma Virus DNA a Eukaryotic Cloning Vector in DNA *Cloning Vol. II a Practical Approach*, D. M. Glover, Ed., IRL Press, Arlington, Va. pp. 213–238 (1985).

In addition, one of the genes for fumonisin esterase or the APAO or trAPAO placed in the appropriate plant expression vector can be used to transform plant cells. The enzyme can then be isolated from plant callus or the transformed cells can be used to regenerate transgenic plants. Such transgenic plants can be harvested, and the appropriate tissues (seed or leaves, for example) can be subjected to large scale protein extraction and purification techniques, and the fumonisin degradation enzymes or APAO can be isolated for use in fumonisin and fumonisin hydrolysis product detoxification processes.

Plant Transformation Methods

Numerous methods for introducing foreign genes into plants are known and can be used to insert an APAO or trAPAO polynucleotide into a plant host including biological and physical plant transformation protocols. See, for example, Miki et al., (1993), "Procedure for Introducing Foreign DNA into Plants", In: *Methods in Plant Molecular Biology and Biotechnology*, Glick and Thompson, eds., CRC Press, Inc., Boca Raton, pages 67–88. The methods chosen vary with the host plant, and include chemical transfection methods such as calcium phosphate, microorganism-mediated gene transfer such as Agrobacterium (Horsch, et al., (1985), *Science* 227:1229–31), electroporation, micro-injection, and biolistic bombardment.

Expression cassettes and vectors and in vitro culture methods for plant cell or tissue transformation and regeneration of plants are known and available. See, for example, Gruber, et al., (1993), "Vectors for Plant Transformation" In: *Methods in Plant Molecular Biology and Biotechnology*, Glick and Thompson, eds. CRC Press, Inc., Boca Raton, pages 89–119.

Agrobacterium-mediated Transformation

The most widely utilized method for introducing an expression vector into plants is based on the natural transformation system of Agrobacterium. *A. tumefaciens* and *A. rhizogenes* are plant pathogenic soil bacteria, which genetically transform plant cells. The Ti and Ri plasmids of *A. tumefaciens* and *A. rhizogenes*, respectively, carry genes responsible for genetic transformation of plants. See, for example, Kado, (1991), *Crit. Rev. Plant Sci.* 10:1. Descriptions of the Agrobacterium vector systems and methods for Agrobacterium-mediated gene transfer are provided in Gruber et al., supra; Miki, et al., supra; and Moloney et al., (1989), *Plant Cell Reports* 8:238.

Similarly, the gene can be inserted into the T-DNA region of a Ti or Ri plasmid derived from *A. tumefaciens*or *A. rhizogenes*, respectively. Thus, expression cassettes can be constructed as above, using these plasmids. Many control sequences are known which when coupled to a heterologous coding sequence and transformed into a host organism show fidelity in gene expression with respect to tissue/organ specificity of the original coding sequence. See, e.g., Benfey, P. N., and Chua, N. H. (1989) *Science* 244: 174–181. Particularly suitable control sequences for use in these plasmids are promoters for constitutive leaf-specific expression of the gene in the various target plants. Other useful control sequences include a promoter and terminator from the nopaline synthase gene (NOS). The NOS promoter and terminator are present in the plasmid pARC2, available from the American Type Culture Collection and designated ATCC 67238. If such a system is used, the virulence (vir) gene from either the Ti or Ri plasmid must also be present, either along with the T-DNA portion, or via a binary system where the vir gene is present on a separate vector. Such systems, vectors for use therein, and methods of transforming plant cells are described in U.S. Pat. No. 4,658,082; U.S. application Ser. No. 913,914, filed Oct. 1, 1986, as referenced in U.S. Pat. No. 5,262,306, issued Nov. 16, 1993 to Robeson, et al.; and Simpson, R. B., et al. (1986) *Plant Mol. Biol.* 6: 403–415 (also referenced in the '306 patent); all incorporated by reference in their entirety.

Once constructed, these plasmids can be placed into *A. rhizogenes* or *A. tumefaciens* and these vectors used to transform cells of plant species, which are ordinarily susceptible to Fusarium or Alternaria infection. Several other transgenic plants are also contemplated by the present invention including but not limited to soybean, corn, sorghum, alfalfa, rice, clover, cabbage, banana, coffee, celery, tobacco, cowpea, cotton, melon and pepper. The selection of either *A. tumefaciens* or *A. rhizogenes* will depend on the plant being transformed thereby. In general *A. tumefaciens* is the preferred organism for transformation. Most dicotyledonous plants, some gymnosperms, and a few monocotyledonous plants (e.g. certain members of the Liliales and Arales) are susceptible to infection with *A. tumefaciens. A. rhizogenes* also has a wide host range, embracing most dicots and some gymnosperms, which includes members of the Leguminosae, Compositae, and Chenopodiaceae. Monocot plants can now be transformed with some success. European Patent Application Publication Number 604 662 A1 to Hiei et al. discloses a method for transforming monocots using Agrobacterium. Saito et al. discloses a method for transforming monocots with Agrobacterium using the scutellum of immature embryos (European Application 672 752 A1). Ishida et al discusses a method for transforming maize by exposing immature embryos to *A. tumefaciens* (Ishida et al., *Nature Biotechnology*, 1996, 14:745–750).

Once transformed, these cells can be used to regenerate transgenic plants, capable of degrading fumonisin. For example, whole plants can be infected with these vectors by wounding the plant and then introducing the vector into the wound site. Any part of the plant can be wounded, including leaves, stems and roots. Alternatively, plant tissue, in the form of an explant, such as cotyledonary tissue or leaf disks, can be inoculated with these vectors, and cultured under conditions, which promote plant regeneration. Roots or shoots transformed by inoculation of plant tissue with *A. rhizogenes* or *A. tumefaciens*, containing the gene coding for the fumonisin degradation enzyme, can be used as a source of plant tissue to regenerate fumonisin-resistant transgenic plants, either via somatic embryogenesis or organogenesis. Examples of such methods for regenerating plant tissue are disclosed in Shahin, E. A. (1985) *Theor. Appl. Genet.* 69:235–240; U.S. Pat. No. 4,658,082; Simpson, R. B., et al. (1986) *Plant Mol. Biol.* 6: 403–415; and U.S. Pat. applications Ser. Nos. 913,913 and 913,914, both filed Oct. 1, 1986, as referenced in U.S. Pat. No. 5,262,306, issued Nov. 16, 1993 to Robeson, et al.; the entire disclosures therein incorporated herein by reference.

Direct Gene Transfer

Despite the fact that the host range for Agrobacterium-mediated transformation is broad, some major cereal crop species and gymnosperms have generally been recalcitrant to this mode of gene transfer, even though some success has recently been achieved in rice (Hiei et al., (1994), *The Plant Journal* 6:271–282). Several methods of plant transformation, collectively referred to as direct gene transfer, have been developed as an alternative to Agrobacterium-mediated transformation.

A generally applicable method of plant transformation is microprojectile-mediated transformation, where DNA is carried on the surface of microprojectiles measuring about 1 to 4 $\mu$m. The expression vector is introduced into plant tissues with a biolistic device that accelerates the microprojectiles to speeds of 300 to 600 m/s which is sufficient to penetrate the plant cell walls and membranes. (Sanford et al., (1987), *Part. Sci. Technol.* 5:27; Sanford, 1988, *Trends Biotech* 6:299; Sanford, (1990), *Physiol. Plant* 79:206; Klein et al., (1992), *Biotechnology* 10:268).

Another method for physical delivery of DNA to plants is sonication of target cells as described in Zang et al., (1991), *BioTechnology* 9:996. Alternatively, liposome or spheroplast fusions have been used to introduce expression vectors into plants. See, for example, Deshayes et al., (1985), *EMBO J.* 4:2731; and Christou et al., (1987), *PNAS USA* 84:3962. Direct uptake of DNA into protoplasts using $CaCl_2$ precipitation, polyvinyl alcohol, or poly-L-omithine has also been reported. See, for example, Hain et al., (1985), *Mol. Gen. Genet.* 199:161; and Draper et al., (1982), *Plant Cell Physiol.* 23:451.

Electroporation of protoplasts and whole cells and tissues has also been described. See, for example, Donn et al., (1990), In: *Abstracts of the VIIth Int'l. Congress on Plant Cell and Tissue Culture IAPTC*, A2-38, page 53; D'Halluin et al., (1992), *Plant Cell* 4:1495–1505; and Spencer et al., (1994), *Plant Mol. Biol.* 24:51–61.

Thus, polynucleotide encoding a polypeptide able to inactivate fumonisin or AP1 can be isolated and cloned in an appropriate vector and inserted into an organism normally sensitive to the Fusarium or its toxins. Furthermore, the polynucleotide imparting fumonisin or AP1 degradative activity can be transferred into a suitable plasmid, and transformed into a plant. Thus, a fumonisin or AP1 degrading transgenic plant can be produced. Organisms expressing the polynucleotide can be easily identified by their ability to degrade fumonisin or AP1. The protein capable of degrading fumonisin or AP1 can be isolated and characterized using techniques well known in the art.

APAO or trAPAO in a Transgenic Plant

Fumonisin esterase reduces but does not eliminate the toxicity of fumonisins. Therefore a second enzymatic modification to further reduce or abolish toxicity is desirable. The partially purified APAO enzyme from *Exophiala spinifera* has little or no activity on intact FB1, a form of fumonisin. However, recombinant APAO enzyme from *Exophiala spinifera*, expressed in *E. coli*, has significant but reduced activity on intact FB1 and other B-series fumonisins. APAO or trAPAO thus could potentially be used without fumonisin esterase since the amine group is the major target for detoxification. Alternatively, the two genes, fumonisin esterase and APAO (or trAPAO) can be used together for degrading toxins.

APAO is predicted to be an enzyme that, when by itself or co-expressed in a heterologous expression system along with fumonisin esterase (either ESP1 or BEST1), will result in the production of 2-oxo pentol (2-OP) from fumonisin B1. The substrate range of recombinant, *E coli*-expressed APAO is limited to fumonisins and their hydrolysis products and does not include amino acids, sphingolipid precursors such as phytosphingosine, or polyamines such as spermidine. Thus, APAO is highly specific for fumonisin-like amines, and thus would have little deleterious effect on other cellular metabolites. In addition, if it is extracellularly localized, it will limit any contact with biologically important amines that might also be substrates. The end result will be a more effective detoxification of fumonisins than can be achieved with esterase alone.

The oxidase activity of APAO is predicted to result in generation of hydrogen peroxide in stoichiometric amounts relative to AP1 or fumonisin oxidized. This may prove to be an additional benefit of this enzyme, since hydrogen peroxide is both antimicrobial and is thought to contribute to the onset of a defense response in plants (Przemylaw, *Biochem J*, 322:681–692 (1997), Lamb, el al., *Ann Rev Plant Physiol Plant Mol Bio* 48:251–275 (1997), and Alverez, et al., *Oxidative Stress and the Molecular Biology of Antioxidant Defenses*, Cold Spring Harbor Press, 815–839 (1997)).

Since one of the embodiments of the present invention is to have both a fumonisin esterase polynucleotide and an APAO or trAPAO polynucleotide present in a plant, there are several ways to introduce more than one polynucleotide in a plant. One way is to transform plant tissue with polynucleotides to both fumonisin esterase and APAO or trAPAO at the same time. In some tissue culture systems it is possible to transform callus with one polynucleotide and then after establishing a stable culture line containing the first polynucleotide, transform the callus a second time with the second polynucleotide. One could also transform plant tissue with one polynucleotide, regenerate whole plants, then transform the second polynucleotide into plant tissue and regenerate whole plants. The final step would then be to cross a plant containing the first polynucleotide with a plant containing the second polynucleotide and select for progeny containing both polynucleotides.

Another method is to create a fusion protein between esterase and APAO or trAPAO, preferably with a spacer region between the two polypeptides. Both enzymes would be active although tethered to each other. In addition, an enzyme cleavage site engineered in the spacer region, would allow cleavage by an endogenous or introduced protease.

Transgenic plants containing both a fumonisin esterase enzyme and/or the APAO enzyme and thus able to degrade fumonisin or a structurally related mycotoxin would be able to reduce or eliminate the pathogenicity of any microorganism that uses fumonisin or a structurally related mycotoxin as a mode of entry to infect a plant. Fungal pathogens frequently use toxins to damage plants and weaken cell integrity in order to gain entry and expand infection in a plant. By preventing the damage induced by a toxin, a plant would be able to prevent the establishment of the pathogen and thereby become tolerant or resistant to the pathogen.

Another benefit of fumonisin degradation is the production of hydrogen peroxide. When fumonisin or AP1 is oxididatively deaminated at C-2, as occurs by exposure to APAO or trAPAO enzyme, hydrogen peroxide is produced as a by-product. Hydrogen peroxide production can trigger enhanced resistance responses in a number of ways. 1) Hydrogen peroxide has direct antimicrobial activity. 2) Hydrogen peroxide acts as a substrate for peroxidases associated with lignin polymerization and hence cell wall strengthening. 3) Via still to be determined mechanisms, hydrogen peroxide acts as a signal for activation of expression of defense related genes, including those that result in stimulation of salicylic acid accumulation. Salicylic acid is thought to act an endogenous signal molecule that triggers expression of genes coding for several classes of pathogenesis-related proteins. Moreover, salicylic acid may set up the oxidative burst and thus act in a feedback loop enhancing its own synthesis. Salicylic acid may also be involved in hypersensitive cell death by acting as an inhibitor of catalase, an enzyme that removes hydrogen peroxide. 4) Hydrogen peroxide may trigger production of additional defense compounds of additional defense compounds such as phytoalexins, antimicrobial low molecular weight compounds. For a review on the role of the oxidative burst and SA please see Lamb, C. and Dixon, R. A., *Ann. Rev. Plant Physiol. Plant Mol. Biol.*, 48: 251–275 (1 997).

Detoxification of Harvested Grain, Silage, or Contaminated Food Crop

The present invention also relates to a method of detoxifying a fumonisin or a structurally related mycotoxin with an APAO enzyme during the processing of grain for animal or human food consumption, during the processing of plant material for silage, or food crops contaminated with a toxin producing microbe, such as but not limited to, tomato. Since the atmospheric ammoniation of corn has proven to be an ineffective method of detoxification (see B. Fitch Haumann, *INFORM* 6:248–257 (1995)), such a methodology during processing is particularly critical where transgenic detoxification is not applicable.

In one embodiment of the present invention, fumonisin degradative enzymes are presented to grain, plant material for silage, or a contaminated food crop, or during the processing procedure, at the appropriate stages of the procedure and in amounts effective for detoxification of fumonisins and structurally related mycotoxins. Detoxification by the enzymes, microbial strains, or an engineered microorganism can occur not only during the processing, but also any time prior or during the feeding of the grain or plant material to an animal or incorporation of the grain or food crop into a human food product, or before or during ingestion of the food crop.

Another embodiment of the present invention is the engineering of a bacterium or fungus to express the detoxification enzymes and then using the bacterium or fungus rather than the enzyme itself There are a number of microbes that could be engineered to express the polynucleotides of the present invention. One could also activate, either inducibly or constitutively, the endogenous genes for fumonisin esterase or APAO. By overexpressing the degradative enzymes and then treating plants, seed, or silage with the microorganism, it would be possible to degrade fumonisin in situ.

The polynucleotides of the invention can be introduced into microorganisms that multiply on plants (epiphytes) to deliver enzymes to potential target crops. Epiphytes can be gram-positive or gram-negative bacteria, for example.

The microorganisms that have been genetically altered to contain at least one degradative polynucleotide and resulting polypeptide may be used for protecting agricultural crops and products. In one aspect of the invention, whole, i.e. unlysed, cells of the transformed organism are treated with reagents that prolong the activity of the enzyme produced in the cell when the cell is applied to the environment of a target plant. A secretion leader may be used in combination with the gene of interest such that the resulting enzyme is secreted outside the host cell for presentation to the target plant.

The degradative enzymes can be fermented in a bacterial host and the resulting bacteria processed and used as a microbial spray. Any suitable microorganism can be used for this purpose. See, for example, Gaertner, et al. (1993) in *Advanced Engineered Pesticides*, (ed. Kim, Marcel Dekker, New York).

The enzymes or microorganisms can be introduced during processing in appropriate manners, for example as a wash or spray, or in dried or lyophilized form or powered form, depending upon the nature of the milling process and/or the stage of processing at which the enzymatic treatment is carried out. See generally, Hoseney, R. C., *Principles of Cereal Science and Technology*, American Assn. of Cereal Chemists, Inc., 1990 (especially Chapters 5, 6 and 7); Jones, J. M., *Food Safety*, Eagan Press, St. Paul, Minn., 1992 (especially Chapters 7 and 9); and Jelen, P., *Introduction to Food Processing*, Restan Publ. Co., Reston, Va., 1985. Processed grain or silage to be used for animal feed can be treated with an effective amount of the enzymes in the form of an inoculant or probiotic additive, for example, or in any form recognized by those skilled in the art for use in animal feed. The enzymes of the present invention are expected to be particularly useful in detoxification during processing and/or in animal feed prior to its use, since the enzymes display relatively broad ranges of pH activity. The esterase from *Exophiala spinifera*, ATCC 74269, showed a range of activity from about pH 3 to about pH 6, and the esterase from the bacterium of ATCC 55552 showed a range of activity from about pH 6 to about pH 9 (U.S. Pat. No. 5,716,820, supra). The APAO enzyme from *Exophiala spinifera* (ATCC 74269) has a pH range of activity from pH 6 to pH 9.

Genetic Engineering of Ruminant Microorganisms

Ruminant microorganisms can be genetically engineered to contain and express either the fumonisin esterase enzymes or APAO, or a combination of the enzymes. The genetic engineering of microorganisms is now an art recognized technique, and ruminant microorganisms so engineered can be added to feed in any art recognized manner, for example as a probiotic or inoculant. In addition, microorganisms capable of functioning as bioreactors can be engineered so as to be capable of mass producing either the fumonisin esterases or the APAO enzyme.

Use of the Fumonisin Esterase and APAO Enzymes for Detection of Reagents for Fumonisins and Related Compounds Another embodiment of the present invention is the use of the enzymes of the present invention as detection reagents for fumonisins and related compounds. The enzymes of the present invention can be used as detection reagents because of the high specificity of the esterase and deaminase enzymes, and the fact that hydrolysis followed by amine oxidation can be monitored by detection of hydrogen peroxide or ammonia using standard reagents (analogous to a glucose detection assay using glucose oxidase). Hydrogen peroxide is often measured by linking a hydrogen peroxide-dependent peroxidase reaction to a colored or otherwise detectable peroxidase product (e.g. Demmano, et al., *European Journal of Biochemistry* 238(3): 785–789 (1996)). Ammonia can be measured using ion-specific electrodes : Fritsche, et al., *Analytica Chimica Acia* 244(2): 179–182 (1991); West, et al., *Analytical Chemistry* 64(5): 533–540 (1992), a herein incorporated by reference) or by GC or other chromatographic method.

For example, recombinant or non-recombinant, active fumonisin esterase (ESP1 or BEST) and APAO proteins are added in catalytic amounts to a sample tube containing an unknown amount of fumonisins (FB1, FB2, FB3, FB4, or partial or complete hydrolysis products of these). The tube is incubated under pH and temperature conditions sufficient to convert any fumonisin in the sample to AP1, and correspondingly the AP1 to 2-OP, ammonia, and hydrogen peroxide. Alternatively, APAO or trAPAO is added in catalytic amounts to a sample tube containing an unknown amount of fumonisins (FB1, FB2, FB3, FB4, or partial or complete hydrolysis products of these). The tube is incubated under pH and temperature conditions sufficient to convert any fumonisin in the sample to 2-oxo FB1, ammonia, and hydrogen peroxide. Then suitable reagents are added for quantification of the hydrogen peroxide or ammonia that were generated stoichiometrically from fumonisins. By comparison with control tubes that received no esterase or APAO enzyme, the amount of fumonisin present can be calculated in direct molar proportion to the hydrogen peroxide or ammonia detected, relative to a standard curve.

This invention can be better understood by reference to the following non-limiting examples. It will be appreciated by those skilled in the art that other embodiments of the invention may be practiced without departing from the spirit and the scope of the invention as herein disclosed and claimed.

EXAMPLE 1

Fungal and bacterial isolates. Exophiala isolates from maize were isolated as described in U.S. Pat. No. 5,716,820, issued Feb. 10, 1998 and pending U.S. application Ser. Nos. 08/888,950 and 08/888,949, both filed Jul. 7, 1997, and herein incorporated by reference.

Isolation methods. Direct isolation of black yeasts from seed was accomplished by plating 100 microliters of seed wash fluid onto YPD or Sabouraud agar augmented with cycloheximide (500 mg/liter) and chloramphenicol (50 mg/liter). Plates were incubated at room temperature for 7–14 days, and individual pigmented colonies that arose were counted and cultured for analysis of fumonisin-degrading ability as described in U.S. Pat. No. 5,716,820, issued Feb. 10, 1998 and pending U.S. application Ser. Nos. 08/888,950 and 08/888,949, both filed Jul. 7, 1997.

Analysis of fumonisins and metabolism products. Analytical thin-layer chromatography was carried out on 100% silanized C18 silica plates (Sigma #T-7020; 10×10 cm; 0.1 mm thick) by a modification of the published method of Rottinghaus (Rottinghaus, et al., *J Vet Diagn Invest*, 4: 326 (1992), and herein incorporated by reference).

To analyze fumonisin esterase activity sample lanes were pre-wet with methanol to facilitate sample application. After application of from 0.1 to 2 μl of aqueous sample, the plates were air-dried and developed in MeOH:4% KCl (3:2) or MeOH:0.2 M KOH (3:2) and then sprayed successively with 0.1 M sodium borate (pH 9.5) and fluorescamine (0.4 mg/ml in acetonitrile). Plates were air-dried and viewed under long wave UV.

For analysis of APAO activity, an alternative method was used. Equal volumes of sample and $^{14}$C-AP1 (1 mg/ml, pH 8, 50 mM sodium phosphate) were incubated at room temperature for one to six days. Analytical thin-layer chromatography was then carried out on C60 HPK silica gel plates (Whatman #4807–700; 10×10 cm; 0.2 mm thick). After application of from 0.1 to 2 μl of aqueous sample, the plates were air-dried and developed in $CHCl_3$: $MeOH:CH_3COOH:H_2O$ (55:36:8:1). Plates were then air dried, and exposed to PhosphorImager screen (Molecular Dynamics) or autoradiographic film. A Storm™ PhosphorImager (Molecular Dynamics) was used to scan the image produced on the screen.

Alkaline hydrolysis of FB1 to AP1. FB1 or crude fumonisin $C_8$ material was suspended in water at 10–100 mg/ml and added to an equal volume of 4 N NaOH in a screw-cap tube. The tube was sealed and incubated at 60° C. for 1 hr. The hydrolysate was cooled to RT and mixed with an equal volume of ethyl acetate, centrifuged at 1000 RCF for 5 minute and the organic (upper) layer recovered. The pooled ethyl acetate layers from two successive extractions were dried under $N_2$ and resuspended in distilled $H_2O$. The resulting material (the aminopentol of FB1 or "AP1") was analyzed by TLC.

Enzyme activity of culture filtrate and mycelium. *Exophiala spinifera* isolate 2141.10 was grown on YPD agar for 1 week, and conidia were harvested, suspended in sterile water, and used at 105 conidia per ml to inoculate sterile Fries mineral salts medium containing 1 mg/ml purified FB1 (Sigma Chemical Co.). After 2 weeks incubation at 28° C. in the dark, cultures were filtered through 0.45 micron cellulose acetate filters, and rinsed with Fries mineral salts. Fungal mycelium was suspended in 15 mL of 0.1% FB1, pH 5.2+1 mM EDTA+3 μg/mL Pepstatin A+1.5 μg/mL Leupeptin and disrupted in a Bead Beaters using 0.1 mm beads and one minute pulses, with ice cooling. Hyphal pieces were collected by filtering through Spin X™ (0.22 μm), and both mycelial supernatant and original culture filtrates were assayed for fumonisin modification by methods outlined above.

Preparation of crude culture filtrate. Agar cultures grown as above were used to inoculate YPD broth cultures (500 ml) in conical flasks at a final concentration of 105 conidia per ml culture. Cultures were incubated 5 days at 28° C. without agitation and mycelia harvested by filtration through 0.45 micron filters under vacuum. The filtrate was discarded and the mycelial mat was washed and resuspended in sterile carbon-free, low mineral salts medium (1 g/liter $NH_3NO_4$; 1 g/liter $NaH_2PO_4$; 0.5 g/liter $MgCl_2$; 0.1 g/liter NaCl; 0.13 g/liter $CaCl_2$; 0.02 g/liter $FeSO_4$ $7H_2O$, pH 4.5) containing 0.5 mg/ml alkaline hydrolyzed crude FB1. After 3–5 days at 28° C. in the dark with no agitation the cultures were filtered through low protein binding 0.45 micron filters to recover the culture filtrate. Phenylmethyl sulfonyl fluoride (PMSF) was added to a concentration of 2.5 mM and the culture filtrate was concentrated using an Amicon™ YM10 membrane in a stirred cell at room temperature, and resuspended in 50 mM sodium acetate, pH 5.2 containing 10 mM $CaCl_2$. The crude culture filtrate (approx. 200-fold concentrated) was stored at −20° C.

To obtain preparative amounts of enzyme-hydrolyzed fumonisin, 10 mg. of FB1(Sigma) was dissolved in 20 mL of 50 mM sodium acetate at pH 5.2+10 mM $CaCl_2$, and 0.25 mL of 200× concentrated crude culture filtrate of 2141.10 was added. The solution was incubated at 37° C. for 14 hours, and then cooled to room temperature. The reaction mixture was brought to approx. pH 9.5 by addition of 0.4 mL of 4 N KOH, and the mixture was extracted twice with 10 mL ethyl acetate. The combined organic layers were dried under $N_2$ and resuspended in $dH_2O$. 2.5 milligrams of organic extracted material were analyzed by Fast Atom Bombardment (FAB) mass spectrometry. The resulting mass spectrum showed a major ion at M/z (+1)=406 mass units, indicating the major product of enzymatic hydrolysis was AP1 which has a calculated molecular weight of 405.

EXAMPLE 2

Preparation of AP1-induced and Non-induced Mycelium.

Liquid cultures of *Exophiala spinifera* isolate 2141.10 were prepared from YPD agar plates (Yeast Extract 10 gm, Bacto-Peptone 20 gm, Dextrose 0.5 gm, and Bacto-Agar 15 gm per liter of water). Aliquots (400–500 uL) of a water suspension of *E. spinifera* cells from YPD agar were spread uniformly onto 150×15 mm YPD agar plates with 4 mm sterile glass beads. The plates were incubated at room temperature for 6–7 days. The mycelia/conidia were transferred from the agar plates into Mineral Salts Medium (MSM) ($Na_2HPO_4 7H_2O$ 0.2 gm, $NH_4Cl$ 1.0 gm, $CaCl_2 2H_2O$ 0.01 gm, $FeSO_4 7H_2O$ 0.02 gm per liter of distilled water, pH 4.5) and centrifuged at 5000× g, 4° C., 20 minutes to pellet the cells. The cell pellet was rinsed once in 40 ml MSM and recentrifuged. The rinsed cell pellet was used to inoculate MSM at a 1:19 ratio of packed cells: MSM. The culture to be induced was supplemented with AP1 to a final concentration of 0.5–1.0 mg/ml and incubated at 28° C., 100 rpm, in the dark to induce catabolic enzymes. The non-induced cultures did not receive AP1 but were place on media containing 4-ABA at the same concentration as AP1. The supernatants were removed by filtration through 0.45 cellulose acetate. The remaining mycelial mat was washed with sterile MSM and then frozen in liquid nitrogen for storage.

EXAMPLE 3

Effect of FB1 and AP1 on Maize Coleoptiles

Maize coleoptiles from 4 day dark-grown germinated maize seeds were excised above the growing point and placed in 96-well microtiter plates in the presence of 60 microliters of sterile distilled water containing FB1 or AP1 at approximately equimolar concentrations of 1.5, 0.5, 0.15, 0.05, 0.015, 0.005, 0.0015, or 0.0005 millimolar, along with water controls. After 2 days in the dark at 28° C the coleoptiles were placed in the light and incubated another 3 days. Injury or lack thereof was evaluated as follows:

| | 0 | .0005 | .0015 | .005 | .015 | .05 | .15 | .5 | 1.5 | mM |
|---|---|---|---|---|---|---|---|---|---|---|
| FB1 | − | − | − | − | +/− | + | + | + | + | |
| AP1 | − | − | − | − | − | − | − | − | + | |

+ = brown necrotic discoloration of coleoptile
− = no symptoms (same as water control)

The results (see table above) indicate there is at least a 30-fold difference in toxicity between FB1 and AP1 to maize coleoptiles of this genotype. This is in general agreement with other studies where the toxicity of the two compounds was compared for plant tissues: In Lemna tissues, AP1 was approx. 40-fold less toxic (Vesonder et al.," *Arch Environ Contam Toxicol* 23: 464–467 (1992).). Studies with both AAL toxin and FB1 in tomato also indicate the hydrolyzed version of the molecule is much less toxic (Gilchrist et al., *Mycopathologia* 117: 57–64 (1992)). Lanprecht et al. also observed an approximate 100-fold reduction in toxicity to tomato by AP1 versus FB1 (Lamprecht et al., *Phytopathology* 84: 383391 (1994))

EXAMPLE 4

Effect of FB1 and AP1 on Maize Tissue Cultured Cells (Black Mexican Sweet, BMS)

FB1 or AP1 at various concentrations was added to suspensions of BMS cells growing in liquid culture medium in 96-well polystyrene plates. After 1 week the cell density in wells was observed under low power magnification and growth of toxin-treated wells was compared to control wells that received water. Growth of BMS cells was significantly inhibited at 0.4 micromolar FB1, but no inhibition was observed until 40 micromolar AP1. This represents an approximate 100-fold difference in toxicity to maize tissue cultured cells. Similarly Van Asch et al. (VanAsch et al., *Phytopathology* 82: 1330–1332 (1992)) observed significant inhibition of maize callus grown on solid medium at 1.4 micromolar FB1. AP1 was not tested in that study, however.

EXAMPLE 5

APAO Activity

A cell-free extract that contains the deaminase activity was obtained by subjecting substrate-induced *Exophiala spinifera* cells to disruption using a Bead Beater™ in 50 mM Na-phosphate, pH 8.0, and recovering the cell-free supernatant by centrifugation and 0.45 micron filtration. Catabolic activity is assayed by incubating extracts with AP1 (hydrolyzed fumonisin B1 backbone) or $^{14}$C-labelled AP1 with the extract and evaluating by TLC on C18 or C60 silica. The product 2-OP has a lower Rf than AP1 and is detected either by radiolabel scan or by $H_2SO_4$ spray/charring of the TLC plate. 2-OP does not react with the amine reagent, fluorescamine that is routinely used to detect AP1 on TLC plates, suggesting that the amine group is missing or chemically modified. Activity is greater at 37° C. than at room temperature, but following 30 min. at 65° C. or 100° C. (no AP1 catabolic activity remained). Activity is maximal at pH 9. At pH 9, complete conversion to 2-OP occurred in 30 minutes. Activity is retained by 30,000 dalton molecular weight cutoff membrane, but only partially retained by 100,000 dalton molecular weight cutoff membrane. Other amine-containing substrates were tested for modification by the crude extract. Fumonisin, with tricarballylic acids attached, is not modified by the extract, indicating that ester-hydrolysis must occur first for the APAO to be able to be effective in modifying FB1 (as noted below, the *E. coli*-expressed, recombinant APAO enzyme does in fact oxidize FB1 although at a lower rate than AP1). Other long-chain bases (sphingosine, sphinganine, and phytosphingosine) are apparently not modified by the crude APAO, suggesting the enzyme(s) is specific for the fumonisin backbone. Preparative amounts of the product, named 2-OP, have also been purified and analyzed by C13 nmr. The results indicate that 2-OP has a keto group at carbon 2 instead of an amine, consistent with an oxidative deamination by an amine oxidase. The C13 nmr data also indicate that 2-OP spontaneously forms an internal hemiketal between C-1 and C-5, resulting in a 5-membered ring with a new chiral center at C-2. All other carbon assignments are as in AP1, thus 2-OP is a compound of composition $C_{22}H_{44}O_6$, FW 404. The product of the enzyme acting on hydrolyzed fumonisin would not be expected to display any significant toxicity.

Other enzymes were tested for their ability to modify AP1. All enzymes were assayed by radiolabeled TLC, as described above, under optimal conditions at 37° Celsius, overnight or longer. The results are as follows:

| Deaminating | EC | Source | Result |
|---|---|---|---|
| Monoamine Oxidase | 1.4.3.4 | bovine plasma | negative |
| D-amino oxidase | 1.4.3.3 | porcine kidney; Type X | negative |
| L-amino oxidase | 1.4.3.2 | *C. adamanteus* venom; Type I | negative |
| Tyramine oxidase | 1.4.3.4 | Anthrobacter spp | negative |
| Methylamine dehydrogenase | 1.4.99.3 | *Paracoccus denitrificans* | negative |
| Aralkyl amine dehydrogenase | 1.4.99.4 | *Alcaligenes faecalis* | negative |
| Phenylalanine ammonia lyase | 4.3.1.5 | *Rhodotorula glutinis*; Type I | negative |
| Histidine ammonia lyase | 4.3.1.3 | *Pseudomonas fluorescens* | negative |
| L-aspartase | 4.3.1.1 | *Hafnia alvei* (*Bacterium cadaveris*) | negative |
| Tyrosine oxidase | 1.14.18.1 | mushroom | negative |
| Lysine oxidase | 1.4.3.14 | *Trichoderma viride* | negative |
| Diamine oxidase | 1.4.3.6 | porcine kidney | negative |

The results were negative for each enzyme tested. Therefore isolates from the American Type Culture Collection (ATCC) were collected. The ATCC isolates selected were listed as containing amine-modifying enzymes or were capable of growth/utilization on amine-containing substrates. The isolates were tested to determine if they could grow on or utilize AP1 as the sole carbon source and if any could modify AP1 to a new compound(s). The nitrogen sources that were used in liquid cultures were AP1 0.1% (w/v), s-butylanine 0.1% (v/v), n-butylamine 0.1% (v/v), and ammonium nitrate 0.2% (w/v). These were prepared in Vogel's Minimal Media (without $NH_4NO_3$) containing 2% sucrose. The isolates were inoculated into the various media and monitored for growth over 2–3 weeks. They were also assayed with the $^{14}C$-radiolabeled TLC assay for AP1 modification. In summary, none of the isolates tested exhibited modification of AP1 in vivo. Clearly the APAO enzyme is unique and unusual in its ability to modify the AP1 toxin.

EXAMPLE 6

Isolation of the trAPAO Polynucleotide

The trAPAO polynucleotide was identified using a proprietary transcript imaging method that compares transcript patterns in two samples and allows cloning of differentially expressed fragments. This technology was developed by CuraGen® (New Haven, Conn.). (see Published PCT patent application no. WO 97/15690, published May 1, 1997, and hereby incorporated by reference) Fluorescently-tagged, PCR amplified cDNA fragments representing expressed transcripts can be visualized as bands or peaks on a gel tracing, and the cDNA from differentially expressed (induced or suppressed) bands can be recovered from a duplicate gel, cloned and sequenced. Known cDNAs can be identified without the need for cloning, by matching the predicted size and partially known sequence of specific bands on the tracing.

In the present invention two RNA samples were obtained from cultures of E. spinifera grown for a specified period in a mineral salts medium containing either AP1 (induced condition), or gamma-aminobutyric acid (ABA; non-induced condition) as a sole carbon source. In the induced condition, fumonisin esterase and APAO enzyme activities are detected, whereas in the non-induced condition these activities are not detected. The methods used for induction of APAO and detection of activity are described earlier (see Example 2 and Example 5). RNA was extracted from induced mycelium by Tri-Reagent methods (Molecular Research Center Inc., Cincinnati, Ohio) only grinding a frozen slurry of tissue and Tri-Reagent with a mortar and pestle until almost melted and adding an additional extraction after the phase separation by extracting the aqueous phase one time with phenol, and two times with a phenol:chloroform:isoamyl alcohol mixture. The RNA's were submitted for CuraGen® transcript imaging to detect cDNA fragments that are induced specifically in the presence AP1. In the resulting gel tracing several bands were found which showed induction of at least 2-fold and up to 79-fold or even 100-fold or more in AP1. In the resulting gel tracing several bands were found which showed induction of at least 10-fold in AP1-grown cells as compared to cells grown in ABA. The sequence of two highly induced bands can be found in Table 1.

TABLE 1

Nucleotide sequence of two CuraGen ® bands that were identified as strongly induced by AP1 in cultures of Exophiala spinifera.

>k0n0-395.5_b (SEQ ID NO: 1)

GGGCCCCGGCGTTCTCGTAGGCTGCGCGGAGTT-
GGTCCCAGACAGACTTTTGTCGTACCTGCTTG-

TABLE 1-continued

Nucleotide sequence of two CuraGen ® bands that were identified as strongly induced by AP1 in cultures of Exophiala spinifera.

GACTGTTGGGACCACTTCCGTCCCGGGTCTCC-
GACCATGAAACAGGTAATGGACCATTGTCGAT-
CGACGTCGATGCTGGTATCTCTGGCAAATGAG-
ATGGGGTCACAGCTCGATTGGAGGACGCCCGA-
GAAGCCTTGTTCGCGCCACCACGGCTTGTCCC-
ATACGAAGACTATCTTGCTATAGTAGCCCAGG-
ATAGAATTTTCCGCCAATGCTTGCTTCTCGGC-
GGGAAGAGGTGGTGAAAATGTCAAGGTGGGAT
ACAAGGTTGTCGGTAACGAAACCANCACCTTT-
TTGCTTCGGAACACGGCGC

>r0c0-182.3_6 (SEQ ID NO: 2)

GAATTTTCCGCCAATGCTTGCTTCTCGGCGGGA-
AGAGGTGGTGAAAATGTCAAGGTGGGATACA
AGGTTGTCGGTAACGAAACCACCACCTTTTTGC-
TTCGGAACACGGCGCCCGAGGCCGATCGTAC-
TGTACAGCCGGATGCCGACTGCTCAATTT-
CAGCGACGGGGGTGTTGAGGTGCAC

Two of the highly induced bands, k0n0-395.5, and r0c0-182.3 showed significant sequence homology to a family of enzymes, flavin-containing amine oxidases (EC 1.4.3.4), that oxidizes primary amines to an aldehyde or ketone, releasing ammonia and hydrogen peroxide (Table 2).

TABLE 2

Identification of a putative flavin amine oxidase from E. spinifera: AP1-induced transcript fragments with amine oxidase homology. BLAST 2.0 default parameters.

| Clone ID | Size | Best Hit | Best Hit Name, source | Prob | from | to | Likely function |
|---|---|---|---|---|---|---|---|
| k0n0-395.5 | 395 bp | P40974 | putrescine oxidase, Micrococcus rubens, EC 1.4.3.10 Length = 478 | 8.0 e-07 | 276 | 333 | oxidation of C-2 amine of AP1 |
| r0c0-182.3 (contigs with k0n0-395) | 182 bp | P12398 | monoamine oxidase type A(MAO-A) [Bos taurus] Length = 527 | 0.0039 | 238 | 296 | oxidation of C-2 amine of AP1 |

The chemical structure of the primary product of AP1 deamination is thought to be a 2-keto compound which cyclizes to a hemiketal at carbons 2 and 5. Therefore it is predicted that this induced enzyme is responsible for deamination of AP1.

Using sequence derived from k0n0-395.5, a partial CDNA was obtained by 3' and 5'RACE-PCR (Chenchik, et al., CLONTECHniques X 1:5–8 (1995); Chenchik, et al., A new method for full-length cDNA cloning by PCR. In A Laboratory Guide to RNA: Isolation, Analysis, and Synthesis. Ed. Krieg, P. A. (Wiley-Liss, Inc.), 273–321 (1996)). A RACE cloning kit from CLONTECH was used, to obtain the RACE amplicons. Briefly, poly A+ RNA is transcribed to make first strand cDNA using a "lock-docking" poly T, CDNA synthesis primer, the second strand is synthesized and the Marathon cDNA adaptor is ligated to both ends of the ds cDNA. Diluted template is then used with the Marathon adapter primer and in separate reactions either a 5' Gene Specific Primer (GSP) or a 3'GSP is used to produce the 3' or 5' RACE amplicon. After characterization of the RACE product(s) and sequencing, full-length cDNAs may be generated by 1) end-to-end PCR using distal 5' and 3' GSPs with the adapter-ligated ds CDNA as template, or 2) the cloned 5' and 3'-RACE fragments may be digested with a restriction enzyme that cuts uniquely in the region of overlap, the fragments isolated and ligated. Subsequently, the RACE-generated full-length cDNAs from 1) and 2) may be cloned into a suitable vector.

In combination with the supplied adapter primer the following gene specific primers were used: for 3' RACE the oligonucleotide N21965: 5'-TGGTTTCGTTACCGACA ACCTTGTATCCC-3' (SEQ ID NO: 3) and for 5' race, the oligonucleotide N21968: 5'-GAGTTGGTCCCAGAC AGACTTTTGTCGT-3' (SEQ ID NO: 4. The polynucleotide sequence of the trAPAO polynucleotide, k0n0-395__6.5, from *Exophiala spinifera* is shown in SEQ ID NO: 5. The polypeptide sequence of trAPAO is shown in SEQ ID NO: 6.

A second clone of APAO containing an unspliced intron was also found. The polynucleotide sequence of trAPAO-I polynucleotide, k0n0-395__5.4, the intron containing clone, from *Exophiala spinifera*, can be found in SEQ ID NO: 7. The polypeptide sequence of trAPAO-1 with the intron spliced out is shown in SEQ ID NO: 8. The polypeptide sequence of trAPAO-1 without the intron spliced out is shown in SEQ ID NO: 9.

EXAMPLE 7

Heterologous Expression of trAPAO

Protein alignments generated with PileUp (GCG) indicate that k0n0-395__6.5 (trAPAO) is similar in size to other flavin amine oxidases and is close to being full length with respect to the amino terminus of their class of proteins. The k0n0-395__6.5 sequence contains a complete β-α-β fold that is required for dinucleotide (FAD) binding, close to the amino end. The k0n0-395 sequence appears to lack only a variable amino terminal segment that varies in length from 5 amino acids in rat monoamine oxidases A & B to 40 amino acids in length in Aspergillus MAO-N. The function of these amino terminal extensions is not known; they are not recognizable as secretion signals. Based on the likely localization of the Exophiala APAO outside the cell membrane, the prediction is that k0n0-395 would have a signal sequence similar to that of the fumonisin esterase cloned from the same organism (U.S. Pat. No. 5,716,820, supra). Using GenomeWalker™, it is possible to clone the 5' end of the transcript and upstream genomic regulatory elements. However, the signal sequence is not expected to be critical to the functionality of the enzyme; in fact, the preferred strategy for heterologous expression in maize and *Pichia pastoris* involves replacing the endogenous signal sequence (if present) with an optimized signal sequence for the organism, e.g. barley alpha amylase for maize and the yeast alpha factor secretion signal for Pichia. In maize transformed with fumonisin esterase, the barley alpha amylase signal-sequence gave higher amounts of functional protein than the native fungal signal, therefore replacement of the native fungal signal sequence is a logical optimization step. Since many of the amine oxidases have a positively charged amino acid near the N-terminus and upstream of the dinucleotide binding site, an additional optimization step included adding a codon for the lysine (K) to the N-terminus of the trAPAO clone (k0n0-395__6.5, SEQ ID NO: 5). This clone is designated K:trAPAO and can be seen in SEQ ID NOS: 10 and 11. The extra lysine is at amino acid 1 and nucleotides 1–3.

EXAMPLE 8

Pichia Expression of trAPAO

For optimum expression of trAPAO in *Pichia pastoris* the alpha mating factor signal peptide was fused in-frame with K:trAPAO coding sequence and can be seen in SEQ ID NOS: 16 and 17. The nucleotide sequence of clone pPicZalphaA:K:trAPAO contains a PCR-amplified insert comprising the k0n0-395 open reading frame with an additional lysine residue at the amino terminus, with a 5' EcoRI site and 3' NotI site for in-frame cloning into the alpha factor secretion vector pPicZalphaA. Nucleotides 1–267 contain the yeast α mating factor secretion signal. The amino acid sequence of shown in SEQ ID NO: 17 contains the trAPAO polypeptide produced from pPicZalphaA:K:trAPAO following transformation into *Pichia pastoris*.

For cloning into expression vectors, two cloning strategies were used. The cDNA k0n0-395__5.4 was generated by using end-to-end PCR using distal 5' and 3' GSPs with the adapter-ligated double stranded cDNA as a template. Each oligonucleotide primer was designed with 5' restriction enzyme sites that contain a 23–25 bp of anchored gene sequence. The 3' primer also included the stop codon. The primer sequences are N23256: 5'-ggggaattcAAAGACAACGTTGCGGACGTGGTAG-3' (SEQ ID NO: 12) and N23259: 5'-ggggcggccgc CTATGCTGCTGGCACCAGGCTAG-3' (SEQ ID NO: 13). A second method was used to generate k0n0-395__6.5. 5' RACE and 3' RACE products using a distal primer containing the necessary restriction enzyme sites, stop codon, etc as described above and paired with a "medial" GSP. The "medial primers" N21965: 5'-TGGTTTCGTTACCG ACAACCTTGTATCCC-3' (SEQ ID NO: 14) for 3' RACE and for 5' race, the oligonucleotide N21968: 5'-GAGTTGGTCCCAGACAGACTMITGTCGT-3' (SEQ ID NO: 15). Adapter-ligated double stranded cDNA was used as template. The isolated 5' and 3'-RACE fragments were digested with a restriction enzyme that cuts uniquely in the region of overlap, in this case Bgl I, isolated and ligated into the expression vector. The digestible restriction sites allow cloning of the inserts in-frame into EcoRI/NotI digested pPicZalphaA. pPicZalphaA is an *E. coli* compatible Pichia expression vector containing a functional yeast alpha factor secretion signal and peptide processing sites, allowing high efficiency, inducible secretion into the culture medium of Pichia. The resulting 1.4 kb bands were cloned into EcoRI/NotI digested pPicZalphaA plasmid.

SEQ ID NO: 16 contains the polynucleotide sequence of clone pPicZalphaA:K:trAPAO, a PCR-amplified insert that comprises the k0n0-395 open reading frame with an additional lysine residue at the amino terminus, and a 5' EcoRI site and 3' NotI site for in-frame cloning into the alpha factor secretion vector pPicZalphaA. SEQ ID NO: 17 contains the amino acid sequence of the trAPAO polypeptide produced from pPicZalphaA:K:trAPAO following transformation into *Pichia pastoris*. The alpha factor secretion signal and a lysine are added.

Pichia was transformed as described in Invitrogen Manual, Easy Select™ Pichia Expression Kit, Version B, #161219, with the trAPAO polynucleotide as described above with either an intron (trAPAO-I, negative control, no expression of active trAPAO since Pichia does not splice introns very efficiently) or without an intron (capable of making an active APAO protein). The Pichia culture fluids and pellets were assayed for APAO activity as described earlier.

The set of frozen six day Pichia culture cell pellets contained two samples with intron (SEQ ID NO: 7) in gene construct, #11, #14, and two samples without intron in gene construct (SEQ ID NO: 5), #6, #52. The six day culture fluids from the same cultures were used to spike with crude fungal enzyme for positive controls.

The 50 µl cell pellets were resuspended in 150 µl cold 50 mM Na-phosphate, pH 8.0, and divided into two fresh 500 µl tubes. One tube was kept on ice with no treatment, the pellet suspension, and one tube was used for lysis. An equal volume of 0.1 mm zirconia-silica beads was added to each tube. The tubes were BeadBeat™ for 15 seconds then cooled on ice 5 minutes. This was repeated three times. The crude lysate was then transferred to another tube for assay or lysate suspension.

The TLC assays were performed as follows, the samples are 1) pellet suspensions; 10 µl; 2) lysate suspensions; 10 µl; 3) media controls-mixed 5 µl media with 5 µl crude fungal enzyme; 10 µl; 4) positive control-used crude fungal enzyme undiluted; 10 µl; 5) substrate control-used 50 mM Na-phosphate, pH8.0; 10 µl. Ten microliters of each sample plus 10 µl of $^{14}$C-AP1 (1 mg/ml, 50 mM Na-phosphate, pH 8) was incubated at room temperature for 6 days. One microliter of the sample was spotted onto C18 and C60 TLC plates. The C18 plates were developed in MeOH:4% KCl (3:2). The C60 plastes were develped in $CHCl_3$:MeOH:$CH_3COOH$:$H_2O$ (55:36:8:1). The plates were then air dried and then exposed to a PhosphorScreen™ for 2–3 days. A Storm™ PhosphorImager was used to develop the images.

A positive TLC result is obtained if an additional radioactive spot appears at a lower Rf of the produced AP1 modification earlier identified as 2-OP, a deaminated product of AP1. In samples #6 and #52 (without intron) the AP1-modifying enzyme activity (conversion of AP1 to 2-OP) was detected in pellet suspensions and pellet lysates, although the majority of activity was associated with the pellet suspensions. In samples #11 and #14 (with intron) a minimal amount of AP1-modifying enzyme activity was detectable in the pellet lysate of #14 only, which indicates Pichia cannot process the intron efficiently.

This experiment verified APAO activity can be detected in Pichia transformants, which verifies that trAPAO as described functions correctly in degrading AP1. The activity is associated with cell suspensions, which show higher activity than pellet lysates. Pellet lysates may show less activity due to release of endogenous proteases during lysis of the cells.

EXAMPLE 9

Expression of trAPAO in *E. coli*

The vector for expressing K:trAPAO in *E. coli* is pGEXAT-1. This vector is a prokaryotic glutathione S-transfcrase (GST) fusion vector for inducible, high-level intracellular expression of genes or gene fragments as fusions with *Schistosoma japonicum* GST. GST gene fusion vectors include the following features, a lac promoter for inducible, high-level expression; an internal lac Iq gene for use in any *E. coli* host; and the thrombin factor Xa or PreScission Protease recognition sites for cleaving the desired protein from the fusion product. The insert of interest, k0n0-395_6.5 (K:trAPAO), was subcloned into the 5' EcoRI site and a 3' NotI site allowing in-frame expression of the GST:K:trAPAO or GST:APAO fusion peptide.

The polynucleotide sequence of the GST:K:trAPAO fusion can be found in SEQ ID NO: 18. The GST fusion with polylinker can be found at nucleotides 1 to 687. The K:trAPAO can be found at nucleotides 688 to 2076. The resulting polypeptide for the GST:K:trAPAO fusion can be seen at SEQ ID NO: 19. Amino acids 1 to 229 represent the GST fusion plus polyliker and amino acids 230 to 692 represent the K:trAPAO portion of the fusion.

*E. coli* was transformed with the pGEX4T-1 vector containing K:trAPAO or GST:APAO as described in BRL catalogue, Life Technologies, Inc. catalogue; Hanahan, D., *J. Mol. Biol.* 166:557 (1983) Jessee, J. *Focus* 6:4 (1984); King, P. V. and Blakesley, R., Focus 8:1, 1 (1986), and hereby incorporated by reference. The transformed *E. coli* was induced by addition of IPTG (isopropyl b-D-thiogalactopyranoside). Four samples of soluble extract and four samples of insoluble inclusion bodies were tested for trAPAO or GST:APAO activity as described in Example 9. APAO activity was present in all soluble samples and two insoluble samples. Highest activity was found at 10 uM IPTG induction. Thus the pGEX-4T-1 vector containing k0n0-395_6.5 construct is capable of producing active APAO enzyme in *E coli*.

EXAMPLE 10

The Complete Nucleotide Sequence of the Exophiala APAO Gene

Using Genome Walker, the complete nucleotide sequence of the Exophiala APAO gene was recovered. The nucleotide sequence described in SEQ ID NO: 5 is missing a portion of the 5' end of the native gene. The missing portion of the 5' end of the native gene is not necessary for expression of an active APAO enzyme, as can be seen in Examples 9 and 10. The complete nucleotide sequence of APAO can be seen in SEQ ID NO: 22. The translation of SEQ ID NO: 22 can be found in SEQ ID NO: 23.

EXAMPLE 11

Expression of APAO and ESP1 in Transgenic Maize Callus

One of the preferred constructs for expression in maize is the nucleotide sequence of the trAPAO fused to the barley alpha amylase signal sequence. The nucleotide sequence of K:trAPAO translational fusion with barley alpha amylase signal sequence, for expression and secretion of the mature trAPAO in maize can be seen in SEQ ID NO: 20. Nucleotides 1–72, represent the barley alpha amylase signal sequence; nucleotides 73–75, represent the added lysine residue; and nucleotides 76–1464, represent the trAPAO cDNA. The amino acid sequence translation of SEQ ID NO: 20 can be found in SEQ ID NO: 21. Amino acids 1 to 24 represent the barley alpha amylase signal sequence and amino acids 25 to 463 is the sequence of K:trAPAO.

Maize embryos were transformed with linear DNA (insert, lacking a bacterial antibiotic resistance marker), derived from constructs containing three transcription units: 1) a PAT selectable marker gene (Wohlieben el al., *Gene* 70, 25–37 (1988)), 2) fumonisin esterase ESP1 fused to a barley alpha amylase signal sequence, and 3) full length APAO without or with an amino-terminal barley alpha amylase signal sequence, (P13603, comprising a PAT selectable marker fused to a 35S promoter, fumonisin esterase ESP1 fused to a barley alpha amylase signal sequence and the ubiquitin promoter, and APAO fused to the ubiquitin promoter and P13611, comprising a PAT selectable marker fused to the 35S promoter, fumonisin esterase ESP1 fused to a barley alpha amylase signal sequence and the ubiquitin promoter and APAO fused to a barley alpha amylase signal sequence and the ubiquitin promoter). In these constructs both ESP1 and APAO were linked to the maize ubiquitin promoter and first intron. In a third construct, the same three transcriptional units were cloned into an Agrobacterium T1 vector (P15258, the construct comprises a PAT selectable marker, fumonisin esterase ESP1 fused to a barley alpha amylase signal sequence and APAO). Stably transformed callus or T0 plants regenerated from callus were tested for ESP1 and APAO activity in buffer extracts of leaf tissue, using radiolabeled FB1 and/or AP1 and C18 thin-layer chromatography. Positive controls consist of non-transformed tissue spiked with E coli-expressed recombinant ESP1 or APAO. The results indicate that both ESP1 and APAO activities can be detected in transgenic maize callus and plants.

Expression of ESP1 and APAO in transgenic callus

| Construct | Sample ID Number | ESP1 activity (TLC) | APAO activity (TLC) |
|---|---|---|---|
| 13603 | 3065.031-2 | + | + |
| 13603 | 3065.034-3 | + | + |
| 13603 | 3065.1117-3 | + | + |
| 13603 | 3065.11s7-n13 | + | + |
| 13603 | 3065.117-2 | + | + |
| 13603 | 3065.1115-2 | + | + |
| 13603 | 3065.1115-6 | + | + |
| 13603 | 3065.1112-1 | + | + |
| 13603 | 3065.118-6 | + | + |
| 13603 | 3065.11s3-1 | + | + |
| 13603 | 3065.11s1-13 | + | + |
| 13603 | 2805.762-2 | + | + |
| 13603 | 3065.1110-2 | + | + |
| 13603 | 3065.039-2 | + | + |
| 13611 | 3065.293-3 | + | + |
| 13611 | 3065.263-1 | + | + |
| 13611 | 3070.24.2.3 | + | + |

Transgenic plants were regenerated from the transgenic callus positive for both ESP1 and APAO activity by standard methods known in the art. Enzyme activity was tested as described previously. As can be seen below transgenic maize plants can successfully express both ESP1 and APAO enzymes.

Expression of APAO and ESP1 in transgenic maize plants (T0)

| Construct | Sample ID Number | ESP1 activity (TLC) | APAO activity (TLC) |
|---|---|---|---|
| 13603 | 910080 | + | + |
| 13603 | 910081 | + | + |
| 13603 | 917065 | + | + |

Another preferred construct for expression of APAO in a plant is targeting the APAO to the peroxisome. Maize embryos were bombarded with insert containing APAO operably linked to ubiquitin promoter and a peroxisomal targeting sequence (Gould, el al., *J Cell Biol* 108:1657–1664 (1989)); ESP1 operably linked to ubiquitin promoter and the barley alpha amylase signal sequence; and a selectable marker of PAT operably linked to the 35S promoter (construct number I14952). Negative controls were unbombarded embryos/callus. Positive controls were unbombarded embryos/callus spiked with purified enzyme. Transformed callus was then tested for ESP 1 or APAO activity as previously described. Out of 67 samples tested 18 samples contained both ESP1 activity and APAO activity. Peroxisomally targeted APAO and apoplast targeted fumonisin esterase can both be successfully expressed in a plant cell.

Another preferred construct for expression of APAO in a plant is targeting the APAO to the mitochondrial membrane. A C-terminal extension is required for targeting monoamine oxidases MAO-A and MAO-B to mammalian outer mitochondrial membranes. An MAO-A, MAO-B, or functionally similar C-terminal extension can be fused in-frame to APAO or trAPAO to facilitate localization of this enzyme to the mitochondrial membrane of maize or other transformed species.

EXAMPLE 12

Comparison of APAO Sequence With Other Sequences

The Exophiala cDNA APAO (SEQ ID NO: 22) contains an 1800 bp open reading frame coding for a 600 amino acid polypeptide (SEQ ID NO: 23) with divergent homology to two classes of proteins. The carboxy three-fourths of APAO (amino acids 137 to 593) is strongly homologous to flavin amine oxidases, a group of enzymes catalyzing the oxidative deamination of primary amines at carbon 1. The amine oxidase function of the carboxy terminal domain was confirmed by expression of a truncated APAO polypeptide (from 137 to 600) in both *Pichia pastoris* and *E. coli*, using AP1 as a substrate (see Example 9). The amino terminal portion of APAO, in contrast, (from approx. 5 to 134) shows significant homology to a group of small deduced open reading frames (ORFs) reported in several bacteria and blue-green algae, as well as several higher organisms. These ORFs code for small proteins of unknown function, ranging in size from 14 to 17 kDA. The juxtaposition of these divergent homologies in a single polypeptide has not been reported previously.

Flavin amine oxidases (E.C. 4.1.4.3) are a group of flavoenzymes found in both higher and lower organisms, and serve a variety of functions in catabolism. They catalyze the oxidative deamination of primary amino groups located at the C-1 position of a variety of substrates, resulting in an aldehyde product plus ammonia and hydrogen peroxide. The APAO enzymes of the present invention are the first flavin amine oxidase known to attack a primary amine not located at C-1 (i.e. C-2 of AP1) and resulting in a keto rather than aldehydic product. However, amino acid oxidases, while not closely related to flavin amine oxidases, are flavoenzymes that oxidize a C-2 amine adjacent to a C-1 carboxyl group.

The monoamine oxidases MAO A & B, (from human, bovine, and trout), are localized in the mitochondrial outer membrane of higher organisms and regulate the level of neurotransmitters. Microbial examples include a fungal amine oxidase (*Aspergillus niger* (niger) MAO-N) involved in amine catabolism, and a bacterial putrescine oxidase from a gram (+) bacterium (*Micrococcus rubens*.). The primary polypeptides vary in length from 478 to 527 amino acids, and share regions of high amino acid sequence conservation at the 5' end as well as at various points through the coding region. Protein alignments generated with PileUp (GCG) indicate that trAPAO contains all conserved domains found in this class of proteins including those near the 5' end.

The amine oxidase domain of trAPAO contains several key features shared by this class of enzymes, including an amino-terminal dinucleotide (ADP) binding region characterized by a beta-alpha-beta stretch containing three invariant glycines (G-X-G-X-X-G) in the beta-alpha turn. In trAPAO, this sequence is (DVVVVGAGLSG) (SEQ ID NO: 54). This region is involved in FAD binding. Absent are several features unique to the mammalian amine oxidases, including several essential cysteine residues (Wu et al., *Mol Pharm* 43:888 (1993)), one of which (Cys406 of MAO-A)

is involved in covalent binding of FAD, and a carboxy-terminal extension that has been demonstrated to be involved in transporting to and anchoring the MAO in the outer mitochondrial membrane. The Aspergillus enzyme MAO-N has been demonstrated to contain non-covalent FAD, and also lacks the conserved cysteine. Therefore it is possible that the APAO enzyme has a non-covalent FAD. The Aspergillus MAO-N has a carboxy-terminal tripeptide Ala-Arg-Leu that is involved in peroxisomal targeting and localization; this sequence is absent from Exophiala MAO.

The amine oxidase domain of trAPAO contains a total of seven cysteines, compared to ten for the Aspergillus enzyme and only two for the Micrococcus enzyme. The mammalian MAO enzymes contain variable numbers of cysteines (at least ten), some of which are highly conserved (including the FAD binding residue mentioned above). The trAPAO sequence also has two putative glycosylation sites (NDS, NQS) towards the amino end.

The purpose of the amino-terminal extension of APAO and the basis for its homology to a group of 14–17 kDa proteins is not clear. In Synechocystis, a similar polypeptide ORF is located immediately upstream of the NADP-dependent glutamine dehydrogenase (gdhA) and has been shown to be required for functional expression of gdhA (Chavez et al, 1995). However, in trAPAO the domain is clearly not necessary for enzymatic activity, as shown by the results of the expression experiments using the truncated APAO. An interesting clue comes from the frequent association of this small ORF with gene clusters involved in oxidoreductase activity in bacteria, or induced by heat stress in mice, suggesting a possible role in redox protection. A byproduct of amine oxidase activity is hydrogen peroxide. Flavoenzymes and other redox enzymes are often susceptible to inactivation by hydrogen peroxide (Schrader et al., *App Microb Biotechnol* 45:458; Aguiree, et al., *J Bacteriol* 171:6243 (1989)), and it is possible that this protein has a protective role against oxidants such as hydrogen peroxide. Alternatively, this domain could be involved in enzyme function, localization or association of the enzyme with other structures. No signal peptide region can be detected in this amino terminal region.

In multiple sequence alignment using GCG PileUp, trA-PAO is most similar to putrescine oxidase of *Micrococcus rubens*, Swissprot accession number P40974, (30% identical amino acids, 40% similar). Homology with several mammalian monoamine oxidases A and B, Swissprot accession numbers P21397 (*Homo Sapiens* mao a), P19643 (*Rattus norvegicus* mao b), P21396 (*Rattus norvegicus* mao a), and P21398 (*Bos taurus* mao a), is somewhat less, ranging from 25 to 28% identity and 36 to 40% similarity. Homology to the only other fungal flavin amine oxidase known, MAO-N from *Aspergillus niger* (Swissprot accession number P46882), is somewhat lower (24% identical, 34% similar). The microbial enzymes are considerably divergent from each other, while the mammalian monoamine oxidases share 65 to 87% identity.

The amino terminal domain (ATD) of APAO also shows homology to a 14.5 kD protein from human and rat phagocytes that shows translational inhibition activity in vitro (Swissprot accession #P52758, P52759) Schmiedeknecht, et al., *Eur J Biochem* 242 (2), 339–351 (1996)), and includes a heat-responsive protein from mouse (Samuel, et al., Hepatology 25 (5), 1213–1222 (1997)). This suggests that this family of proteins is involved in regulating cellular metabolism. No example exists in which this domain is fused to a larger protein domain, however, making APAO unique. Without intending to be limited by theory, all of this suggests, that this domain plays a regulatory role in APAO gene expression, possibly to prevent translation of the message when it is not needed. This raises the question of how translation of the message is restored when active enzyme is required by the Exophiala cell. Possibly there are alternative start sites that begin downstream of the inhibitor domain; or proteolysis, complexing, degradation, or phosphorylation/dephosphorylation of the inhibitor domain when it is not needed. The first possibility is less likely because there are no other ATG codons prior to the ATG at 122–124 that constitutes the predicted start site of APAO. The second possibility cannot be easily tested, although there is a casein kinase site in the ATD. Alternative roles for the ATD include oligomerization of the APAO protein, or anchoring the protein to some intracellular site, such as the membrane.

A parallel example of regulatory control over another flavoenzyme, human flavin monooxygenase 4 (FMO-4), by a C-terminal extention has been reported (Itagaki, et al., *J of Biol Chem* 271(33): 20102–20107 (1996)). In this case the introduction of a stop codon prior to the 81 base C-terminal extension allowed expression of active enzyme in heterologous systems. The role of the C-terminal portion was not elucidated, however. In another example, alternative splicing led to a shorter gene product that complexed with and interfered with the function of the normally spliced version (Quinet, et al., *J of Biol Chem* 268(23): 16891–16894 (1993)). In another case, an alternative splicing-generated insert in another protein led to inhibition of cell growth (Bhat, et al., *Protein Engineering* 9(8): 713–718 (1996)). In yet another variation, fas/Apo1 splicing variants prevent apoptosis, apparently through a 49 amino acid domain shared by all variants ((Papoff, et al., *J of Immunology* 156(12): 4622–4630 (1996)).

EXAMPLE 13

Making a Fusion Protein Containing Fumonisin Esterase and AP Amine Oxidase Activity in the Same Polypeptide The enzyme activities of fumonisin esterase and APAO can be combined in a single polypeptide by using the open reading frames together either with or without a spacer region between the two polypeptides. This creates a hybrid protein with dual enzyme activities that can be exported as a unit to the apoplast, and will allow both enzyme activities to be conveniently localized to the same area of the cell wall. The two cDNAs can be combined in either order, but the preferred method is to link them in the order $NH^3$-Esterase:APAO-COOH. The spacer, if present, may consist of a short stretch of amino acids such as GGGSGGGS, or a set of amino acids that comprises a protease cleavage site that can be acted on by an apoplastic protease. This would result in the production of stoichiometric amounts of both esterase and APAO enzymes in the apoplast.

The esterase-APAO fusion protein can be made with either the fumonisin esterase from *E. spinifera* (ESP1) or fumonisin esterase from bacterium (BEST1). Since the pH range for maximum activity of BEST1 is similar to that of APAO (range 6.0 to 8.0), these may present the most effective combination in fusion form. In addition, any of the polynucleotides of the present invention may be used for an esterase-APAO fusion. As described in previous examples these fusion sequences can be placed in the appropriate expression vectors and used to express proteins in either bacteria or plants.

The nucleotide sequence of ESP1 contains three nucleotide differences and three corresponding amino acid differences for the ESP1 sequence disclosed in pending U.S. application Ser. Nos. 08/888,950 and 08/888,949, both filed Jul. 7, 1997. Both the sequences disclosed in the present application and the sequences disclosed in the pending US applications contain functional fumonisin esterase genes. For the purposes of the present invention, either the original ESP1 sequences or the ESP1 sequences may be used in combination with the APAO sequences or in fusion sequences. The nucleotide sequence of a BAA:ESP1:trAPAO construct for plant expression can be found in SEQ ID NO: 24 and the translation in SEQ ID NO: 25. The nucleotide sequence for a BAA:BEST1:K:trAPAO construct for plant expression can be found in SEQ ID NO: 26 and the translation in SEQ ID NO: 27. The nucleotide sequence of a GST:ESP1:K:trAPAO fusion for bacterial expression in a pGEX-4T-1 or similar vector can be found in SEQ ID NO: 28 and the translation in SEQ ID NO: 29. The nucleotide sequence for a GST:BEST1:K:trAPAO fusion for bacterial expression in a pGEX-4T-1 or similar vector can be seen in SEQ ID NO: 30 and the translation in SEQ ID NO: 31.

EXAMPLE 14

APAO Substrate Studies

The following assay was used to determine the substrate specificity of the APAO enzyme. Reaction mix: 436 µl of 200 mM Na-phosphate, pH8.0; 50 µl substrate (10 mM); 2 µl Amplex Red (1 mg in 200 µl DMSO); and 2 µl of Peroxidase (5000 U/ml). The APAO enzyme was recombinant enzyme produced as GST fusion in $E.$ $coli$, purified over a glutathione affinity column and cleaved with thrombin to remove the GST. All components were mixed at room temperature. The initial rate was determined in a spectrophotometer at 572 nm over one minute by absorbance units/second (BLANK). Ten microliters of APAO at 70 ug/ml was added and mixed. The initial rate was again determined at 572 nm over one minute in absorbance units/second (SAMPLE). The rates were converted to absorbance units/minute. The BLANK value was subtracted from the SAMPLE value. The absorbance units were converted to $\mu$M $H_2O_2$ wherein 1 $\mu$M $H_2O_2$ equals 0.138 absorbance units at pH 8.0.

| SUBSTRATES FOR APAO | |
|---|---|
| SUBSTRATE | RATE µM $H_2O_2$/min |
| 1 mM Fumonisin B1 | 0.1429 |
| 1 mM AP1 | 0.8876 |
| 0.5 mg/mL Fumonisin B2 | 0.3058 |
| 1 mM Fumonisin B3 | 0.1449 |
| 0.5 mg/mL Fumonisin B4 | 0.1728 |
| 1 mM norepinephrine | 0.0087 |
| 1 mM epinephrine | 0.0071 |
| 1 mM dopamine | 0.0040 |
| 1 mM spermine | 0.0002 |

NOT SUBSTRATES FOR APAO (defined as compounds resulting in less than 1% conversion to hydrogen peroxide by APAO relative to AP1 under similar conditions of time, pH, temperature, and substrate concentration): 2-phenylethylamine, spermidine, EDTA-Na$_2$, tryptamine, putrescine, benzamidine, serotonin, cadaverine, Pefabloc SC, tyramine, 1,3-diaminopropane, leupeptin, histamine, hydroxylamine, aprotinin, deprenyl, Fumonisin C4, isoniazid, sphingosine, phenelzine, sphinganine, phytosphingosine, D-alanine, DL-alanine, L-arginine, L-asparagine, L-aspartic acid, D-aspartic acid, L-cysteine, L-glutamine, L-glutamic acid, glycine, L-histidine, L-isoleucine, L-leucine, L-lysine, DL-lysine, L-methionine, DL-methionine, L-phenylaiamine, L-proline, L-threonine, L-tryptophan, L-tyrosine, L-valine.

EXAMPLE 15

Removal of Glycosylation Sites From APAO.

Some cytosolic enzymes, when engineered for secretion by fusion with a heterologous signal peptide, lack function due to glycosylation at one or more potential glycosylation sites (amino acid consensus sequence N-X-S/T) that are not normally glycosylated in the native environment (Farrell L B, Beachy R N, *Plant Mol Biol* 15(6):821–5 (1990)). Since APAO lacks a recognizable signal sequence, it may be cytoplasmically localized in *Exophiala spinifera*, although secretion by some other method not involving a signal peptide cannot be ruled out. APAO contains two potential glycosylation sites, which can potentially be glycosylated, when APAO is secreted in a plant or other eukaryotic cell. These glycosylation sites can be eliminated without affecting protein function by means of site-directed mutagenesis using standard protocols (such as kits available from CLON-TECH Laboratories, Inc. (Palo Alto, Calif.)).

SEQ ID NO: 32 shows the amino acid sequence of a GST:APAO in which two amino acids of APAO have been changed by site-directed mutagenesis to eliminate two potential glycosylation sites. The first mutation changes asparagine at amino acid 201 of APAO to serine, and the second mutation changes serine at amino acid 206 of APAO to asparagine. Other mutations at either amino acid 200, 201, 202, 203, 204, 205, 206, or 207 of APAO, or a combination of these, can also be engineered to accomplish the removal of the glycosylation signal (Meliquist, J. L., Kasturi, L., Spitalnik, S. L., and Shakin-Eshelman, S. H., 1998, The amino acid following an Asn-X-Ser/Thr sequence is an important determinant of n-linked core glycosylation efficiency. Biochemistry 37:6833).

Other modifications to APAO can be made to improve its expression in a plant system, including site-directed mutagenesis to remove selected cysteine residues, which may be detrimental to proper folding when the protein is secreted into the endomembrane system for delivery to the apoplast. Cysteines are present at residues 64, 109, 167, 292, 351, 359, 387, 461, and 482, and may or may not be involved in disulfide crosslinking in mature, folded APAO. Using standard methods of site-directed mutagenesis, one or more of these residues can be substituted with alanine or other suitable amino acid, resulting in a modified version of APAO that retains its activity and specificity but displays better activity and stability in an extracellular environment. It is possible that one or more cysteines is involved in covalent attachment of the FAD moiety to the APAO protein, and elimination of this cysteine would be expected to reduce or abolish activity.

EXAMPLE 16

Other APAO Polynucleotides From *Exophiala spinifera* and *Rhinocladiella atrovirens*

Using primers designed from the APAO isolated from *Exophiala spinifera*, ATCC 74269(Table 15), three new APAO polynucleotides were isolated from *Exophiala spinifera* (isolates ESP002 and ESP003), designated ESP002_

C2, ESP002_C3 and ESP003_C12 and three new APAO polynucleotides from *Rhinociadielia afrovirens* (isolate RAT011) designated RAT011_C1, RAT011_C2, RAT011_C4. The strains used to isolate the polynucleotides are described below.

| Isolate | Genus species | Source | FB1 degrader | APAO homologs isolated |
|---|---|---|---|---|
| ESP002 | *Exophiala spinifera* | Palm, ATCC 26089 | Yes | ESP002_c2 in pGEX4T1<br>ESP002_c3 in pGEX4T1 |
| ESP003 | *Exophiala spinifera* | Maize seed | Yes | ESP003_c12 in pGEX4T1 |
| RAT011 | *Rhinocladiella atrovirens* | Maize seed | Yes | RAT011_c1 in pGEM11Zf+<br>RAT011_c2 in pGEX4T1<br>RAT011_c4 in pGEM11Zf+ |

| Growth conditions and production of culture material |
|---|
| 1. Streak 150 × 15 mm YPD plates with a glycerol aliquot of the above isolates. |
| 2. Grow at 28° C. in the dark until there is sufficient growth for inoculating liquid medium usually at least two weeks. |
| 3. Mycelia and spores were scraped from the plates or agar cubes used to inoculate 50 mls YPD broth in 250 ml baffled flasks. |
| 4. Flasks of culture material were grown at 28° C. in the dark at ~125 rpm. |
| 5. After sufficient growth was obtained the cultures were harvested by pelleting the culture in 50 ml centrifuge tubes at 3400 rpm for 15 min. |
| 6. The supernatant was discarded and the pellets were frozen at −20° C. |

| YPD broth and agar medium | | | |
|---|---|---|---|
| Amount per liter: | Yeast Extract | 10 g | |
| | Bactopeptone | 20 g | |
| | Dextrose | 0.5 g | |
| | Bactoagar | 15 g | (for agar media only) |

DNA Isolation

The DNA was isolated according to a modified version of a plant CTAB DNA extraction protocol (Saghai-Maroof M A, et al., *Proc Natl Acad Sci, USA*, 81:8014–8018 (1984)) as follows.

1. Place 0.2–0.5 g (dry weight) lyophilized fungal *mycelium* in a 50 ml disposable centrifuge tube, break up mat with a spatula or glass rod. Shake briefly.
2. Add 10 ml (per 0.5 g mat) of CTAB extraction buffer. Gently mix to wet all the powdered mat.
3. Place in 65° C. water bath for 30 minutes.
4. Cool. Add an equal volume of phenol:chloroform. Shake briefly to mix.
5. Centrifuge 20 minutes at 3400 rpm.
6. To the aqueous phase add an equal volume of chloroform:isoamyl alcohol (24:1). Shake briefly to mix.
7. Centrifuge 15 minutes at 3400 rpm.
8. To aqueous phase add an equal volume of isopropanol.
9. Centrifuge for 30 minutes at 3400 rpm to pellet precipitated DNA.
10. Rinse DNA pellet with 70% ethanol.
11. Air dry pellet.
12. Resuspend pellet in 1–5 ml TE containing 20 ug/ml RNase A.

CTAB Extraction Buffer 0.1 M Tris, pH 7.5
1% CTAB (mixed hexadecyl trimethyl ammonium bromide)
0.7 M NaCl
10 mM EDTA
1% 2-mercaptoethanol
Add proteinase K to a final concentration of 0.3 mg/ml prior to use.

Primer Design

Primers used were gene specific primers based on APAO polynucleotide sequence (SEQ ID NO: 22) with restriction enzymes sites for cloning. The 5'-primer, 26194, contained the restriction enzyme recognition site, EcoRI. The complementary 3'-primer, 23259, contained the restriction enzyme recognition site, NotI.

26194
  5' ggggaattcATGGCACTTGCACCGAGC-TACATCAATC 3', 37-mer (SEQ ID NO: 34)

23259
  5' gggGCGGCCGCCTATGCTGCTGGCAC-CAGGCTAG 3', 34-mer (SEQ ID NO: 13)

PCR conditions

| 1. The PCR cocktail: per 50 ul reaction per 0.2 ml tube | 10 mM dNTPs | 1 ul |
|---|---|---|
| | 10× Advantage polymerase buffer | 5 ul |
| | HPLC water | 38 ul |
| | 10 uM primer 26194 | 2 ul |
| | 10 uM primer 23259 | 2 ul |
| | 50× Advantage polymerase mix (Clontech) | 1 ul |
| | Template, genomic DNA, 50 ng/ul | 1 ul |

2. Thermocycling conditions:

| MJ PTC-100 AgV Thermocycler: | | | |
|---|---|---|---|
| Step | 1 | 95° | 2 minutes |
| | 2 | 95° | 30 seconds |
| | 3 | 60° | 1 minute |
| | 4 | 72° | 1 minute 30 seconds |
| | 5 | Go to step 2, 34× more | |
| | 6 | 72° | 5 minutes |
| | 7 | 4° | Hold |
| | 8 | End | |

3. PCR products were analyzed on a 1% LE-agarose, TAE plus ethidium bromide gel. Bands of about 1900 bp were seen on the gel. The band was not present in the no DNA control reaction.

Cloning Protocols

1. DNA was extracted from excised gel fragments using a QIAGEN Gel Extraction Kit (Catalog number 28704, QIAGEN, Santa Clara, Calif.).

2. PCR fragments were digested with EcoRI and NotI to free up the sites for cloning into EcoRI and NotI digested vector, either pGEX4T1 (Phamacia) or pGEM11Zf+ (Promega).
3. Digests were cleaned up and desalted used a QIAquick PCR Purification Kit (Catalog number 28104).
4. Isolated fragment was quantified and checked for purity on a 1% LE-agarose, TAE+ ethidium bromide gel.
5. Fragments were ligated into compatible sites in either pGEX4T1 (Pharmacia) or PGEM11Zf+ (Promega).
6. After heat inactivation Library efficiency DH5 competent E. coli were transformed with a small amount of the ligation reaction.
7. LB+ carbenicillin, 50 ug/ml, plates were spread with an aliquot of the transformation mix, grown overnight at 37° C.
8. Colonies were screened for full-length insert using a PCR miniprep method utilizing vector primers flanking the multiple cloning region.
9. Positive clones were identified and overnight cultures grown for plasmid isolation and verification by sequencing.
10. Positive clones are identified as follows:

| | |
|---|---|
| DH5 :pGEX4T1:ESP002FL_c2 | (from palm tree isolate) |
| DH5 :pGEX4T1:ESP002FL_c3 | (from palm tree isolate) |
| DH5 :pGEX4T1:ESP003FL_c12 | (from maize isolate) |
| DH5 :pGEM11Zf+:RAT011FL_c1 | (from maize isolate) |
| DH5 :pGEM11Zf+:RAT011FL_c4 | (from maize isolate) |
| DH5 :pGEX4T1:RAT011FL_c2 | (from maize isolate) |

**Important note:
These are genomic clones containing two introns

Sequence Results

Three APAO polynucleotides and related polypeptides were isolated from Exophiala spinifera (isolates ESP002 and ESP003), designated ESP002_C2, (SEQ ID NOS: 35 and 36) ESP002_C3 (SEQ ID NOS: 37 and 38) and ESP003_C12 (SEQ ID NOS: 39 and 40). Three APAO polynucleotides were isolated from Rhinocladiella atrovirens (isolate RAT011) designated RAT001_C1 (SEQ ID NOS: 41 and 42), RAT011_C2 (SEQ ID NOS: 43 and 44), and RAT011_C4 (SEQ ID NOS: 45 and 46). Introns were detected by comparison of the genomic sequence with the cDNA sequence of APAO from E. spinifera 214.10 (SEQ ID NO: 22), and by identifying putative intron splice junctions in the gap domains (Shab, el al., Journal of Molecluar and Applied Genetics 2:111–126 (1983)).

Plasmids containing the polynucleotide sequences of the invention were deposited with American Type Culture Collection (ATCC), Manassas, Va., and assigned Accession No. 98812, 98813, 98814, 98815, 98816, (all deposited on Jul. 15, 1998) and PTA-32 (deposited on May 7, 1999). The deposits will be maintained under the terms of the Budapest Treaty on the International Recognition of the Deposit of Microorganisms for the Purposes of Patent Procedure. The deposits were made merely as a convenience for those of skill in the art and are not an admission that a deposit is required under 35 U.S.C. § 112.

Preliminary sequence results were entered into GCG, and nucleotide and protein alignments were done in a pileup using a software program called Genedoc for shading and homology comparisons (Nicholas, et al., EMBNEW.NEWS 4:14 (1997; or at the Internet site www.cris.com/~Ketchup/genedoc.shtml). The first APAO (SEQ ID NO: 22) sequences were included for comparison. Comparing the reference sequence SEQ ID NO: 22 to the other homologs sequence identities range from 96 to 99% (identities are lower since APAO introns were not included). Homologies are slightly higher comparing Exophiala genes sequences. At the amino acid sequence level the comparison of the reference SEQ ID NO: 23) to the other homologs yielded sequence identities of approximately 97%.

All publications and patent applications in this specification are indicative of the level of ordinary skill in the art to which this invention pertains. All publications and patent applications are herein incorporated by reference to the same extent as if each individual publication or patent application was specifically and individually indicated by reference.

The invention has been described with reference to various specific and preferred embodiments and techniques. However, it should be understood that many variations and modifications may be made while remaining within the spirit and scope of the invention.

What is claimed is:

1. An isolated polynucleotide encoding a protein having fumonisin degrading activity, said polynucleotide selected from the group consisting of:

a) a polynucleotide having at least 90% sequence identity to the polynucleotide as set forth in SEQ ID NO:35;

b) a polynucleotide having at least 95% sequence identity to the polynucleotide as set forth in SEQ ID NO:35; and c) a polynucleotide complementary to the polynucleotide of a) or b).

2. A recombinant expression comprising an isolated polynucleotide encoding a protein having fumonisin degrading activity, said polynucleotide selected from the group consisting of:

a) a polynucleotide having at least 90% sequence identity to the polynucleotide as set forth in SEQ ID NO:35;

b) a polynucleotide having at least 95% sequence identity to the polynucleotide as set forth in SEQ ID NO:35; and c) a polynucleotide complementary to the polynucleotide of a) or b).

3. A vector comprising a recombinant expression comprising an isolated polynucleotide encoding a protein having fumonisin degrading activity, said polynucleotide selected from the group consisting of:

a) a polynucleotide having at least 90% sequence identity to the polynucleotide as set forth in SEQ ID NO:35;

b) a polynucleotide having at least 95% sequence identity to the polynucleotide as set forth in SEQ ID NO:35; and c) a polynucleotide complementary to the polynucleotide of a) or b).

4. A host cell comprising a recombinant expression comprising an isolated polynucleotide encoding a protein having fumonisin degrading activity, said polynucleotide selected from the group consisting of:

a) a polynucleotide having at least 90% sequence identity to the polynucleotide as set forth in SEQ ID NO:35;

b) a polynucleotide having at least 95% sequence identity to the polynucleotide as set forth in SEQ ID NO:35; and c) a polynucleotide complementary to the polynucleotide of a) or b).

5. The host cell of claim 4 wherein the cell is a plant cell.

6. The host cell of claim 5, wherein the plant cell is from a plant selected from the group consisting of maize, sorghum, wheat, tomato, soybean, alfalfa, sunflower, canola cotton, and rice.

7. A transformed plant comprising an isolated polynucleotide encoding a protein having fumonisin degrading activity, said polynucleotide selected from the group consisting of:

a) a polynucleotide having at least 90% sequence identity to the polynucleotide as set forth in SEQ ID NO:35;

b) a polynucleotide having at least 95% sequence identity to the polynucleotide as set forth in SEQ ID NO:35; and c) a polynucleotide complementary to the polynucleotide of a) or b).

8. A plant seed comprising an isolated polynucleotide encoding a protein having fumonisin degrading activity, said polynucleotide selected from the group consisting of:

a) a polynucleotide having at least 90% sequence identity to the polynucleotide as set forth in SEQ ID NO:35;

b) a polynucleotide having at least 95% sequence identity to the polynucleotide as set forth in SEQ ID NO:35; and c) a polynucleotide complementary to the polynucleotide of a) or b).

* * * * *

UNITED STATES PATENT AND TRADEMARK OFFICE
CERTIFICATE OF CORRECTION

PATENT NO. : 6,737,562 B1
DATED : May 18, 2004
INVENTOR(S) : Duvick et al.

It is certified that error appears in the above-identified patent and that said Letters Patent is hereby corrected as shown below:

Column 217,
Line 32, should read:
2. A recombinant expression cassette comprising an isolated poly-
Line 42, should read:
3. A vector comprising a recombinant expression cassette com-
Line 52, should read:
4. A host cell comprising a recombinant expression cassette com- Signed and Sealed this Seventh Day of December, 2004

JON W. DUDAS
*Director of the United States Patent and Trademark Office*

UNITED STATES PATENT AND TRADEMARK OFFICE
CERTIFICATE OF CORRECTION

PATENT NO. : 6,737,562 B1
DATED : May 18, 2004
INVENTOR(S) : Duvick et al.

It is certified that error appears in the above-identified patent and that said Letters Patent is hereby corrected as shown below:

Column 217,
Line 32, should read:
2. A recombinant expression cassette comprising an isolated poly-
Line 42, should read:
3. A vector comprising a recombinant expression cassette com-
Line 52, should read:
4. A host cell comprising a recombinant expression cassette com- Signed and Sealed this Eighteenth Day of January, 2005

JON W. DUDAS
*Director of the United States Patent and Trademark Office*